(12) United States Patent
Sengupta et al.

(10) Patent No.: US 10,071,103 B2
(45) Date of Patent: Sep. 11, 2018

(54) TREATMENTS FOR RESISTANT ACNE

(71) Applicant: VYOME BIOSCIENCES PVT. LTD., New Delhi (IN)

(72) Inventors: Shiladitya Sengupta, Delhi (IN); Suresh Rameshlal Chawrai, Pune (IN); Shamik Ghosh, Delhi (IN); Sumana Ghosh, Delhi (IN); Nilu Jain, New Delhi (IN); Suresh Sadhasivam, Salem (IN); Richard Buchta, Melbourne (AU); Anamika Bhattacharyya, Delhi (IN)

(73) Assignee: VYOME BIOSCIENNCES PVT. LTD., New Delhi (IN)

( * ) Notice: Subject to any disclaimer, the term of this patent is extended or adjusted under 35 U.S.C. 154(b) by 0 days.

(21) Appl. No.: 15/115,143

(22) PCT Filed: Jan. 29, 2015

(86) PCT No.: PCT/IN2015/000057
§ 371 (c)(1),
(2) Date: Jul. 28, 2016

(87) PCT Pub. No.: WO2015/114666
PCT Pub. Date: Aug. 6, 2015

(65) Prior Publication Data
US 2016/0346294 A1  Dec. 1, 2016

(30) Foreign Application Priority Data

Jan. 29, 2014 (IN) .............................. 269/DEL/2014
Nov. 10, 2014 (IN) ........................... 3247/DEL/2014

(51) Int. Cl.
| | | |
|---|---|---|
| A61K 31/55 | (2006.01) | |
| A61K 31/192 | (2006.01) | |
| A61K 45/06 | (2006.01) | |
| A61K 47/02 | (2006.01) | |
| A61K 47/08 | (2006.01) | |
| A61K 47/10 | (2017.01) | |
| C07D 513/04 | (2006.01) | |
| A61K 31/4709 | (2006.01) | |
| A61K 9/00 | (2006.01) | |
| A61K 47/18 | (2017.01) | |
| A61K 47/32 | (2006.01) | |
| A61K 47/36 | (2006.01) | |
| A61K 47/38 | (2006.01) | |

(52) U.S. Cl.
CPC ............ *A61K 31/55* (2013.01); *A61K 9/0014* (2013.01); *A61K 31/192* (2013.01); *A61K 31/4709* (2013.01); *A61K 45/06* (2013.01); *A61K 47/02* (2013.01); *A61K 47/08* (2013.01); *A61K 47/10* (2013.01); *A61K 47/183* (2013.01); *A61K 47/32* (2013.01); *A61K 47/36* (2013.01); *A61K 47/38* (2013.01); *C07D 513/04* (2013.01)

(58) Field of Classification Search
CPC .... A61K 31/55; A61K 9/0014; A61K 31/192; A61K 31/4709; A61K 45/06; A61K 47/02; A61K 47/08; A61K 47/10; A61K 47/183; A61K 47/32; A61K 47/36; A61K 47/38
USPC ................................................... 514/210.16
See application file for complete search history.

(56) References Cited

U.S. PATENT DOCUMENTS

| | | |
|---|---|---|
| 4,668,664 A | 5/1987 | Rougier et al. |
| 5,607,980 A | 3/1997 | McAtee et al. |
| 6,255,279 B1 | 7/2001 | Christophers et al. |
| 2005/0209157 A1 | 9/2005 | Owen |
| 2005/0245545 A1 | 11/2005 | Kase et al. |
| 2005/0282755 A1 | 12/2005 | Hart et al. |
| 2006/0008538 A1 | 1/2006 | Wu et al. |
| 2007/0134729 A1 | 6/2007 | Christensen et al. |
| 2007/0197501 A1 | 8/2007 | Schulz et al. |
| 2011/0144329 A1* | 6/2011 | Shawer ............... C07D 223/12 540/605 |
| 2016/0058775 A1* | 3/2016 | Prasad ................... A61K 8/342 424/401 |

FOREIGN PATENT DOCUMENTS

| | | |
|---|---|---|
| CN | 103524492 A | 1/2014 |
| EP | 0251330 A2 | 1/1998 |
| JP | 2009196934 A | 9/2009 |
| WO | 2006/100495 A1 | 9/2006 |
| WO | 2007/070518 A2 | 6/2007 |
| WO | 2008/035078 A1 | 3/2008 |
| WO | 2012/177770 A1 | 12/2012 |
| WO | 2012/177986 A2 | 12/2012 |
| WO | 2014/167554 A2 | 10/2014 |
| WO | 2014/195872 A1 | 12/2014 |

OTHER PUBLICATIONS

Betriu et al., "Erythromycin and Clindamycin Resistance and Telithromycin Susceptibility in *Streptococcus agalactiae*", Antimicrobial Agents and Chemotherapy 47(3):1112-1114 (2003).
Bryskier et al., "Dual β-lactam-fluoroquinolone compounds: a novel approach to antibacterial treatment", Expert Opinion on Investigational Drugs 6(10):1479-1499 (1997).
Cambau et al., "Target specificity of the new fluoroquinolone besifloxacin in *Streptococcus pneumoniae, Staphylococcus aureus* and *Escherichia coli*", Journal of Antimicrobial Chemotherapy 63:443-450 (2009).
De Lucca et al., "Antifungal peptides: Origin, activity, and therapeutic potential", Revista Iberoamericana de Micologia 17:116-120 (2000).

(Continued)

*Primary Examiner* — Yevgeny Valenrod
(74) *Attorney, Agent, or Firm* — Nixon Peabody LLP; David S. Resnick; Ravinderjit Braich

(57) ABSTRACT

The present disclosure relates generally to novel molecules, compositions, and formulations for treatment of bacterial infections in general and more specifically to bacterial infections with antibiotic resistant pathogens.

16 Claims, 14 Drawing Sheets

(56) References Cited

OTHER PUBLICATIONS

Elitropi et al., "New Cephalosporins and 7α-Methoxy Cephalosporins Chemistry and Biological Activities", The Journal of Antibiotics 32(9):900-908 (1979).

Epand et al., "Diversity of antimicrobial peptides and their mechanisms of action", Biochimica et Biophysica Acta 1462:11-28 (1999).

Haas et al., "Besifloxacin, a Novel Fluoroquinolone, Has Broad-Spectrum In Vitro Activity against Aerobic and Anaerobic Bacteria", Antimicrobial Agents and Chemotherapy 53(8):3552-3560 (2009).

Jeremy et al., "Inflammatory Events Are Involved in Acne Lesion Initiation", Journal of Investigative Dermatology 121(1):20-27 (2003).

Kabara et al., "Fatty Acids and Derivatives as Antimicrobial Agents", Antimicrobial Agents and Chemotherapy 2(1):23-28 (1972).

Kato et al., "Comparison of In Vitro Activities of DU-6859a and Other Fluoroquinolones Against Japanese Isolates of Anaerobic Bacteria", Clinical Infectious Diseases 23(Suppl 1):S31-S35 (1996).

Keren et al., "Specialized Persister Cells and the Mechanism of Multidrug Tolerance in *Escherichia coli*", Journal of Bacteriology 186(24):8172-8180 (2004).

Kim et al., "Activation of Toll-Like Receptor 2 in Acne Triggers Inflammatory Cytokine Responses", The Journal of Immunology 169:1535-1541 (2002).

Lau et al., "Scope and Limitations of The Co-Drug Approach to Topical Drug Delivery", Current Pharmaceutical Design 14(8):794-802 (2008).

Lee et al., "Protease-activated receptor-2 mediates the expression of inflammatory cytokines, antimicrobial peptides, and matrix metalloproteinases in keratinocytes in response to Propionibacterium acnes", Archives of Dermatological Research 302:745-756 (2010).

Liu et al., "Cutting Edge: All-trans Retinoic Acid Down-Regulates TLR2 Expression and Function", The Journal of Immunology 174:2467-2470 (2005).

Mouser et al., "Propionibacterium acnes-Reactive T Helper-1 Cells in the Skin of Patients with Acne Vulgaris", The Journal of Investigative Dermatology 121(5):1226-1228 (2003).

Nagy et al., "Propionibacterium acnes and lipopolysaccharide induce the expression of antimicrobial peptides and proinflammatory cytokines/chemokines in human sebocytes", Microbes and Infection 8:2195-2205 (2006).

Regoes et al., "Pharmacodynamic Functions: a Multiparameter Approach to the Design of Antibiotic Treatment Regimens", Antimicrobial Agents and Chemotherapy 48(10):3670-3676 (2004).

Schlunzen et al., "Structural basis for the interaction of antibiotics with the peptidyl transferase centre in eubacteria", Nature 413:814-821 (2001).

Taglietti et al., "Novel Topical Drug Delivery Systems and Their Potential Use in Acne Vulgaris", Skin Therapy Letter 1-5 (2008).

Thiboutot et al., "IL-17: A Key Player in the P. acnes Inflammatory Cascade?", Journal of Investigative Dermatology 134:307-310 (2014).

Toyoda et al., "An Overview of Topical Antibiotics for Acne Treatment", Dermatology 196(1):130-134 (1998).

Zasloff M., "Antimicrobial peptides of multicellular organisms", Nature 415:389-395 (2002).

Miller et al., "SOS Response Induction by β-Lactams and Bacterial Defense Against Antibiotic Lethality", Science 305:1629-1631 (2004).

Ye et al., "Synthesis and antibacterial activity of pyridonecarboxylic acid derivatives containing 2-methyl-5-nitroimidazol", Acta Pharmaceutica Sinica 38(4):260-263 (2003).

\* cited by examiner

TREATMENTS FOR RESISTANT ACNE

RELATED APPLICATIONS

This application claims benefit priority of Indian Patent Application No. 269/DEL/2014, filed Jan. 29, 2014 and No. 3247/DEL/2014, filed Nov. 10, 2014, the content of both applications is incorporated herein by reference in their entirety.

FIELD OF THE INVENTION

The present disclosure relates generally to novel molecules, compositions, and formulations for treatment of bacterial infections in general and more specifically to bacterial infections with antibiotic-tolerant pathogens.

BACKGROUND OF THE INVENTION

Acne vulgaris is a skin condition that affects over 85% of all people. Acne is a term for a medical condition of plugged pores typically occurring on the face, neck, and upper torso. Following are four primary factors that are currently known to contribute to the formation of acne vulgaris; (1) increased sebum output resulting in oily, greasy skin; (2) increased bacterial activity, normally due to an overabundance of *Propionibacterium acnes* bacteria; (3) plugging (hypercornification) of the follicle or pilosebaceous duct; and (4) and inflammation. The plugged pores result in blackheads, whiteheads, pimples or deeper lumps such as cysts or nodules. Severe cases of acne can result in permanent scarring or disfiguring.

Though acne vulgaris is multifactorial, a commensal skin bacteria (*P. acnes*) plays a major role in the formation of acne lesion. It is an infection of pilosebacious glands, oil glands in the skin. In most cases sudden breakouts of acne can be correlated with sudden increased production of sebum in the affected individual. During adolescence androgen hormones play a crucial role. It leads to overproduction of sebum by the pilosebaceous gland. The situation gets further accentuated by irregular shedding of dead skin from lining of hair follicles. As the dead skin cells clump together in the oily environment, they can form plugs which block the pores of the hair follicles. A pore clogged by the shedding skin is referred to as a comedo.

This creates a very conducive anaerobic condition for *P. acnes* bacteria to grow. Hyperproliferation of *P. acnes* leads to destruction of follicular walls and it sends a danger signal to the host immune system. *P. acnes* may trigger an innate immune reaction both in very early (microcomedogenic) and in late (inflammatory) acne lesions via the activation of Toll like receptors 2 (TLR2) on inante immune cells. TLR activation ultimately triggers the expression various cytokines (like IL-6, IL-8, IL-12, IL-17 etc) and chemokines that stimulate recruitment of other host immune cells [Jeremy et al, 2003; Thibout et al, 2014]. Acne lesions range in severity from blackheads, whiteheads and pimples to more serious lesions such as deeper lumps, cysts and nodules.

Although various over-the-counter products are commercially available to counteract acne condition, such as anti-acne agents for topical use, including salicylic acid; sulfur; lactic acid; glycolic acid; pyruvic acid; urea; resorcinol; N-acetylcysteine; retinoic acid; isotretinoin; tretinoin; adapalene; tazoretene; antibacterials such as clindamycin, tetracyclines, and erythromycin; vitamins such as folic acid and nicotinamide; minerals such as zinc; benzoyl peroxide; octopirox; triclosan; azelaic acid; phenoxyethanol; phenoxypropanol; and flavinoids, these agents tend to lack in potential to mitigate the acne condition and may have negative side effects when devised in conventional topical formulations. A key challenge that has limited the use of topical formulations is the absence of formulations with the desired physicochemical properties and high drug loading, which maintains a concentration significantly higher than the MIC at the site of application by facilitating the right degree of penetration over time but with minimal systemic exposure. A formulation that addresses these unmet needs can be a significant advance in the treatment of acne.

Furthermore, as articulated in [Taglietti et al, 2008], when it comes to the delivery of a drug to a specific site, topical formulations that are efficacious are probably among the most challenging products to develop. Once the product is applied on the skin, a complex interaction occurs between the formulation, the active compounds, and the skin itself. The penetration of the active compound(s) into the skin follows Fick's first law of diffusion, which describes the transfer rate of solutes as a function of the concentration of the various ingredients, the size of the treatment surface area, and the permeability of the skin. However, the skin's permeability can be influenced by many factors, such as the drying, moisturizing, or occluding effects of the excipients in the formulation, which, in combination, can modulate the release of the product at the treatment site. In acne, the site of action is inside the pilosebaceous unit and, therefore, an efficacious anti-acne formulation should facilitate the penetration of the active compound(s) into this extremely lipophilic environment. An effective topical formulation therefore needs to provide a stable chemical environment in a suitable dispensing container in order to accommodate multiple compounds that may have different, if not incompatible, physicochemical characteristics [Tagleitti et al, 2008]. Once applied, a topical formulation must interact with the skin environment, which can influence the rate of the release of the compound(s) in order to achieve adequate skin absorption, and exert additional physical effects on the skin, such as drying, occluding, or moisturizing [Tagleitti et al, 2008]. For example, even if an active agent is very potent, and is effective via a systemic route, in the case of topical administration can behave completely differently, i.e. if the desired concentration is not reached in the pilosebaceous (or skin) unit, it will not serve as an effective anti-acne therapy. Similarly, a molecule or drug can behave entirely differently if formulated with different compositions, which we demonstrate later in an example. Similarly, two molecule or active agents may behave entirely differently in the same formulation or composition. Therefore, every new molecule that needs to be formulated for topical skin application poses a novel and independent challenge as it is impossible to predict which composition and ratio of active and excipients will provide the desired efficacy benefit.

Furthermore, an emerging condition is the evolution of strains of *P. acnes*, which do not respond to the antibiotic agents such as clindamycin, tetracyclines and erythromycin currently approved for the treatment of acne. While the earlier dogmawas that antibiotics failure arises due to selection of 'resistant' strains, i.e. a mutation resulting in alteration of the target of the antibiotic rendering it ineffective, emerging evidence suggests that antibiotic failure is more complex than this simple understanding. The assumption was that if resistance develops, i.e. the target of an antibiotic is altered, it is possible to treat the condition by changing to an alternative antibiotic, the target of which is still intact in the bacteria. However, recent knowledge has rendered this assumption as false. For example, Regoes et al, 2004 demonstrates that even in the absence of any resistance, a subset of bacteria can just exhibit tolerance to an antibiotic, i.e. not undergo lysis. This could arise due to physiological (metabolic) and morphological changes observed in bacteria exposed to antibiotics. For example, in a study published in Science, [Miller et al, 2004] showed that a transient induction of SOS response by ampicillin can protect E. coli against the bactericidal effects of ampicillin. Regoes et al, 2004 suggested that tolerance mechanisms could cross over between some antibiotics, i.e. Antibiotic A might be rendered ineffective due to development of resistance, but it is possible that Antibiotic B, which has an entirely different target/mechanism of action, and is shown to be active in a different or sensitive bacterial strain, may also be rendered ineffective in the resistant strain due to shared tolerance mechanisms. Indeed, massive changes in gene expression leading to alteration in the syntheses of proteins of metabolic and stress response pathways and cell division during exposure of E. coli to ampicillin and ofloxacin have been observed, and a number of these alterations in the gene expression levels were shared between bacteria exposed to ampicillin and ofloxacin, suggesting a bacteria not responding to ampicillin may not respond to ofloxacin although both agents have different targets. We saw a similar observation in screening a library of antibiotics against different strains of P. acnes that are sensitive or non-responsive to clindamycin (a lincosamide). As shown in FIG. 1A, the strain of P. acnes non-responsive to clindamycin also showed increased survival capability in the presence of roxithromycin (a macrolide), which targets a different site from clindamycin. [Keren et al, 2004]. Specialized persister cells and the mechanism of multidrug tolerance in Escherichia coli. J. Bacteriol. 186:8172-8180) suggested that random fluctuations in gene expression are responsible for the formation of specialized persister cells. As argued by Regoes et al, 2004, phenotypic tolerance to antibiotic could actually prevent clearance. As a result, while there remains a need in the art for compositions, formulations and methods for treating acne that is not responding to the currently used agents, especially clindamycin-, minocydine-, erythromycin-, and/ or doxycycline, the probability of tolerance makes itimprobable to predict a drug that may work against P. acnes.

Furthermore, it is increasingly becoming evident that subtle changes in chemical structure of a molecule can dramatically change activity of the molecules against target protein. For example erythromycin (a macrolide) and clindamycin bind to similar 50S ribosomal unit but crystal structure [Schulzen et al, 2001] showed different mode of binding between the agents and amino acid residues present in 50S ribosomal sub-unit. There are known bacterial strains of P. acnes that are resistant to clindamycin but can be either non-responsive or susceptible to erythromycin and vice versa. Interestingly, telithromycin, which is a semisynthetic derivative of erythromycin works well in a bacterial strain that is resistant to both erythromycin and clindamycin [Beitru et al, 2003]. Similarly, in another example, the introduction of 8-chloro group dramatically enhanced the potency of moxifloxacin but a similar change in gatifloxacin had no effect against S. aureus, S. pneumonia, and E. coli. Additionally, molecules of the same class can have different affinity for the same protein target but in different bacteria. For example it has been found that both besifloxacin and moxifloxacin effectively bind to DNA gyrase than ciprofloxacin in S. aureus. In contrary ciprofloxacin binding towards DNA gyrase is more effective in E. coli than moxifloxacin or besifloxacin. Similarly, besifloxacin is found to be best effective molecule against S. pneumonia followed by moxifloxacin and ciprofloxacin. [Cambau et al, 2009]. It is therefore not possible to predict the activity of a molecule against a bacteria or microbe based on its similarity in structure another drug that shows activity against the same microbe or a different microbe, even though they might have similar mechanisms of action. Indeed, as shown in FIG. 1, we observed that molecules that were verisimilar in structure had completely distinct activity against P. acnes, i.e. where one was inactive the other was very potent against both clindamycin-susceptible and -non-resistant P. acnes (FIGS. 1A and 1B). In another example, which we discuss later, we observed a non-lincosamide molecule that was very effective in a P. acnes strain resistant to clindamycin but not active in a clindamycin-sensitive P. acnes (FIGS. 1A and 1B). The identification of an effective drug that works against both sensitive as well as clindamycin-, minocycline-, erythromycin-, or doxycycline-nonresponder P. acnes therefore emerges through serendipity during systematic screening in P. acnes.

Furthermore, while an emerging problem is the development of resistant strains of microbes that are not responding to antimicrobial compounds and compositions well known in the art, there remains a need in the art for a more effective antibiotic that not only works against resistant microbes but also reduces the risk of development of resistance by the microbes to this new antibiotic. Thus molecules that are efficacious antibiotics and also 'prevent' or reduce the development of resistance can be a major advancement in the treatment of microbial diseases.

The inflammatory character of acne has been correlated with the host immune response targeting Propionibacterium acnes, In vitro studies demonstrate that P. acnes whole cells or cell fractions stimulate cytokine and matrix metalloproteinase release from immune cells, keratinocytes, and sebocytes [Kim et al., 2002; Liu et al., 2005; Nagy et al., 2006; Lee et al., 2010] Though P. acnes are long been present in the follicular area, they come in direct contact with immune cells in dermis only after follicular rupture, The innate immune system recognizes P. acnes via TLR2 [Kim et al., 2002], leading to the secretion of inflammatory cytokines, including IL-6, IL-8, IL-12 etc. Follicular rupture happens very late in the disease process. But there are multiple evidences which suggest that the adaptive immune response also has a significant role in the inflammation observed even in early stages of acne, resulting from the recruitment of activated T helper 1 (Th1) lymphocytes to early acne lesions [Mouser et al., 2003]1. A potential treatment of acne therefore needs to resolve inflammation, and should be able to target these inflammatory pathways.

An ideal treatment for acne therefore need molecules that can work at two or more targets. Molecules that work against both antibiotic-sensitive as well as clindamycin-, minocycline-, erythromycin- and doxycycline-tolerant or non-responsive strains of P. acnes and can additionally inhibit the P. acnes-activated inflammatory mediator/s, or molecules that target two or more cellular targets in these microbes while additionally exerting an inhibitory effect on the P. acnes-activated inflammatory mediator/s, and is formulated in an optimal formulation that enables the desired concentration of the active agent on the skin or pilosebaceous region following topical application can emerge as a powerful strategy for the treatment of acne.

SUMMARY

DART

A series of novel DART (Dual Action Rational Therapeutics) molecules were designed and synthesized for treatment of bacterial infections caused by both susceptible and resistant gram positive and gram negative bacteria and specially for curing acne and different skin and skin structure infections and additionally prevent the development of resistance. DART molecules can mount its activity through two distinct mechanisms of action in a microbe (such as a bacteria), and create less chance in mutation development at both target sites in the bacteria. Additionally, it can also act at the host level by modulating the immune response, such as altering the levels of inflammatory cytokines.

The design of DART comprises of two active domains. The two active domains can be selected from different families, for example, β-lactam, β-lactam derivatives, 2- and 4-quinolones, quinolones having halogenated atom specially fluorine atom attached at C-6 or C-7 position of the central ring system, fluoroquinolone with halogenated atom specially chlorine atom attached at C-8 position of the central ring system, tetracycline, oxazolidinone, hydroxypyridones, derivatives of hydroxypyridones, pleuromutilin, azoles, nitroimidazoles, monoxycarbolic acid class, fusidic acid, sulfonamide, sulfonamide derivatives, retinoids, different fatty acids (saturated, unsaturated), propylene glycol and glycerol derivatives of different fatty acids and a strategic combination from each of the families. The design was made strategically by arranging the two active domains in the right steric arrangement for both the active domains to maintain their function against bacteria or fungus. Overall these molecules possess faster bacterial killing with reduction in inflammation and activity against resistant pathogens. These molecules also show a lower risk of development of resistance.

In some embodiments, the DART molecule has at least two chemical domains. Each of said chemical domains binds to a distinct or different active site in a target cell. In a preferred embodiment, a third chemical domain may be present. In a further preferred embodiment, said two chemical domains may be bound together through a said third domain. In some embodiments, the DART molecule has at least two distinct or different anti-bacterial mechanisms of action. In some embodiments, the DART molecule has at least two distinct or different anti-acne mechanisms of action. Without limitations, the DARTs can act on the same target or on different targets, for example, the bacteria and the host. In some embodiments, the DART acts on at least two different targets. In some embodiments, at least one of the targets is different than that affected by conventional antibiotics.

In some embodiments, the DART molecule has a β-lactam ring and a quinolone nucleus, or a quinolone nucleus and a nitro-heterocycle, or a β-lactam ring and a nitroheterocycle.

In some embodiments, the DART has at least two distinct anti-bacterial mechanisms of action, for example inhibits DNA gyrase or topoisomerase IV and transpeptidase-mediated cross-linking of peptidoglycans; inhibits isoprenyl pyrophosphate and transpeptidase-mediated cross-linking of peptidoglycans; inhibits isoprenyl pyrophosphate and DNA gyrase of topoisomerase IV; inhibits folate synthesis and DNA gyrase of topoisomerase IV; inhibits folate synthesis and transpeptidase-mediated cross-linking of peptidoglycans; inhibits DNA gyrase or topoisomerase IV and the 30S ribosomal sub-unit in bacteria; inhibits DNA gyrase or topoisomerase IV and the 50S sub-unit in bacteria; inhibits transpeptidase-mediated cross-linking of peptidoglycans and the 30S or the 50S ribosomal sub-unit in bacteria; inhibits folate synthesis and the 30S or the 50S sub-unit in bacteria; or inhibits isoprenyl pyrophosphate and the 30S or the 50S sub-unit in bacteria, or causes DNA modification, such as inducing DNA nicks while inhibiting the induction of negative supercoils in DNA; or altering the fluidity of the cell membrane while exerting an activity on the DNA; or altering the levels of metal ions in a cell while inducing DNA changes. In some embodiments, the first mechanism of action is an anti-bacterial action and the second mechanism of action is anti-inflammatory or immunomodulatory.

In some embodiments, the DART molecule has at least two distinct treating acne mechanisms of action and modulates at least two different targets. In some embodiments, the first mechanism is an antibacterial action and the second mechanism of action is inhibition of keratinocyte proliferation and differentiation. In some embodiments, the DART molecule has two distinct acne treating mechanisms of action and wherein the first mechanism is an antibacterial action and the second mechanism of action is anti-inflammatory. In some embodiments, the DART molecule is effective against forms of *Propionbacterium acnes* that respond poorly to clindamycin-, or doxycycline-, or erythromycin-, or minocycline-containing anti-acne products. In some embodiments, they are effective against one or more of clindamycin-, minocycline-, erythromycin-, and/or doxycycline-tolerant or resistant strains of *Propionbacterium acnes*. In some embodiments, it prevents the development of resistance in *P. acnes*.

In some embodiments, the DART molecule has at least two distinct anti-bacterial mechanisms of action and modulates at least two different targets against a pathogen. Non limiting examples of such pathogens are: *Bartonella henselae, Borrelia burgdorferi, Campylobacter jejuni, Campylobacter fetus, Chlamydia trachomatis, Chlamydia pneumoniae, Chylamydia psittaci, Simkania negevensis, Escherichia coli* (e.g., O157:H7 and K88), *Ehrlichia chafeensis, Clostridium botulinum, Clostridium perfringens, Clostridium tetani, Enterococcus faecalis, Haemophilius influenzae, Haemophilius ducreyi, Coccidioides immitis, Bordetella pertussis, Coxiella burnetii, Ureaplasma urealyticum, Mycoplasma genitalium, Trichomatis vaginalis, Helicobacter pylori, Helicobacter hepaticus, Legionella pneumophila, Mycobacterium tuberculosis, Mycobacterium bovis, Mycobacterium africanum, Mycobacterium leprae, Mycobacterium asiaticum, Mycobacterium avium, Mycobacterium celatum, Mycobacterium celonae, Mycobacterium fortuitum, Mycobacterium genavense, Mycobacterium haemophilum, Mycobacterium intracellulare, Mycobacterium kansasii, Mycobacterium malmoense, Mycobacterium marinum, Mycobacterium scrofulaceum, Mycobacterium simiae, Mycobacterium szulgai, Mycobacterium ulcerans, Mycobacterium xenopi, Corynebacterium diptheriae, Rhodococcus equi, Rickettsia aeschlimannii, Rickettsia africae, Rickettsia conorii, Arcanobacterium haemolyticum, Bacillus anthracis, Bacillus cereus, Lysteria monocytogenes, Yersinia pestis, Yersinia enterocolitica, Shigella dysenteriae, Neisseria meningitides, Neisseria gonorrhoeae, Streptococcus bovis, Streptococcus hemolyticus, Streptococcus mutans, Streptococcus pyogenes, Streptococcus pneumoniae, Staphylococcus aureus, Staphylococcus epidermidis, Staphylococcus pneumoniae, Staphylococcus saprophyticus, Vibrio cholerae, Vibrio parahaemolyticus, Salmonella typhi, Salmonella paratyphi, Salmonella enteritidis, Treponema pallidum, Candida, Cryptcooccus, Cryptosporidium, Giardia lamblia, Microsporidia, Plasmodium vivax, Pneumocystis carinii, Toxoplasma gondii, Trichophyton mentagrophytes, Enterocytozoon bieneusi, Cyclospora cayetanensis, Encephalitozoon hellem, Encephalitozoon cuniculi*, among other bacteria, archaea, protozoa, and fungi.

In some embodiments, the first and second domains independently have antibacterial activity against a *Staphylococcus* species. Examples of *Staphylococcus* species include, but are not limited to, *S. aureus* group (e.g., *S. aureus, S. simiae*), *S. auricularis* group (e.g., *S. auricularis*), *S. carnosus* group (e.g., *S. carnosus, S. condimenti, S. massiliensis, S. piscifermentans, S. simulans*), *S. epidermidis* group (e.g., *S. capitis, S. caprae, S. epidermidis, S. saccharolyticus*), *S. haemolyticus* group (e.g., *S. devriesei, S. haemolyticus, S. hominis*), *S. hyicus-intermedius* group (e.g., *S. chromogenes, S. felis, S. delphini, S. hyicus, S. intermedius, S. lutrae, S. microti, S. muscae, S. pseudintermedius, S. rostri, S. schleiferi*), *S. lugdunensis* group (e.g., *S. lugdunensis*), *S. saprophyticus* group (e.g., *S. arlettae, S. cohnii, S. equorum, S. gallinarum, S. kloosii, S. leei, S. nepalensis, S. saprophyticus, S. succinus, S. xylosus*), *S. sciuri* group (e.g., *S. fleurettii, S. lentus, S. sciuri, S. stepanovicii, S. vitulinus*), *S. simulans* group (e.g., *S. simulans*), and *S. warneri* group (e.g., *S. pasteuri, S. warneri*).

Without limitations, the DARTS can be in the form of particles, powders, suspensions, dispersions, emulsions, liposomes, micelles, globules, solutions, vesicles, aggregates, creams, gels, and the like.

The disclosure also provides formulations comprising DARTs as the active pharmaceutical ingredient (API).

Antibiotics

The disclosure also provides formulations comprising antibiotic agents, which are not DARTs, as the API. In some embodiments, the antibiotic agent is a8-chloro fluoroquinolone. Exemplary 8-chloro fluoroquinolones include, but are not limited to, besifloxacin, clinafloxacin and sitafloxacin. In some embodiments, the formulation comprises besifloxacin as the API.

In various embodiments, the API can be micronized, suspended, or solubilized. In some embodiments, the API can be in the form of particles, powders, suspensions, dispersions, emulsions, liposomes, micelles, globules, solutions, vesicles, aggregates, and the like. In some embodiments, the API can in the form of a drug carrier.

In some embodiments, the API can be coated. In some other embodiments, the API can be uncoated.

Without limitations, the formulation can be in a form selected from the group consisting of lotions, creams, gels, emulgel, oils, serums, powders, sprays, ointments, solutions, suspensions, dispersions, pastes, foams, peels, films, masks, patches, sticks, rollers, cleansing liquid washes, cleansing solid bars, pastes, foams, powders, shaving creams, impregnated fabric), and the like. In some embodiments, the formulation is in a form selected from the group consisting of gel, cream, spary, face wash, soap bar, body wash, lotion, suspended drug loaded gel, suspended drug loaded cream, and any combinations thereof.

In some embodiments, the API or the formulation can be used to treat acne not responding to antibiotics. Specifically, it exerts greater efficacy against forms of *Propionbacterium acnes* that respond poorly to clindamycin-, or doxycycline-, or erythromycin-, or minocycline-containing anti-acne products.

In some embodiments, the API or the formulation can be used to treat acne by exerting an anti-inflammatory effect.

In some embodiments, the API or the formulation can be used to treat acne by killing strains of *Propionbacterium acne* that are sensitive to one or more of clindamycin-, minocycline-, erythromycin-, and/or doxycycline and additionally exerting a greater efficacy by inhibiting *P. acnes*-mediated inflammatory pathways (i.e. dual mechanisms of action).

Combinations

The disclosure also provides formulations comprising a combination of two or more antibiotic agents. For example, an 8-chloro fluoroquinolone in combination with another anti-acne agent. In some embodiments, the formulation comprises two or more different 8-chloro fluoroquinolones. In some embodiments, the formulation comprises besifloxacin and a retinoid, such as adapalene.

In some embodiments, the formulation comprises an anti-acne agent and an anti-inflammatory agent. For example, the formulation can comprise an 8-chloro fluoroquinolone and an anti-inflammatory agent.

In some embodiments, the two or more antibiotic agents can be a DART molecule or two or more different DART molecules. In some embodiments, one of the two or more antibiotic agent is a DART and the other is not a DART molecule.

As described herein, the disclosure provides formulations comprising DART and/or non-DART antibiotic agent as the API. As such, exemplary API's for the formulations include DARTs, anti-bacterial, anti-fungal and anti-acne agents. In some embodiments, the API can be in the form of a drug carrier, i.e., the API can be nanotized, coated, made into vesicles, liposome, emulsions, and the like for the formulation. Without limitations the formulation or the composition can be formulated for administration by any appropriate route known in the art including, but not limited to, topical (including buccal and sublingual) and oral or parenteral routes, including intravenous, intramuscular, subcutaneous, transdermal, airway (aerosol), pulmonary, and nasal administration.

The DARTs and formulations disclosed herein can be used for treating bacterial infections due to Gram-positive or Gram-negative bacteria. Additionally, the DARTs are effective against resistant forms of pathogens. Furthermore, the DARTs are effective in preventing the development of resistant forms of pathogens. Thus, the DARTs and formulations disclosed herein can be used for treating antibiotic tolerant or resistant bacterial infections. Exemplary bacterial infections include, but are not limited to, infection by *Bartonella henselae, Borrelia burgdorferi, Campylobacter jejuni, Campylobacter fetus, Chlamydia trachomatis, Chlamydia pneumoniae, Chylamydia psittaci, Simkania negevensis, Escherichia coli* (e.g., O157:H7 and K88), *Ehrlichia chafeensis, Clostridium botulinum, Clostridium perfringens, Clostridium tetani, Enterococcus faecalis, Haemophilius influenzae, Haemophilius ducreyi, Coccidioides immitis, Bordetella pertussis, Coxiella burnetii, Ureaplasma urealyticum, Mycoplasma genitalium, Trichomatis vaginalis, Helicobacter pylori, Helicobacter hepaticus, Legionella pneumophila, Mycobacterium tuberculosis, Mycobacterium bovis, Mycobacterium africanum, Mycobacterium leprae, Mycobacterium asiaticum, Mycobacterium avium, Mycobacterium celatum, Mycobacterium celonae, Mycobacterium fortuitum, Mycobacterium genavense, Mycobacterium haemophilum, Mycobacterium intracellulare, Mycobacterium kansasii, Mycobacterium malmoense, Mycobacterium marinum, Mycobacterium scrofulaceum, Mycobacterium simiae, Mycobacterium szulgai, Mycobacterium ulcerans, Mycobacterium xenopi, Corynebacterium diptheriae, Rhodococcus equi, Rickettsia aeschlimannii, Rickettsia africae, Rickettsia conorii, Arcanobacterium haemolyticum, Bacillus* anthracis, Bacillus cereus, Lysteria monocytogenes, Yersinia pestis, Yersinia enterocolitica, Shigella dysenteriae, Neisseria meningitides, Neisseria gonorrhoeae, Streptococcus bovis, Streptococcus hemolyticus, Streptococcus mutans, Streptococcus pyogenes, Streptococcus pneumoniae, Staphylococcus aureus, Staphylococcus epidermidis, Staphylococcus pneumoniae, Staphylococcus saprophyticus, Vibrio cholerae, Vibrio parahaemolyticus, Salmonella typhi, Salmonella paratyphi, Salmonella enteritidis, Treponema pallidum, Candida, Cryptcooccus, Cryptosporidium, Giardia lamblia, Microsporidia, Plasmodium vivax, Pneumocystis carinii, Toxoplasma gondii, Trichophyton mentagrophytes, Enterocytozoon bieneusi, Cyclospora cayetanensis, Encephalitozoon hellem, Encephalitozoon cuniculi*, among other bacteria, archaea, protozoa, and fungi. In some embodiments, infection is with a *Staphylococcus* species.

In some embodiments, the DARTS and formulations disclosed herein can be used for treating acne. In some embodiments, the DARTS and formulations disclosed herein are effective against forms of *Propionbacterium acnes* that respond poorly to clindamycin-, or doxycycline-, or erythromycin-, or minocycline-containing anti-acne products. In some embodiments, the DARTs and formulations disclosed herein are effective against one or more of clindamycin-, minocycline-, erythromycin-, and/or doxycycline-tolerant or resistant strains of *Propionbacterium acnes*. For treating infections, the DART or the formulation disclosed herein can be administered once or daily to the subject as a single dose or a plurality of doses.

BRIEF DESCRIPTION OF THE DRAWINGS

FIG. 2A—Agarose gel electrophoresis showing effect of compound 91 on super-coiling of *E. coli* plasmid DNA by DNA Gyrase. FIG. 2B—Percentage of DNA super-coiling by DNA gyrase in presence increasing concentrations of compound 91.

DETAILED DESCRIPTION OF THE INVENTION

Figure 1A:
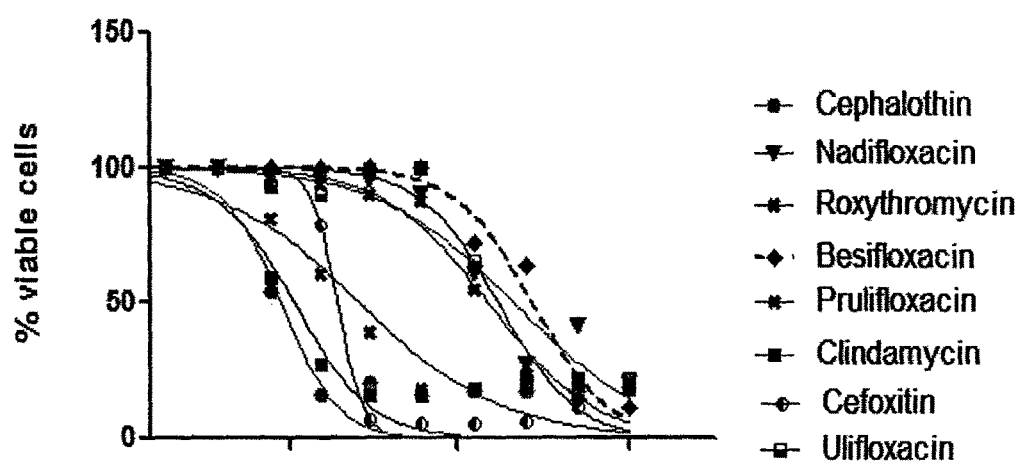
FIGS. 1A and 1B shows dose response curves of different antibiotics against both MTCC1951 and CCARM 9010 strains of *P. acnes*. While MTCC1951 is killed by clindamycin, the drug has no effect on CCARM9010. Different antibiotics behave differently and unpredictably on the different strains belong to a different family from Clindamycin.

Acne vulgaris is a skin condition that affects over 85% of all people. Acne is a term for a medical condition of plugged pores typically occurring on the face, neck, and upper torso. Following are four primary factors that are currently known to contribute to the formation of acne vulgaris; (1) increased sebum output resulting in oily, greasy skin; (2) increased bacterial activity, normally due to an overabundance of *Propionibacterium acnes* bacteria; (3) plugging (hypercornification) of the follicle or pilosebaceous duct; and (4) and inflammation. The plugged pores result in blackheads, whiteheads, pimples or deeper lumps such as cysts or nodules. Severe cases of acne can result in permanent scarring or disfiguring.

As articulated in http://thescienceofacne.com/antibiotic-susceptibility-of-*propionibacterium-acnes*/results from studies over last four decades clearly demonstrate that over time *P. acnes* bacteria has become increasingly resistant to certain classes of antibiotics. Particularly important are observations that a significant percentage of the bacteria isolated from acne patients are now resistant to the most common antibiotics used in acne treatment: Clindamycin, Erythromycin, Tetracycline, Doxycycline and Minocycline. Additionally, such resistant or antibiotic-tolerant strains can cause relapse of acne, and also cause other diease states. There is a need for antibiotics that can kill *P. acnes* while minimizing the probability of development of mutant or tolerant strains that can survive the antibiotic exposure, and those that can work against strains that are not responding to the current drugs. Additionally, if these novel molecules can target additional steps in acne formation, such as inflammation, then the clinical outcome in acne can be greater than existing therapies.

Skin is a major organ of the body, and performs many essential functions besides acting as a barrier, such as maintaining homeostasis. Besides acne, there are many other skin diseases that are caused by bacterial colonization of the skin. The most common bacteria for mild to moderate skin infection are *Staphylococcus* and *Streptococcus* e.g., Acute Bacterial Skin and Skin Structure Infection (ABSSSI). Such bacteria can infect the skin of both pediatric and adult patients; mainly develop during hospitalization or living in a nursing home, while gardening, or while swimming. Some people are at particular risk of developing skin infections, for example, people suffering with diabetes, human immunodeficiency virus (HIV) or AIDS or other immune disorders, or hepatitis, and who is undergoing chemotherapy or treatment with other drugs that suppress the immune system.

Common skin bacterial infections include cellulitis, erysipelas, impetigo, folliculitis, and furuncles and carbuncles. Cellulitis is a painful, erythematous infection of the dermis and subcutaneous tissue characterized by warmth, edema, and advancing borders and is usually caused by *Streptococcus* or *Staphylococcus* species. Erysipelas is a superficial form of cellulitis with sharply demarcated borders and is caused almost exclusively by *Streptococcus*. Impetigo is also caused by *Streptococcus* or *Staphylococcus* and can lead to lifting of the stratum corneum resulting in the commonly seen bullous effect. Folliculitis is an inflammation of the hair follicles, and it is most commonly caused by *Staphylococcus*. If the infection of the follicle is deeper and involves more follicles, it moves into the furuncle and carbuncle stages and usually requires incision and drainage. Two different kinds of skin diseases occurred due to the toxins produced by the bacteria include, Staphylococcal Scaled Skin Syndrome (SSSS) which usually affects children less than 5 years old, adults with kidney failure and the other one is Toxic Shock Syndrome. There is more chance of colonization of *S. aureus* is found with patients suffering from eczema and atopic dermatitis, a type of inflammatory, relapsing, non-contagious, itchy skin disorder. Thus *Staphylococcus aureus* infection plays an important role in atopic dermatitis (AD) or atopic eczema (AE). Unfortunately, some strains of *Staphylococcus* have become resistant to methicillin and other similar antibiotics which are known as MRSA. Recently it has been found that more than one-half of all cases of skin bacterial infections caused by MRSA species. The infections associated with MRSA species cannot be cured with traditional penicillin-related drugs. Instead, MRSA must be treated with alternate antibiotics.

However as articulated in http://thescienceofacne.com/antibiotic-susceptibility-of-*propionibacterium-acnes*/"Not all antibiotics are created equal". The same is true for bacteria. Some types of antibiotics are highly effective against certain types of bacteria, while essentially worthless against others. Moreover, antibiotic susceptibility and resistance is a dynamic process that is constantly changing. Over time, certain types of bacteria may gain or lose resistance to particular antibiotics. The primary problem with standard, laboratory-based antibiotic resistance testing is that the susceptibility of a bacteria to an antibiotic is often different when it is growing on a petri dish versus when it is growing on your body. This is because bacteria are not static organisms, they adapt to their environment. A *P. acnes* bacteria growing in a follicle and feeding on sebum has a different metabolic profile than one growing on a petri dish and feeding on a bacterial nutrition supplement. Furthermore, bacteria modulate expression of surface proteins, cell wall structures and genes depending on their environment, and these changes can have a profound effect on their susceptibility to a particular antibiotic. As a result, in the case of topical antibiotics for treatment of skin bacterial conditions, a priori knowledge does not exist, i.e. there is no mechanism to predict that an antibiotic will be effective against *P. acnes* acnes or any other skin bacterial condition until it has been tested on the bacterial strain. For example, as shown in http://thescienceofacne.com/antibiotic-susceptibility-of-*propionibacterium-acnes*/, *P. acnes* was reported to be highly resistant to a nitroimidazole (metronidazole) or a tetracycline (lymecycline) but partially responsive to doxycycline (another tetracycline), and showing no resistance to ciprofloxacin but resistant to another fluoroquinolone, Levofloxacin. It is therefore impossible to predict which antibiotic will work based on a priori activity in other bacterial strains. There is a need for a systematic development of novel antibiotics that show activity against acne.

In this regard DART molecules can act as an ideal drug candidate to acne caused by *P. acnes*, and additionally for the treatment of other skin and skin structure infections caused by other bacteria such as MRSA. DARTs were designed to contain two distinct chemical domains, selected from different families as mentioned earlier, for example a β-lactam ring and a quinolone nucleus, or a quinolone nucleus and nitro-heterocycle, or a β-lactam ring and a nitroheterocycle, which confers two distinct mechanisms of action. This creates less chance in mutation development at both target sites of bacteria resulting in less resistance development against these antibiotics. Some of the molecules can exert additional anti-inflammatory mechanisms to reduce host inflammatory response, further enhancing the anti-acne efficacy.

The embodiments of the various aspects disclosed herein are based on the molecules designed by the inventors, which can act on at least two different or distinct targets. Generally, the molecule includes at least two different or distinct chemical domains. Each of said chemical domains binds to a distinct or different active site in a target cell. The said chemical domains can be bound together through a third domain. As used herein, the term "chemical domain" means a part of a molecule that is involved in a desired property. For example, a chemical domain can be part of the molecule involved in binding of the molecule with a target or involved in modulating an activity of the target.

In some embodiments, the first and second chemical domains independently have anti-bacterial or bactericidal activity. In some embodiments, the first and second domain can independently comprise an antibacterial agent. As used herein, the term "antibacterial agent" or "antibiotic agent" is defined as a compound having either a bactericidal or bacteriostatic effect upon bacteria contacted by the compound. As used herein, the term "bactericidal" is defined to mean having a destructive killing action upon bacteria. As used herein, the term "bacteriostatic" is defined to mean having an inhibiting action upon the growth of bacteria. Examples of antibacterial agents include, but are not limited to, macrolides or ketolides such as erythromycin, azithromycin, clarithromycin, dirithromycin, troleandomycin, spiramycin, telithromycin, carbomycin a, josamycin, kitasamycin, midecamycin acetate, oleandomycin, solithromycin, spiramycin, troleandomycin, cethromycin, solithromycin, spiramycin, ansamycin, oleandomycin, carbomycin and tylosin; beta-lactams including penicillin, cephalosporin and carbapenems such as carbapenem, imipenem and meropenem; monolactams such as penicillin g, penicillin v, methicillin, oxacillin, cloxacillin, dicloxacillin, nafcillin, ampicillin, azlocillin, amoxicillin, carbenicillin, ticarcillin, mezlocillin, piperacillin, azlocillin, temocillin, flucloxacillin, cepalothin, cephapirin, cephradine, cephaloridine, cefazolin, cefamandole, cefuroxime, cephalexin, cefprozil, cefaclor, loracarbef, cefoxitin, cefmetazole, cefotaxime, ceftizoxime, ceftriaxone, cefoperazone, ceftazidime, cefixime, cefpodoxime, ceftibuten, cefdinir, cefpirome, cefepime, cefadroxil, cefalothin, cefalexin, cefuroxime, cefditoren, ceftazidime, ceftizoxime, ceftaroline fosamil, ceftaroline, ceftobiprole, aztreonam, ertapenem, doripenem and cilastatin; penicillin combinations such as amoxicillin/clavulanate, ampicillin/sulbactam, piperacillin/tazobactam and ticarcillin/clavulanate; quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin, pazufloxacin, besifloxacin, ulifloxacin, prulifloxacin, cinoxacin, piromidic acid, pipemidic acid, rosoxacin, rufloxacin, balofloxacin, tosufloxac in, delafloxacin, nemonoxacin; antibacterial sulfonamides and antibacterial sulphanilamides, including para-aminobenzoic acid, sulfadiazine, silver sulfadiazine, sulfisoxazole, sulfamethoxazole, sulfadimethoxine, sulfadoxine, sulfamethizole and sulfathalidine, mafenide, sulfacetamide, sulfisomidine, sulfanilimide, sulfasalazine and sulfonamidochrysoidine; aminoglycosides such as streptomycin, neomycin, kanamycin, paromycin, gentamicin, tobramycin, amikacin, netilmicin, spectinomycin, sisomicin, dibekalin, isepamicin, dihydrostreptomycin, framycetin, ribostamycin, arbekacin, bekanamycin, dibekacin, hygromycin b, verdamicin and, astromicin; tetracyclines tetracycline, chlortetracycline, demeclocycline, minocycline, oxytetracycline, methacycline, doxycycline, clomocycline, lymecycline, meclocycline, penimepicycline, and rolitetracycline; rifamycins such as rifampicin (also called rifampin), rifapentine, rifabutin, bezoxazin, orifamycin and rifaximin; lincosamides such as lincomycin and clindamycin; lipopeptide like daptomycin; glycopeptides such as vancomycin, telavancin and teicoplanin; streptogramins such as quinupristin and daflopristin; ansamycins such as geldanamycin, herbimycin, rifaximin; oxazolidinones such as linezolid, eperezolid, posizolid, radezolid, ranbezolid, sutezolid and tedizolid; pleuromutilins such as retapamulin, tiamulin, valnemulin; steroid antibacterials such as fusidic acid; amphenicols such as chloramphenicol, azidamfenicol, thiamphenicol, florfenicol; nitrofurans such as furazolidone, nitrofurantoin; streptogramins such as pristinamycin, quinupristin/dalfopristin virginiamycin; other antibacterials such as arsphenamine, fosfomycin, mupirocin, platensimycin, tigecycline, trimethoprim, polymyxin, bacitracin, colistin, colymycin, metronidazole, cotrimoxazole and phosphonomycin; and anti-mycobacterial drugs such as clofazimine, dapsone, capreomycin, cycloserine, ethambutol, ethionamide, isoniazid, pyrazinamide, rifampicin, rifabutin, rifapentine, streptomycin. in some embodiments, the antibacterial agent can be selected from the group consisting of azithromycin, roxithromycin, ceftaroline, cefotaxime, cefoxitin, ceftriaxone, cephalothin, minocycline, nadifloxacin, moxifloxacin, besifloxacin, ulifloxacin, prulifloxacin, retapamulin, metronidazole, ornidazole and any combinations thereof. In some embodiments, antibacterial agent can be hyaluronic acid or a derivative thereof.

In some embodiments of the DART molecule, the first and second domains independently have anti-acne activity. In some embodiments, the first and second chemical domains are independently an anti-acne agent. As used herein, the term "anti-acne agent" refers to any chemical that is effective in the treatment of acne and/or the symptoms associated therewith. Anti-acne agents are well known in the art such as U.S. Pat. App. Pub. No. 2006/0008538 and U.S. Pat. No. 5,607,980, content of both of which is incorporated herein by reference. Examples of useful anti-acne agents include, but are not limited to keratolytics, such as salicylic acid, derivatives of salicylic acid, and resorcinol; retinoids, such as retinoic acid, tretinoin, adapalene, tazarotene; sulfur-containing D- and L-amino acids and their derivatives and salts; lipoic acid; antibiotics and antimicrobials, such as benzoyl peroxide, triclosan, chlorhexidine gluconate, octopirox, tetracycline, 2,4,4'-trichloro-2'-hydroxy diphenyl ether, 3,4,4'-trichlorobanilide, nicotinamide, tea tree oil, rofecoxib, azelaic acid and its derivatives, phenoxyethanol, phenoxypropanol, phenoxisopropanol, ethyl acetate, clindamycin, erythromycin, and meclocycline; sebostats, such as flavonoids; and bile salts, such as scymnol sulfate and its derivatives, deoxycholate, and cholate; and combinations thereof. These agents are well known and commonly used in the field of personal care.

In some embodiments, the anti-acne agent can be an antimicrobial peptide having activity against *P. acnes*. Antimicrobial peptides are ubiquitous in nature and play an important role in the innate immune system of many species [Zasloff et al., 2002; and Epand et al., 1999]. The antimicrobial peptide can be a naturally occurring peptide or an analog thereof, or it can be a synthetic peptide. As used herein an "analog" refers to a naturally-occurring antimicrobial peptide that has been chemically modified to improve its effectiveness and/or reduce its toxic side effects. The antimicrobial peptide can be a peptide known to be effective against Gram positive bacteria. Non-limiting examples include lantibiotics, such as nisin, subtilin, epidermin and gallidermin; defensins; attacins, such as sarcotoxin; cecropins, such as cecropin A, bactericidin, and lepidopteran; magainins; melittins; histatins; brevinins; and combinations thereof. Additionally, antimicrobial peptides having activity against *P. acnes* have been reported, for example, in U.S. Pat. App. Pub. No. 2005/0282755; No. 2005/02455452; and No. 2005/0209157, and U.S. Pat. No. 6,255,279, content of all of which is incorporated herein by reference. Suitable examples of antimicrobial peptides having reported activity against *P. acnes* include, but are not limited to, novispirins (Hogenhaug, supra), and those described in U.S. Pat. App. Pub. No. 2007/0265431, content of which is incorporated herein by reference. In some embodiments, the antimicrobial peptide can be cathilicidine and its derivatives.

In some embodiments, the anti-bacterial agent can be free fatty acid (FFA) or fatty acid derivatives or fatty acid esters of propylene glycol (PG) or glycerol (G) derivatives and any combinations thereof. For example, lauric acid, stearic acid, myristic acid, oleic acid, linoleic acid, myristoleic acid, palmitooleic acid, linoleic acid, linolenic acid, sapienic acid, different polyunsaturated FAs (PUFA), propylene glycol monolaurate, glycerol mono and/or di laurate, propylene glycol monoloeate, glycerol mono and/or di oleate and other derivatives known in art. Fatty acids are well known antimicrobial agent [Kabara et al., 1972] and their activity varies with chain length, degree of unsaturation and number of fatty acid ester present in propylene glycol or glycerol backbones. The prime target of FAs and derivatives is bacterial cell membrane, which is non-specific in nature. Disruption of bacterial membrane causes disruption in cellular electron transport activity or oxidative phosphorylation or inhibition to a particular enzyme activity or diminishing cellular energy production or impairment of nutrient uptake or auto-oxidation of degradation products or generation of toxic peroxidation or direct lysis of bacterial cells. Their broad spectrum of non-specific activity makes them as a promising antimicrobial candidate for treatment and prevention of antimicrobial infections caused by number of gram-positive and gram-negative bacteria that generates various skin and skin structure infections. In some embodiments, the FA and derivatives alone or in combination with any antibiotics or covalent conjugates with any antibiotics (e.g. DARTs) are effective against antibiotic prone *Propionbacterium acnes* as well as *P. acnes* that respond poorly to clindamycin-, or doxycycline-, or erythromycin-, or minocycline-containing anti-acne products. In some embodiments, they are effective against one or more of clindamycin-, minocycline-, erythromycin-, and/or doxycycline-tolerant or resistant strains of *Propionbacterium acnes*. In some embodiments, it prevents the development of resistant forms of pathogens In some embodiments, the first and second anti-acne agents in the DART or formulations disclosed herein are selected independently from the group consisting of acetretin, adapalene, alitretinoin, azelaic acid, Azithromycin, benzoyl peroxide, Besifloxacin, bexarotene, Cefotaxime, Cefoxitin, Ceftaroline, Ceftobiprole, Ceftriaxone, Cephalothin, clindamycin, erythromycin, etretinate, Garenoxacin, glycolic acid, isotretinoin, lactic acid, Minocycline, Moxifloxacin, N-acetylcystein, Nadifloxacin, octopirox, phenoxyethanol, phenoxypropanol, Prulifloxacin, pyruvic acid, Radezolid (RX-1741), resorcinol, Retapamulin, retinoic acid, Roxithromycin, salicylic acid, Sitafloxacin, sodium sulfacetamide, spirinolactone, sulfacetamide, sulfur, tazarotene, tretinoin, triclosan, ulifloxacin, metronidazole, ornidazole, urea, and any combinations thereof.

In some embodiments, the first and second chemical domains are independently an antifungal agent. As used herein, the term "antifungal agent" is intended to mean a substance capable of inhibiting or preventing the growth, viability and/or reproduction of a fungal cell. Preferable antifungal agents are those capable of preventing or treating a fungal infection in an animal or plant. A preferable antifungal agent is a broad spectrum antifungal agent. However, an antifungal agent can also be specific to one or more particular species of fungus.

Examples of antifungal agents include, but are not limited to, azoles (e.g., Fluconazole, Isavuconazole, Itraconazole, Ketoconazole, Miconazole, Clortrimazole, Voriconazole, Posaconazole, Ravuconazole, Ciclopirox, etc.), polyenes (e.g., natamycin, lucensomycin, nystatin, amphotericin B, etc.), echinocandins (e.g., Cancidas), pradimicins (e.g., beanomicins, nikkomycins, sordarins, allylamines, etc.), Triclosan, Piroctone and its olamine salt, fenpropimorph, terbinafine, and derivatives and analogs thereof. Additional antifungal agents include those described, for example, in Int. Pat. Pub. No. WO2001/066551, No. WO2002/090354, No. WO2000/043390, No. WO2010/032652, No. WO2003/008391, No. WO2004/018485, No. WO2005/006860, No. WO2003/086271, No. WO2002/067880; in U.S. Pat. App. Pub. No. 2008/0194661, No. 2008/0287440, No. 2005/0130940, No. 2010/0063285, No. 2008/0032994, No. 2006/0047135, No. 2008/0182885; and in U.S. Pat. No. 6,812,238; No. 4,588,525; No. 6,235,728; No. 6,265,584; No. 4,942,162; and No. 6,362,172, content of all of which is incorporated herein by reference.

In some embodiments, the antifungal agent is a pyrithione salt. Examples of useful pyrithione salts include, but are not limited to, zinc pyrithione, sodium pyrithione, potassium pyrithione, lithium pyrithione, ammonium pyrithione, copper pyrithione, calcium pyrithione, magnesium pyrithione, strontium pyrithione, silver pyrithione, gold pyrithione, manganese pyrithione, and combinations thereof. Non-metal pyrithione salts such as the ethanolamine salt, chitosan salt, and the disulfide salt of pyrithione (which is commercially available as OMADINE MDS or OMDS), can also be used. The pyrithione salt can be used in any particulate form, including, but not limited to, crystalline form such as platelets, rods, needles, blocks, round and amorphous, regularly or irregularly shaped particles.

In some embodiments, the pyrithione salt is zinc pyrithione. Zinc pyrithione is best known for its use in treating dandruff and seborrhoeic dermatitis. It also has antibacterial properties and is effective against many pathogens from the *Streptococcus* and *Staphylococcus* genera. Its other medical applications include treatments of psoriasis, eczema, ringworm, fungus, athlete's foot, dry skin, atopic dermatitis, tinea, and vitiligo.

In some embodiments, the antifungal agent is an antifungal peptide. Antifungal peptides are well known in the art (see for example, De Lucca et al., 2000]. The antifungal peptide can be a naturally occurring peptide or an analog thereof, or it can be a synthetic peptide. As used herein, the term "analog" refers to a naturally occurring antifungal peptide that has been chemically modified to improve its effectiveness and/or reduce its toxic/side effects. Exemplary antifungal peptides can include, but are not limited to, syringomycins, syringostatins, syringotoxins, nikkomycins, echinocandins, pneumocadins, aculeacins, mulundocadins, cecropins, alpha-defensins, beta-defensins, novispirins, and combinations thereof. Other antifungal peptides include those described, for example, in U.S. Pat. No. 6,255,279 and U.S. Pat. App. Pub. No. 2005/0239709; No. 2005/0187151; No. 2005/0282755, and No. 2005/0245452, content all of which is incorporated herein by reference.

In some embodiments, the first chemical domain is an anti-bacterial agent and the second chemical domain is anti-acne agent or an antifungal agent.

Without limitations, the first and the second chemical domains in the DART can be bound to each other covalently. One of skill in the art is well aware of different functional groups in chemical domains that can be used for covalently binding a first chemical domain with a second chemical domain. For example, the first chemical domain can comprise a functional group selected from the group consisting of an amino group, a N-substituted amino group, a carboxyl group, a carbonyl group, an acid anhydride group, an aldehyde group, a hydroxyl group, an epoxy group, a thiol, a disulfide group, an alkenyl group, a hydrazine group, a hydrazide group, a semicarbazide group, a thiosemicarbazide group, an amide group, an aryl group, an ester group, an ether group, a glycidyl group, a halo group, a hydride group, an isocyanate group, a urea group, a urethane group, and any combinations thereof for binding with the second chemical domain. In some embodiments, the second chemical domain comprises a functional group selected from the group consisting of an amino group, a N-substituted amino group, a carboxyl group, a carbonyl group, an acid anhydride group, an aldehyde group, a hydroxyl group, an epoxy group, a thiol, a disulfide group, an alkenyl group, a hydrazine group, a hydrazide group, a semicarbazide group, a thiosemicarbazide group, an amide group, an aryl group, an ester group, an ether group, a glycidyl group, a halo group, a hydride group, an isocyanate group, a urea group, a urethane group, and any combinations thereof for binding with the first chemical domain. In some embodiments, the first and second chemical domains are bound to each other via same functional group. In some embodiments, the first and second chemical domains are bound to each other via different functional groups.

In some embodiments, the third domain can enhance or increase an activity of at least one of the chemical domains. For example, the activity of at least one of the chemical domains is increased or enhanced relative to when the third domain is absent. In some embodiments, the third domain can increase or enhance antibacterial activity of at least one of the chemical domains in the DART. In some embodiments, the third domain can increase or enhance anti-acne activity of at least one of the chemical domains in the DART. In some embodiments, the third domain can increase or enhance anti-inflammatory activity of at least one of the chemical domains in the DART.

In some embodiments, the third domain itself has biological activity. For example, the third domain can be an active agent. In some embodiments, the third domain can have anti-bacterial or anti-fungal activity. In some embodiments, the third domain can have anti-inflammatory activity.

The third domain of the DARTs can be a direct bond or an atom such as oxygen or sulfur, a unit such as $NR^1$, C(O), C(O)O, C(O)NH, SS, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^1)_2$, C(O), C(O)O, cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In some embodiments, the first and second chemical domains are covalently bound to each other via a third domain comprising at least one cleavable group. A cleavable group is one which is sufficiently stable under a first set of conditions and can be cleaved to release the two parts the cleavable group is holding together. In a preferred embodiment, the cleavable group is cleaved at least 10 times or more, preferably at least 100 times faster under a first reference condition (which can, e.g., be selected to mimic or represent intracellular conditions) than under a second reference condition (which can, e.g., be selected to mimic or represent conditions found in the blood or serum).

Cleavable groups are susceptible to cleavage agents, e.g., pH, redox potential or the presence of degradative molecules. Generally, cleavage agents are more prevalent or found at higher levels or activities at the desired site of action of the molecule comprising the cleavable group. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

Exemplary cleavable groups include, but are not limited to, redox cleavable groups (e.g., —S—S— and —C(R)$_2$—S—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid cleavable groups (e.g., hydrazones, esters, and esters of amino acids, —C=NN— and —OC(O)—); ester-based cleavable groups (e.g., —C(O)O—); peptide-based cleavable groups, (e.g., groups that are cleaved by enzymes such as peptidases and proteases, e.g., —NHCHR$^A$C(O)NHCHR$^B$C(O)—, where R$^A$ and R$^B$ are the R groups of the two adjacent amino acids). A peptide based cleavable group comprises two or more amino acids. In some embodiments, the peptide-based cleavable group comprises the amino acid sequence that is the substrate for a peptidase or a protease found in/secreted by *P. acnes*.

In some embodiments, the cleavable group is an acid labile group. Generally, an acid cleavable group is cleavable in an acidic environment with a pH of about 6.5 or lower (e.g., about 6.5, 6.0, 5.5, 5.0, 4.5, 4.0, 3.5, 3.0, or lower), or by agents such as enzymes that can act as a general acid.

In some embodiments, the first and second chemical domains are covalently bound together by a third domain selected from the group consisting of 11-hydroxyundecenic acid; 1,10-decanediol; 1,3-propanediol; 1,5-pentanedil; 10-hydroxydecenic acid; succinic; lactic acid; 3-hydroxypropionic acid; and any combinations thereof.

In some embodiments, the third domain can be linker, e.g., a cleavable or non-cleavable linker.

The first chemical domain can be bound to the second chemical domain or the domain connecting the first and second chemical domains via a direct bond or an atom such as oxygen or sulfur, a unit such as NH, C(O), C(O)O, C(O)NH, SS, SO, $SO_2$, or $SO_2NH$.

Similarly, the second chemical domain can be bound to the first chemical domain or the domain connecting the first and second chemical domains via a direct bond or an atom such as oxygen or sulfur, a unit such as NH, C(O), C(O)O, C(O)NH, SS, SO, $SO_2$, or $SO_2NH$.

The DARTs can be synthesized using methods known in the art. Exemplary methods for synthesizing the DARTs are described in the Examples section herein. See Examples 2 to 10.

In some embodiments, the DART can be selected from those shown in Tables 1A & 1B.

TABLE 1A

Exemplary DARTs Set-1

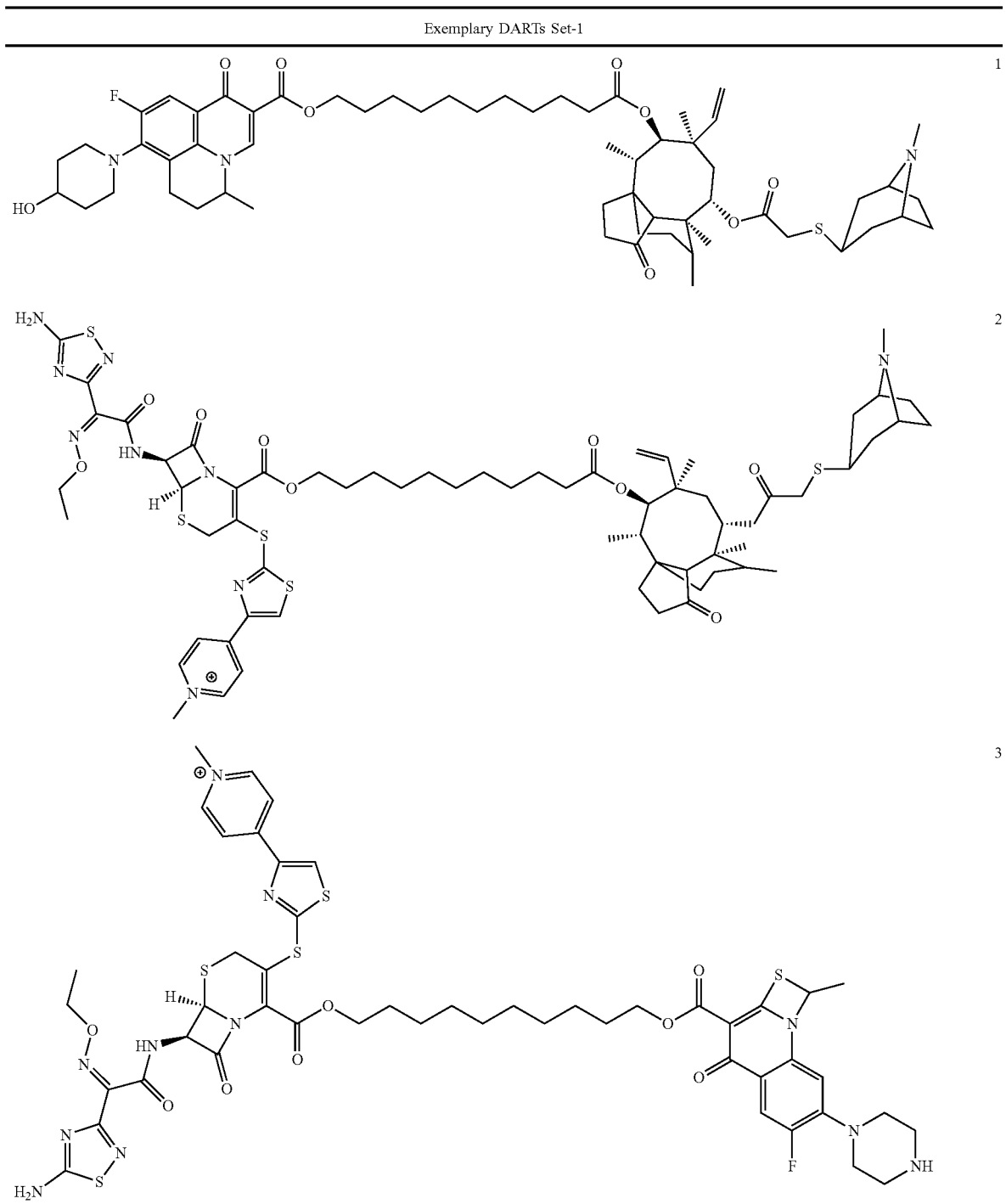

TABLE 1A-continued
Exemplary DARTs Set-1
4
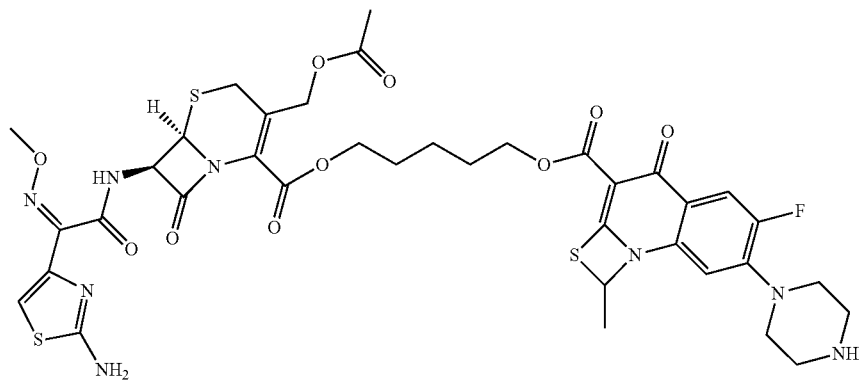 [SMILES: CO/N=C(\C(=O)N[C@@H]1C(=O)N2C(C(=O)OCCCCCOC(=O)c3c4n(c5cc(N6CCNCC6)c(F)cc5c3=O)C(C)S4)=C(COC(C)=O)CS[C@H]12)c1csc(N)n1]
5
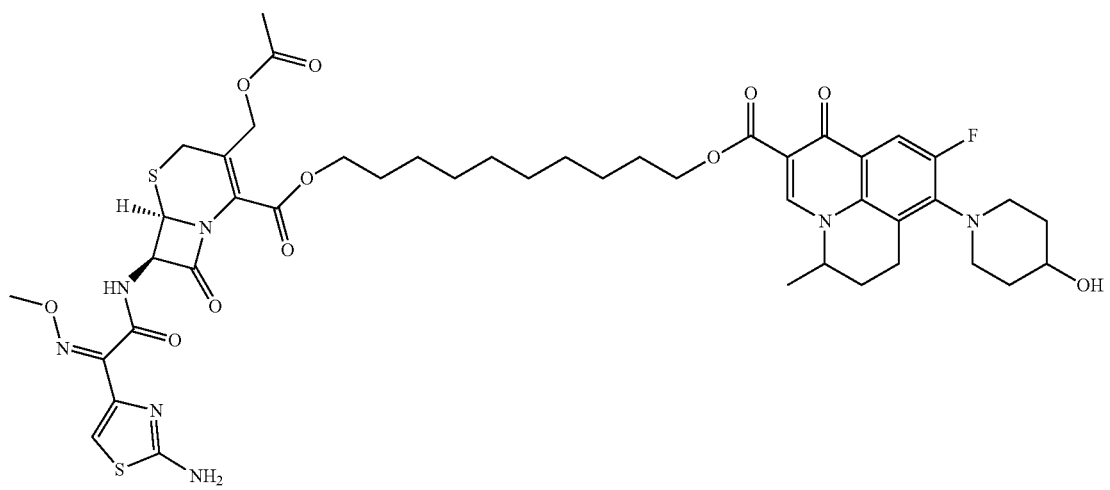 [SMILES: CO/N=C(\C(=O)N[C@@H]1C(=O)N2C(C(=O)OCCCCCCCCCCOC(=O)c3cn4c5c(c(N6CCC(O)CC6)c(F)cc5c3=O)CCC4C)=C(COC(C)=O)CS[C@H]12)c1csc(N)n1]
6
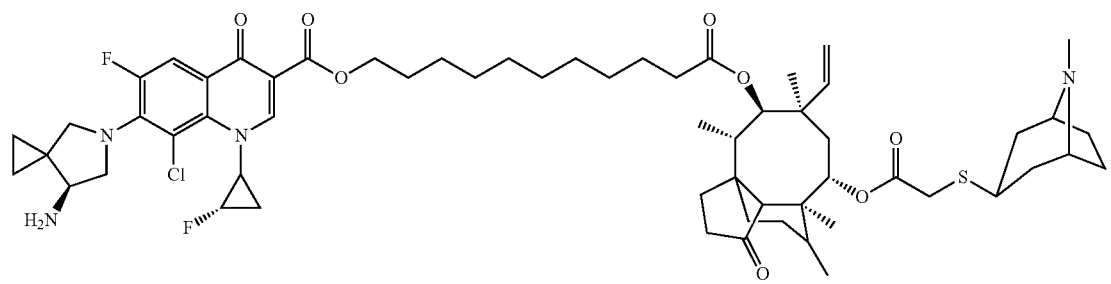 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)CCCCCCCCCCOC(=O)c1cn(C2C[C@@H]2F)c2c(Cl)c(N3C[C@@H](N)C4(CC4)C3)c(F)cc2c1=O]

TABLE 1A-continued
Exemplary DARTs Set-1
7
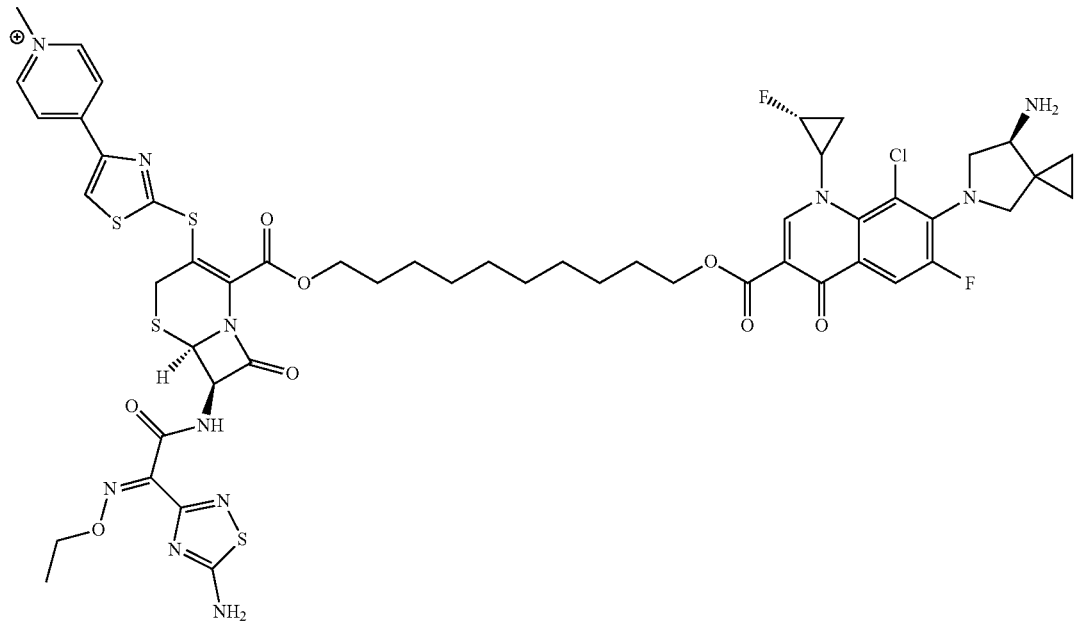 [SMILES: CCO/N=C(/C(=O)N[C@@H]1C(=O)N2C(C(=O)OCCCCCCCCCCOC(=O)c3cn(C4C[C@H]4F)c4c(Cl)c(N5C[C@@H](N)C6(CC6)C5)c(F)cc4c3=O)=C(Sc3nc(-c4cc[n+](C)cc4)cs3)CS[C@H]12)c1nsc(N)n1]
8
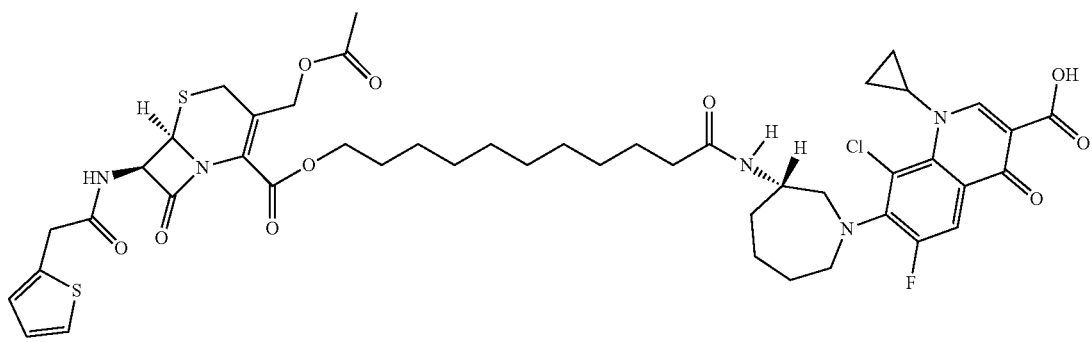 [SMILES: CC(=O)OCC1=C(C(=O)OCCCCCCCCCCC(=O)N[C@H]2CCCCN(c3c(F)cc4c(=O)c(C(=O)O)cn(C5CC5)c4c3Cl)C2)N2C(=O)[C@@H](NC(=O)Cc3cccs3)[C@H]2SC1]
9
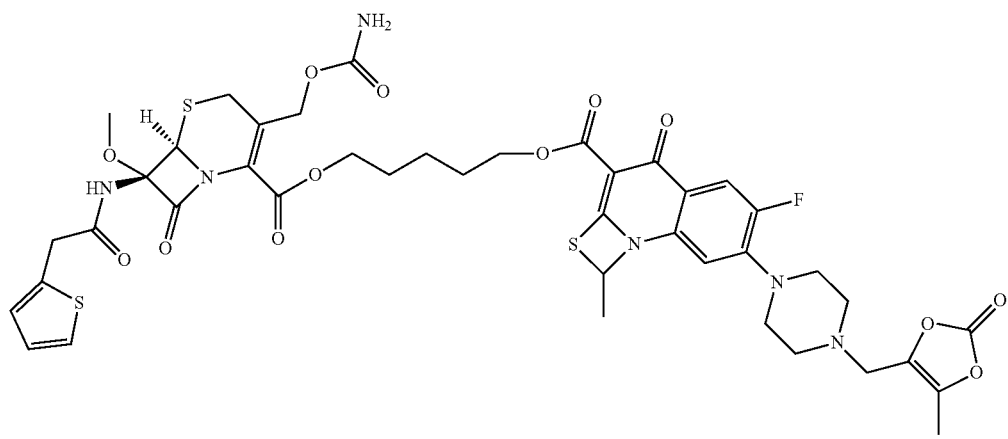 [SMILES: CO[C@@]1(NC(=O)Cc2cccs2)C(=O)N2C(C(=O)OCCCCCOC(=O)c3c4n(c5cc(N6CCN(Cc7oc(=O)oc7C)CC6)c(F)cc5c3=O)C(C)S4)=C(COC(N)=O)CS[C@@H]21]

TABLE 1A-continued
Exemplary DARTs Set-1
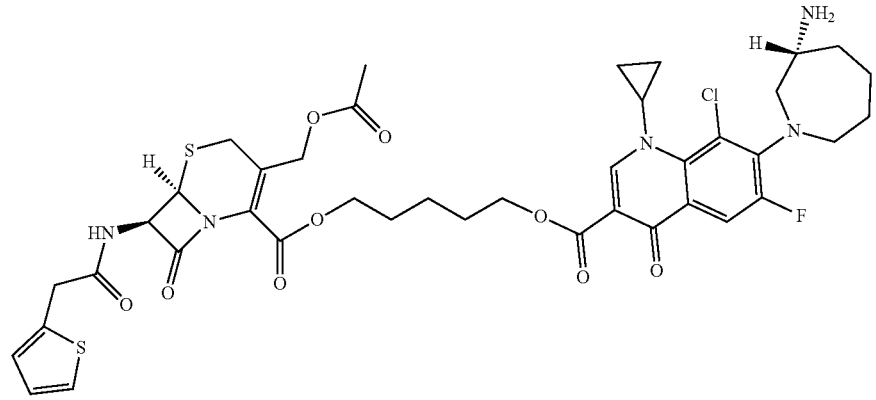 [SMILES: CC(=O)OCC1=C(C(=O)OCCCCCOC(=O)c2cn(C3CC3)c3c(Cl)c(N4CCCC[C@@H](N)C4)c(F)cc3c2=O)N2C(=O)[C@@H](NC(=O)Cc3cccs3)[C@H]2SC1]
10
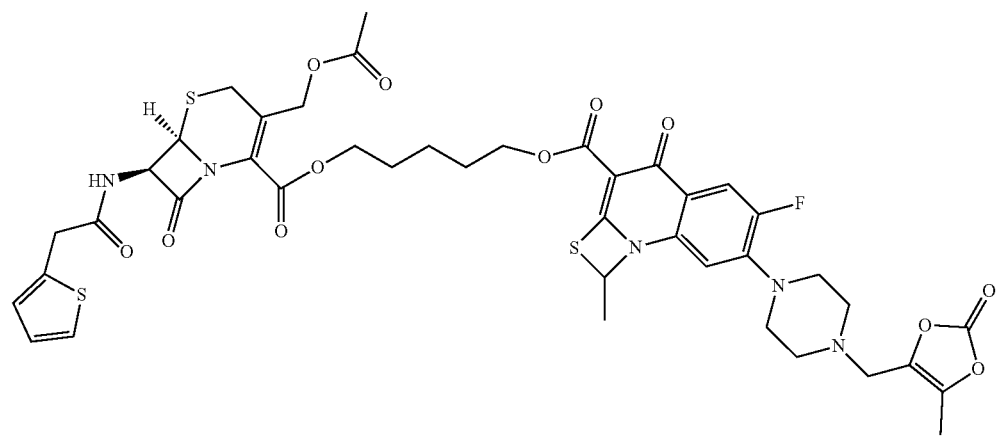 [SMILES: CC(=O)OCC1=C(C(=O)OCCCCCOC(=O)c2c3n(c4cc(N5CCN(Cc6oc(=O)oc6C)CC5)c(F)cc4c2=O)C(C)S3)N2C(=O)[C@@H](NC(=O)Cc3cccs3)[C@H]2SC1]
11
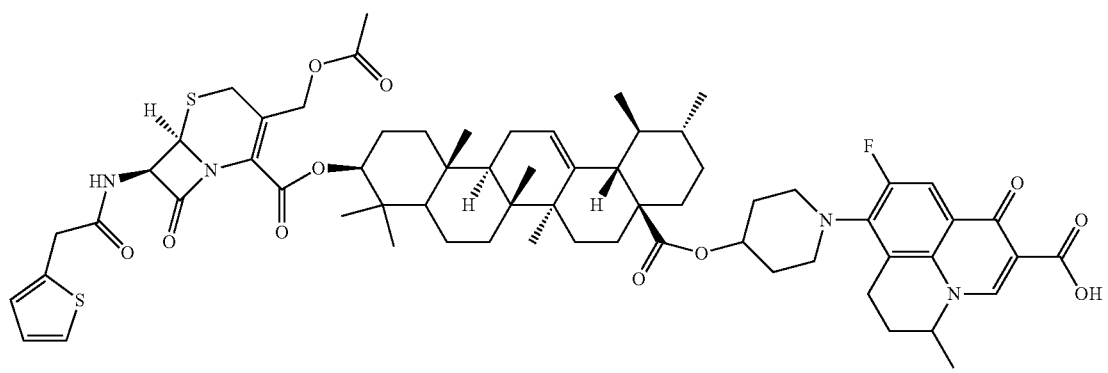
12
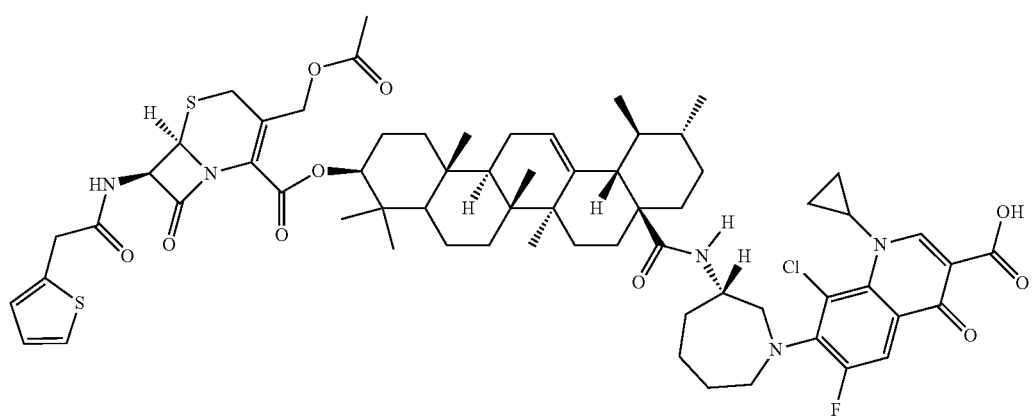
13

TABLE 1A-continued
Exemplary DARTs Set-1
14
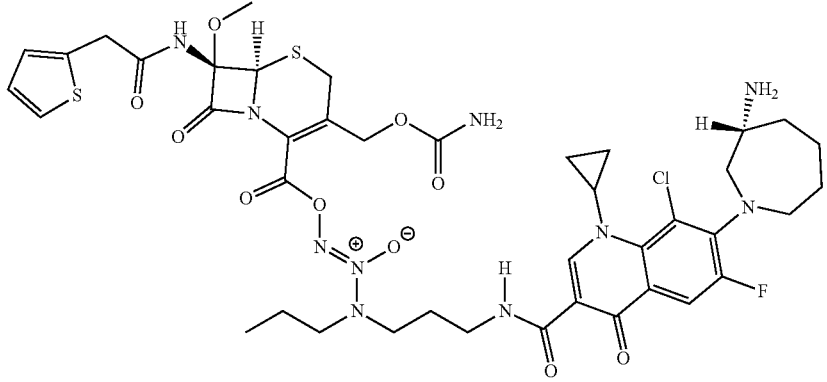 [SMILES: CCCN(CCCNC(=O)c1cn(C2CC2)c2c(Cl)c(N3CCCC[C@@H](N)C3)c(F)cc2c1=O)/[N+]([O-])=N/OC(=O)C1=C(COC(N)=O)CS[C@H]2N1C(=O)[C@]2(NC(=O)Cc1cccs1)OC]
15
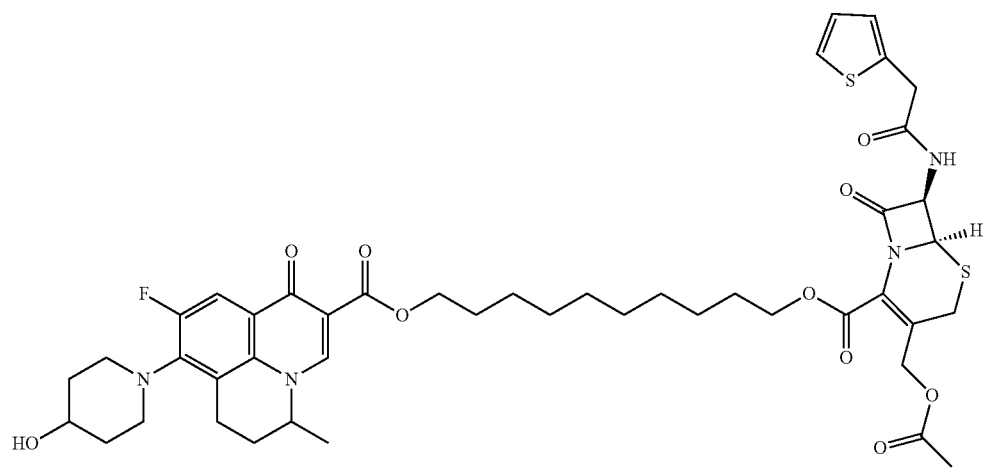 [SMILES: CC(=O)OCC1=C(C(=O)OCCCCCCCCCCOC(=O)c2cn3c4c(c(N5CCC(O)CC5)c(F)cc4c2=O)CCC3C)N2C(=O)[C@@H](NC(=O)Cc3cccs3)[C@H]2SC1]
16
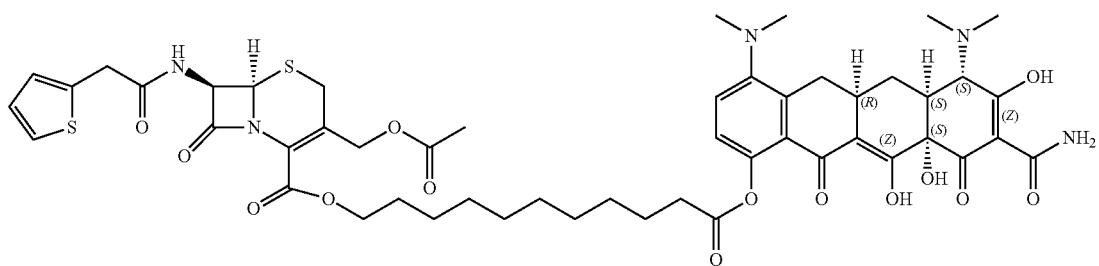
17
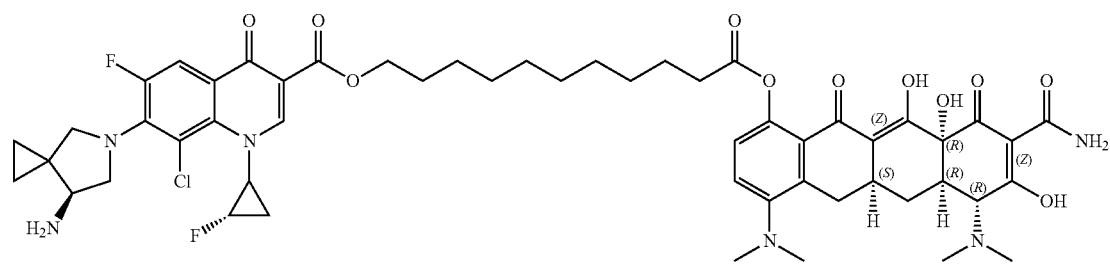

| TABLE 1A-continued |
| --- |
| Exemplary DARTs Set-1 |
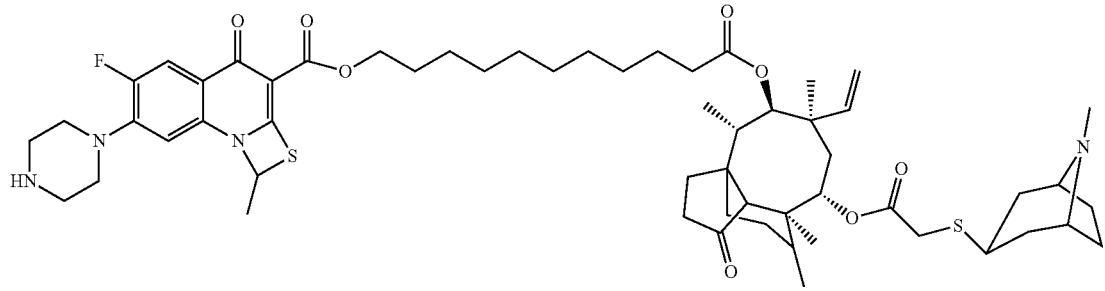 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)CCCCCCCCCCOC(=O)c1c2n(c3cc(N4CCNCC4)c(F)cc3c1=O)C(C)S2] 18
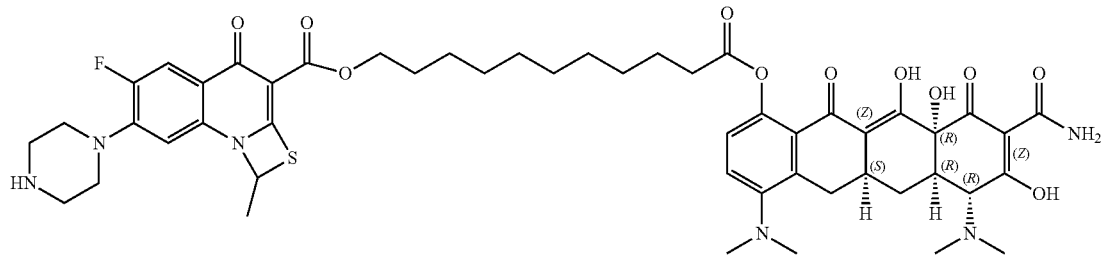 19
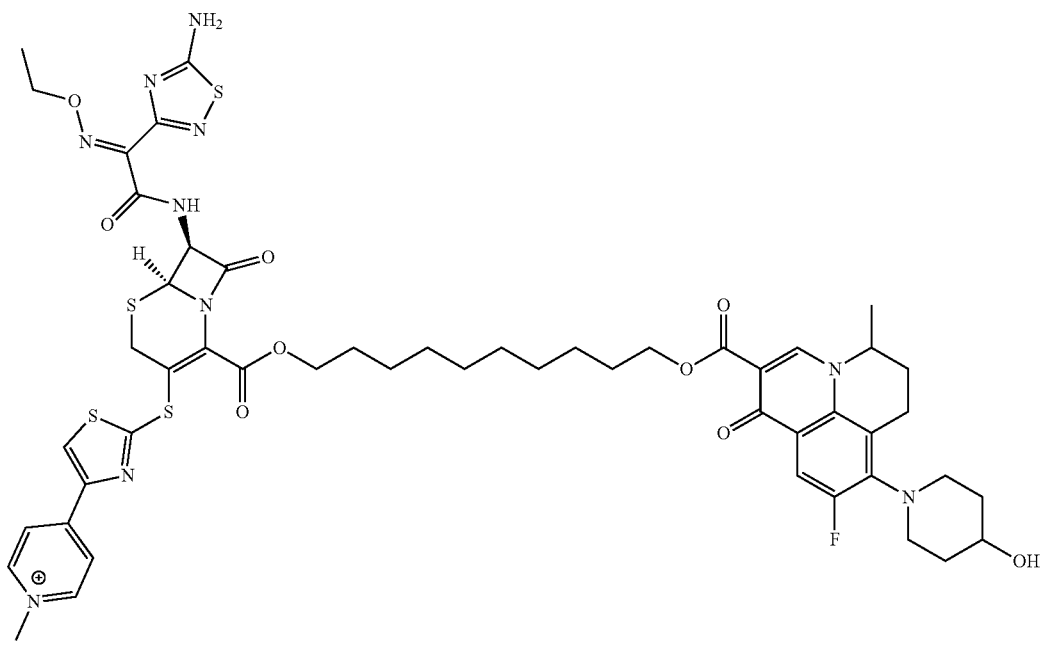 [SMILES: CCO/N=C(/C(=O)N[C@H]1C(=O)N2C(C(=O)OCCCCCCCCCCOC(=O)c3cn4c5c(c(N6CCC(O)CC6)c(F)cc5c3=O)CCC4C)=C(Sc3nc(-c4cc[n+](C)cc4)cs3)CS[C@@H]12)c1nsc(N)n1] 20
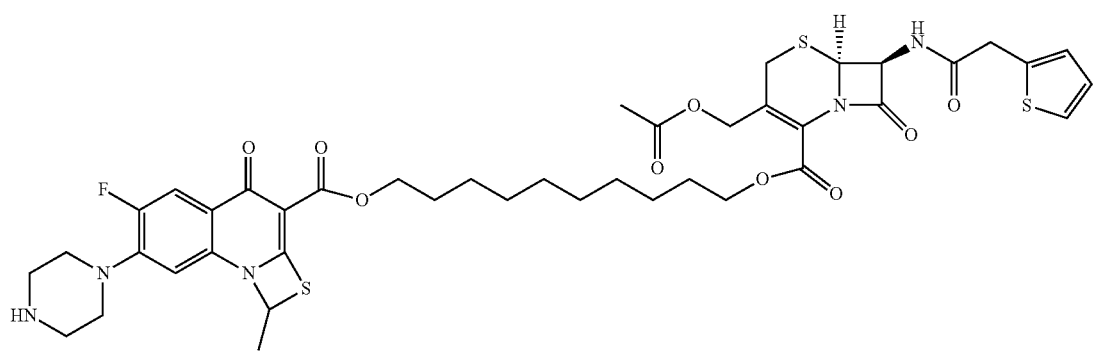 [SMILES: CC(=O)OCC1=C(C(=O)OCCCCCCCCCCOC(=O)c2c3n(c4cc(N5CCNCC5)c(F)cc4c2=O)C(C)S3)N2C(=O)[C@H](NC(=O)Cc3cccs3)[C@@H]2SC1] 21

31 32
TABLE 1A-continued
Exemplary DARTs Set-1
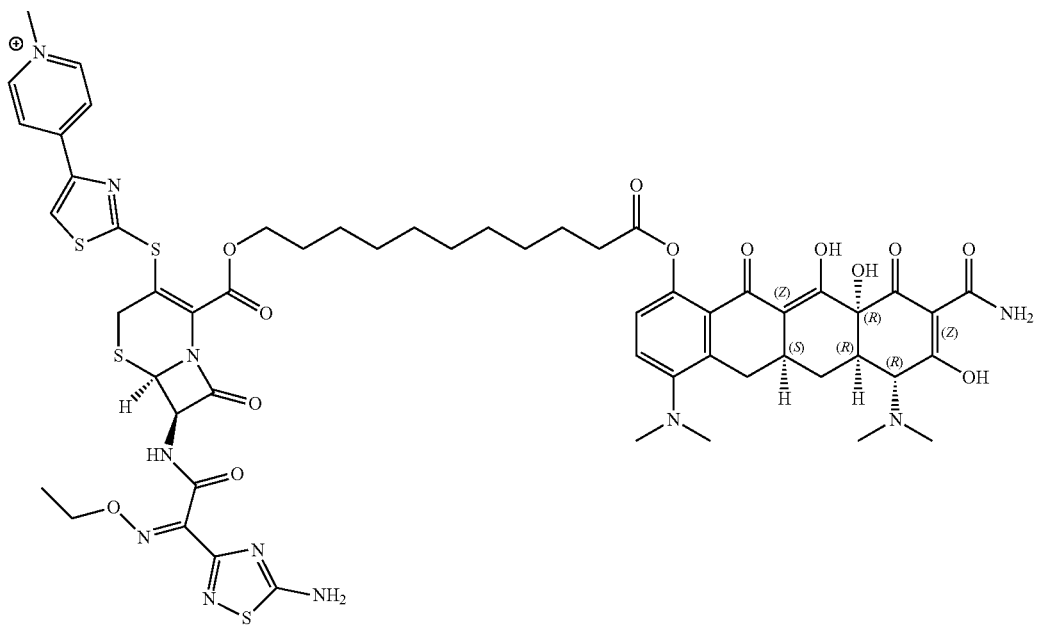
22
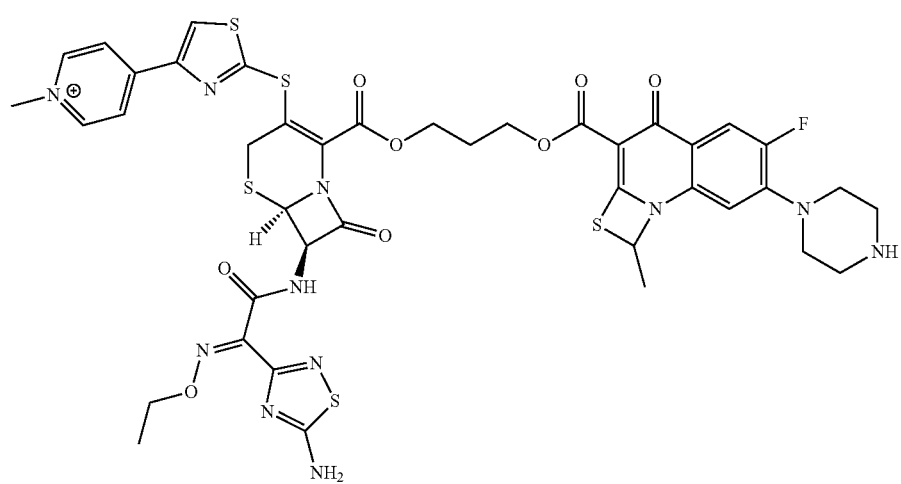 [SMILES: CCO/N=C(/C(=O)N[C@@H]1C(=O)N2C(C(=O)OCCCOC(=O)c3c4n(c5cc(N6CCNCC6)c(F)cc5c3=O)C(C)S4)=C(Sc3nc(-c4cc[n+](C)cc4)cs3)CS[C@H]12)c1nsc(N)n1]
23
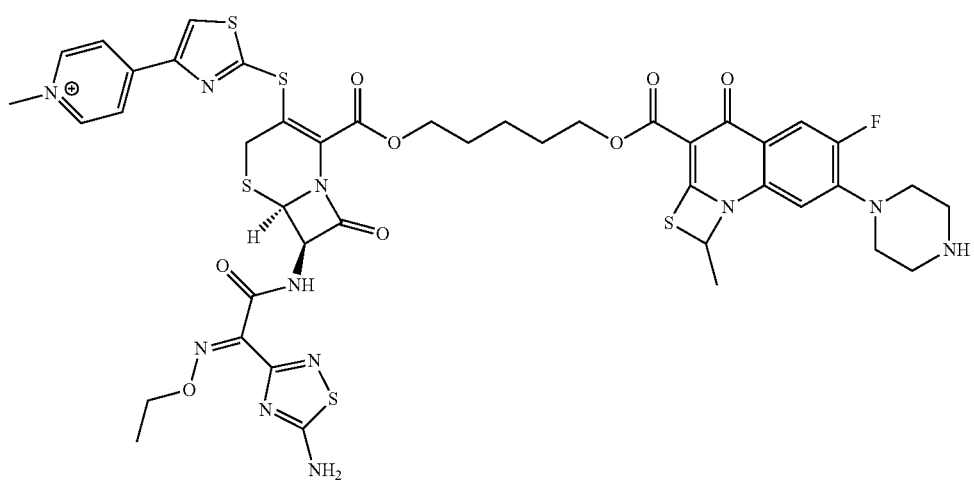 [SMILES: CCO/N=C(/C(=O)N[C@@H]1C(=O)N2C(C(=O)OCCCCCOC(=O)c3c4n(c5cc(N6CCNCC6)c(F)cc5c3=O)C(C)S4)=C(Sc3nc(-c4cc[n+](C)cc4)cs3)CS[C@H]12)c1nsc(N)n1]
24

TABLE 1A-continued
Exemplary DARTs Set-1
25
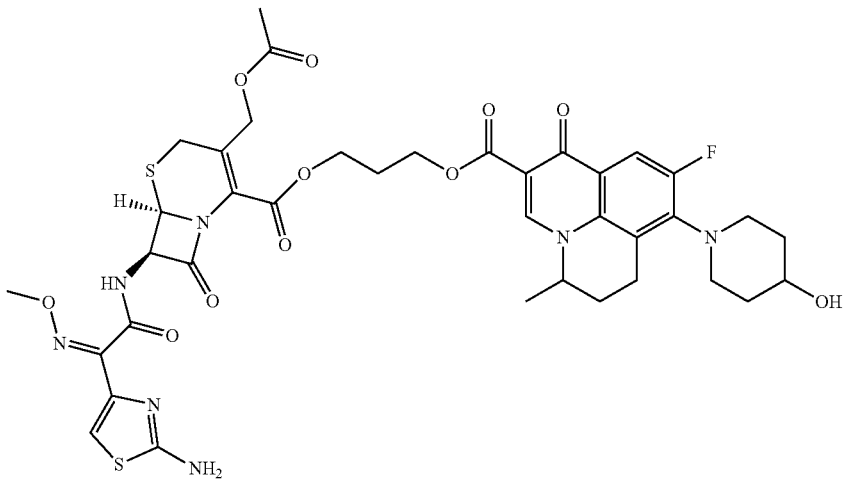 [SMILES: CO/N=C(\C(=O)N[C@@H]1C(=O)N2C(C(=O)OCCCOC(=O)c3cn4c5c(c(N6CCC(O)CC6)c(F)cc5c3=O)CCC4C)=C(COC(C)=O)CS[C@H]12)c1csc(N)n1]
26
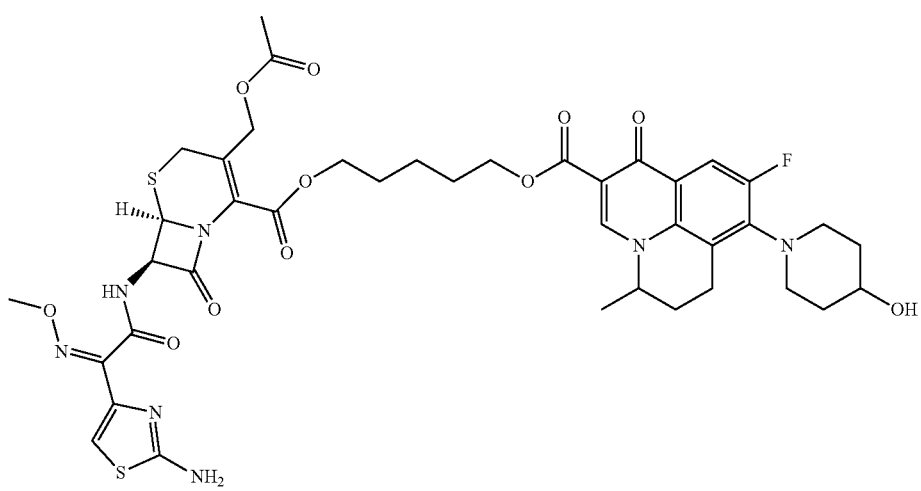 [SMILES: CO/N=C(\C(=O)N[C@@H]1C(=O)N2C(C(=O)OCCCCCOC(=O)c3cn4c5c(c(N6CCC(O)CC6)c(F)cc5c3=O)CCC4C)=C(COC(C)=O)CS[C@H]12)c1csc(N)n1]
27
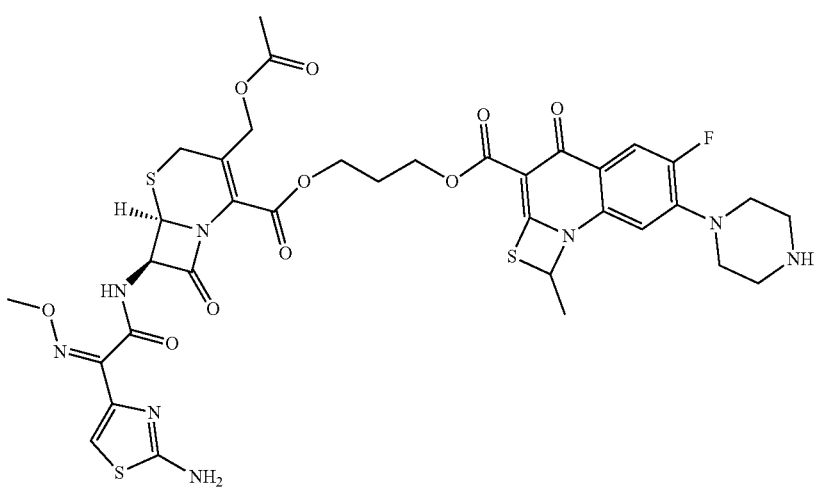 [SMILES: CO/N=C(\C(=O)N[C@@H]1C(=O)N2C(C(=O)OCCCOC(=O)c3c4n(c5cc(N6CCNCC6)c(F)cc5c3=O)C(C)S4)=C(COC(C)=O)CS[C@H]12)c1csc(N)n1]

TABLE 1A-continued
Exemplary DARTs Set-1
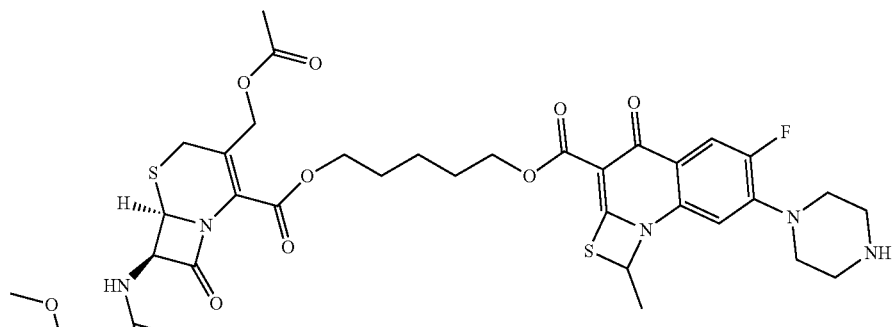
28
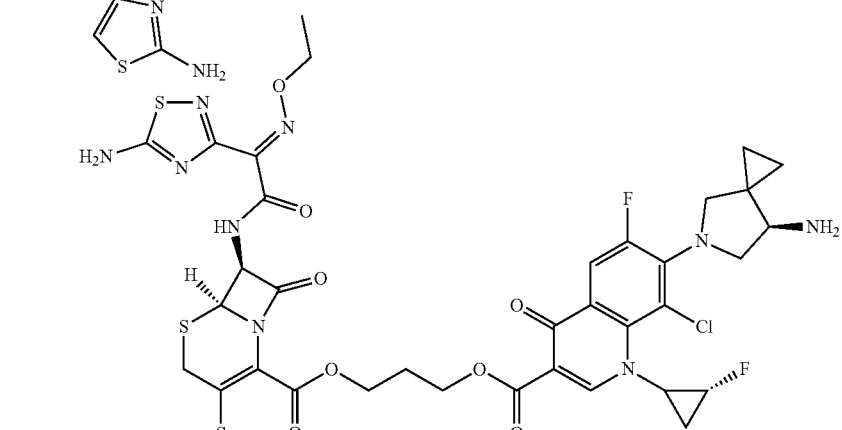
29
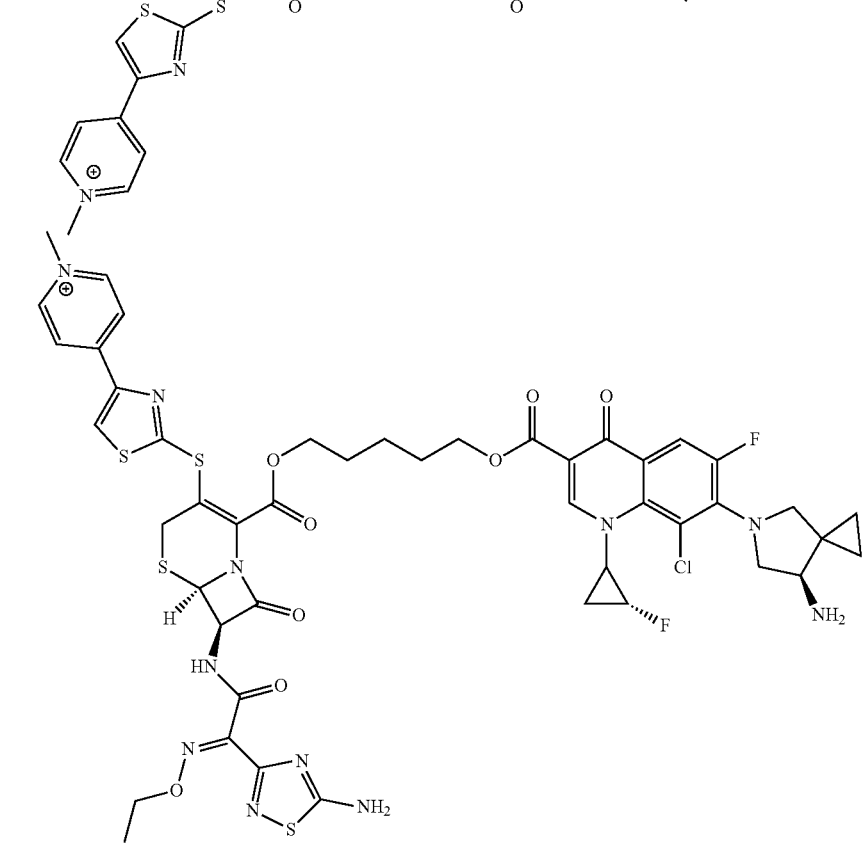
30

TABLE 1A-continued
Exemplary DARTs Set-1
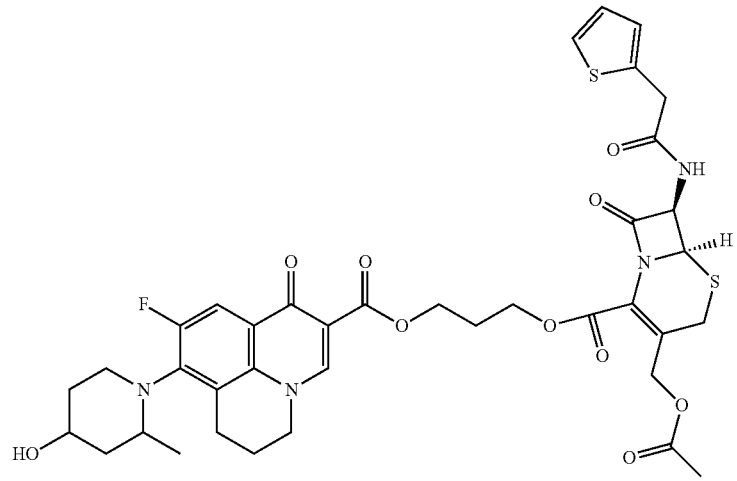 [SMILES: CC(=O)OCC1=C(C(=O)OCCCOC(=O)c2cn3c4c(c(N5CCC(O)CC5C)c(F)cc4c2=O)CCC3)N2C(=O)[C@@H](NC(=O)Cc3cccs3)[C@H]2SC1]
31
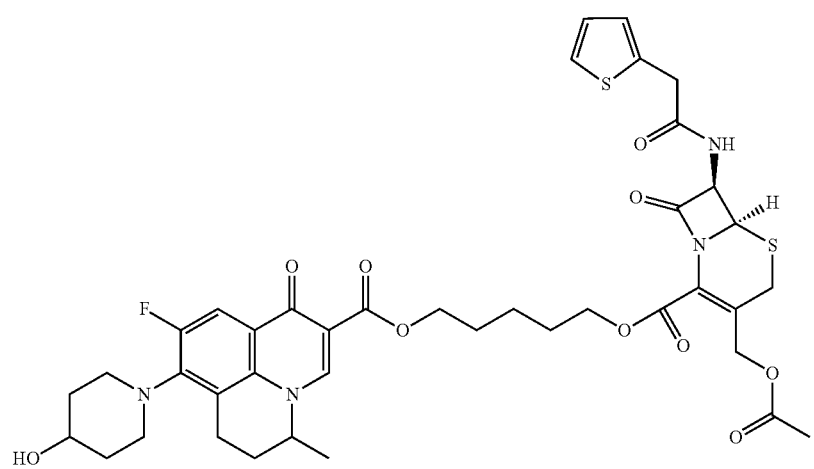 [SMILES: CC(=O)OCC1=C(C(=O)OCCCCCOC(=O)c2cn3c4c(c(N5CCC(O)CC5)c(F)cc4c2=O)CCC3C)N2C(=O)[C@@H](NC(=O)Cc3cccs3)[C@H]2SC1]
32
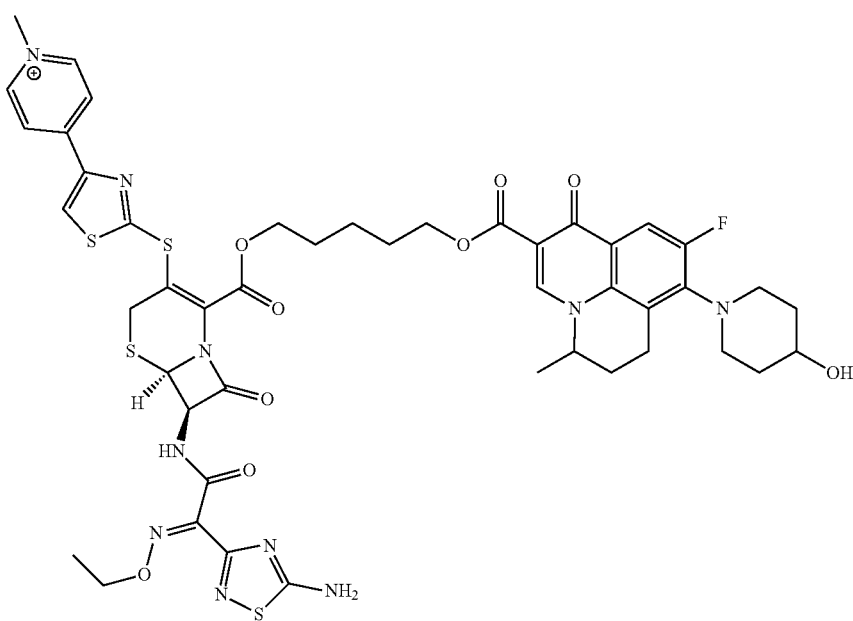 [SMILES: CCO/N=C(/C(=O)N[C@@H]1C(=O)N2C(C(=O)OCCCCCOC(=O)c3cn4c5c(c(N6CCC(O)CC6)c(F)cc5c3=O)CCC4C)=C(Sc3nc(-c4cc[n+](C)cc4)cs3)CS[C@H]12)c1nsc(N)n1]
33

TABLE 1A-continued
Exemplary DARTs Set-1
34
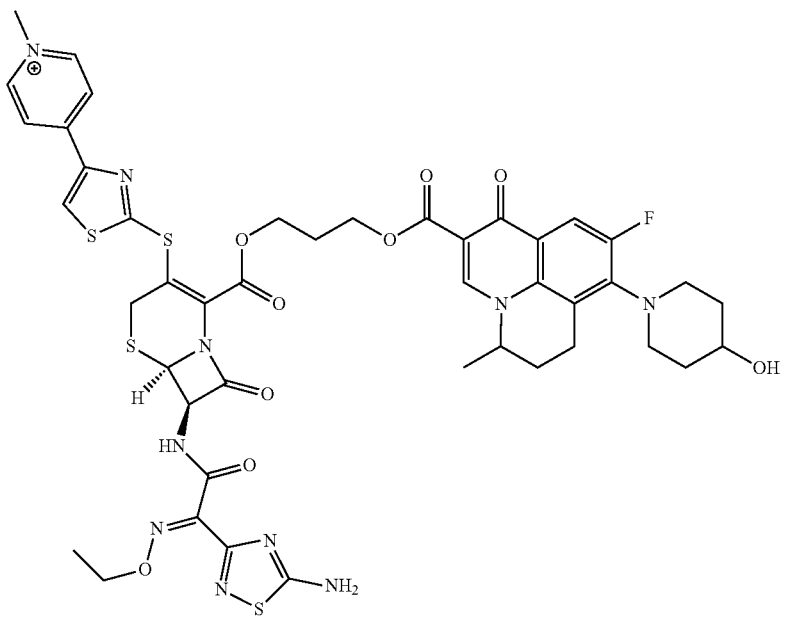 [SMILES: CCO/N=C(/C(=O)N[C@@H]1C(=O)N2C(C(=O)OCCCOC(=O)c3cn4c5c(c(N6CCC(O)CC6)c(F)cc5c3=O)CCC4C)=C(Sc3nc(-c4cc[n+](C)cc4)cs3)CS[C@H]12)c1nsc(N)n1]
35
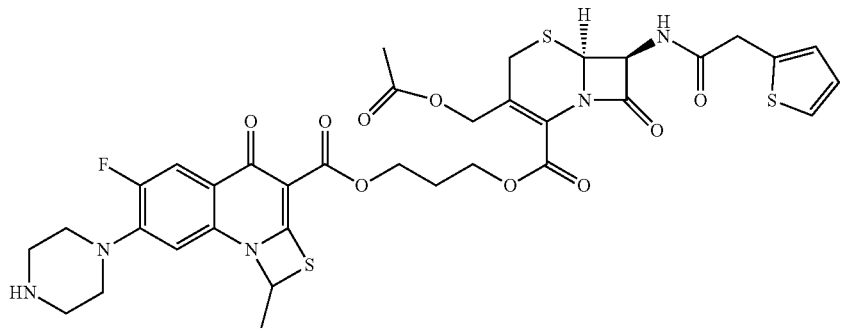 [SMILES: CC(=O)OCC1=C(C(=O)OCCCOC(=O)c2c3n(c4cc(N5CCNCC5)c(F)cc4c2=O)C(C)S3)N2C(=O)[C@H](NC(=O)Cc3cccs3)[C@@H]2SC1]
36
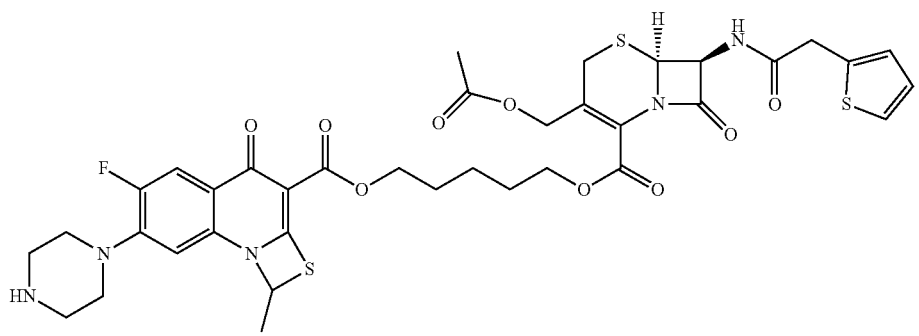 [SMILES: CC(=O)OCC1=C(C(=O)OCCCCCOC(=O)c2c3n(c4cc(N5CCNCC5)c(F)cc4c2=O)C(C)S3)N2C(=O)[C@H](NC(=O)Cc3cccs3)[C@@H]2SC1]

TABLE 1A-continued
Exemplary DARTs Set-1
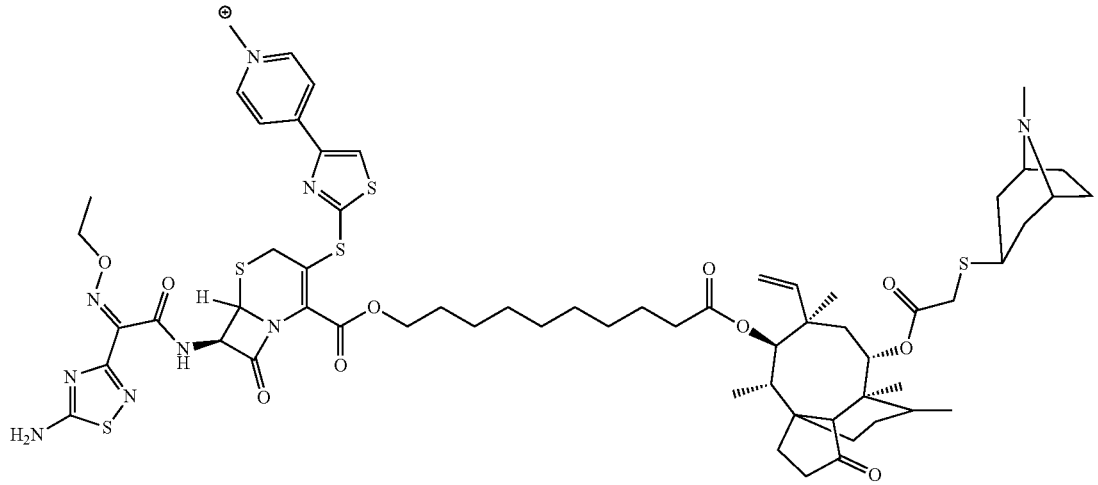
37
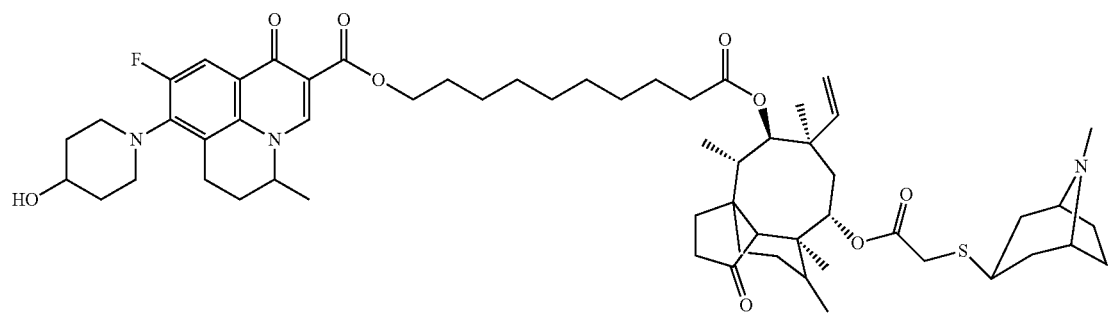 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)CCCCCCCCCOC(=O)c1cn2c3c(c(N4CCC(O)CC4)c(F)cc3c1=O)CCC2C]
38
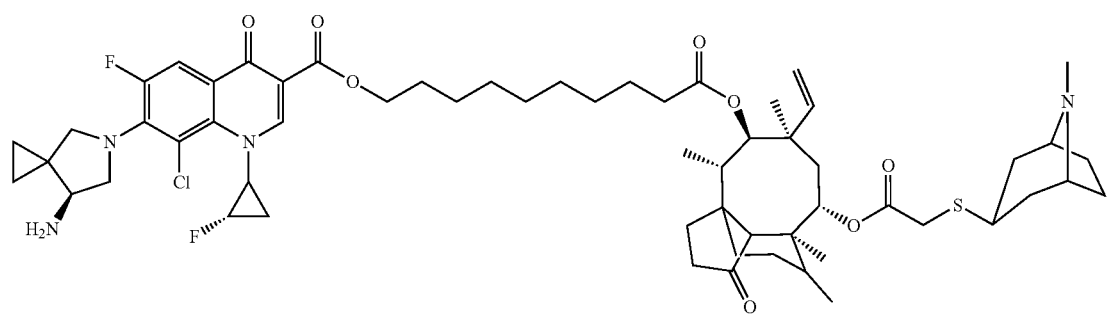 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)CCCCCCCCCOC(=O)c1cn(C2C[C@@H]2F)c2c(Cl)c(N3C[C@@H](N)C4(CC4)C3)c(F)cc2c1=O]
39
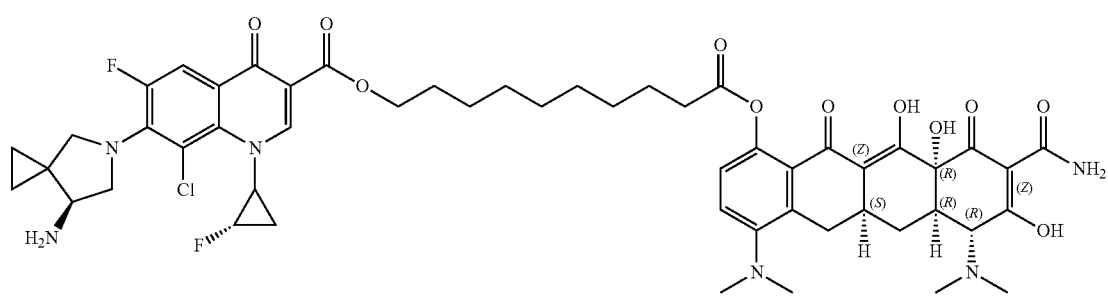
40

TABLE 1A-continued
Exemplary DARTs Set-1
41
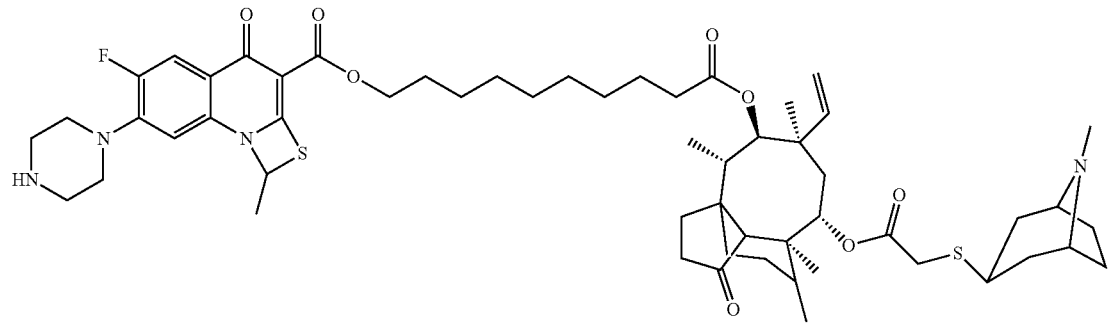 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)CCCCCCCCCOC(=O)c1c2n(c3cc(N4CCNCC4)c(F)cc3c1=O)C(C)S2]
42
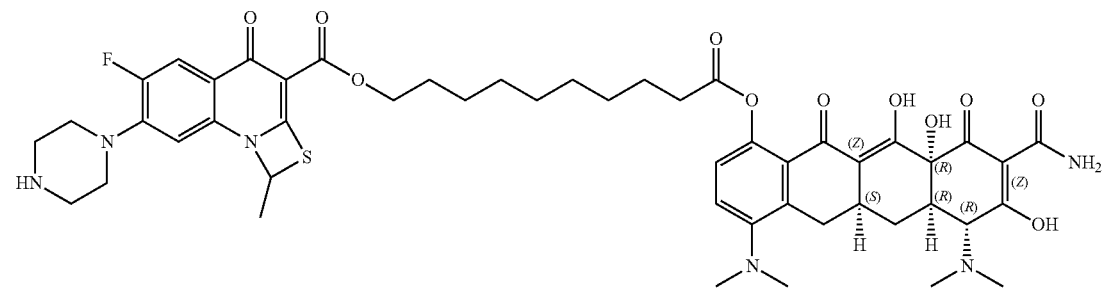
43
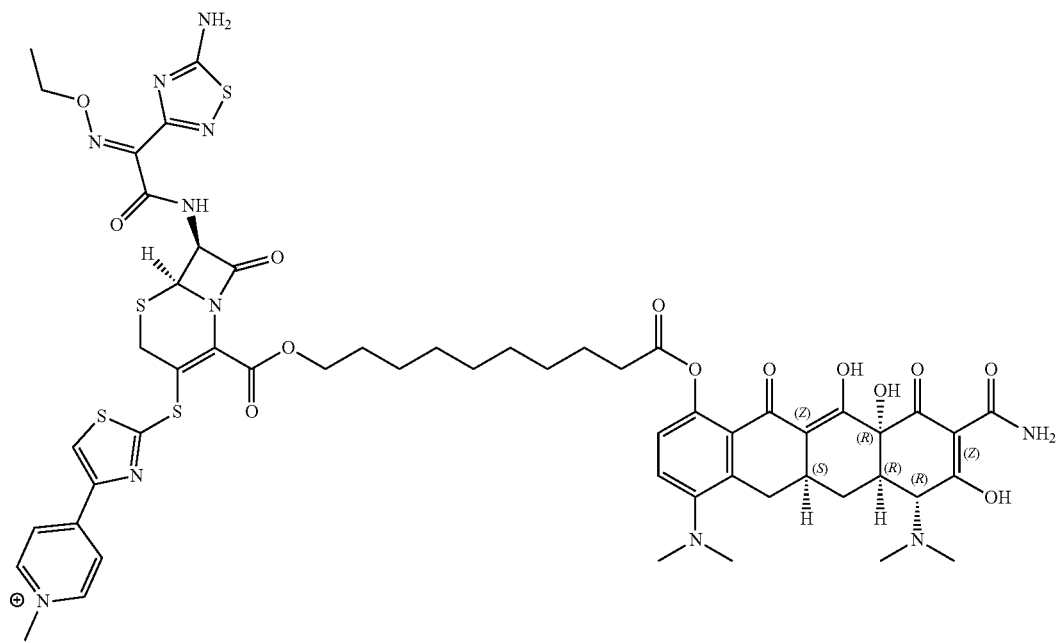

TABLE 1A-continued
Exemplary DARTs Set-1
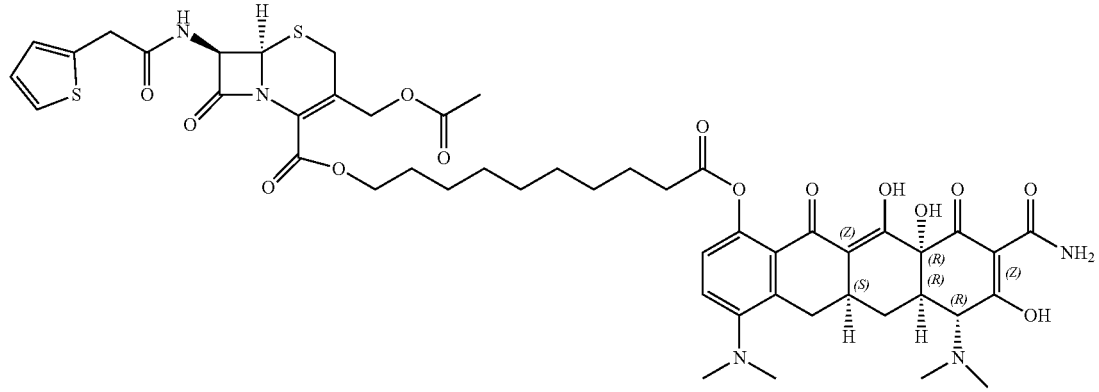
44
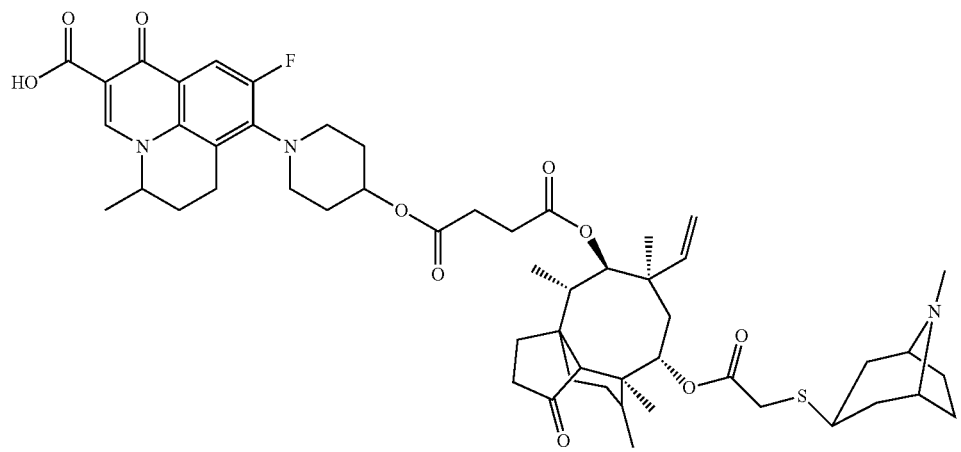 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)CCC(=O)OC1CCN(c2c(F)cc3c(=O)c(C(=O)O)cn4c3c2CCC4C)CC1]
45
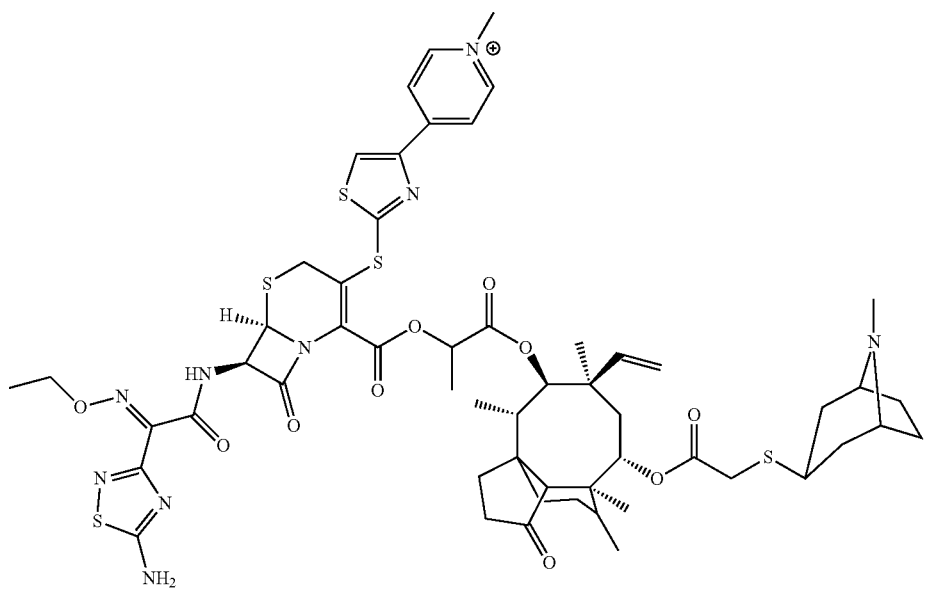 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)C(C)OC(=O)C1=C(Sc2nc(-c3cc[n+](C)cc3)cs2)CS[C@@H]2[C@H](NC(=O)/C(=N/OCC)c3nsc(N)n3)C(=O)N12]
46

TABLE 1A-continued
Exemplary DARTs Set-1
47
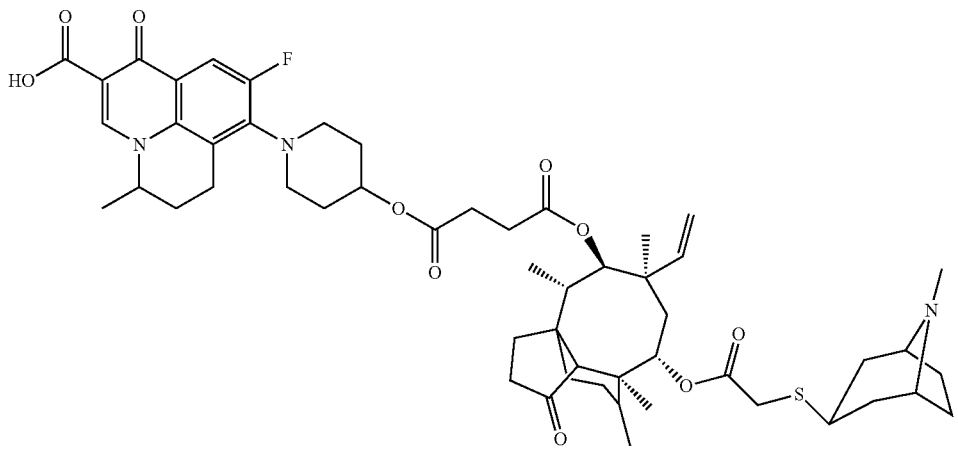 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)CCC(=O)OC1CCN(c2c(F)cc3c(=O)c(C(=O)O)cn4c3c2CCC4C)CC1]
48
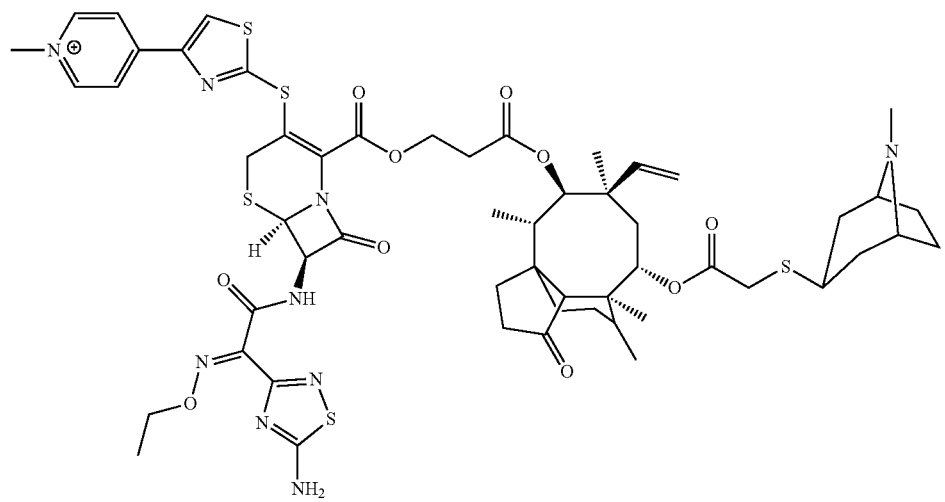 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)CCOC(=O)C1=C(Sc2nc(-c3cc[n+](C)cc3)cs2)CS[C@@H]2[C@H](NC(=O)/C(=N/OCC)c3nsc(N)n3)C(=O)N12]
49
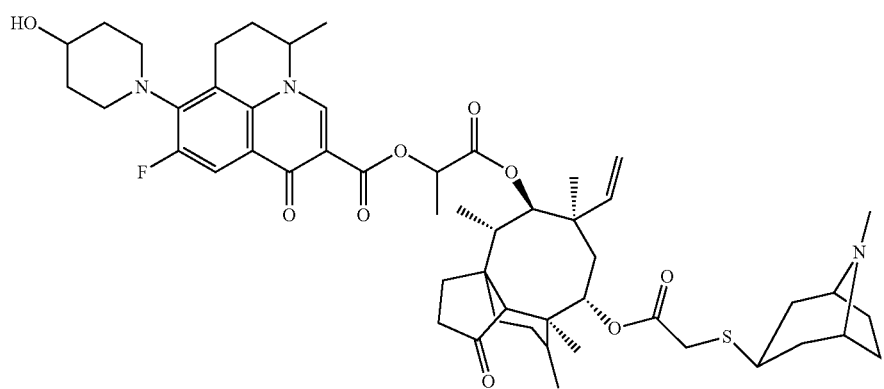 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)C(C)OC(=O)c1cn2c3c(c(N4CCC(O)CC4)c(F)cc3c1=O)CCC2C]

49 50
TABLE 1A-continued
Exemplary DARTs Set-1
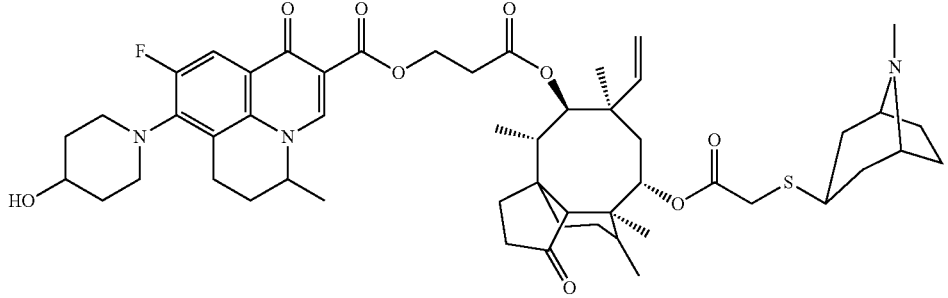 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)CCOC(=O)c1cn2c3c(c(N4CCC(O)CC4)c(F)cc3c1=O)CCC2C]
50
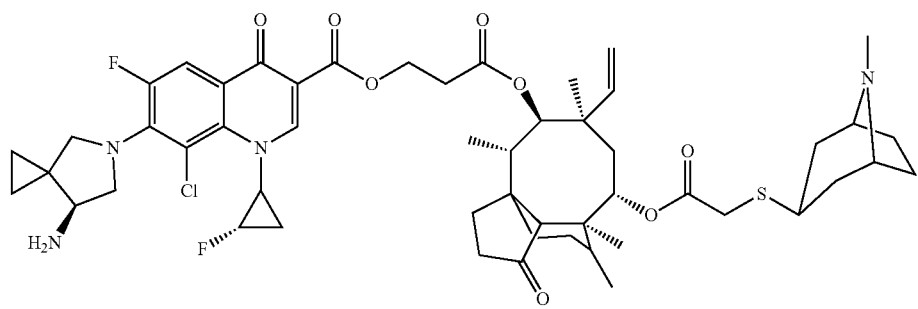 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)CCOC(=O)c1cn(C2C[C@@H]2F)c2c(Cl)c(N3C[C@@H](N)C4(CC4)C3)c(F)cc2c1=O]
51
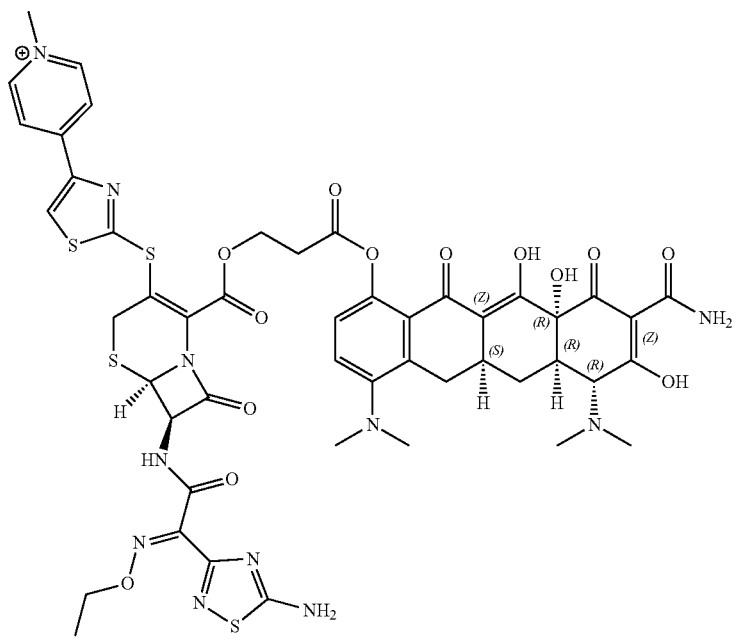
52
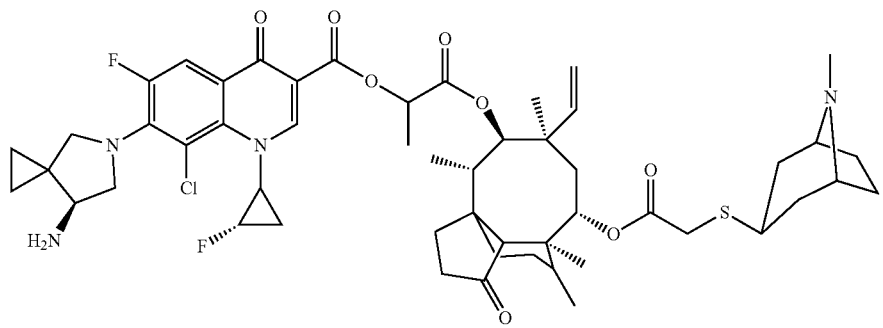 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)C(C)OC(=O)c1cn(C2C[C@@H]2F)c2c(Cl)c(N3C[C@@H](N)C4(CC4)C3)c(F)cc2c1=O]
53

TABLE 1A-continued
Exemplary DARTs Set-1
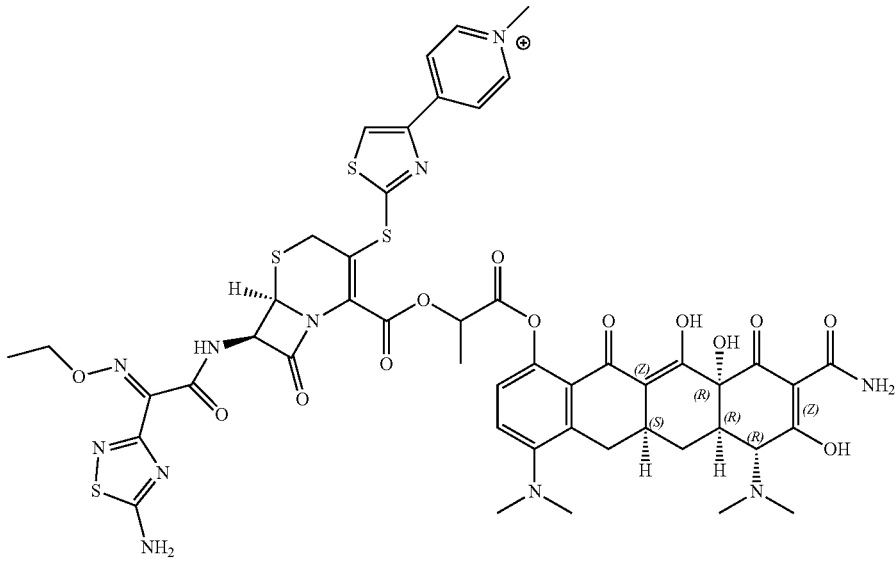
54
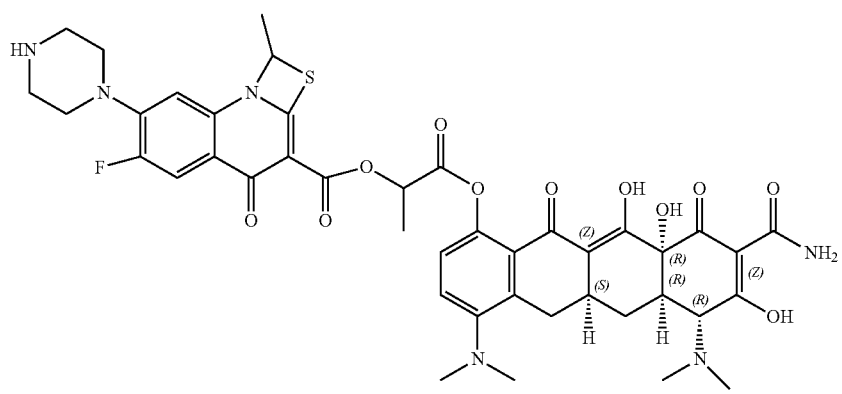
55
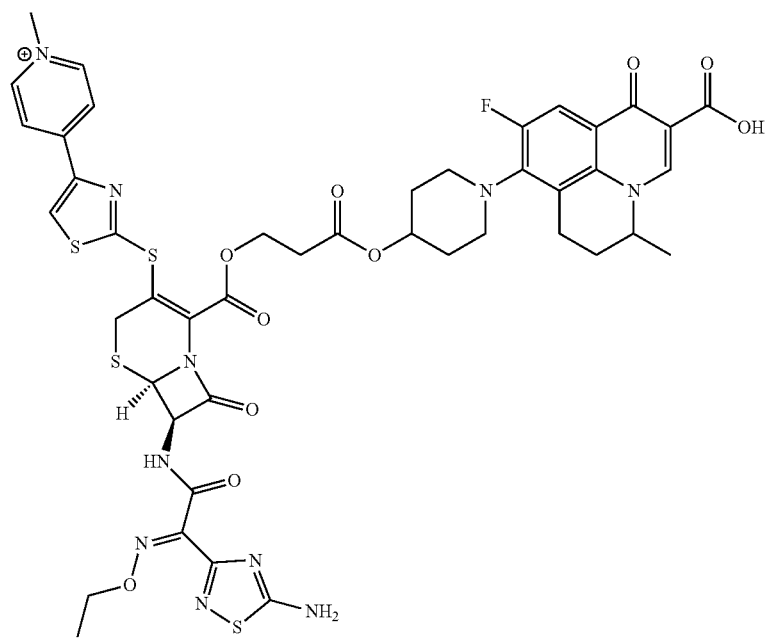 [SMILES: CCO/N=C(/C(=O)N[C@@H]1C(=O)N2C(C(=O)OCCC(=O)OC3CCN(c4c(F)cc5c(=O)c(C(=O)O)cn6c5c4CCC6C)CC3)=C(Sc3nc(-c4cc[n+](C)cc4)cs3)CS[C@H]12)c1nsc(N)n1]
56

TABLE 1A-continued
Exemplary DARTs Set-1
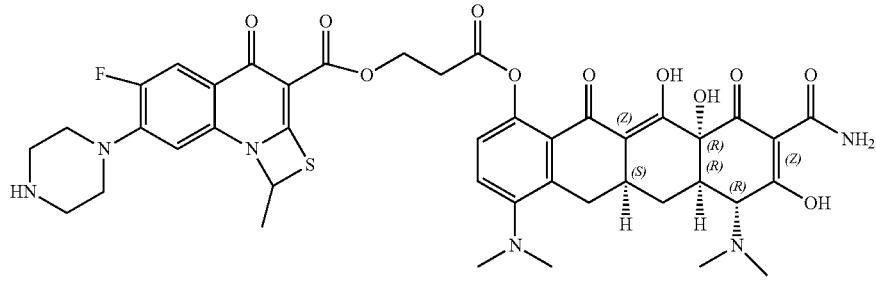
57
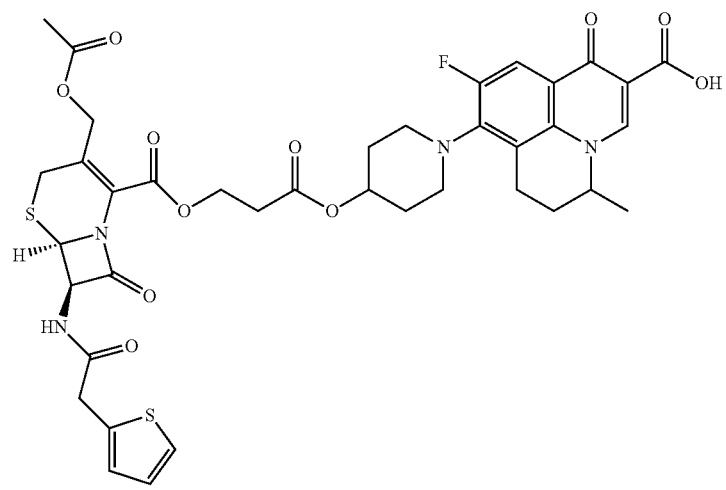 [SMILES: CC(=O)OCC1=C(C(=O)OCCC(=O)OC2CCN(c3c(F)cc4c(=O)c(C(=O)O)cn5c4c3CCC5C)CC2)N2C(=O)[C@@H](NC(=O)Cc3cccs3)[C@H]2SC1]
58
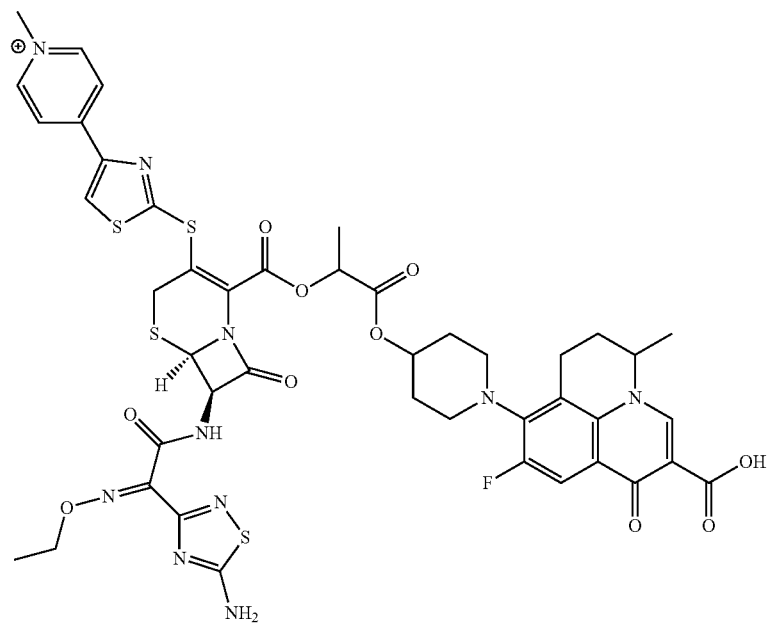 [SMILES: CCON=C(C(=O)N[C@@H]1C(=O)N2C(C(=O)OC(C)C(=O)OC3CCN(c4c(F)cc5c(=O)c(C(=O)O)cn6c5c4CCC6C)CC3)=C(Sc3nc(-c4cc[n+](C)cc4)cs3)CS[C@H]12)c1nsc(N)n1]
59

TABLE 1A-continued
Exemplary DARTs Set-1
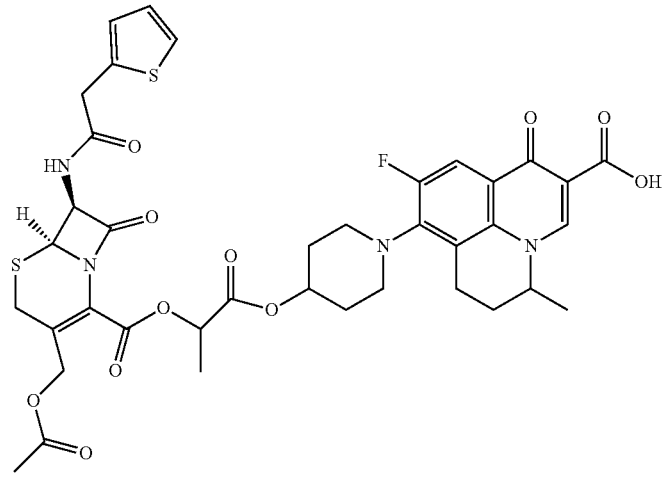 [SMILES: CC(=O)OCC1=C(C(=O)OC(C)C(=O)OC2CCN(c3c(F)cc4c(=O)c(C(=O)O)cn5c4c3CCC5C)CC2)N2C(=O)[C@H](NC(=O)Cc3cccs3)[C@@H]2SC1]
60
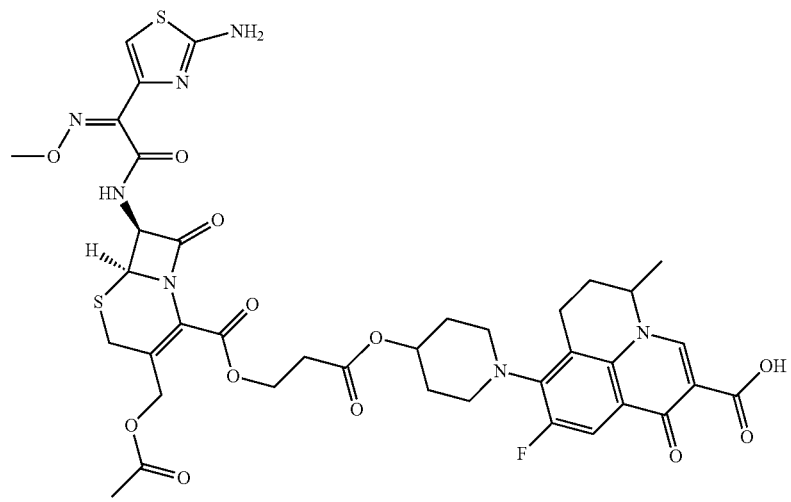 [SMILES: CO/N=C(\C(=O)N[C@H]1C(=O)N2C(C(=O)OCCC(=O)OC3CCN(c4c(F)cc5c(=O)c(C(=O)O)cn6c5c4CCC6C)CC3)=C(COC(C)=O)CS[C@@H]12)c1csc(N)n1]
61
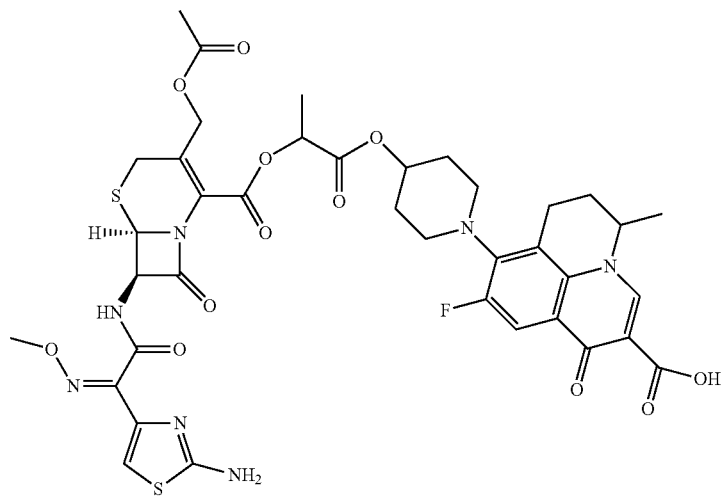 [SMILES: CO/N=C(\C(=O)N[C@@H]1C(=O)N2C(C(=O)OC(C)C(=O)OC3CCN(c4c(F)cc5c(=O)c(C(=O)O)cn6c5c4CCC6C)CC3)=C(COC(C)=O)CS[C@H]12)c1csc(N)n1]
62

TABLE 1A-continued
Exemplary DARTs Set-1
63
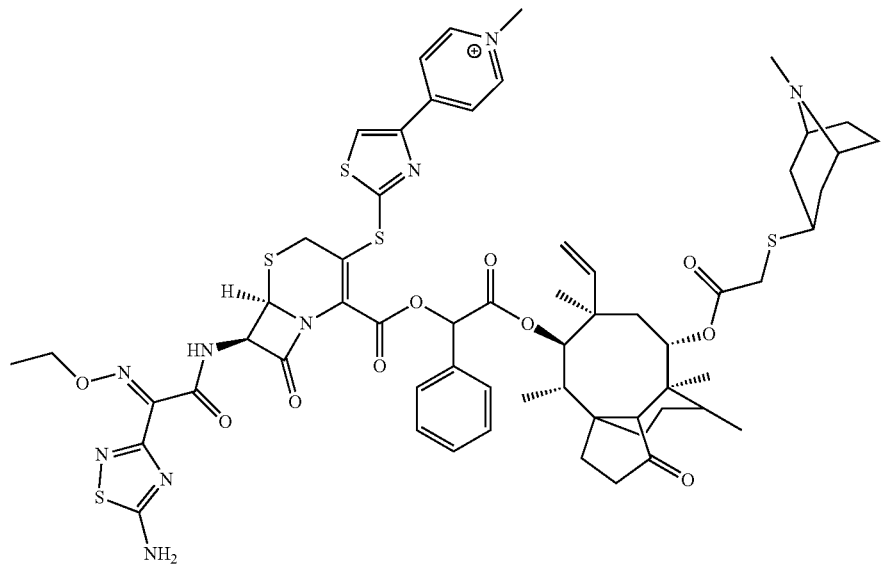 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)C(OC(=O)C1=C(Sc2nc(-c3cc[n+](C)cc3)cs2)CS[C@@H]2[C@H](NC(=O)/C(=N/OCC)c3nsc(N)n3)C(=O)N12)c1ccccc1]
64
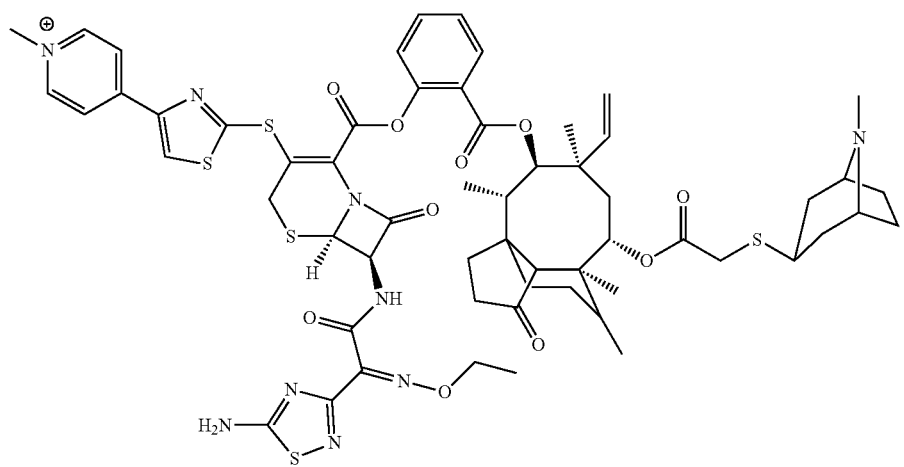 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)c1ccccc1OC(=O)C1=C(Sc2nc(-c3cc[n+](C)cc3)cs2)CS[C@@H]2[C@H](NC(=O)C(=NOCC)c3nsc(N)n3)C(=O)N12]
65
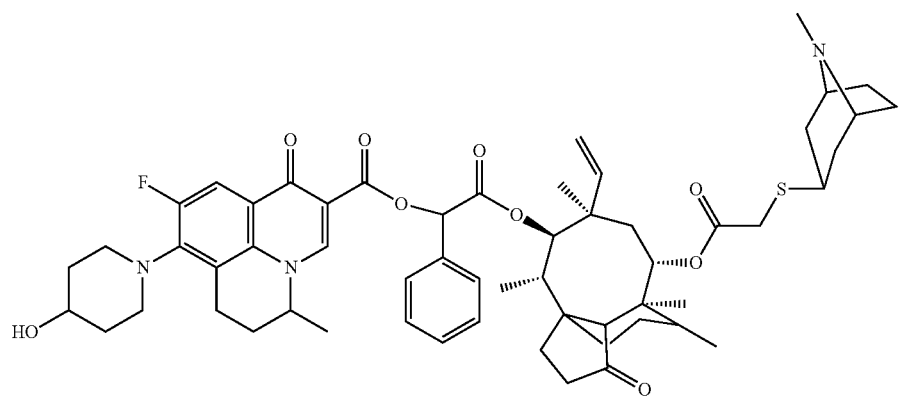 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)C(OC(=O)c1cn2c3c(c(N4CCC(O)CC4)c(F)cc3c1=O)CCC2C)c1ccccc1]

TABLE 1A-continued
Exemplary DARTs Set-1
66
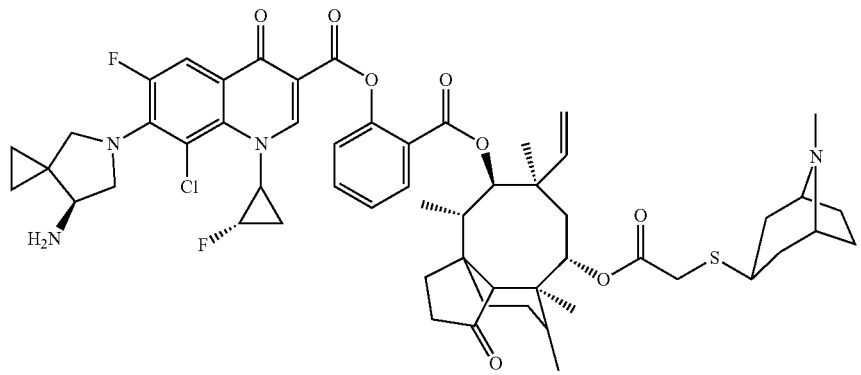 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)c1ccccc1OC(=O)c1cn(C2C[C@@H]2F)c2c(Cl)c(N3C[C@@H](N)C4(CC4)C3)c(F)cc2c1=O]
67
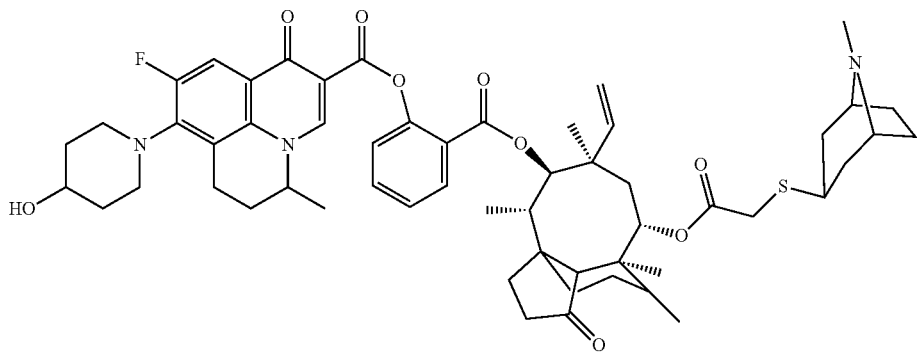 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)c1ccccc1OC(=O)c1cn2c3c(c(N4CCC(O)CC4)c(F)cc3c1=O)CCC2C]
68
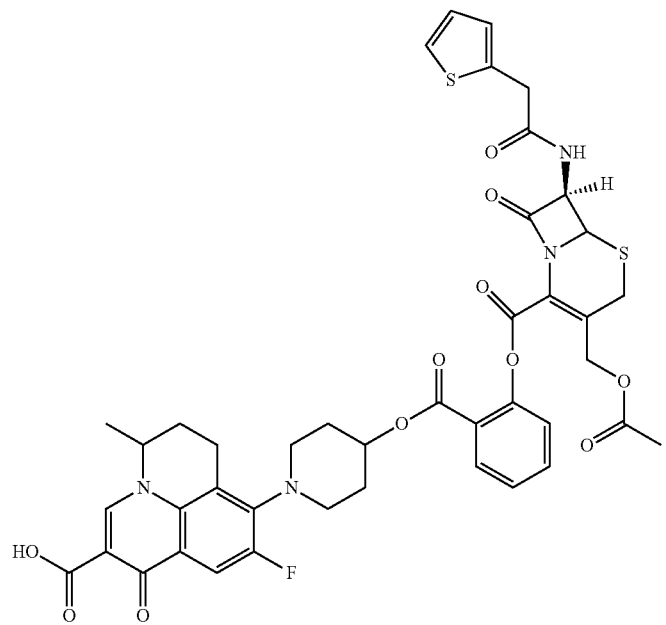 [SMILES: CC(=O)OCC1=C(C(=O)Oc2ccccc2C(=O)OC2CCN(c3c(F)cc4c(=O)c(C(=O)O)cn5c4c3CCC5C)CC2)N2C(=O)[C@@H](NC(=O)Cc3cccs3)C2SC1]

TABLE 1A-continued
Exemplary DARTs Set-1
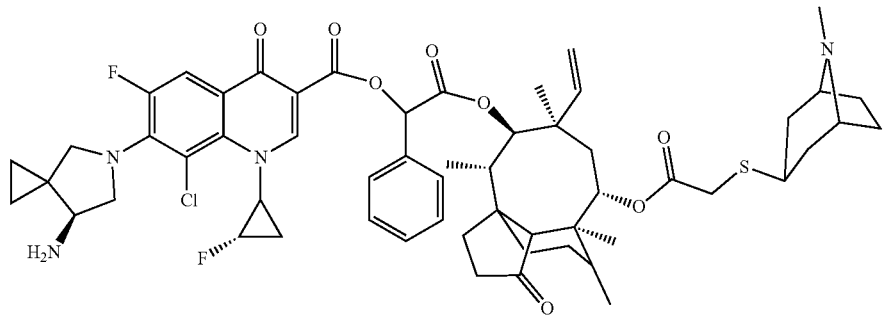 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)C(OC(=O)c1cn(C2C[C@@H]2F)c2c(Cl)c(N3C[C@@H](N)C4(CC4)C3)c(F)cc2c1=O)c1ccccc1]
69
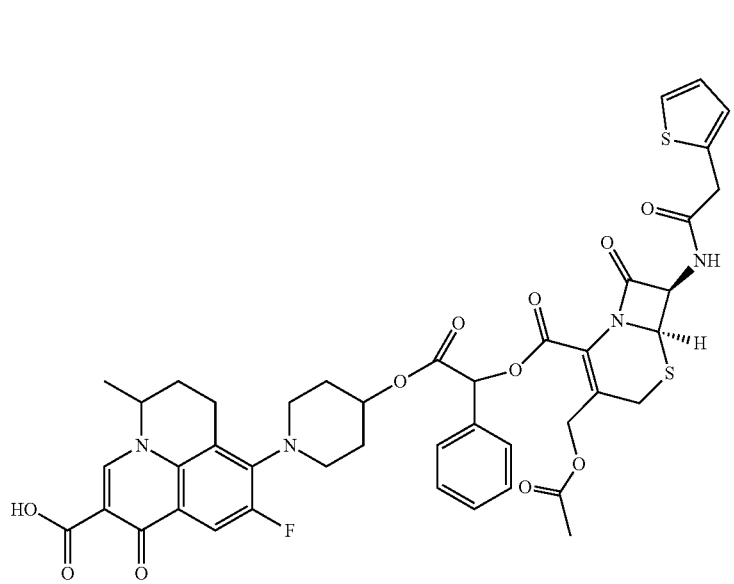 [SMILES: CC(=O)OCC1=C(C(=O)OC(C(=O)OC2CCN(c3c(F)cc4c(=O)c(C(=O)O)cn5c4c3CCC5C)CC2)c2ccccc2)N2C(=O)[C@@H](NC(=O)Cc3cccs3)[C@H]2SC1]
70
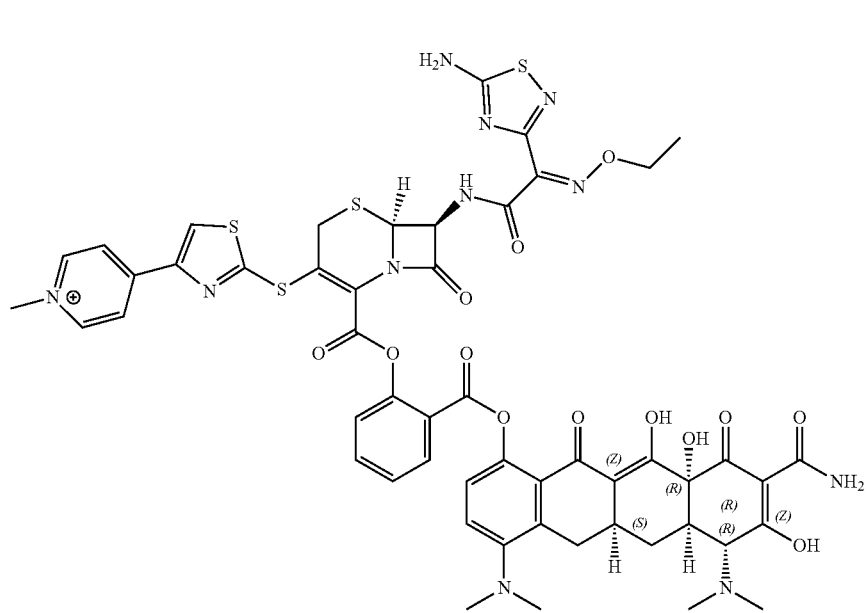
71

TABLE 1A-continued
Exemplary DARTs Set-1
72
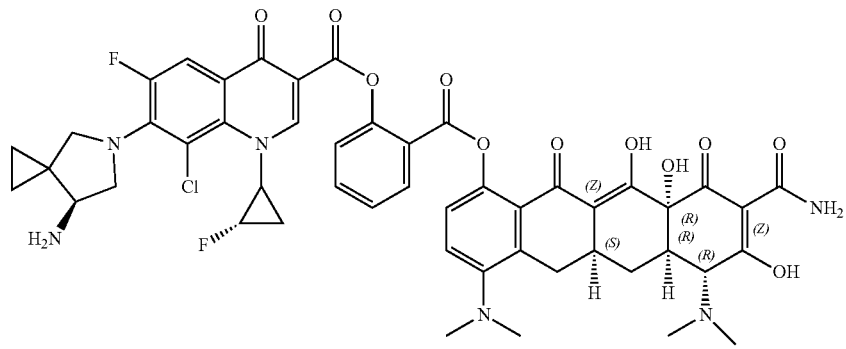
73
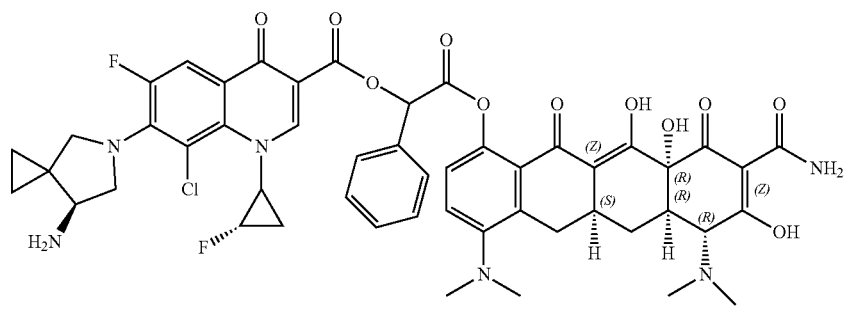
74
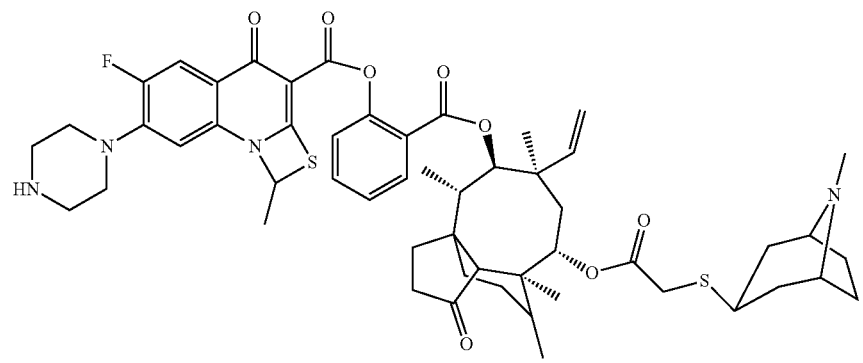 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)c1ccccc1OC(=O)c1c2n(c3cc(N4CCNCC4)c(F)cc3c1=O)C(C)S2]
75
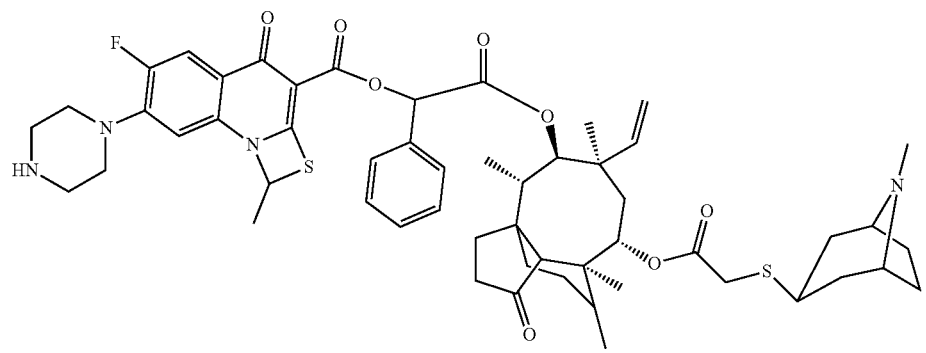 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)C(OC(=O)c1c2n(c3cc(N4CCNCC4)c(F)cc3c1=O)C(C)S2)c1ccccc1]

US 10,071,103 B2
65 66
TABLE 1A-continued
Exemplary DARTs Set-1
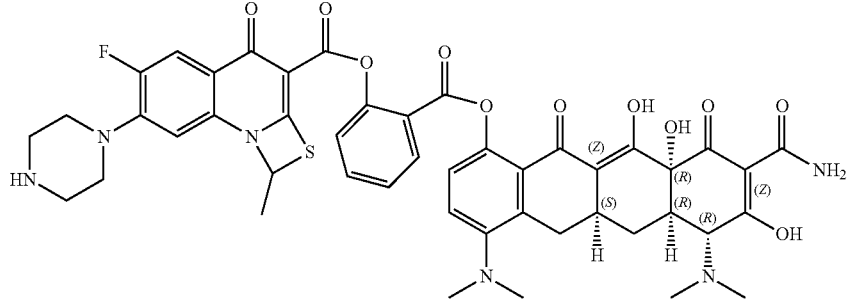
76
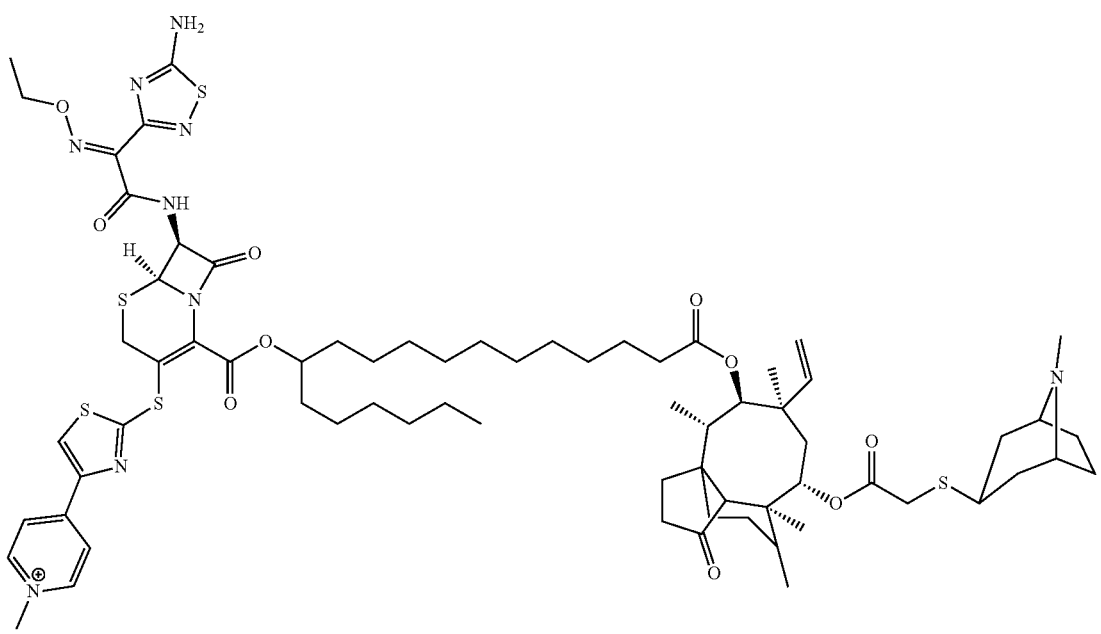 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)CCCCCCCCCCC(CCCCCC)OC(=O)C1=C(Sc2nc(-c3cc[n+](C)cc3)cs2)CS[C@H]2[C@@H](NC(=O)/C(=N/OCC)c3nsc(N)n3)C(=O)N12]
77
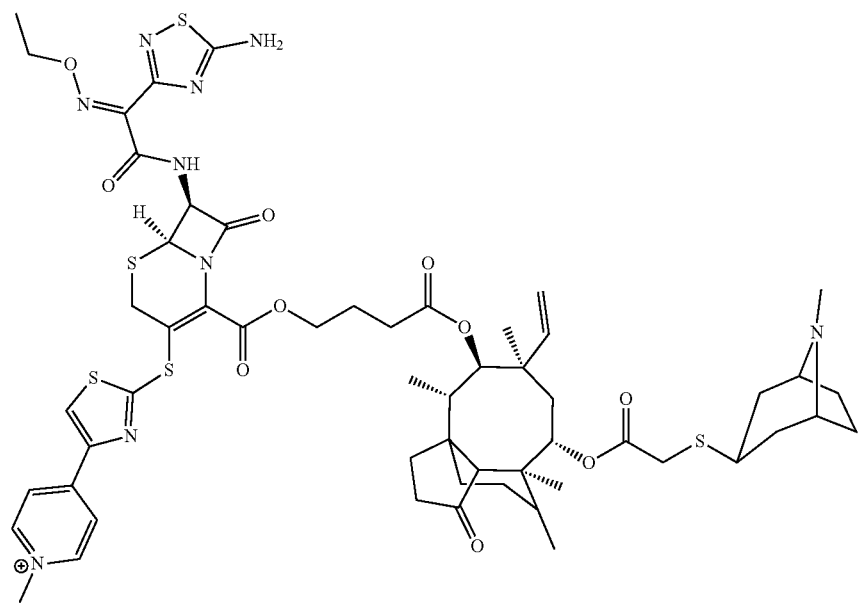 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)CCCOC(=O)C1=C(Sc2nc(-c3cc[n+](C)cc3)cs2)CS[C@H]2[C@@H](NC(=O)/C(=N/OCC)c3nsc(N)n3)C(=O)N12]
78

TABLE 1A-continued
Exemplary DARTs Set-1
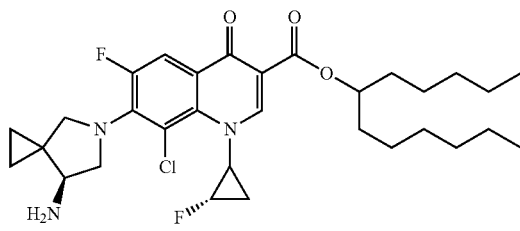
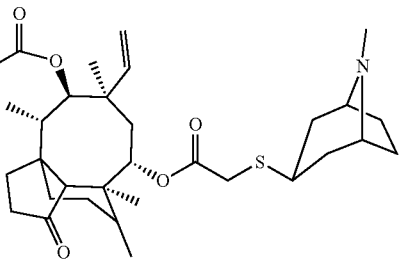
79
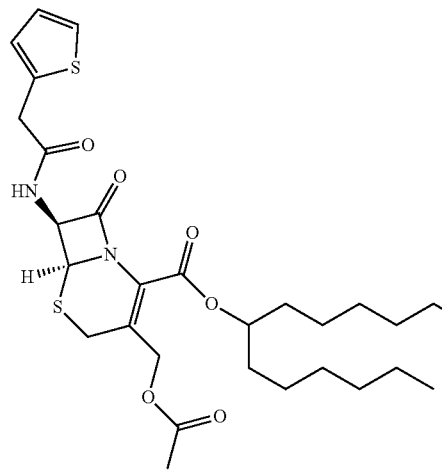
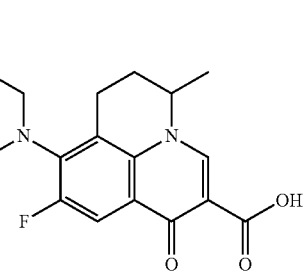
80
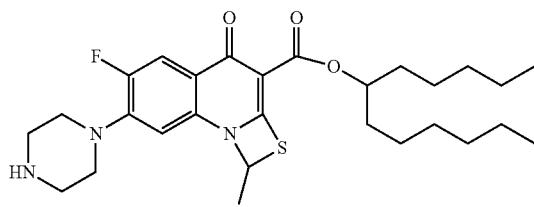
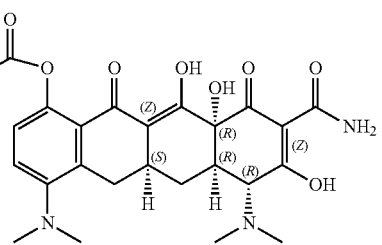
81
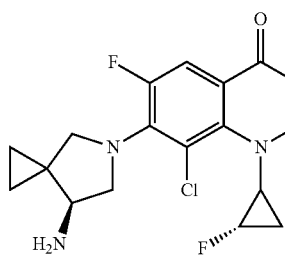
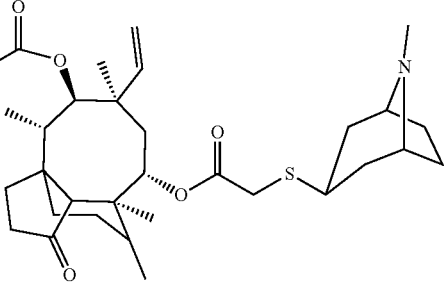
82

TABLE 1A-continued
Exemplary DARTs Set-1
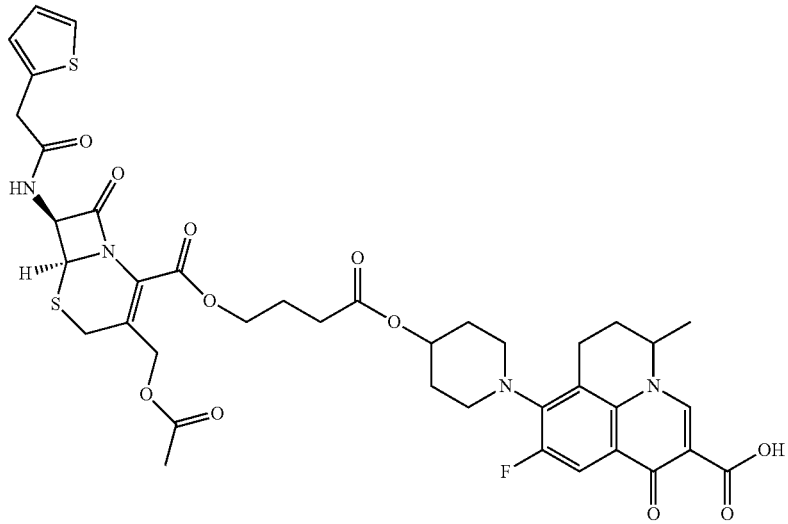 [SMILES: CC(=O)OCC1=C(C(=O)OCCCC(=O)OC2CCN(c3c(F)cc4c(=O)c(C(=O)O)cn5c4c3CCC5C)CC2)N2C(=O)[C@H](NC(=O)Cc3cccs3)[C@@H]2SC1]
83
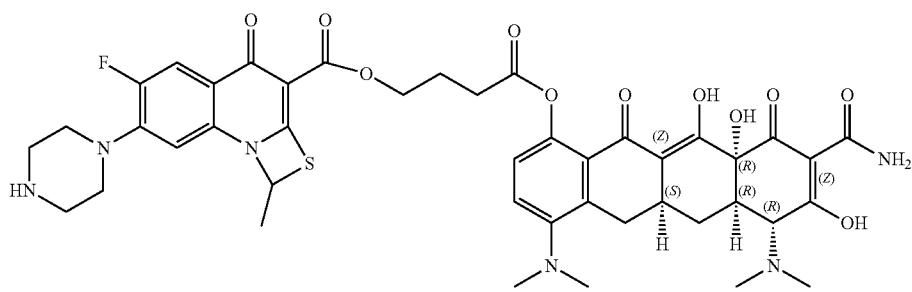
84
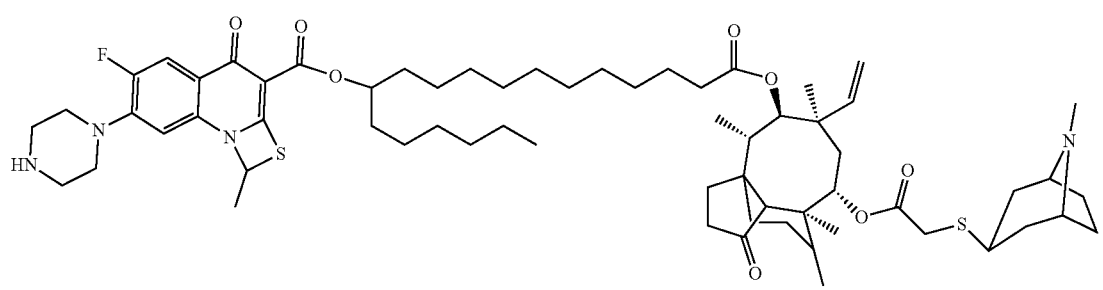 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)CCCCCCCCCCC(CCCCCC)OC(=O)c1c2n(c3cc(N4CCNCC4)c(F)cc3c1=O)C(C)S2]
85
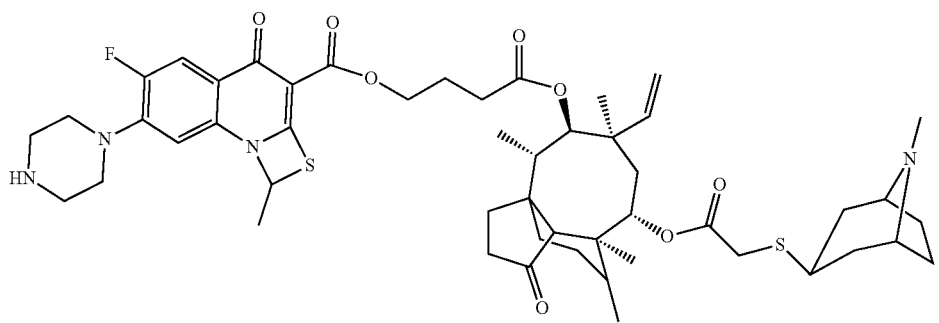 [SMILES: C=C[C@@]1(C)C[C@H](OC(=O)CSC2CC3CCC(C2)N3C)[C@@]2(C)C(C)CCC3(CCC(=O)C32)[C@H](C)[C@H]1OC(=O)CCCOC(=O)c1c2n(c3cc(N4CCNCC4)c(F)cc3c1=O)C(C)S2]
86

TABLE 1A-continued
Exemplary DARTs Set-1
87
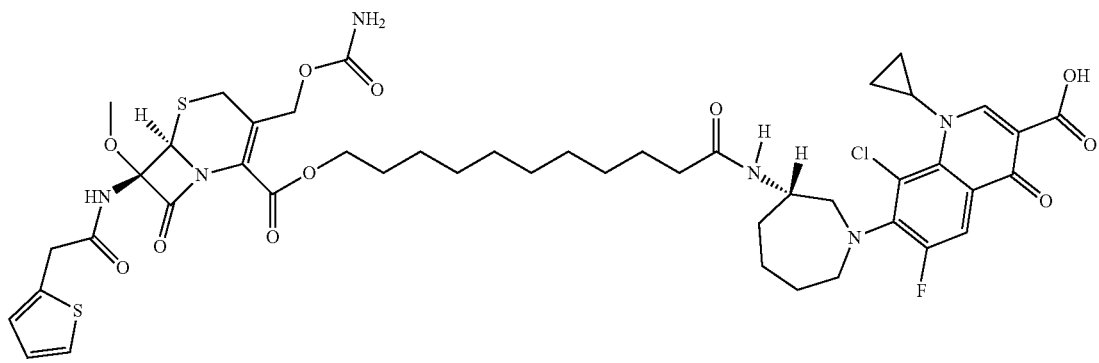 [SMILES: CO[C@@]1(NC(=O)Cc2cccs2)C(=O)N2C(C(=O)OCCCCCCCCCCC(=O)N[C@H]3CCCCN(c4c(F)cc5c(=O)c(C(=O)O)cn(C6CC6)c5c4Cl)C3)=C(COC(N)=O)CS[C@@H]21]
88
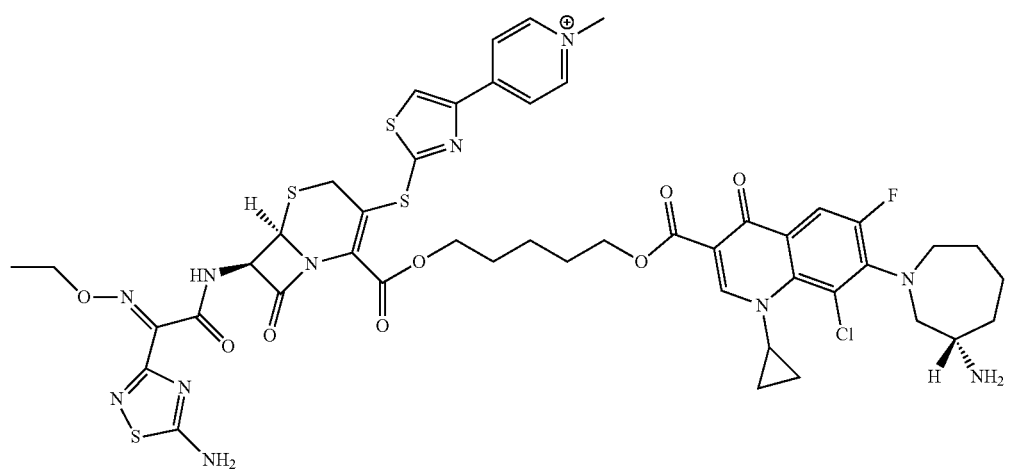 [SMILES: CCO/N=C(/C(=O)N[C@@H]1C(=O)N2C(C(=O)OCCCCCOC(=O)c3cn(C4CC4)c4c(Cl)c(N5CCCC[C@H](N)C5)c(F)cc4c3=O)=C(Sc3nc(-c4cc[n+](C)cc4)cs3)CS[C@H]12)c1nsc(N)n1]
89
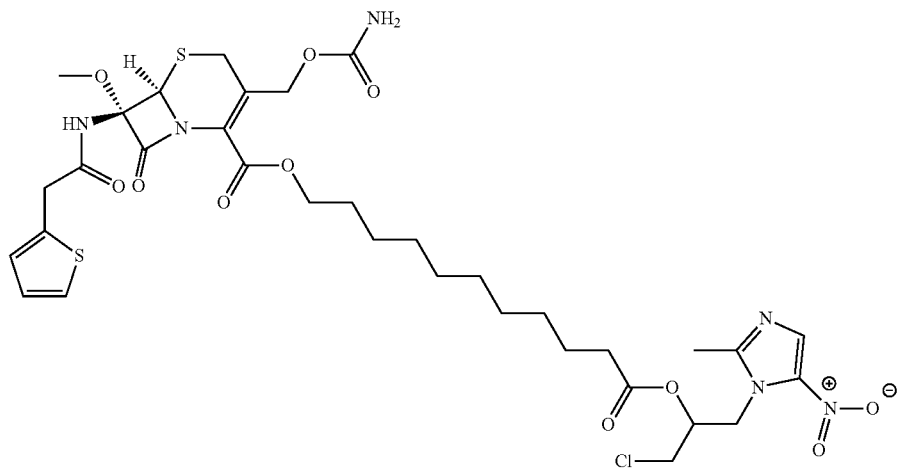 [SMILES: CO[C@@]1(NC(=O)Cc2cccs2)C(=O)N2C(C(=O)OCCCCCCCCCCC(=O)OC(CCl)Cn3c([N+](=O)[O-])cnc3C)=C(COC(N)=O)CS[C@@H]21]

TABLE 2A
Exemplary DARTs Set-2
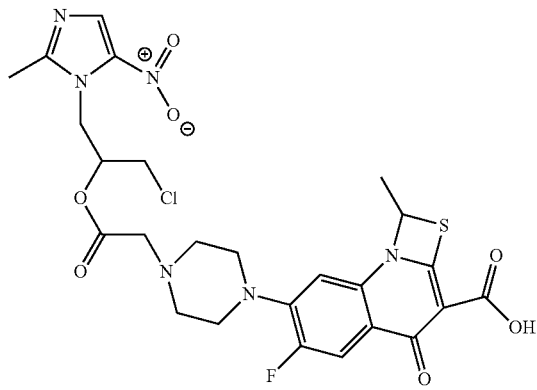 [SMILES: Cc1ncc([N+](=O)[O-])n1CC(CCl)OC(=O)CN1CCN(c2cc3c(cc2F)c(=O)c(C(=O)O)c2n3C(C)S2)CC1]
90
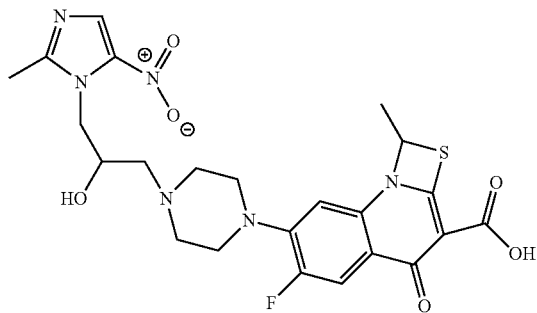 [SMILES: Cc1ncc([N+](=O)[O-])n1CC(O)CN1CCN(c2cc3c(cc2F)c(=O)c(C(=O)O)c2n3C(C)S2)CC1]
91
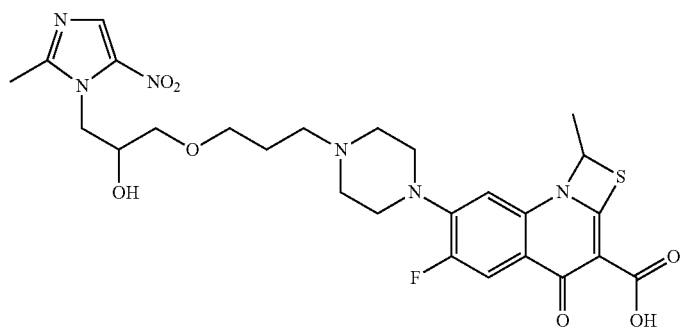 [SMILES: Cc1ncc([N+](=O)[O-])n1CC(O)COCCCN1CCN(c2cc3c(cc2F)c(=O)c(C(=O)O)c2n3C(C)S2)CC1]
92
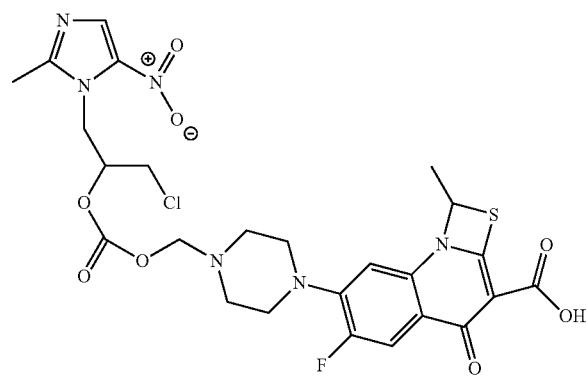 [SMILES: Cc1ncc([N+](=O)[O-])n1CC(CCl)OC(=O)OCN1CCN(c2cc3c(cc2F)c(=O)c(C(=O)O)c2n3C(C)S2)CC1]
93

TABLE 2A-continued
Exemplary DARTs Set-2
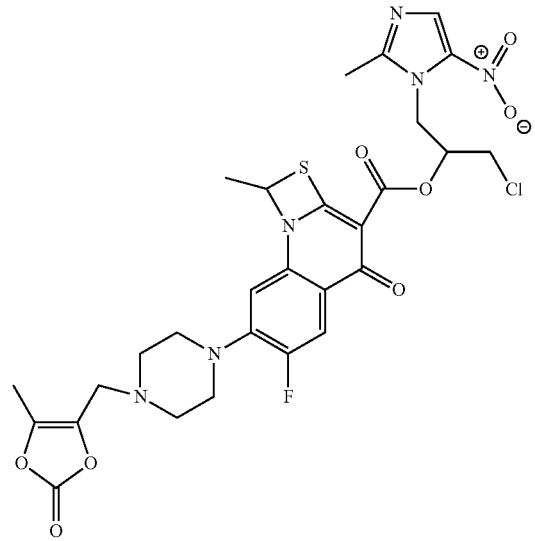 [SMILES: Cc1oc(=O)oc1CN1CCN(c2cc3c(cc2F)c(=O)c(C(=O)OC(CCl)Cn2c([N+](=O)[O-])cnc2C)c2n3C(C)S2)CC1]
94
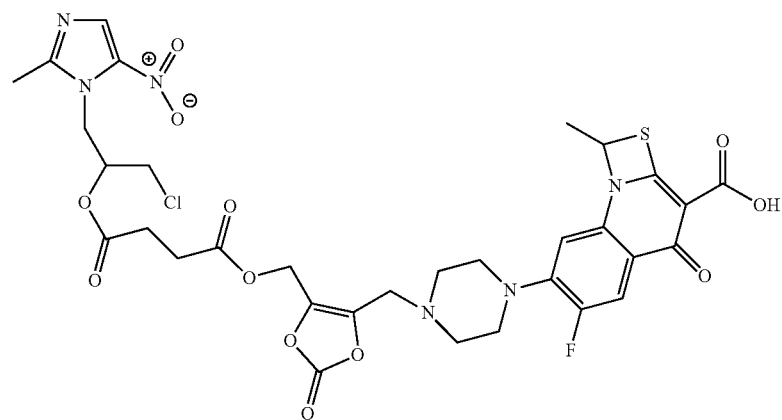 [SMILES: Cc1ncc([N+](=O)[O-])n1CC(CCl)OC(=O)CCC(=O)OCc1oc(=O)oc1CN1CCN(c2cc3c(cc2F)c(=O)c(C(=O)O)c2n3C(C)S2)CC1]
95
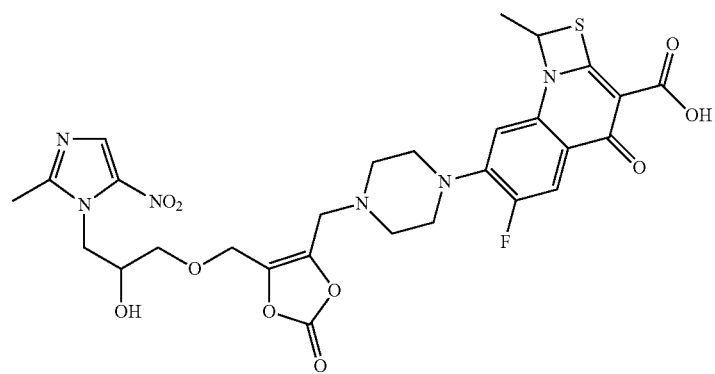 [SMILES: Cc1ncc([N+](=O)[O-])n1CC(O)COCc1oc(=O)oc1CN1CCN(c2cc3c(cc2F)c(=O)c(C(=O)O)c2n3C(C)S2)CC1]
96

TABLE 2A-continued
Exemplary DARTs Set-2
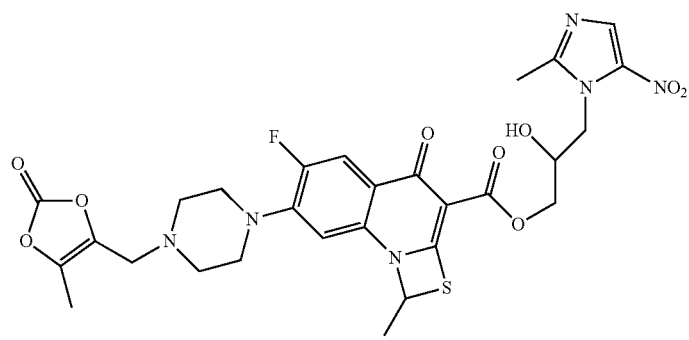 [SMILES: Cc1oc(=O)oc1CN1CCN(c2cc3c(cc2F)c(=O)c(C(=O)OCC(O)Cn2c([N+](=O)[O-])cnc2C)c2n3C(C)S2)CC1]
97
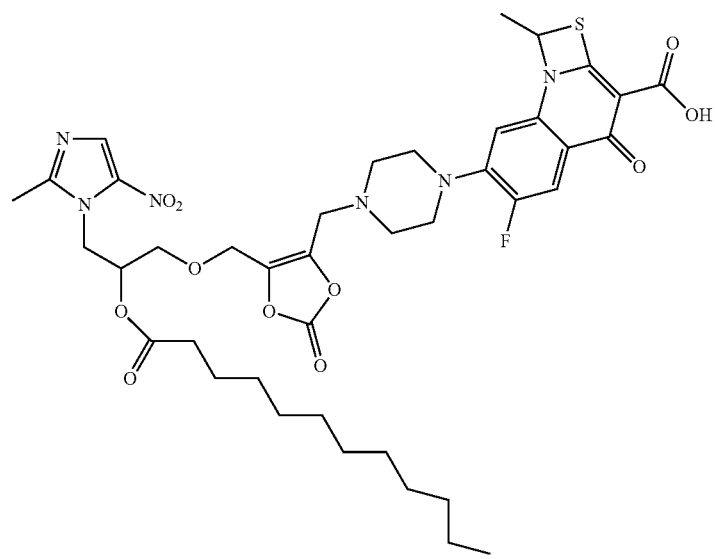 [SMILES: CCCCCCCCCCCC(=O)OC(COCc1oc(=O)oc1CN1CCN(c2cc3c(cc2F)c(=O)c(C(=O)O)c2n3C(C)S2)CC1)Cn1c([N+](=O)[O-])cnc1C]
98
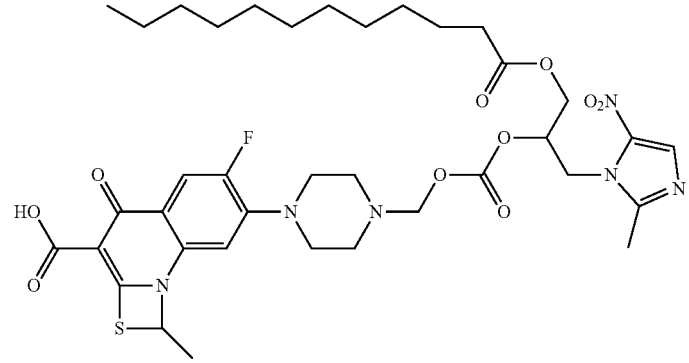 [SMILES: CCCCCCCCCCCC(=O)OCC(Cn1c([N+](=O)[O-])cnc1C)OC(=O)OCN1CCN(c2cc3c(cc2F)c(=O)c(C(=O)O)c2n3C(C)S2)CC1]
99
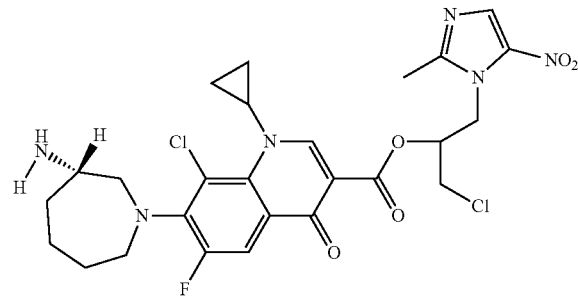 [SMILES: Cc1ncc([N+](=O)[O-])n1CC(CCl)OC(=O)c1cn(C2CC2)c2c(Cl)c(N3CCCC[C@H](N)C3)c(F)cc2c1=O]
100

TABLE 2A-continued
Exemplary DARTs Set-2
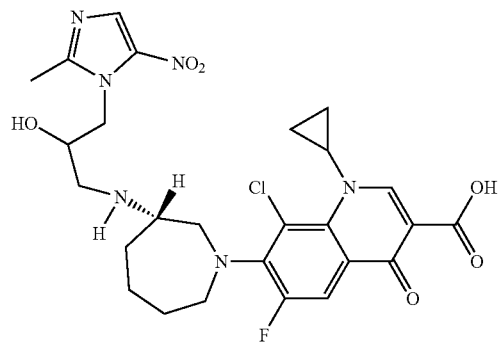 [SMILES: Cc1ncc([N+](=O)[O-])n1CC(O)CN[C@H]1CCCCN(c2c(F)cc3c(=O)c(C(=O)O)cn(C4CC4)c3c2Cl)C1]
101
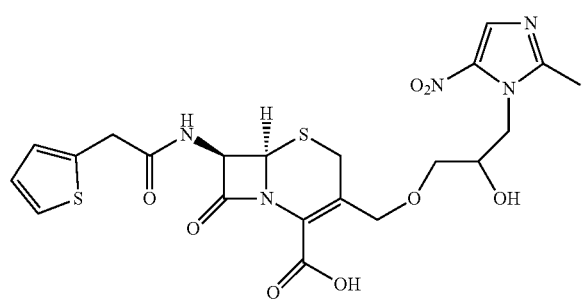 [SMILES: Cc1ncc([N+](=O)[O-])n1CC(O)COCC1=C(C(=O)O)N2C(=O)[C@@H](NC(=O)Cc3cccs3)[C@H]2SC1]
102
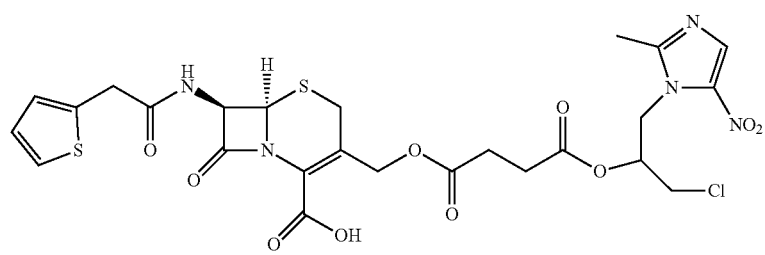 [SMILES: Cc1ncc([N+](=O)[O-])n1CC(CCl)OC(=O)CCC(=O)OCC1=C(C(=O)O)N2C(=O)[C@@H](NC(=O)Cc3cccs3)[C@H]2SC1]
103
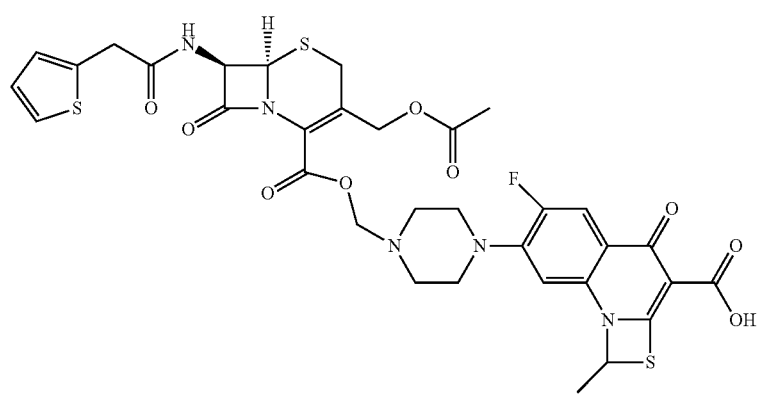 [SMILES: CC(=O)OCC1=C(C(=O)OCN2CCN(c3cc4c(cc3F)c(=O)c(C(=O)O)c3n4C(C)S3)CC2)N2C(=O)[C@@H](NC(=O)Cc3cccs3)[C@H]2SC1]
104
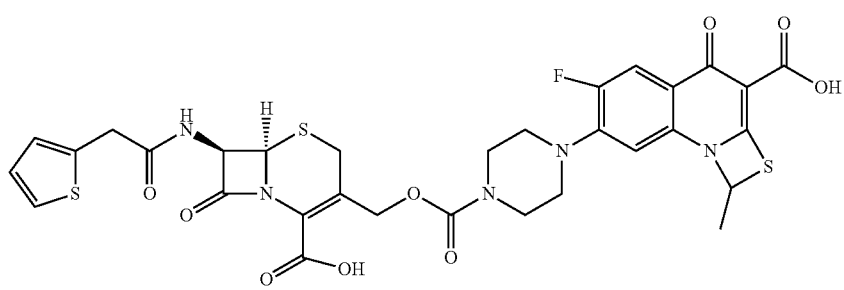 [SMILES: CC1Sc2c(C(=O)O)c(=O)c3cc(F)c(N4CCN(C(=O)OCC5=C(C(=O)O)N6C(=O)[C@@H](NC(=O)Cc7cccs7)[C@H]6SC5)CC4)cc3n21]
105

US 10,071,103 B2
TABLE 2A-continued
Exemplary DARTs Set-2
106
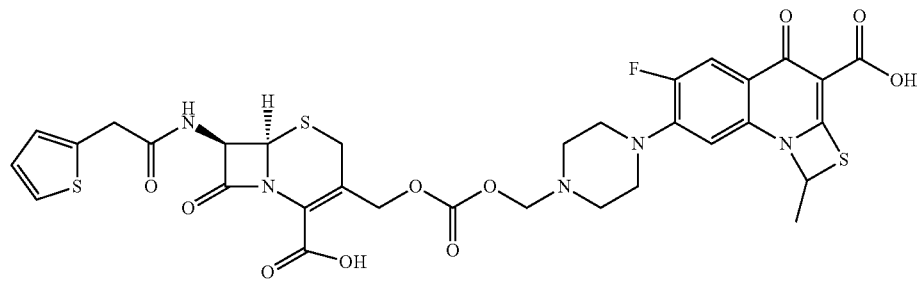 [SMILES: CC1Sc2c(C(=O)O)c(=O)c3cc(F)c(N4CCN(COC(=O)OCC5=C(C(=O)O)N6C(=O)[C@@H](NC(=O)Cc7cccs7)[C@H]6SC5)CC4)cc3n21]
107
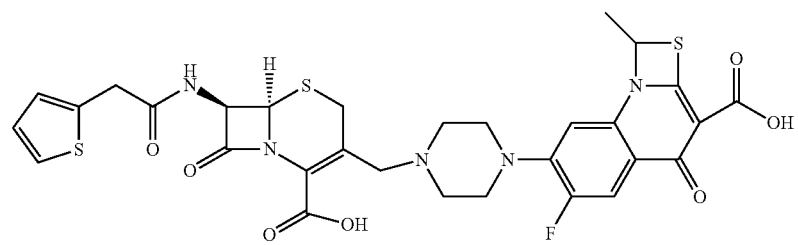 [SMILES: CC1Sc2c(C(=O)O)c(=O)c3cc(F)c(N4CCN(CC5=C(C(=O)O)N6C(=O)[C@@H](NC(=O)Cc7cccs7)[C@H]6SC5)CC4)cc3n21]
108
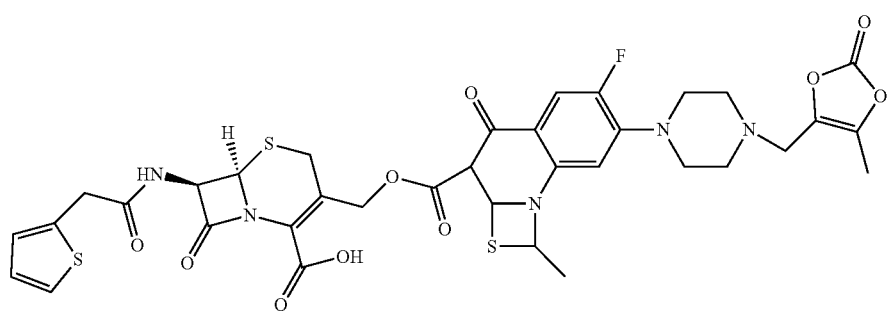 [SMILES: Cc1oc(=O)oc1CN1CCN(c2cc3c(cc2F)C(=O)C(C(=O)OCC2=C(C(=O)O)N4C(=O)[C@@H](NC(=O)Cc5cccs5)[C@H]4SC2)C2SC(C)N32)CC1]
109
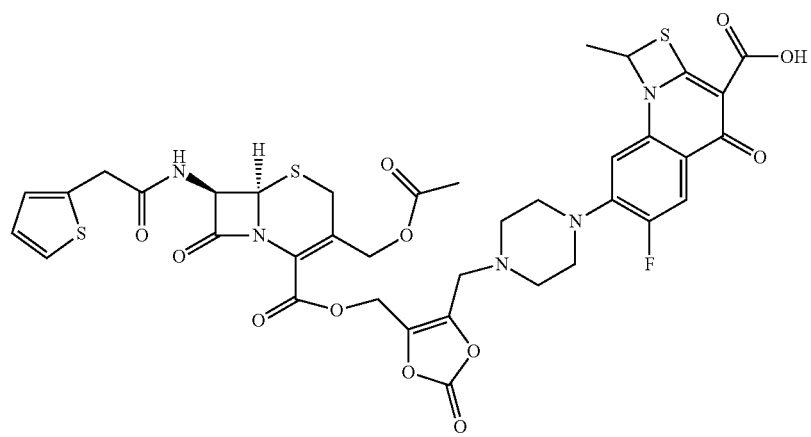 [SMILES: CC(=O)OCC1=C(C(=O)OCc2oc(=O)oc2CN2CCN(c3cc4c(cc3F)c(=O)c(C(=O)O)c3n4C(C)S3)CC2)N2C(=O)[C@@H](NC(=O)Cc3cccs3)[C@H]2SC1]

TABLE 2A-continued
Exemplary DARTs Set-2
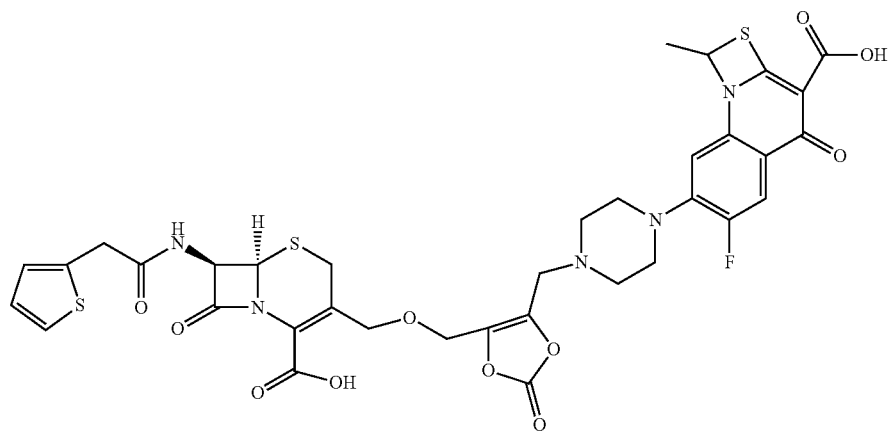 [SMILES: CC1Sc2c(C(=O)O)c(=O)c3cc(F)c(N4CCN(Cc5oc(=O)oc5COCC5=C(C(=O)O)N6C(=O)[C@@H](NC(=O)Cc7cccs7)[C@H]6SC5)CC4)cc3n21]
110
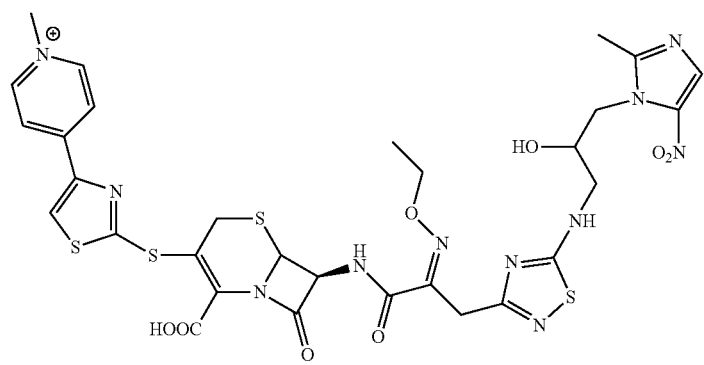 [SMILES: CCO/N=C(/Cc1nsc(NCC(O)Cn2c([N+](=O)[O-])cnc2C)n1)C(=O)N[C@H]1C(=O)N2C(C(=O)O)=C(Sc3nc(-c4cc[n+](C)cc4)cs3)CSC12]
111
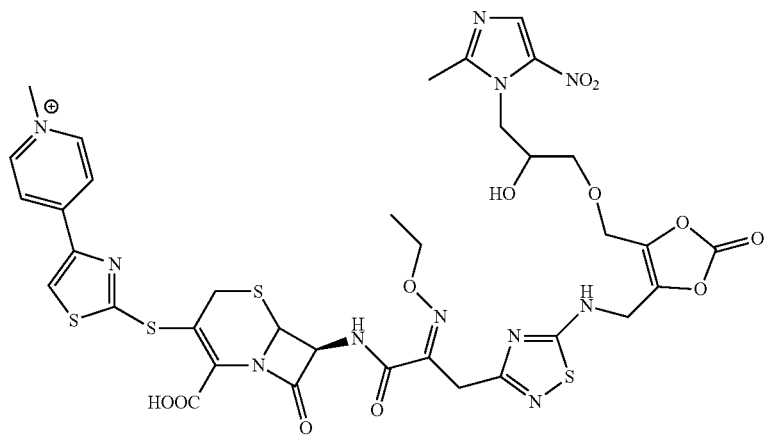 [SMILES: CCO/N=C(/Cc1nsc(NCc2oc(=O)oc2COCC(O)Cn2c([N+](=O)[O-])cnc2C)n1)C(=O)N[C@H]1C(=O)N2C(C(=O)O)=C(Sc3nc(-c4cc[n+](C)cc4)cs3)CSC12]
112
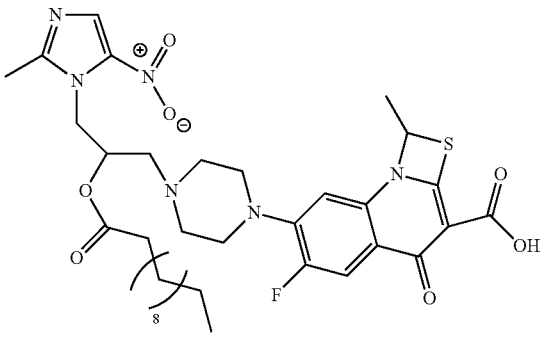
113

TABLE 2A-continued
Exemplary DARTs Set-2
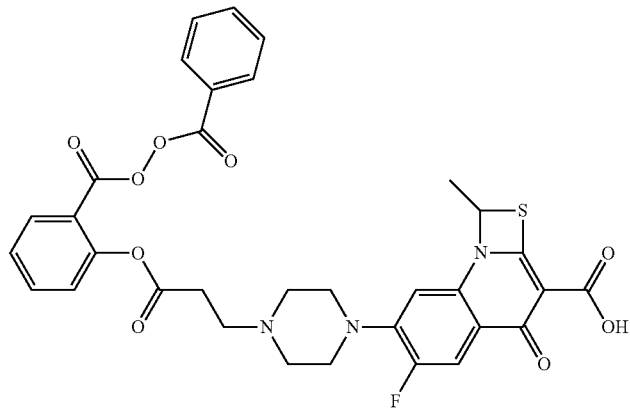 [SMILES: CC1Sc2c(C(=O)O)c(=O)c3cc(F)c(N4CCN(CCC(=O)Oc5ccccc5C(=O)OOC(=O)c5ccccc5)CC4)cc3n21]
114
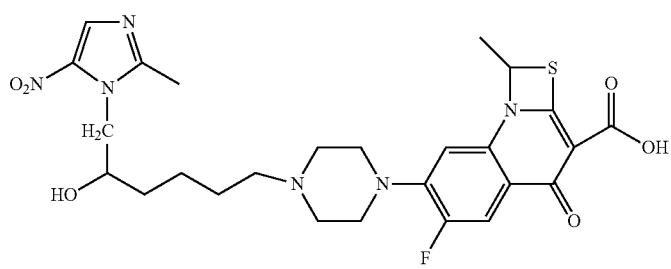 [SMILES: Cc1ncc([N+](=O)[O-])n1CC(O)CCCCN1CCN(c2cc3c(cc2F)c(=O)c(C(=O)O)c2n3C(C)S2)CC1]
115
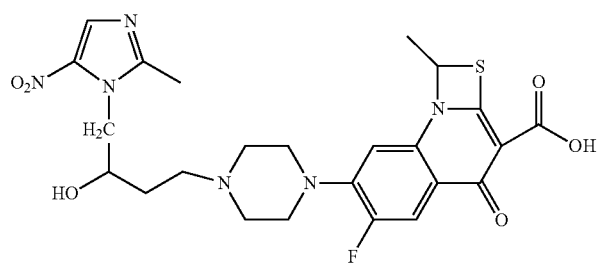 [SMILES: Cc1ncc([N+](=O)[O-])n1CC(O)CCN1CCN(c2cc3c(cc2F)c(=O)c(C(=O)O)c2n3C(C)S2)CC1]
116
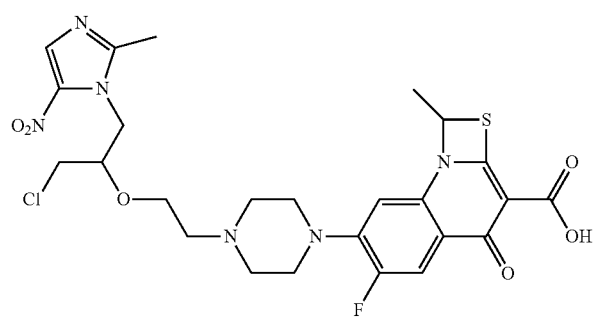 [SMILES: Cc1ncc([N+](=O)[O-])n1CC(CCl)OCCN1CCN(c2cc3c(cc2F)c(=O)c(C(=O)O)c2n3C(C)S2)CC1]
117
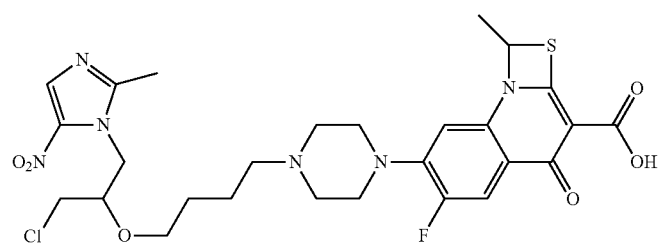 [SMILES: Cc1ncc([N+](=O)[O-])n1CC(CCl)OCCCCN1CCN(c2cc3c(cc2F)c(=O)c(C(=O)O)c2n3C(C)S2)CC1]
118

TABLE 2A-continued
Exemplary DARTs Set-2
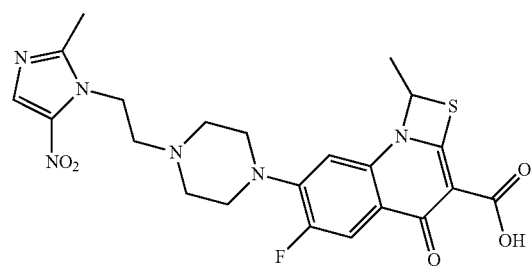 [SMILES: Cc1ncc([N+](=O)[O-])n1CCN1CCN(c2cc3c(cc2F)c(=O)c(C(=O)O)c2n3C(C)S2)CC1]
119
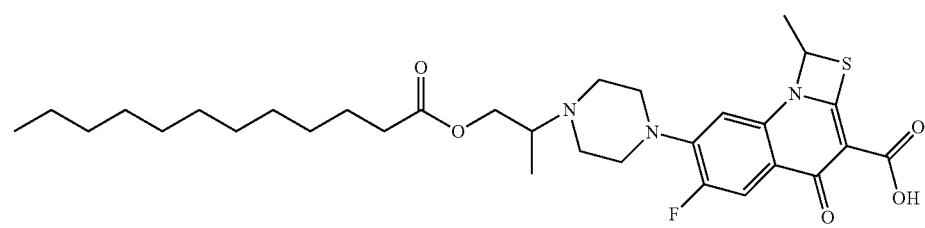 [SMILES: CCCCCCCCCCCC(=O)OCC(C)N1CCN(c2cc3c(cc2F)c(=O)c(C(=O)O)c2n3C(C)S2)CC1]
120
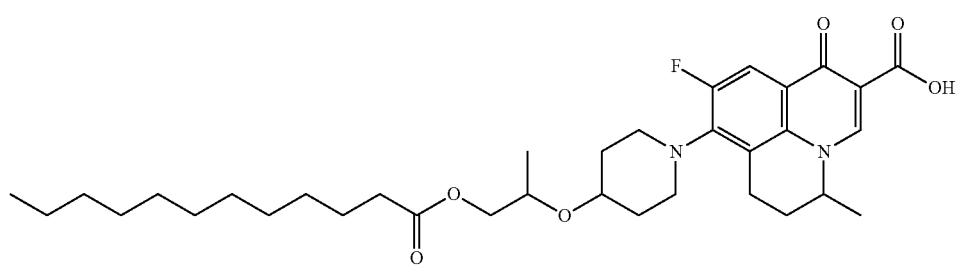 [SMILES: CCCCCCCCCCCC(=O)OCC(C)OC1CCN(c2c(F)cc3c(=O)c(C(=O)O)cn4c3c2CCC4C)CC1]
121
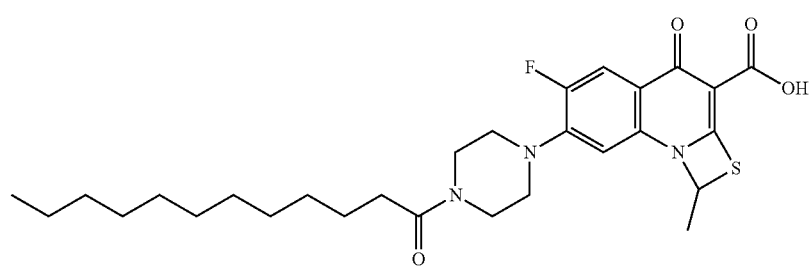 [SMILES: CCCCCCCCCCCC(=O)N1CCN(c2cc3c(cc2F)c(=O)c(C(=O)O)c2n3C(C)S2)CC1]
122
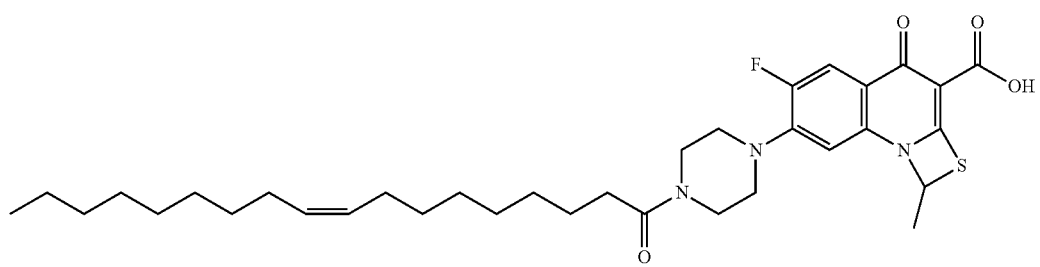 [SMILES: CCCCCCCC/C=C\CCCCCCCC(=O)N1CCN(c2cc3c(cc2F)c(=O)c(C(=O)O)c2n3C(C)S2)CC1]
123
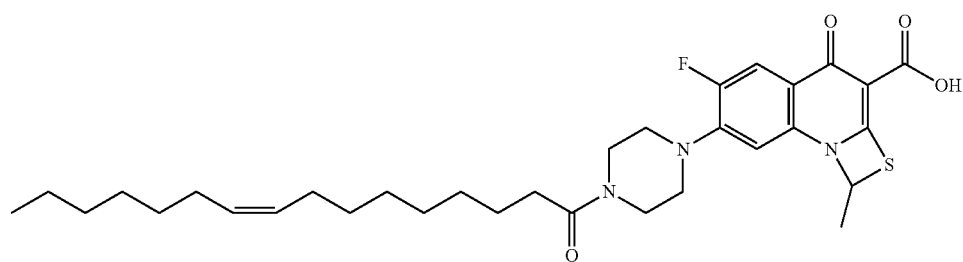 [SMILES: CCCCCC/C=C\CCCCCCCC(=O)N1CCN(c2cc3c(cc2F)c(=O)c(C(=O)O)c2n3C(C)S2)CC1]
124

TABLE 2A-continued
Exemplary DARTs Set-2
| | |
|---|---|
| 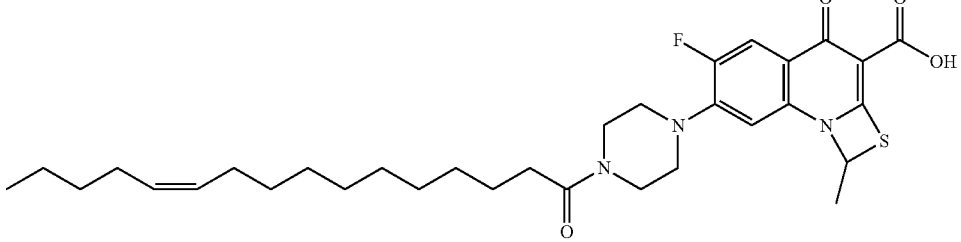 | 125 |
| 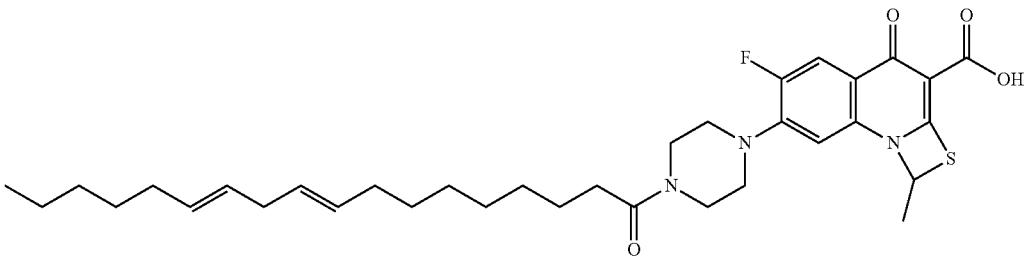 [SMILES: CCCCC/C=C/C/C=C/CCCCCCCC(=O)N1CCN(c2cc3c(cc2F)c(=O)c(C(=O)O)c2n3C(C)S2)CC1] | 126 |
| 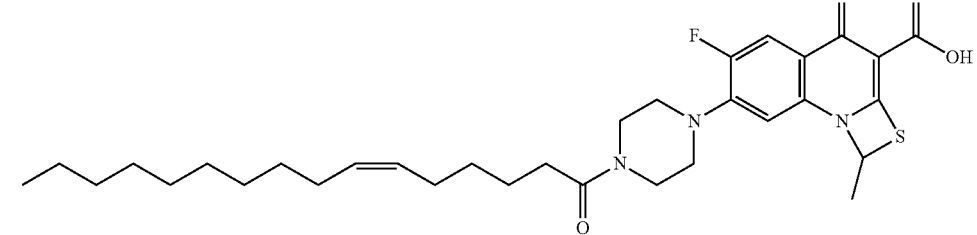 | 127 |
| 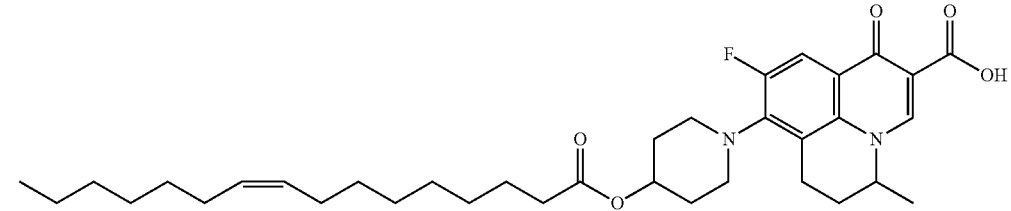 [SMILES: CCCCCC/C=C\CCCCCCCC(=O)OC1CCN(c2c(F)cc3c(=O)c(C(=O)O)cn4c3c2CCC4C)CC1] | 128 |
| 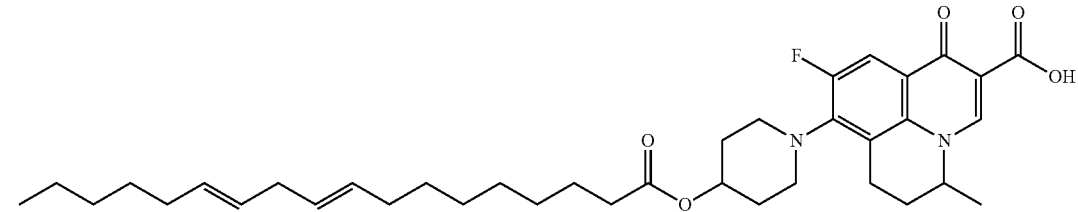 [SMILES: CCCCC/C=C/C/C=C/CCCCCCCC(=O)OC1CCN(c2c(F)cc3c(=O)c(C(=O)O)cn4c3c2CCC4C)CC1] | 129 |

TABLE 2A-continued

Exemplary DARTs Set-2

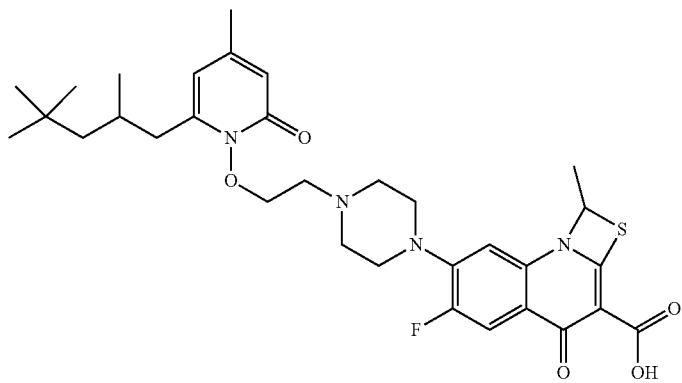 [SMILES: Cc1cc(CC(C)CC(C)(C)C)n(OCCN2CCN(c3cc4c(cc3F)c(=O)c(C(=O)O)c3n4C(C)S3)CC2)c(=O)c1]

130

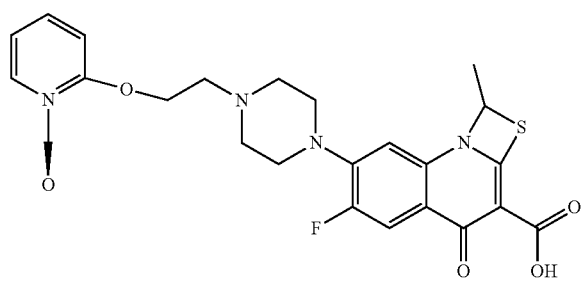

131

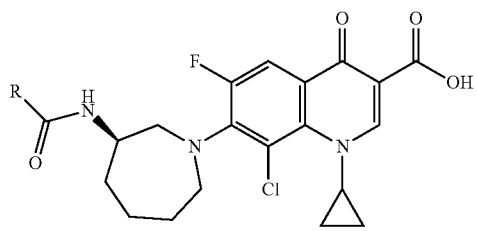

132

R = Lauric acid, oleic, palmitoleic acid, myrstoleic acid, linoleic acid, linolenic acid

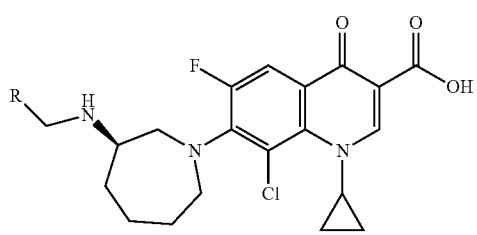

133

R = FA-ester of propylene glycole and glyceol and their derivatives

The present invention also provides formulations comprising DART as the API. Various features of the formulations are described in more detail vide infra.

Antibiotics (Non-DART)

The present invention also envisages compounds which are not DARTs. Accordingly, the invention also provides formulations comprising an antibiotic agent which is not a DART, i.e., a formulation comprising a non-DART antibiotic agent as the API. For example, the present invention describes the use of 8-chloro fluoroquinolones for the treatment of acne conditions, especially those caused by resistant forms of *P. acnes*. It is a sub class of fluoroquinolones where C8 position is substituted with chlorine. Thus, in some embodiments, the disclosure provides a formulation comprising 8-chloro fluoroquinolone as the API. Exemplary 8-chloro fluoroquinolones include, but are not limited to, besifloxacin, sitafloxacin, and clinafloxacin. In some embodiments, the formulation comprises besifloxacin.

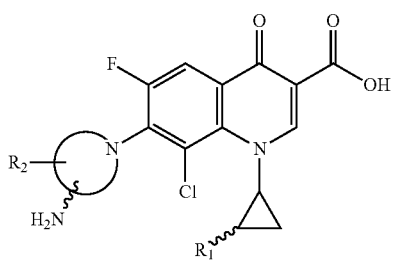

8-Chloro fluoroquinolones
R₁ = H, F
R₂ = H, Cyclopropyl

Examples -

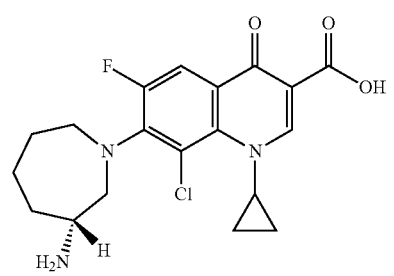

Besifloxacin

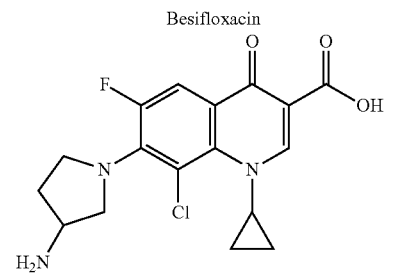

Clinafloxacin

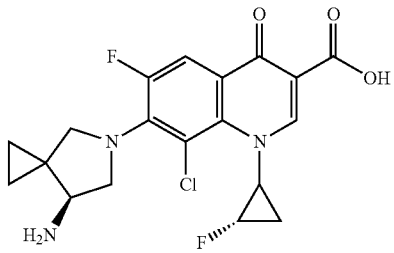

Sitafloxacin

Without wishing to be bound by a theory, micronization of an antibiotic agent, such as besifloxacin, can have an impact on its bioactivity. For example, micronization can enhance antibiotic agent's bioactivity or its retention at a desired site. Further, micronization can also affect the antibiotic agent's stability and amounts in a formulation. Moreover, micronization can also allow optimizing properties of formulations comprising micronized besifloxacin. Accordingly, without limitations, the API in the formulation, (e.g., the antibiotic agent) can be in the form of particles, powders, suspensions, dispersions, emulsions, liposomes, micelles, globules, solutions, vesicles, aggregates, and the like.

In some embodiments, the API, for example, but not limited to, besifloxacin or DART, can be micronized, i.e., formed as a particle.

Generally, the micronized API has a size in the range from about 0.2 μm to about 15 μm. In some embodiments, the micronized API has a size in the range from about 1 μm to about 10 μm. In some embodiments, the micronized API has a size in the range from about 1.5 μm to about 9 μm. In some embodiments, the micronized API has a size in the range from about 2 μm to about 8 μm.

In some embodiments, the API is in the form of a particle and comprises a surface modifier on the surface thereof. Generally a surface modifier is a molecule that can change the surface of the particle (such as by coating) in question and help in adhering the whole particle, hence, to the specific surface(s). Generally, the surface modification does not involve chemical bonding alterations or creation of any chemical bond. The surface modifier just physically associates with the particle.

The surface modifier can be selected from the group consisting of lipids, oils, polymers, peptides, proteins, carbohydrates, glycolipids, phospholipids, lipoproteins, cationic molecules, and any combinations thereof. The surface modifier can form a coating layer on the particle surface. Without limitations, the particle can be partially or fully coated with the surface modifier.

Some non-limiting exemplary formulations comprising a micronized antibiotic agent, e.g., besifloxacin, are described in Examples 18-20 and shown in Table 18.

In some embodiments, the formulation can be a spray formulation. Exemplary non-limiting spray formulations are described in Example 23 and Table 19. In some embodiments, the formulation can be in the form of a face wash. Exemplary non-limiting face wash formulations are described in Example 24, and Table 20. In some embodiments, the formulation can be in the form of a soap bar. Exemplary non-limiting soap bar formulations are described in Example 25 and Table 21. In some embodiments, the formulation can be in the form of a body wash. Exemplary non-limiting body wash formulations are described in Example 26, and Table 22. In some embodiments, the formulation can be in the form of a lotion. Exemplary non-limiting lotion formulations are described in Example 27, and Table 23.

Surfactants are known to solubilize hydrophobic substances by reducing the interfacial tension. Accordingly, in some embodiments, the antibiotic agent can be solubilized with a surfactant before forming the formulation. In-addition to surfactants, co-solvents or co-surfactants can also help in solubilization of the poorly water-soluble compounds by increasing the wetting property or reducing the interfacial tension of the hydrophobic molecule. Some exemplary surfactants and co-surfactants can include, but are not limited to, sodium lauryl sulfate, tween 80, tween 20, span 20, and any combinations thereof. Exemplary co-solvents for solubilizing the antibiotic agent, such as besifloxacin, can include propylene glycol monocaprylate and diethylene glycol monoethyl ether. Additional surfactants, co-surfactants and co-solvents that are amenable for solubilizing the antibiotic agent are described elsewhere in the disclosure. Without wishing to be bound by a theory, solubilizing the antibiotic agent, e.g., besifloxacin, can provide formulations that are within FDA prescription guidelines and limits of inactive excipients or ingredients. Non-limiting exemplary formulations comprising a solubilized API, e.g., antibiotic agent such as besifloxacin, are described in Examples 28, 31 and 33, and shown in Tables 24, 27 and 30-32.

Preparation of drug-loaded (suspended form) gel via conventional methods usually leads to exposure of the drug to a wide range of pH conditions, which can lead to, in some instances, solubilization of the drug, and then reprecipitation. This solubilization-reprecipitation phenomenon in most cases leads to change in original particle size, impurity profile or crystal pattern, or others. In order to circumvent this issue, the inventors have used an inventive approach to prepare different suspended drug-loaded formulations. Thus, in some embodiments, the formulation is in form of a suspended gel with negligible or minimal drug solubilization-reprecipitation. In the suspended drug formulations, the API particles are dispersed in a carrier media, such as, but not limited to, glycerol, and processed to the desired formulation. Exemplary suspended gel formulations are described in Example 24, 26, 28, 29, 30, 31 and 32 and shown in Tables 25, 27, 29, 33, 34, 37 and 38. Exemplary suspended drug loaded cream formulations are described in Examples 30 and 32 and Tables 26 and 28.

In addition to the various components, the formulation can also comprise one or more viscosity modifiers. In some embodiments, the viscosity modifier is a polymer. Exemplary polymeric viscosity modifiers include, but are not limited to, carbopol, hydroxypropyl cellulose, hydroxypropyl methyl cellulose, hydroxyethyl cellulose, and sodium hyaluronate. In some other embodiments, the viscosity modifier is a non-polymeric viscosity modifier or gelling agent. Additional exemplary viscosity modifiers are described elsewhere in the disclosure. Exemplary formulations comprising various viscosity modifiers are described in Example 33 and Tables 29-32.

According to published literature there may be some kind of physical and/or chemical interaction between carbopol and fluoroquinolones. For which, there may be a need to prepare formulations without carbopol or carbopol-like-polymers to avoid any incompatibility issues during the product shelf life. Accordingly, in some embodiments, the formulation is essentially free ofd viscosity modifiers. Exemplary formulations that are essentially free of a viscosity modifier are described in Example 32 and Table 28.

In some embodiments, the API can be coated with a molecule selected from the group consisting of lipids, oils, polymers, peptides, proteins, carbohydrates, glycolipids, phospholipids, lipoproteins, cationic molecules, and any combinations thereof. Without limitations, the API can be partially or fully coated with the coating molecule. Exemplary formulations comprising coated or non-coated API are described in Example 46 and Tables 52 and 53.

It is noted that various formulations features discussed in more detail vide infra are applicable to the formulation comprising antibiotic agent, e.g., besifloxacin, described herein.

Combination

In some embodiments, the formulation comprises two or more antibiotic agents. For example, the formulation can comprise two or more different anti-acne agents. In some embodiments, the formulation comprises an 8-chloro fluoroquinolones alone or in combination with another anti-acne agent. Exemplary 8-chloro fluoroquinolones include, but are not limited to, besifloxacin, sitafloxacin, and clinafloxacin. In some embodiments, the formulation comprises besifloxacin. In some embodiments, the formulation comprises besifloxacin and adapalene.

Without limitations, the two or more antibiotic agents can be in the same form or different forms. For example, the first and second anti-biotic agents can be independently micronized, suspended, or solubilized for the API. Accordingly, in some embodiments, both the first anti-biotic agent and the second anti-biotic agent are micronized. In some embodiments, the first anti-biotic agent is micronized and the second anti-biotic agent is solubilized. In some embodiments, the first anti-biotic agent is micronized and the second anti-biotic agent is suspended in the formulation. In some embodiments, the first anti-biotic agent is solubilized and the second anti-biotic agent is micronized. In some embodiments, both the first anti-biotic agent the second anti-biotic agent are solubilized. In some embodiments, the first anti-biotic agent is solubilized and the second anti-biotic agent is suspended. In some embodiments, the first anti-biotic agent is suspended and the second anti-biotic agent is micronized. In some embodiments, the first anti-biotic agent is suspended and the second anti-biotic agent is solubilized. In some embodiments, both the first anti-biotic agent and the second antibiotic agent are suspended.

In some embodiments, the formulation comprises besifloxacin and adapalene, wherein besifloxacin is solubilized and adapalene is suspended. In some other embodiments, the formulation comprises besifloxacin and adapalene, wherein both the besifloxacin and adapalene are solubilized. Exemplary formulation comprising both besifloxacin and adapalene are described in Examples 18, 23-27 and 31 and Tables 18-23 and 27.

It is noted that various formulations features discussed in more detail vide infra are applicable to the formulation comprising two or more antibiotic agents described herein.

Features Applicable to DART, Non-DART, and Combination APIs

Furthermore, as articulated in http://thescienceofacne.com/antibiotic-susceptibility-of-*propionibacterium-acnes*/). 'The second major limitation of treatment of acne is that antibiotics are not evenly dispersed throughout the different tissues in the body. Many antibiotics do not effectively accumulate in the follicle and/or sebaceous glands, and therefore do not effectively reach the bacteria responsible for acne. Even if a bacteria is highly susceptible to a particular antibiotic in lab-based testing, if that antibiotic does not make it to the site of infection at a sufficient concentration, it is not going to be an effective treatment. As a result there can be major differences in the effectiveness of oral antibiotics and topical antibiotics used in acne treatments.' This extends to all bacterial diseases of the skin. There is a need to develop unique optimal topical formulations and is described later.

Skin, e.g., micro-cracks, sweat or secretion pores, and hair follicles can act as reservoirs for drug carriers of particular sizes. Efficacy of active agents, e.g., antifungal and antibacterial formulations can be enhanced using infundibular delivery. A drug carrier can enhance the delivery of active agent on sebum filled hair follicles and also exhibit fusogenecity of such drug carriers to lipophilic microbial cell wall/cell membrane. This allows retention of the drug carrier on the skin, followed by slow and continuous release of the DART or antibacterial agent from the drug carrier. Exemplary drug carriers include, but are not limited to, microparticles, nanoparticles, vesicles, liposomes, emulsions, globules, and solutions.

In addition to the API (e.g., DART and/or other antibacterial agent), the drug carrier can further comprise one or more additional components. For example, the drug carrier can further comprise a compound selected from the group consisting of lipids, oils, polymers, peptides, proteins, carbohydrates, glycolipids, phospholipids, lipoproteins, cationic molecules, and any combinations thereof. The API, e.g., DART or other anti-bacterial agent, can be present in the core of the drug carrier and the additional component can form a coating layer over the core. Without limitation, the coating can be a functional or non-functional coating. By functional coating is meant a coating that imparts one or more desirable properties to the drug carrier, such as enhanced targeting or retention at site of action, increase in the activity of the API, or having a desired activity itself.

In some embodiments, DART and/or other anti-bacterial agent can be formed as a particle. In addition to the API (e.g., DART and/or other anti-bacterial agent), the particle can further comprise a compound selected from the group consisting of lipids, oils, polymers, peptides, proteins, carbohydrates, glycolipids, phospholipids, lipoproteins, cationic molecules, and any combinations thereof. The API, e.g., DART or other anti-bacterial agent, can be present in the core of the particle and the additional component can form a coating layer over the core.

In some embodiments, the particle comprises a surface modifier on the surface thereof. Generally a surface modifier is a molecule that can change the surface of the particle (such as by coating) in question and help in adhering the whole particle, hence, to the specific surface(s). Generally, the surface modification does not involve chemical bonding alterations or creation of any chemical bond. The surface modifier just physically associates with the particle.

The surface modifier can be selected from the group consisting of lipids, oils, polymers, peptides, proteins, carbohydrates, glycolipids, phospholipids, lipoproteins, cationic molecules, and any combinations thereof. The surface modifier can form a coating layer on the particle surface. Without limitations, the particle can be partially or fully coated with the surface modifier.

In some embodiments, the drug carriers and formulations disclosed herein can further comprise an active agent, i.e., an active agent in addition to the DART and/or anti-bacterial agent. As used herein, the term "active agent" means a compound or composition that has a particular desired activity. For example, an active agent can be a therapeutic compound. Without limitations the active agent can be selected from the group consisting of small organic or inorganic molecules, saccharines, oligosaccharides, polysaccharides, peptides; proteins, peptide analogs and derivatives, peptidomimetics, nucleic acids, nucleic acid analogs and derivatives, antibodies, antigen binding fragments of antibodies, lipids, extracts made from biological materials, naturally occurring or synthetic compositions, and any combinations thereof.

In some embodiments, the active agent can be selected from the group consisting of antifungal agents, antibacterial agents, antimicrobial agents, anti-acne agents, antioxidant agents, cooling agents, soothing agents, wound healing agents, anti-inflammatory-agents, penetration enhancers, permeation enhancers, anti-oxidants, anti-aging agents, anti-wrinkle agents, skin whitening or bleaching agents, ultraviolet (UV) light absorbing or scattering agents, skin depigmentation agents, regenerative agents, scar healing agents, dyes or coloring agents, deodorizing agents, fragrances, keratolytic agent, and any combinations thereof. In some embodiments, the active agent can be a keratolytic agent.

In some embodiments, the active agent is an anti-inflammatory agent. As used herein the term "anti-inflammatory agent" refers to a compound (including its analogs, derivatives, prodrugs and pharmaceutically salts) which can be used to treat inflammation or inflammation related disease or disorder. Exemplary anti-inflammatory agents include, but are not limited to, the known steroidal anti-inflammatory and non-steroidal anti-inflammatory drugs (NSAIDs). Exemplary steroidal anti-inflammatory agents include but are not limited to 21-acetoxypregnenolone, alclometasone, algestone, amcinonide, beclomethasone, betamethasone, budesonide, chloroprednisone, clobetasol, clobetansone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furcate, paramethosone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, derivatives thereof and mixtures thereof. Exemplary nonsteroidal anti-inflammatory agents include but are not limited to COX inhibitors (COX-1 or COX nonspecific inhibitors) and selective COX-2 inhibitors. Exemplary COX inhibitors include but are not limited to salicylic acid derivatives such as aspirin, sodium salicylate, choline magnesium trisalicylate, salicylate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam); alkanones such as nabumetone; derivatives thereof and mixtures thereof. Exemplary COX-2 inhibitors include but are not limited to diarylsubstituted furanones such as refecoxib; diaryl-substituted pyrazoles such as celecoxib; indole acetic acids such as etodolac and sulfonanilides such as nimesulide; derivatives thereof and mixtures thereof.

In some embodiments, the active agent is an anti-aging agent. As used herein, the term "anti-aging agent" means a compound or composition that inhibits or reduces signs of aging, such as wrinkles, fine lines, and other manifestations of photodamage. Examples of anti-aging agents include, but are not limited to, flavonoids such as quercetin, hesperidin, quercitrin, rutin, tangeritin, and epicatechin; CoQ10; inorganic sunscreens such as tianium dioxide and zinc oxide; organic sunscreens such as octyl-methyl cinnamates and derivatives thereof; retinoids; vitamins such as vitamin E, vitamin A, vitamin C (ascorbic acid), vitamin B, and derivatives thereof such as vitamin E acetate, vitamin C palmitate, and the like; antioxidants including alpha hydroxy acid such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrrolactic acid, alpha-hydroxyisovaleric acid, ethyl pyruvate, galacturonic acid, glucopehtonic acid, glucopheptono 1,4-lactone, gluconic acid, gluconolactone, glucuronic acid, glucurronolactone, glycolic acid, isopropyl pyruvate, methyl pyruvate, mucic acid, pyruvia acid, saccharic acid, saccaric acid 1,4-lactone, tartaric acid, and tartronic acid; beta hydroxy acids such as beta-hydroxybutyric acid, beta-phenyl-lactic acid, beta-phenylpyruvic acid; botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, rice, safflower, and mixtures thereof.

In some embodiments, the active agent is an ultraviolet (UV) light absorbing or scattering agent. Ultraviolet light absorbing agents include, for example, ultraviolet absorber of benzoic acid system such as para-aminobenzoic acid (hereinafter, abbreviated as PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA methyl ester and the like; ultraviolet absorber of anthranilic acid system such as homomenthyl-N-acetyl anthranilate and the like; ultraviolet absorber of salicylic acid system such as amyl salicylate, menthyl salicylate, homomenthyl salicylate, octyl salicylate, phenyl salicylate, benzyl salicylate, p-isopropanol phenyl salicylate and the like; ultraviolet absorber of cinnamic acid system such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate(2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, glyceryl mono-2-ethylhexanoyl-dipara-methoxy cinnamate, methyl-bis(trimethylsiloxane)silylisopentyl trimethoxy cinnamate and the like; 3-(4'-methylbenzylidene)-d,l-camphor; 3-benzylidene-d,l-camphor; urocanic acid, urocanic acid ethyl ester; 2-phenyl-5-methylbenzoxazole; 2,2'-hydroxy-5-methylphenylbenzotriazole; 2-(2'-hydroxy-5'-t-octylphenyl)benzotriazole; 2-(2'-hydroxy-5'-methylphenylbenzotriazole; dibenzaladine; dianisoylmethane, 4-methoxy-4'-t-butyldibenzoylmethane; 5-(3,3-dimethyl-2-norbornylidene)-3-pentane-2-one; dimorpholinopyridazinone; and combinations thereof. Ultraviolet light scattering agents include, for example, powders such as titanium oxide, particulate titanium oxide, zinc oxide, particulate zinc oxide, ferric oxide, particulate ferric oxide, ceric oxide and the like.

In some embodiments, the active agent is an anti-wrinkle agent, e.g., a dermatological anti-wrinkle agent. Anti-wrinkle agents include, without limitations, flavonoids such as quercetin, hesperidin, quercitrin, rutin, tangeritin, and epicatechin; CoQ10; vitamin C; hydroxy acids including $C_2$-$C_{30}$ alpha-hydroxy acids such as glycolic acid, lactic acid, 2-hydroxy butanoic acid, malic acid, citric acid tartaric acid, alpha-hydroxyethanoic acid, hydroxycaprylic acid and the like; beta hydroxy acids including salicylic acid and polyhydroxy acids including gluconolactone (G4); and mixtures of these acids. Further anti-wrinkleagentsinclude retinoic acid and gamma-linolenic acid.

In some embodiments, the active agent is a skin whitening or bleaching agent. Skin whitening and bleaching agents include hydrogen peroxide, zinc peroxide, sodium peroxide, hydroquinone, 4-isopropylcatechol, hydroquinone monobenzyl ether, kojic acid; lactic acid; ascorbyl acid and derivatives such as magnesium ascorbyl phosphate; arbutin; and licorice root. Sunless tanning actives include dihydroxyacetone (DHA); glyceryl aldehyde; tyrosine and tyrosine derivatives such as malyltyrosine, tyrosine glucosinate, and ethyl tyrosine; phospho-DOPA, indoles and derivatives; and mixtures thereof. Other skin whitening agents include sugar amines, such as glucosamine, N-acetyl glucosamine, glucosamine sulfate, mannosamine, N-acetyl mannosamine, galactosamine, N-acetyl galactosamine, their isomers (e.g., stereoisomers), and their salts (e.g., HCl salt); and N-acyl amino acid compounds, such as N-acyl phenylalanine, N-acyl tyrosine, their isomers, including their D and L isomers, salts, derivatives, and mixtures thereof. An example of a suitable N-acyl amino acid is N-undecylenoyl-L-phenylalanine.

In some embodiments, the active agent is a skin depigmentation agent. Examples of suitable depigmentation agents include, but are not limited to, soy extract; soy isoflavones; retinoids such as retinol; kojic acid; kojic dipalmitate; hydroquinone; arbutin; transexamic acid; vitamins such as niacin and vitamin C; azelaic acid; linolenic acid and linoleic acid; placertia; licorice; and extracts such as chamomile and green tea; and salts and prodrugs thereof.

In some embodiments, the active agent is an antioxidant agent. As used herein, the term "antioxidant agent" refers to any molecule capable of slowing, reducing, inhibiting, or preventing the oxidation of other molecules. Examples of antioxidants include, but are not limited to, hydrophilic antioxidants, lipophilic antioxidants, and mixtures thereof. Non-limiting examples of hydrophilic antioxidants include chelating agents (e.g., metal chelators) such as ethylenediaminetetraacetic acid (EDTA), citrate, ethylene glycol tetraacetic acid (EGTA), 1,2-bis(o-aminophenoxy)ethane-N,N,N',N'-tetraacetic acid (BAPTA), diethylene triamine pentaacetic acid (DTPA), 2,3-dimercapto-1-propanesulfonic acid (DMPS), dimercaptosuccinic acid (DMSA), α-lipoic acid, salicylaldehyde isonicotinoyl hydrazone (SIH), hexyl thioethylamine hydrochloride (HTA), desferrioxamine, salts thereof, and mixtures thereof. Additional hydrophilic antioxidants include ascorbic acid (vitamin C), cysteine, glutathione, dihydrolipoic acid, 2-mercaptoethane sulfonic acid, 2-mercaptobenzimidazole sulfonic acid, 6-hydroxy-2,5,7,8-tetramethylchroman-2-carboxylic acid, sodium metabisulfite, salts thereof, and mixtures thereof. Non-limiting examples of lipophilic antioxidants include vitamin E isomers such as α-, β-, γ-, and δ-tocopherols and α-, β-, γ-, and δ-tocotrienols; polyphenols such as 2-tert-butyl-4-methyl phenol, 2-tert-butyl-5-methyl phenol, and 2-tert-butyl-6-methyl phenol; butylated hydroxyanisole (BHA) (e.g., 2-tert-butyl-4-hydroxyanisole and 3-tert-butyl-4-hydroxyanisole); butylhydroxytoluene (BHT); tert-butylhydroquinone (TBHQ); ascorbyl palmitate; n-propyl gallate; salts thereof; and mixtures thereof. One of skill in the art will appreciate that antioxidants can be classified as primary antioxidants, secondary antioxidants, or metal chelators based upon the mechanisms in which they act. Primary antioxidants quench free radicals which are often the source of oxidative pathways, whereas secondary antioxidants function by decomposing the peroxides that are reactive intermediates of the pathways. Metal chelators function by sequestering the trace metals that promote free radical development. In some embodiments, the antioxidant agent is resveratrol.

In some embodiments, the active agent is a wound healing agent. As used herein, the term "wound healing agent" means active agents that are effective for promoting natural wound healing processes over days, weeks, or months. Exemplary wound healing agents include, but are not limited to, proteinaceous growth factors, vascular endothelial growth factors, anti-proliferant agent, antimicrobials, and anti-inflammatory agents.

In some embodiments, the active agent is a soothing agent. As used herein, the term "soothing agent" means a molecule which helps in reducing the discomfort of the skin and/or scalp, for example by soothing the feelings of itching. Exemplary soothing agents include, but are not limited to, aloe, avocado oil, green tea extract, hops extract, chamomile extract, colloidal oatmeal, calamine, cucumber extract, sodium palmate, sodium palm kernelate, butyrospermum parkii (i.e., shea butter), menthe piperita (i.e., peppermint) leaf oil, sericin, pyridoxine (a form of vitamin B6), retinyl palmitate and/or other forms of vitamin A, tocopheryl acetate and/or other forms of vitamin E, lauryl laurate, hyaluronic acid, aloe barbadensis leaf juice powder, *euterpe oleracea* (i.e., acai berry) fruit extract, riboflavin (i.e., vitamin B2), thiamin HCl and/or other forms of vitamin B1, and/any combinations thereof.

In some embodiments, the active agent is a cooling agent. As used herein, the term "cooling agent" refers to molecules which provide a sensation of cooling on application. Some exemplary cooling agents include, but are not limited to, WS-3; WS-23; menthol; 3-substituted-P-menthanes; N-substituted-P-menthane-3-carboxamides; isopulegol; 3-(1-menthoxy)propane-1,2-diol; 3-(1-menthoxy)-2-methylpropane-1,2-diol; p-menthane-2,3-diol; p-menthane-3,8-diol; 6-isopropyl-9-methyl-1,4-dioxaspiro[4,5]decane-2-methanol; menthyl succinate and its alkaline earth metal salts; trimethylcyclohexanol; N-ethyl-2-isopropyl-5-methylcyclohexanecarboxamide; Japanese mint oil; peppermint oil; menthone; menthone glycerol ketal; menthyllactate; 3-(1-menthoxy)ethan-1-ol; 3-(1-menthoxy)propan-1-ol; 3-(1-menthoxy)butan-1-ol; 1-menthylacetic acid N-ethylamide; 1-menthyl-4-hydroxypentanoate; 1-menthyl-3-hydroxybutyrate; N,2,3-trimethyl-2-(1-methylethyl)-butanamide; n-ethyl-t-2-c-6 nonadienamide; N,N-dimethyl menthyl succinamide; menthyl pyrrolidone carboxylate; and the like.

In some embodiments, the active agent is a coloring agent. As used herein, the term "coloring agent" means any substance that can be employed to produce a desired color. Gen. Such coloring agents are approved for human consumption pursuant an appropriate governmental agency and/or act, such as the Food and Drug Administration (FDA)/Federal Food Drug and Cosmetic Act (FD&C) in the US or an analogous agency of the European Union. For example, the coloring agent can be a food-grade dye or a lake. A "dye" is a water soluble compound, which is available as a powder, granule, liquid or other special purpose form. A "lake" is a water insoluble form of a dye. Exemplary coloring agents include, but are not limited to, FD&C Blue No. 1 (Brilliant Blue), FD&C Blue No. 2 (Indigotine), FD&C Green No. 3 (Fast Green), FD&C Red No. 3 (Erythrosine), FD&C Red No. 40 (Allura Red), FD&C Yellow No. 5 (Tartrazine), FD&C Yellow No. 6 (Sunset Yellow), annatto extract, anthocyanis, aronia/redfruit, beet juice, beet powder, beta-carotene, beta-apo-8-carotenal, black currant, burnt sugar, canthaxanthin, caramel, carbo medicinalis, carmine, carmine/beta-carotene, carmine blue, carminic acid, carrot, carrot oils, chlorophyll, chlorophyllin, cochineal extract, copper-chlorophyll, copper-chlorophyllin, curcumin, curcumin/Cu-chlorophyllin, elderberry, grape, grape skin extracts, hibiscus, lutein, mixed carotenoids, paprika, paprika extract, paprika oleoresin, riboflavin, saffron, spinach, stinging nettle, titanium dioxide, turmeric, and combinations thereof. Preferred coloring agents according to the present invention are FD&C Blue No. 1 (Brilliant Blue), FD&C Blue No. 2 (Indigotine), FD&C Green No. 3 (Fast Green), FD&C Red No. 3 (Erythrosine), FD&C Red No. 40 (Allura Red), FD&C Yellow No. 5 (Tartrazine), FD&C Yellow No. 6 (Sunset Yellow), and any combinations thereof.

In some embodiments; the active agent is a fragrance. Exemplary fragrances include; but are not limited to, 2,4-dimethyl-3-cyclohexene-1-carbaldehyde; isocyclocitral; menthone; isomenthone; ROMASCONE® (methyl 2,2-dimethyl-6-methylene-1-cyclohexanecarboxylate); nerone; terpineol; dihydroterpineol; terpenyl acetate; dihydroterpenyl acetate; dipentene; eucalyptol; hexylate; rose oxide; PERYCOROLLE® ((S)-1,8-p-menthadiene-7-ol); 1-p-menthene-4-ol; (1RS,3RS,4SR)-3-p-mentanyl acetate; (1R,2S,4R)-4,6,6-trimethyl-bicyclo[3,1,1]heptan-2-ol; DOREMOX® (tetrahydro-4-methyl-2-phenyl-2H-pyran); cyclohexyl acetate; cyclanol acetate; Fructalate (1,4-cyclohexane diethyldicarboxylate); KOUMALACTONE® ((3ARS,6SR,7ASR)-perhydro-3,6-dimethyl-benzo[B]furan-2-one); Natactone ((6R)-perhydro-3,6-dimethyl-benzo[B]furan-2-one); 2,4,6-trimethyl-4-phenyl-1,3-dioxane; 2,4,6-trimethyl-3-cyclohexene-1-carbaldehyde; (E)-3-methyl-5-(2,2,3-trimethyl-3-cyclopenten-1-yl)-4-penten-2-ol; (1'R,E)-2-ethyl-4-(2',2',3'-trimethyl-3'-cyclopenten-1'-yl)-2-buten-1-ol; POLYSANTOL® ((1'R,E)-3,3-dimethyl-5-(2',2',3'-trimethyl-3'-cyclopenten-1'-yl)-4-penten-2-ol); fleuramone; PARADISONE® (methyl-(1R)-cis-3-oxo-2-pentyl-1-cyclopentane acetate); Veloutone (2,2,5-Trimethyl-5-pentyl-1-cyclopentanone); NIRVANOL® (3,3-dimethyl-5-(2,2,3-trimethyl-3-cyclopenten-1-yl)-4-penten-2-ol); 3-methyl-5-(2,2,3-trimethyl-3-cyclopenten-1-yl)-2-pentanok damascones; NEOBUTENONE® (1-(5,5-dimethyl-1-cyclohexen-1-yl)-4-penten-1-one); nectalactone ((1'R)-2-[2-(4'-methyl-3'-cyclohexen-1'-yl)propyl]cyclopentanone); alpha-ionone; beta-ionone; damascenone; DYNASCONE® (mixture of 1-(5,5-dimethyl-1-cyclohexen-1-yl)-4-penten-1-one and 1-(3,3-dimethyl-1-cyclohexen-1-yl)-4-penten-1-one); DORINONE® beta (1-(2,6,6-trimethyl-1-cyclohexen-1-yl)-2-buten-1-one); ROMANDOLIDE® ((1S,1'R)-[1-(3',3'-Dimethyl-1'-cyclohexyl)ethoxycarbonyl]methyl propanoate); 2-tert-butyl-1-cyclohexyl acetate; LIMBANOL® (1-(2,2,3,6-tetramethyl-cyclohexyl)-3-hexanol); trans-1-(2,2,6-trimethyl-1-cyclohexyl)-3-hexanol; (E)-3-methyl-4-(2,6,6-trimethyl-2-cyclohexen-1-yl)-3-buten-2-one; terpenyl isobutyrate; LORYSIA® (4-(1,1-dimethylethyl)-1-cyclohexyl acetate); 8-methoxy-1-p-menthene; HELVETOLIDE® ((1S,1'R)-2-[1-(3',3'-dimethyl-1'-cyclohexyl) ethoxy]-2-methylpropyl propanoate); para tert-butyl-cyclohexanone; menthenethiol; 1-methyl-4-(4-methyl-3-pentenyl)-3-cyclohexene-1-carbaldehyde; allyl cyclohexylpropionate; cyclohexyl salicylate; Methyl cedryl ketone; Verdylate; vetyverol; vetyverone; 1-(octahydro-2,3,8,8-tetramethyl-2-naphtalenyl)-1-ethanone; (5RS,9RS,10SR)-2,6,9,10-tetramethyl-1-oxaspiro[4.5]deca-3,6-diene and the (5RS,9SR,10RS) isomer; 6-ethyl-2,10,10-trimethyl-1-oxaspiro[4.5]deca-3,6-diene; 1,2,3,5,6,7-hexahydro-1,1,2,3,3-pentamethyl-4-indenone; HIVERNAL® (a mixture of 3-(3,3-dimethyl-5-indanyl)propanal and 3-(1,1-dimethyl-5-indanyl)propanal); Rhubofix® (3',4-dimethyl-tricyclo[6.2.1.0(2,7)]undec-4-ene-9-spiro-2'-oxirane); 9/10-ethyldiene-3-oxatricyclo[6.2.1.0(2,7)]undecane; POLYWOOD® (perhydro-5,5,8A-trimethyl-2-naphthalenyl acetate); octalynol; CETALOX® (dodecahydro-3a,6,6,9a-tetramethyl-naphtho [2,1-b]furan); tricyclo[5.2.1.0(2,6)]dec-3-en-8-yl acetate and tricyclo[5.2.1.0(2,6)]dec-4-en-8-yl acetate as well as tricyclo[5.2.1.0(2,6)]dec-3-en-8-yl propanoate and tricyclo[5.2.1.0(2,6)]dec-4-en-8-yl propanoate; camphor; borneol; isobornyl acetate; 8-isopropyl-6-methyl-bicyclo[2.2.2]oct-5-ene-2-carbaldehyde; camphopinene; cedramber (8-methoxy-2,6,6,8-tetramethyl-tricyclo[5.3.1.0(1,5)]undecane); cedrene; cedrenol; cedrol; FLOREX® (mixture of 9-ethylidene-3-oxatricyclo[6.2.1.0(2,7)]undecan-4-one and 10-ethylidene-3-oxatricyclo[6.2.1.0(2,7)]undecan-4-one); 3-methoxy-7,7-dimethyl-10-methylene-bicyclo[4.3.1]decane; CEDROXYDE® (trimethyl-13-oxabicyclo-[10.1.0]-trideca-4,8-diene); Ambrettolide LG ((E)-9-hexadecen-16-olide); HABANOLIDE® (pentadecenolide); muscenone (3-methyl-(4/5)-cyclopentadecenone); muscone; EXAL- TOLIDE® (pentadecanolide); EXALTONE® (cyclopentadecanone); (1-ethoxyethoxy)cyclododecane; Astrotone; LILIAL®; rosinol; and the like.

In some embodiments, the active agent is an antifungal agent. Examplary antifungal agents are described elsewhere in the disclosure. As used herein, the terms "fungus" or "fungi" include a variety of nucleated, spore-bearing organisms which are devoid of chlorophyll. Examples include yeasts, mildews, molds, rusts, and mushrooms. Examples of fungi include, but are not limited to *Aspergillus* fumigates, *Aspergillus flavus, Aspergillus nidulans, Candida albicans, Candida glabrata, Candida guilliermondii, Candida krusei, Candida lusitaniae, Candida parapsilosis, Candida tropicalis, Cryptococcus neoformans, Issatchenkia orientalis, Coccidioides, Paracoccidioides, Histoplasma, Blastomyces, Trichophyton rubrum*, and *Neurospora crassa*. In some embodiments, fungus is of the genus *Malassezia* (e.g., *M. furfur, M. pachydermatis, M. globosa, M. restricta, M. slooffiae, M. sympodialis, M. nana, M. yamatoensis, M. dermatis*, and *M. obtuse*). In one embodiment, the fungus is *Trichophyton rubrum*.

In some embodiments, the active agent is an antibacterial agent. Exemplary anti-bacterial agents are described elsewhere in the disclosure.

In some embodiments, the active agent is an anti-scarring agent. As used herein, an "anti-scarring agent" refers to any agent which inhibit fibrosis or scarring. Useful anti-scarring agents can inhibit one or more aspect of the fibrosis process. For example, in certain embodiments, the anti-scarring agent inhibits inflammation; collagen production in, or release from, cells; and/or is an anti-infective or antifungal agent. In some embodiments, the anti-scarring agent is selected from the group consisting of (−)-arctigenin, 6. The device of claim 1 or claim 2 wherein the anti-scarring agent is selected from an angiogenesis inhibitor, a 5-HT inhibitor, a beta 1 integrin antagonist, a beta tubulin inhibitor, a bisphosphonate compound selected from risedronate and an analogue or derivative thereof, a blocker of enzyme production in Hepatitis C, a bone mineralization promoter, a Bruton's tyrosine kinase inhibitor, a calcineurin inhibitor, a calcium channel blocker, a CaM kinase II inhibitor, a caspase 3 inhibitor, a cathepsin B inhibitor, a cathepsin K inhibitor, a cathepsin L inhibitor, a CB1/CB2 receptor agonist, a CC chemokine receptor antagonist, a CD40 antagonist, a cell cycle inhibitor, a cell cycle inhibitor, a chemokine receptor antagonist, a chymase inhibitor, a clotting factor, a collagenase antagonist, a cual integrin inhibitor, a CXCR antagonist, a cyclic GMP agonist, a cyclin dependent kinase inhibitor, a cyclooxygenase 1 inhibitor, a D2 dopamine receptor antagonist, a DHFR inhibitor, a diuretic, a DNA alkylating agent, a DNA methylation inhibitor, a DNA methylation promoter, a DNA methylation promoter, a DNA synthesis inhibitor, a DNA topoisomerase inhibitor, a dopamine antagonist, a farnesyltransferase inhibitor, a farnexyl transferase inhibitor, a fibrinogen antagonist, a G protein agonist, a glycosylation inhibitor, a heat shock protein 90 antagonist, a histamine receptor antagonist, a histone deacetylase inhibitor, a histone deacetylase inhibitor, a JAK2 inhibitor, a JAK3 enzyme inhibitor, a JNK inhibitor, a kinase inhibitor, a kinesin antagonist, a leukotriene inhibitor and antagonist, a lysyl hydrolase inhibitor, a MAP kinase inhibitor, a matrix metalloproteinase inhibitor, a microtubule inhibitor, a microtubule inhibitor, a muscarinic receptor inhibitor, a neurokinin antagonist, a nitric oxide agonist, a nitric oxide synthase inhibitor, a NO synthase inhibitor, a norepinephrine reuptake inhibitor, a NSAID agent, a p38 MAP kinase inhibitor, a palmitoyl-protein thioesterase inhibitor, a PDGF receptor kinase inhibitor, a peptidylglycine alpha-hydroxylating monooxygenase inhibitor, a peptidyl-prolyl cis/trans isomerase inhibitor, a Peptidyl-Prolyl Cis/Trans isomerase Inhibitor, a peroxisome proliferator-activated receptor (PPAR) agonist, a pesticide, a phosphatase inhibitor, a phosphodiesterase inhibitor, a PKC inhibitor, a PKC inhibitor, a platelet activating factor antagonist, a platelet aggregation inhibitor, a polymorphonuclear neutrophil inhibitor, a prolyl hydroxylase inhibitor, a prostaglandin inhibitor, a protein synthesis inhibitor, a protein tyrosine kinase inhibitor, a purineoreceptor P2X antagonist, a pyruvate dehydrogenase activator, a Raf kinase inhibitor, a RAR/RXT antagonist, a reducing agent, a retinoic acid receptor antagonist, a retinoic acid receptor antagonist, a selective serotonin reuptake inhibitor, a serine protease inhibitor, a serotonin receptor inhibitor, a sheddase inhibitor, a sodium channel inhibitor, a steroid, a steroid, a stromelysin inhibitor, a superoxide anion generator, a TACE inhibitor, a telomerase inhibitor, a TGF beta inhibitor, a thromboxane A2 receptor inhibitor, a TNF-alpha antagonist, a Toll receptor inhibitor, a tryptase inhibitor, a tubulin antagonist, a tumor necrosis factor antagonist, a tyrosine kinase inhibitor, a VEGF inhibitor, a vitamin D receptor agonist, ampicillin sodium salt, an acetylcholinesterase inhibitor, an actin polymerization and stabilization promoter, an adenylate cyclase agonist, an ALK-5 receptor antagonist, an alpha adrenergic receptor antagonist, an androgen inhibitor, an anesthetic compound, an angiotensin II receptor agonist, an antibiotic selected from the group consisting of apigenin, an anti-coagulant, an anti-emetic agent, an anti-inflammatory compound, an anti-metabolite and antineoplastic agent, an anti-microbial agent, an anti-microbial agent, an anti-neoplastic agent, an anti-oxidant, an anti-proliferative agent, an anti-psychotic compound, an anti-spasmodic agent, an antithrombotic agent, an anti-viral agent, an apoptosis activator, an apoptosis activator, an apoptosis antagonist, an aromatase inhibitor, an AXOR12 agonist, an elastase inhibitor, an elF-2a inhibitor, an elongation factor-1 alpha inhibitor, an endothelial growth factor antagonist, an endothelial growth factor receptor kinase inhibitor, an endotoxin antagonist, an epothilone and tubulin binder, an estrogen agonist, an estrogen receptor antagonist, an FGF inhibitor, an FGF receptor kinase inhibitor, an FLT-3 kinase inhibitor, an FXR antagonist, an HMG-CoA reductase inhibitor, an HMGCoA reductase inhibitor, an ICAM inhibitor, an IL, an IL-2 inhibitor, an immunosuppressant, an inhibitor of type III receptor tyrosine kinase, an inosine monophosphate inhibitor, an interleukin antagonist, an intracellular calcium flux inhibitor, an intracellular calcium flux inhibitor, an intracellular calcium influx inhibitor, an irreversible inhibitor of enzyme methionine aminopeptidase type 2, an isozyme selective delta protein kinase C inhibitor, an MCP-CCR2 inhibitor, an MEK1/MEK 2 inhibitor, an MIF inhibitor, an mTOR inhibitor, an mTOR kinase inhibitor, an NF kappa B inhibitor, an ornithine decarboxylase inhibitor, an S-adenosyl-L-homocysteine hydrolase inhibitor, an SDF-1 antagonist, an SRC inhibitor, an Syk kinase inhibitor, an α-glucosidase inhibitor, an Integrin antagonist, and a immuno-modulator selected from Bay 11-7085, and IRAK antagonist, ICE, idazoxan hydrochloride, protein kinase B inhibitor, protein kinase C stimulant, purine nucleoside analogue, puromycin, reversible inhibitor of ErbB1 and ErbB2, ribonucleoside triphosphate reductase inhibitor, any combination thereof. In some embodiments, the anti-scarring agent can be selected from ZD-6474, AP-23573, synthadotin, S-0885, aplidine, ixabepilone, IDN-5390, SB-2723005, ABT-518, combretastatin, anecortave acetate, SB-715992, temsirolimus, adalimumab, erucylphosphocholine, alphastatin, etanercept, humicade, gefitinib, isotretinoin, radicicol, clobetasol propionate, homoharringtonine, trichostatin A, brefeldin A, thapsigargin, dolastatin, cerivastatin, jasplakinolide, herbimycin A, pirfenidone, vinorelbine, 17-DMAG, tacrolimus, loteprednol etabonate, juglone, prednisolone, puromycin, 3-BAABE, cladribine, mannose-6-phosphate, 5-azacytidine, Ly333531 (ruboxistaurin), and simvastatin.

In some embodiments, the active agent is a skin regenerating agent. Some skin regenerating agents can act as anti-scarring agents.

In some embodiments, the drug carrier comprises an additional anti-acne agent. In some embodiments, the additional anti-acne agent can be selected from the group consisting of acetretin, adapalene(s), alitretinoin, alpha- or beta-hydroxy acids, antibiotics, antimicrobial peptides, antimicrobials, azelaic acid, benzoyl peroxide, bexarotene, bile salts, biofilm inhibitors, clindamycin, erythromycin, etretinate, glycolic acid, isotretinoin, keratolytic agents, lactic acid, lipoic acid, N-acetylcystein, natural anti-acne agents, octopirox, phenoxyethanol, phenoxypropanol, pyruvic acid, resorcinol, retinoic acid, retinoid(s), salicylic acid, sebostats, sodium sulfacetamide, spironolactone, sulfur, sulfur containing D- or L-amino acids, tazarotene, tea tree oil, tretinoin, triclosan, urea, and any combinations thereof.

The drug carrier disclosed herein can comprise any amount of the API (e.g., DART or other agent). For example, the drug carrier can comprise about 0.01% to about 99% (w/w) of the API. For example, the particle can comprise between about 0.01% to about 20% (w/w) of the API. In some embodiments, the API comprises greater than 1% (w/w), greater than 5% (w/w), greater than 10% (w/w), greater than 15% (w/w), greater than 20% (w/w), greater than 25% (w/w), greater than 30% (w/w), greater than 35% (w/w), greater than 40% (w/w), greater than 45% (w/w), greater than 50% (w/w), greater than 55% (w/w), greater than 60% (w/w), greater than 65% (w/w), greater than 70% (w/w), greater than 75% (w/w), greater than 80% (w/w), greater than 85% (w/w), greater than 90% (w/w), or greater than 95% (w/w) of the total weight of the drug carrier. In some embodiments, the content of API in the drug carrier can range from about 75% to about 97% (w/w). In some other embodiments, the content of API in the drug carrier can range from about 3% to about 25% (w/w).

A lipid for use in the drug carriers or formulations disclosed herein can be selected from the group consisting of fatty acids, fatty alcohols, glycerolipids (e.g., monoglycerides, diglycerides, and triglycerides), phospholipids, glycerophospholipids, sphingolipids, sterol lipids, prenol lipids, saccharolipids, polyketides, and any combination thereof. In some embodiments, the lipid can be selected from the group consisting of 1,3-Propanediol Dicaprylate/Dicaprate; 10-undecenoic acid; 1-dotriacontanol; 1-heptacosanol; 1-nonacosanol; 2-ethyl hexanol; Androstanes; Arachidic acid; Arachidonic acid; arachidyl alcohol; Behenic acid; behenyl alcohol; Capmul MCM C10; Capric acid; capric alcohol; capryl alcohol; Caprylic acid; Caprylic/Capric Acid Ester of Saturated Fatty Alcohol C12-C18; Caprylic/Capric Triglyceride; Caprylic/Capric Triglyceride; Ceramide phosphorylcholine (Sphingomyelin, SPH); Ceramide phosphorylethanolamine (Sphingomyelin, Cer-PE); Ceramide phosphorylglycerol; Ceroplastic acid; Cerotic acid; Cerotic acid; ceryl alcohol; Cetearyl alcohol; Ceteth-10; cetyl alcohol; Cholanes; Cholestanes; cholesterol; cis-11-eicosenoic acid; cis-11-octadecenoic acid; cis-13-docosenoic acid; cluytyl alcohol; coenzyme Q10 (CoQ10); Dihomo-γ-linolenic; Docosahexaenoic acid; egg lecithin; Eicosapentaenoic acid; Eicosenoic acid; Elaidic acid; elaidolinolenyl alcohol; elaidolinoleyl alcohol; elaidyl alcohol; Erucic acid; erucyl alcohol; Estranes; Ethylene glycol distearate (EGDS); Geddic acid; geddyl alcohol; glycerol distearate (type I) EP (Precirol ATO 5); Glycerol Tricaprylate/Caprate; Glycerol Tricaprylate/Caprate (CAPTEX® 355 EP/NF); glyceryl monocaprylate (Capmul MCM C8 EP); Glyceryl Triacetate; Glyceryl Tricaprylate; Glyceryl Tricaprylate/Caprate/Laurate; Glyceryl Tricaprylate/Tricaprate; glyceryl tripalmitate (Tripalmitin); Henatriacontylic acid; Heneicosyl alcohol; Heneicosylic acid; Heptacosylic acid; Heptadecanoic acid; Heptadecyl alcohol; Hexatriacontylic acid; isostearic acid; isostearyl alcohol; Lacceroic acid; Lauric acid; Lauryl alcohol; Lignoceric acid; lignoceryl alcohol; Linoelaidic acid; Linoleic acid; linolenyl alcohol; linoleyl alcohol; Margaric acid; Mead; Melissic acid; melissyl alcohol; Montanic acid; montanyl alcohol; myricyl alcohol; Myristic acid; Myristoleic acid; Myristyl alcohol; neodecanoic acid; neoheptanoic acid; neononanoic acid; Nervonic; Nonacosylic acid; Nonadecyl alcohol; Nonadecylic acid; Nonadecylic acid; Oleic acid; oleyl alcohol; Palmitic acid; Palmitoleic acid; palmitoleyl alcohol; Pelargonic acid; pelargonic alcohol; Pentacosylic acid; Pentadecyl alcohol; Pentadecylic acid; Phosphatidic acid (phosphatidate, PA); Phosphatidylcholine (lecithin, PC); Phosphatidylethanolamine (cephalin, PE); Phosphatidylinositol (PI); Phosphatidylinositol bisphosphate (PIP2); Phosphatidylinositol phosphate (PIP); Phosphatidylinositol triphosphate (PIP3); Phosphatidylserine (PS); polyglyceryl-6-distearate; Pregnanes; Propylene Glycol Dicaprate; Propylene Glycol Dicaprylocaprate; Propylene Glycol Dicaprylocaprate; Psyllic acid; recinoleaic acid; recinoleyl alcohol; Sapienic acid; soy lecithin; Stearic acid; Stearidonic; stearyl alcohol; Tricosylic acid; Tridecyl alcohol; Tridecylic acid; Triolein; Undecyl alcohol; undecylenic acid; Undecylic acid; Vaccenic acid; α-Linolenic acid; γ-Linolenic acid; a fatty acid salt of 10-undecenoic acid, adapalene, arachidic acid, arachidonic acid, behenic acid, butyric acid, capric acid, caprylic acid, cerotic acid, cis-11-eicosenoic acid, cis-11-octadecenoic acid, cis-13-docosenoic acid, docosahexaenoic acid, eicosapentaenoic acid, elaidic acid, erucic acid, heneicosylic acid, heptacosylic acid, heptadecanoic acid, isostearic acid, lauric acid, lignoceric acid, linoelaidic acid, linoleic acid, montanic acid, myristic acid, myristoleic acid, neodecanoic acid, neoheptanoic acid, neononanoic acid, nonadecylic acid, oleic acid, palmitic acid, palmitoleic acid, pelargonic acid, pentacosylic acid, pentadecylic acid, recinoleaic acid (e.g. zinc recinoleate), sapienic acid, stearic acid, tricosylic acid, tridecylic acid, undecylenic acid, undecylic acid, vaccenic acid, valeric acid, α-linolenic acid, or γ-linolenic acid; paraffin; and any combinations thereof. In some embodiments, the lipid can be a fatty acid comprising 11 or fewer carbons. For example the fatty acid can comprise 6, 7, 8, 9, 10, or 11 carbons.

Without wishing to be bound by a theory, it is believed that fatty acid salts can be also used in the particles to potentiate anti-bacterial activity, e.g., anti-acne activity and provide stability in compositions comprising said drug carriers. Accordingly, in some embodiments, the lipid is a fatty acid salt. Without limitations, the fatty acid salt can be selected from the group consisting of zinc, sodium, potassium, lithium, ammonium, copper, calcium, magnesium, strontium, manganese, and combinations thereof. The drug carrier can comprise any amount of the lipid component. For example, the drug carrier can comprise between about 0.01% to about 99% (w/w) of the lipid component. In some embodiments, the lipid component comprises greater than 0.1% (w/w), greater than 0.5% (w/w), greater than 1%

(w/w), greater than 2% (w/w), greater than 3% (w/w), greater than 4% (w/w), greater than 5% (w/w), greater than 6% (w/w), greater than 7% (w/w), greater than 8% (w/w), greater than 9% (w/w), greater than 10% (w/w), greater than 11% (w/w), greater than 12% (w/w), greater than 13% (w/w), greater than 14% (w/w), greater than 15% (w/w), greater than 16% (w/w), greater than 17% (w/w), greater than 18% (w/w), greater than 19% (w/w), greater than 20% (w/w), greater than 25% (w/w), greater than 30% (w/w), greater than 35% (w/w), greater than 40% (w/w), greater than 45% (w/w), or greater than 50% (w/w) of the total weight of the drug carrier. Typically, the content of the lipid component in the drug carriers are in the range of about 2-25% (w/w).

Ratio of the active agent (e.g., DART or other antibacterial agent) to the total lipid component of the coating layer can be any desired ratio. For example, ratio of the active agent to the total lipid component can range from about 100:1 to about 1:100. In some embodiments, the ratio of the active agent to the total lipid component can range from about 75:1 to about 1:75, from about 50:1 to about 1:50, from about 25:1 to about 1:25, from about 20:1 to about 1:20, from about 15:1 to about 1:15, from about 5:1 to about 1:5, or from about 25:1 to about 1:5. In some embodiments, the ratio of the active agent to the total lipid component is about 30:1, about 25:1, about 20:1, about 15:1, about 10:1, about 5:1, or about 1:1. The ratio can be based on weight, mass, or moles.

Thickness of the coating layer can range from nanometers to millimeters. For example, the coating layer thickness can range from about 1 nm to about 5000 nm, from about 5 nm to about 2500 nm, from about 10 nm to about 2000 nm, from about 50 nm to about 1500 nm, from about 20 nm to about 1000 nm, from about 1 nm to about 1000 nm, from about 1 nm to about 500 nm, from about 1 nm to about 250 nm, from about 1 nm to about 200 nm, from about 1 nm to about 150 nm, from about 1 nm to about 100 nm, from about 2 nm to about 50 nm, or from about 5 nm to about 25 nm.

In some embodiments, the drug carrier can comprise two or more (e.g., 1, 2, 3, 4, 5, 6, 7, 8, 9, 10, or more) lipids, i.e., the carrier can comprise a first lipid and a second lipid. For example, the coating layer can comprise a second lipid that is different from the first lipid.

Exemplary proteins for use in the drug carriers or formulations disclosed herein can include, but are not limited to, Actin, Albumin, Amaranth Protein, Ammonium Hydrolyzed Animal Protein, Animal protein, Barley Protein, Brazil Nut Protein, Casein, Collagen, Collagen protein hydrolyzed, Conchiolin Protein, corn protein, Cottonseed Protein, Elastin, Extensin, Fibroin, Fibronectin, Fish Protein, Gadidae Protein, Gelatin, Glutein, Glycoproteins, Hazelnut Protein, Hemoglobin, Hemp Seed Protein, Honey Protein, Hydrolyzed Actin, Hydrolyzed Amaranth Protein, Hydrolyzed animal protein, Hydrolyzed Barley Protein, Hydrolyzed Brazil Nut Protein, Hydrolyzed Conchiolin Protein, Hydrolyzed corn protein, Hydrolyzed Cottonseed Protein, Hydrolyzed Elastin, Hydrolyzed Extensin, Hydrolyzed Fibroin, Hydrolyzed Fibronectin, Hydrolyzed Fish Protein, Hydrolyzed Gadidae Protein, Hydrolyzed Gadidae Protein, Hydrolyzed Gelatin, Hydrolyzed Hair Keratin, Hydrolyzed Hazelnut, Hydrolyzed Hazelnut Protein, Hydrolyzed Hemoglobin, Hydrolyzed Hemp Seed Protein, Hydrolyzed Honey Protein, Hydrolyzed Keratin, Hydrolyzed Lupine Protein, Hydrolyzed Maple Sycamore Protein, Hydrolyzed Milk Protein, Hydrolyzed Oat Protein, Hydrolyzed Pea Protein, Hydrolyzed Potato Protein, Hydrolyzed Reticulin, Hydrolyzed Royal Jelly Protein, Hydrolyzed Sericin, Hydrolyzed Serum Protein, Hydrolyzed Sesame Protein, Hydrolyzed Soy Protein, Hydrolyzed Soymilk Protein, Hydrolyzed Spinal Protein, Hydrolyzed Spongin, Hydrolyzed Sweet Almond Protein, Hydrolyzed Vegetable Protein, Hydrolyzed Wheat Gluten, Hydrolyzed Wheat Protein, Hydrolyzed Whey Protein, Hydrolyzed Yeast Protein, Hydrolyzed Yogurt Protein, Hydrolyzed Zein, Integrin, Jojoba protein HP, Hydrolyzed, keratin, Lupine Protein, Maple Sycamore Protein, MEA-Hydrolyzed Collagen, MEA-Hydrolyzed Silk, Milk Protein, Myosin, Oat Protein, Pea Protein, polylysine, Potato Protein, Reticulin, Rice Quat, Royal Jelly Protein, Sericin, Serum Protein, Sesame Protein, Silk powder, Sodium Hydrolyzed Casein, Soy Protein, Soy Rice Peptides, Soymilk Protein, Spinal Protein, Spongin, Sweet Almond Protein, Vegetable Protein, Wheat Gluten, Whey Protein, Yeast Protein, Yogurt Protein, Zein, and Zinc Hydrolyzed Collagen.

In some embodiments, the protein is an albumin. The albumin can be a naturally occurring albumin, an albumin related protein or a variant thereof such as a natural or engineered variant. Variants include polymorphisms, fragments such as domains and subdomains, fragments and/or fusion proteins. An albumin can comprise the sequence of an albumin protein obtained from any source. A number of proteins are known to exist within the albumin family. Accordingly, the albumin can comprise the sequence of an albumin derived from one of serum albumin from African clawed frog (e.g., see Swissprot accession number P08759-1), bovine (e.g., see Swissprot accession number P02769-1), cat (e.g., see Swissprot accession number P49064-1), chicken (e.g., see Swissprot accession number P19121-1), chicken ovalbumin (e.g., see Swissprot accession number P01012-1), cobra ALB (e.g., see Swissprot accession number Q91134-1), dog (e.g., see Swissprot accession number P49822-1), donkey (e.g., see Swissprot accession number QSXLE4-1), European water frog (e.g., see Swissprot accession number Q9YGH6-1), blood fluke (e.g., see Swissprot accession number AAL08579 and Q95VB7-1), Mongolian gerbil (e.g., see Swissprot accession number O35090-1 and JC5838), goat (e.g., see Swissprot accession number B3VHM9-1 and as available from Sigma as product no. A2514 or A4164), guinea pig (e.g., see Swissprot accession number Q6WDN9-1), hamster (see DeMarco et al. (2007). International Journal for Parasitology 37(11): 1201-1208), horse (e.g., see Swissprot accession number P35747-1), human (e.g., see Swissprot accession number P02768-1), Australian Lung-fish (e.g., see Swissprot accession number P83517), macaque (Rhesus monkey) (e.g., see Swissprot accession number Q28522-), mouse (e.g., see Swissprot accession number P07724-1), North American bull frog (e.g., see Swissprot accession number P21847-1), pig (e.g., see Swissprot accession number P08835-1), pigeon (e.g. as defined by Khan et al, 2002, 1112. J. Biol. Macromol, 30(3-4), 171-8), rabbit (e.g., see Swissprot accession number P490 65-1), rat (e.g., see Swissprot accession number P02770-1), salamander (e.g., see Swissprot accession number Q8UW05-1), salmon ALB1 (e.g., see Swissprot accession number P21848-1), salmon ALB2 (e.g., see Swissprot accession number Q03156-1), sea lamprey (e.g., see Swissprot accession number Q91274-1 and 042279-1) sheep (e.g., see Swissprot accession number P14639-1), Sumatran orangutan (e.g., see Swissprot accession number Q5NVH5-1), tuatara (e.g., see Swissprot accession number Q8JIA9-1), turkey ovalbumin (e.g., see Swissprot accession number O73860-1), Western clawed frog (e.g., see Swissprot accession number Q6D.I95-1), and includes variants and fragments thereof as defined herein. Many naturally occurring mutant forms of albumin are known. Many are described in Peters, (1996, All About Albumin: Biochemistry, Genetics and Medical Applications, Academic Press, Inc., San Diego, Calif., p. 170-181), content of which is incorporated herein by reference. The term albumin also encompasses albumin variants, such as genetically engineered forms, mutated forms, and fragments etc. having one or more binding sites that are analogous to a binding site unique for one or more albumins as defined above. By analogous binding sites in the context of the invention are contemplated structures that are able to compete with each other for binding to one and the same ligand structure. In one embodiment, albumin is bovine serum albumin, egg albumin, hydrolyzed lactalbumin, or lactalbumin, including variants and fragments thereof. In one embodiment, the protein is egg albumin.

The protein can comprise between about 0.01% to about 99% (w/w) of the drug carrier. In some embodiments, the protein component comprises greater than 0.1% (w/w), greater than 0.5% (w/w), greater than 1% (w/w), greater than 2% (w/w), greater than 3% (w/w), greater than 4% (w/w), greater than 5% (w/w), greater than 6% (w/w), greater than 7% (w/w), greater than 8% (w/w), greater than 9% (w/w), greater than 10% (w/w), greater than 11% (w/w), greater than 12% (w/w), greater than 13% (w/w), greater than 14% (w/w), greater than 15% (w/w), greater than 16% (w/w), greater than 17% (w/w), greater than 18% (w/w), greater than 19% (w/w), greater than 20% (w/w), greater than 25% (w/w), greater than 30% (w/w), greater than 35% (w/w), greater than 40% (w/w), greater than 45% (w/w), or greater than 50% (w/w) of the total weight of the drug carriers. Typically, the content of the protein component in the drug carriers are in the range of about 1-25% (w/w), about 0.1-10% (w/w), about 0.5-5% (w/w), or about 1-1.5% (w/w).

Ratio of the active agent (e.g., DART or other antibacterial agent) to the protein component can be any desired ratio. For example, ratio of the active agent to the protein component can range from about 100:1 to about 1:100. In some embodiments, the ratio the active agent to the protein can range from about 100:1 to about 1:1, from about 90:1 to about 10:1, from about 85:1 to about 15:1, from about 80:1 to about 25:1, or from 75:1 to about 50:1. In some embodiments, the ratio of the active agent to the protein component is about 75:1. The ratio can be based on weight, mass, or moles.

Generally, any cationic molecule can be used in the drug carriers or formulations disclosed herein. As used herein the term "cationic molecule" refers to a molecule that carries a net positive charge. In some embodiments, the cationic molecule is a polyamine. Exemplary cationic molecules include, but are not limited to, Putrescine (Butane-1,4-diamine), Cadaverine (Pentane-1,5-diamine), Spermidine, Spermine, Cyclen (1,4,7,10-tetrazacyclododecane), Cyclam (1,4,8,11-Tetraazacyclotetradecane), Linear Polyethyleneimine (Poly(iminoethylene)), Norspermidine, p-Phenylenediamine (1,4-diaminobenzene), Diethylenetriamine (N-(2-aminoethyl)-1,2-ethanediamine), thermospermine, Tris(2-aminoethyl)amine, Hexamethylenediamine, Beta-lysine (3,6-diaminohexanoic acid), m-Phenylenediamine (1,3-diaminobenzene), Diaminopropane (1,2-Diaminopropane), Ethylenediamine dihydroiodide, and polyamine D 400 (Polyoxyalkyleneamine D 400).

The cationic molecule can comprise between about 0.01% to about 99% (w/w) of the drug carrier. In some embodiments, the cationic molecule comprises greater than 0.1% (w/w), greater than 0.5% (w/w), greater than 1% (w/w), greater than 2% (w/w), greater than 3% (w/w), greater than 4% (w/w), greater than 5% (w/w), greater than 6% (w/w), greater than 7% (w/w), greater than 8% (w/w), greater than 9% (w/w), greater than 10% (w/w), greater than 11% (w/w), greater than 12% (w/w), greater than 13% (w/w), greater than 14% (w/w), greater than 15% (w/w), greater than 16% (w/w), greater than 17% (w/w), greater than 18% (w/w), greater than 19% (w/w), greater than 20% (w/w), greater than 25% (w/w), greater than 30% (w/w), greater than 35% (w/w), greater than 40% (w/w), greater than 45% (w/w), or greater than 50% (w/w) of the total weight of the drug carriers. Typically, the content of the cationic molecule in the drug carriers are in the range of about 1-25% (w/w), about 0.1-10% (w/w), about 0.5-5% (w/w), or about 1-1.5% (w/w).

Ratio of the active agent (e.g., DART or other antibacterial agent) to the protein component can be any desired ratio. For example, ratio of the active agent to the protein component can range from about 100:1 to about 1:100. In some embodiments, the ratio the active agent to the protein can range from about 100:1 to about 1:1, from about 90:1 to about 10:1, from about 85:1 to about 15:1, from about 80:1 to about 25:1, or from 75:1 to about 50:1. In some embodiments, the ratio of the active agent to the protein component is about 75:1. The ratio can be based on weight, mass, or moles.

Generally, any carbohydrate molecule can be used in the drug carriers or formulations disclosed herein. In some embodiments, the carbohydrate is a polysaccharide. Exemplary polysaccharides include cellulose derivatives such as hydroxyethyl-cellulose, hydroxy propyl-methyl-cellulose and carboxymethyl-cellulose; glycosaminoglycans such as hyaluronic acid, chondroitin sulfate, chitin and chitosan; starch derivatives such as starch/hydroxyethyl starch; agarose; and alginate and combinations thereof. In some embodiments, the carbohydrate can be selected from the group consisting of chitosan and their derivatives, alginates and their derivatives, pullulan, their derivatives The carbohydrate can comprise between about 0.01% to about 99% (w/w) of the drug carrier. In some embodiments, the carbohydrate comprises greater than 0.1% (w/w), greater than 0.5% (w/w), greater than 1% (w/w), greater than 2% (w/w), greater than 3% (w/w), greater than 4% (w/w), greater than 5% (w/w), greater than 6% (w/w), greater than 7% (w/w), greater than 8% (w/w), greater than 9% (w/w), greater than 10% (w/w), greater than 11% (w/w), greater than 12% (w/w), greater than 13% (w/w), greater than 14% (w/w), greater than 15% (w/w), greater than 16% (w/w), greater than 17% (w/w), greater than 18% (w/w), greater than 19% (w/w), greater than 20% (w/w), greater than 25% (w/w), greater than 30% (w/w), greater than 35% (w/w), greater than 40% (w/w), greater than 45% (w/w), or greater than 50% (w/w) of the total weight of the drug carriers. Typically, the content of the carbohydrate in the drug carriers are in the range of about 1-25% (w/w), about 0.1-10% (w/w), about 0.5-5% (w/w), or about 1-1.5% (w/w).

Ratio of the active agent (e.g., DART or other antibacterial agent) to the carbohydrate can be any desired ratio. For example, ratio of the active agent to the carbohydrate can range from about 100:1 to about 1:100. In some embodiments, the ratio the active agent to the carbohydrate can range from about 100:1 to about 1:1, from about 90:1 to about 10:1, from about 85:1 to about 15:1, from about 80:1 to about 25:1, or from 75:1 to about 50:1. In some embodiments, the ratio of the active agent to the carbohydrate is about 75:1. The ratio can be based on weight, mass, or moles.

In some embodiments, the drug carrier further comprises an excipient. In some embodiments, the excipient is a wetting agent. Without limitations, the wetting agent can be selected from alkyl sulfates, e.g. sodium lauryl sulfate, sodium stearyl sulfate, sodium oleyl sulfate and sodium cetyl sulfate, alkyl aryl sulfonates, e.g. sodium dodecylbenzene sulfonate and dialkyl sodium sulfosuccinates, e.g. sodium bis-(2-ethylhexyl)sulfosuccinate, and most preferably sodium lauryl sulfate. Further examples of the pharmaceutically acceptable wetting agent include benzethonium chloride, cetylpyridinium chloride, docusatesodium, poloxamer, polysorbate and sorbitan esters.

In some embodiments, the excipient is a stabilizer, e.g., a surface stabilizer. Suitable surfacestabilizers can preferably be selected from known organic and inorganic pharmaceutical excipients. Such excipients include various polymers, low molecular weight oligomers, natural products, and surfactants with high and low hydrophilic lipophilic balance (HLB). Preferred surfacestabilizers include nonionic and ionic surfactants. Two or more surfacestabilizers can be used in combination. Representative examples of surfacestabilizers include sodium docusate, cetyl pyridinium chloride, gelatin, casein, lecithin (phosphatides), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Specialty Chemicals)); polyethylene glycols (e.g., Carbowaxs 3350® and 1450®, and Carbopol 934® (Union Carbide)), dodecyl trimethyl ammonium bromide, polyoxyethylene stearates, colloidal silicon dioxide, phosphates, sodium dodecylsulfate, carboxymethylcellulose calcium, hydroxypropyl celluloses (e.g., HPC, HPC-SL, and HPC-L), hydroxypropyl methylcellulose (HPMC), carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), polyvinylpyrrolidone (PVP), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); a charged phospholipid such as dimyristoyl phophatidyl glycerol, dioctylsulfosuccinate (DOSS); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (American Cyanamid)); Duponol P®, which is a sodium lauryl sulfate (DuPont); Tritons X-200®, which is an alkyl aryl polyether sulfonate (Rohm and Haas); Crodestas F-1 10®, which is a mixture of sucrose stearate and sucrose distearate (Croda Inc.); p-isononylphenoxypoly-(glycidol), also known as Olin-IOG® or Surfactant 10-G® (Olin Chemicals, Stamford, Conn.); Crodestas SL-40® (Croda, Inc.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; and the like. Most of these surfacestabilizers are known pharmaceutical excipients and are described in detail in the Handbook of Pharmaceutical Excipients, published jointly by the American Pharmaceutical Association and The Pharmaceutical Society of Great Britain (The Pharmaceutical Press, 1986), content of which is incorporated herein by reference in its entirety. In one embodiment, the excipient is sodium docusate.

Generally, the drug carriers have an average diameter of from about 5 nm to about 20,000 nm. In some embodiments, the drug carriers have an average diameter of from about 5 nm to about 5,000 nm. In some embodiments, the drug carriers have an average diameter of from about 50 nm to about 2500 nm. In some embodiments, the drug carriers have an average diameter of from about 100 nm to about 2000 nm. In some embodiments, the drug carriers have an average diameter of from about 150 nm to about 1700 nm. In some embodiments, the drug carriers have an average diameter of from about 200 nm to about 1500 nm. In some embodiment, the drug carriers have an average diameter of about 260 nm. In one embodiment, the drug carriers have an average diameter of about 30 nm to about 150 nm. In some embodiments, the drug carriers have an average diameter of about 100 nm to about 1000 nm, from about 200 nm to about 800 nm, from about 200 nm to about 700 nm, or from about 300 nm to about 700 nm.

Generally, the drug carriers disclosed herein can be of any shape or form, e.g., spherical, rod, elliptical, cylindrical, capsule, or disc.

In some embodiments, the drug carrier can be micro-sized and have a size of about 1 μm to about 1000 μm. In some embodiments, the drug carrier can be nano-sized and have size of about 0.1 nm to about 1000 nm. In some embodiments, the drug carrier is a microparticle or a nanoparticle. As used herein, the term "microparticle" refers to a particle having a particle size of about 1 μm to about 1000 μm. As used herein, the term "nanoparticle" refers to particle having a particle size of about 0.1 nm to about 1000 nm.

It will be understood by one of ordinary skill in the art that particles usually exhibit a distribution of sizes around the indicated "size." Unless otherwise stated, the terms "drug carrier size" and "particle size" as used herein refer to the mode of a size distribution of drug carriers or particles, i.e., the value that occurs most frequently in the size distribution. Methods for measuring the drug carrier or particle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

In some embodiments, the drug carrier can be substantially spherical. What is meant by "substantially spherical" is that the ratio of the lengths of the longest to the shortest perpendicular axes of the drug carrier cross section is less than or equal to about 1.5. Substantially spherical does not require a line of symmetry. Further, the drug carriers can have surface texturing, such as lines or indentations or protuberances that are small in scale when compared to the overall size of the drug carrier and still be substantially spherical. In some embodiments, the ratio of lengths between the longest and shortest axes of the drug carrier is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1. Without wishing to be bound by a theory, surface contact is minimized in drug carriers that are substantially spherical, which minimizes the undesirable agglomeration of the drug carriers upon storage. Many crystals or flakes have flat surfaces that can allow large surface contact areas where agglomeration can occur by ionic or non-ionic interactions. A sphere permits contact over a much smaller area.

In some embodiments, the drug carriers have substantially the same particle size. Drug carriers having a broad size distribution where there are both relatively big and small drug carriers allow for the smaller drug carriers to fill in the gaps between the drug carriers, thereby creating new contact surfaces. A broad size distribution can result in larger spheres by creating many contact opportunities for binding agglomeration. The drug carriers described herein are within a narrow size distribution, thereby minimizing opportunities for contact agglomeration. What is meant by a "narrow size distribution" is a particle size distribution that has a ratio of the volume diameter of the 90th percentile of the small spherical particles to the volume diameter of the 10th percentile less than or equal to 5. In some embodiments, the volume diameter of the 90th percentile of the small spherical particles to the volume diameter of the 10th percentile is less than or equal to 4.5, less than or equal to 4, less than or equal to 3.5, less than or equal to 3, less than or equal to 2.5, less than or equal to 2, less than or equal to 1.5, less than or equal to 1.45, less than or equal to 1.40, less than or equal to 1.35, less than or equal to 1.3, less than or equal to 1.25, less than or equal to 1.20, less than or equal to 1.15, or less than or equal to 1.1.

Geometric Standard Deviation (GSD) can also be used to indicate the narrow size distribution. GSD calculations involved determining the effective cutoff diameter (ECD) at the cumulative less than percentages of 15.9% and 84.1%. GSD is equal to the square root of the ratio of the ECD less than 84.17% to ECD less than 15.9%. The GSD has a narrow size distribution when GSD<2.5. In some embodiments, GSD is less than 2, less than 1.75, or less than 1.5. In one embodiment, GSD is less than 1.8.

While, the drug carriers are discussed in terms of coated particles, there are at least eight types of drug carriers that can be formulated with the active agent and one or more additional components. Different types of drug carriers can be as follows: ((1) drug carriers comprising a core formed by the active agent to which the additional component absorbs/adsorbs or the additional component forms one or more coating layers on the drug carrier core; (2) drug carriers comprising a generally homogeneous mixture of the active agent and the additional component; (3) drug carriers comprising a core comprising a generally homogeneous mixture of the active agent and the additional component, and the additional component forms one or more coating layers on the drug carrier core; (4) drug carriers comprising a core formed by the additional component and the active agent forms one or more coating layers on the drug carrier core; (5) drug carriers comprising a core comprising a generally homogeneous mixture of the active agent and the additional component, and the active agent forms one or more coating over the drug carrier core; (6) drug carrier comprising a core of material other than the active agent and the additional component, and a mixture of the active agent and the additional component forms one or more coating layers on the drug carrier core; (7) drug carriers comprising a core comprising a generally homogeneous mixture of the active agent and the additional component, and a material other than the active agent or the additional component forms one or more coating layers on the drug carrier core; (8) liposomes comprising the active agent; (9) emulsions, e.g., oil/water/oil or water/oil/water emulsions; (10) micelles; (11) globules; (12) suspensions; (13) dispersions; (14) vesicles; (15) aggregates; and (16) drug carrier comprising any of the drug carriers of (1)-(15) and further comprising one or more layers of a material other than the active agent or the additional component. In drug carriers of (16), the further layer can be the outermost layer, a first layer on the core, interspersed between the layers described in (1)-(15), or any combinations thereof. Without limitations, the coating layer can comprise components other than indicated above. For example, the above indicated coating component can be mixed with other molecules or compositions to form the coating layer. This can be useful in instances wherein the specified component may not be able to form a coating layer by itself. In some embodiments, the particle comprises a core comprising the active agent and the additional component forms one or more (e.g., 1, 2, 3, 4, 5, 6, 7, 8, 9, 10 or more) coating layers on the core.

In some embodiments, the drug carrier can be in the form of a liposome. As used herein, a liposome is a structure having lipid-containing membranes enclosing an aqueous interior. Liposomes can have one or more lipid membranes. Oligolamellar, large vesicles and multilamellar vesicles have multiple, usually concentric, membrane layers. Liposomes with several nonconcentric membranes, i.e., several smaller vesicles contained within a larger vesicle, are termed multivesicular vesicles.

Liposomes can further comprise one or more additional lipids and/or other components such as sterols, e.g., cholesterol. Additional lipids can be included in the liposome compositions for a variety of purposes, such as to prevent lipid oxidation, to stabilize the bilayer, to reduce aggregation during formation or to attach ligands onto the liposome surface. Any of a number of additional lipids and/or other components can be present, including amphipathic, neutral, cationic, anionic lipids, and programmable fusion lipids. Such lipids and/or components can be used alone or in combination. In addition to the lipids, the liposome can comprise one or more of the additives described in the disclosure.

Liposome compositions can be prepared by a variety of methods that are known in the art. See e.g., U.S. Pat. Nos. 4,235,871; 4,737,323; 4,897,355 and 5,171,678; published International Applications WO 96/14057 and WO 96/37194; Feigner, P. L. et al., *Proc. Natl. Acad. Sci., USA* (1987) 8:7413-7417, Bangham, et al. *M. Mol. Biol.* (1965) 23:238, Olson, et al. *Biochim. Biophys. Acta* (1979) 557:9, Szoka, et al. *Proc. Natl. Acad. Sci.* (1978) 75: 4194, Mayhew, et al. *Biochim. Biophys. Acta* (1984) 775:169, Kim, et al. *Biochim. Biophys. Acta* (1983) 728:339, and Fukunaga, et al. *Endocrinol.* (1984) 115:757.

In some embodiments, the drug carrier can be micelle. As used herein, "micelles" are a particular type of molecular assembly in which amphipathic molecules are arranged in a spherical structure such that all hydrophobic portions on the molecules are directed inward, leaving the hydrophilic portions in contact with the surrounding aqueous phase. The converse arrangement.

In some embodiments, the drug carrier can be an emulsion. As used herein, "emulsion" is a heterogeneous system of one liquid dispersed in another in the form of droplets. Emulsions are often biphasic systems comprising two immiscible liquid phases intimately mixed and dispersed with each other. Either of the phases of the emulsion can be a semisolid or a solid, as is the case of emulsion-style ointment bases and creams. The active agent can be present as a solution in either the aqueous phase, oily phase or itself as a separate phase.

In some embodiments, the drug carrier can be formulated as microemulsions. As used herein, "microemulsion" refers to a system of water, oil and amphiphile which is a single optically isotropic and thermodynamically stable liquid solution. Microemulsions also include thermodynamically stable, isotropically clear dispersions of two immiscible liquids that are stabilized by interfacial films of surface-active molecules.

The application of emulsion formulations via dermatological, oral and parenteral routes and methods for their manufacture have been reviewed in the literature, for example see Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., volume 1, p. 245; and Block, in Pharmaceutical Dosage Forms, Lieberman, Rieger and Banker (Eds.), 1988, Marcel Dekker, Inc., New York, N.Y., volume 1, p. 335, contents of which are herein incorporated by reference in their entirety.

The drug carrier can be fabricated using methods and instruments well known in the art. For example, the drug carriers can be made using microprecipitation, encapsulation, deaggregation, hybrid of deaggregation and encapsulation, homogenization, hybrid of deaggregation and hot homogenization, or any combinations thereof. In some embodiments, the process of making the particles comprises the step of selecting particles of a desired size.

Formulation Features Applicable to DART, Non-DART and Combination API

The disclosure provides a composition or formulation comprising a DART. The disclosure also provides a composition or formulation comprising an anti-bacterial agent as the API, wherein the anti-bacterial agent is not a DART molecule. In some embodiments, the formulation comprises two or more different APIs, e.g., two different DARTs, two different anti-bacterial agents which are not DART, or a DART molecule and an anti-bacterial agent which is not a DART. In some embodiments, the DART or the antibacterial agent is formulated as drug carrier for the API. Without limitations the formulation or the composition can be formulated for administration by any appropriate route known in the art including, but not limited to, topical (including buccal and sublingual) and oral or parenteral routes, including intravenous, intramuscular, subcutaneous, transdermal, airway (aerosol), pulmonary, nasal, and rectal administration. Exemplary modes of administration include, but are not limited to, topical, injection, infusion, instillation, inhalation, or ingestion. "Injection" includes, without limitation, intravenous, intramuscular, intra-arterial, intrathecal, intraventricular, intracapsular, intraorbital, intracardiac, intradermal, intraperitoneal, intralymphnodal, transtracheal, subcutaneous, subcuticular, intra-articular, sub capsular, subarachnoid, intraspinal, intracerebral, spinal, and intracisternal injection and infusion. In some embodiments, the formulation can be in the form of an oral dosage, injectable, aerosol or inhalant.

In some embodiments, the formulation can comprise two or more (e.g., two, three, four, five or more) different anti-bacterial agents as the API. For example, the formulation can comprise two different anti-acne agents as the API.

In some embodiments, the formulation comprises 8-chloro besifloxacin and another anti-acne agent as the API. In one embodiment, the formulation comprises besifloxacin and adapalene as the API.

The formulations disclosed herein can comprise several types of cosmetically-acceptable topical vehicles including, but not limited to solutions, colloidal suspensions, dispersions, emulsions (microemulsions, nanoemulsions, multiple and non-aqueous emulsions), hydrogels, and vesicles (liposomes, niosomes, novasomes). Components and formulation methods of suitable cosmetically-acceptable topical vehicles are well known in the art and are described, for example, in U.S. Pat. No. 6,797,697 and U.S. Pat. App. Pub. No. 2005/0142094 and No. 2005/0008604, Int. Pat. App. Pub. No. 2006/029818 and No. 2000/062743, content of all of which is incorporated herein by reference. Those skilled in the art will appreciate the various methods for producing these various product forms.

In some embodiments, the formulation can be in the form of a cream, oil, lotion, serum, gel, sunscreen, nail varnish, ointment, foam, spray, aerosol, powder, stick, solution, suspension, dispersion, paste, peel, and impregnated fabric (e.g. a "wipe" or tissue). Generally, the composition comprises an effective amount of the active agent. As used here, the term "effective amount" is that amount of the formulation containing the active agent necessary to achieve the desired improvement. In some embodiments, the formulation is a topical formulation.

In some embodiments, the formulation can be in a form selected from the group consisting of lotions, creams, gels, emulgel, oils, serums, powders, sprays, ointments, solutions, suspensions, dispersions, pastes, foams, peels, films, masks, patches, sticks, rollers, cleansing liquid washes, cleansing solid bars, pastes, foams, powders, shaving creams, impregnated fabric (e.g. a "wipe" or tissue), and the like.

In some embodiments, the formulation is an anti-bacterial formulation. In some embodiments, the composition is an anti-bacterial composition in the form of a skin care composition. As defined herein, the term "skin care composition" refers to materials applied topically to the skin that benefit, improve, or enhance the condition of the skin, or treat skin suffering from an infectious or diseased condition. Such skin care compositions include bases such as soap bases, cosmetic bases, medicament bases, cream bases, emollient bases, and combinations thereof, as well as other bases known in the art.

Without limitations, the formulation can comprise any desired amount of the API. For example, the formulation can comprise from about 0.01% to about 99% (w/w or w/v) of the API. In some embodiments, the formulation can comprise from about 0.1% to about 75% (w/w or w/v), from about 1% to about 50% (w/w or w/v), from about 1.5% to about 40% (w/w or w/v), API. In some embodiments, the formulation can comprise from about 2.5%, 3%, 3.5%, 4%, 4.5%, 5%, 7.5%, 10%, 12.5%, 15%, 17.5%, 20%, 22.5%, or 25% (w/w or w/v) of the API.

In some embodiments, the formulation can comprises, in addition to the API, one or more zinc compounds. Without wishing to be bound by a theory, zinc compounds can help to suppress sebum secretion and reduce acne inflammation. Exemplary zinc compounds include, but are not limited to, zinc acetate, zinc methionine, zinc pyrrolidone carboxylic acid, zinc sulfide, zinc gluconate, zinc picolinate, zinc sulphate, zinc citrate, etc. Without limitations, the formulation can comprise any desired amount of the zinc compound. For example, the formulation can comprise from about 0.01% to about 99% (w/w or w/v) of the zinc compound. In some embodiments, the formulation can comprise from about 0.1% to about 75% (w/w or w/v), from about 1% to about 50% (w/w or w/v), from about 1.5% to about 40% (w/w or w/v), from about 2% to about 25% (w/w or w/v), or from about 2.5% to about 25% (w/w or w/v) of the zinc compound. In some embodiments, the formulation can comprise from about 2.5%, 3%, 3.5%, 4%, 4.5%, 5%, 7.5%, 10%, 12.5%, 15%, 17.5%, 20%, 22.5%, or 25% (w/w or w/v) of the zinc compound.

In some embodiments, the formulation can further comprise one or more excipients. Without limitations, the excipient can be selected from the group consisting of emulsifiers, preservatives, surfactants, oils, lipids, waxes, stabilizers, rheology modifiers or thickening agents (gelling agent), emollients, moisturizers, conditioning agents, fragrances/perfumes, potentiating agents, preservatives, opacifiers, antioxidants, cooling agents, film forming agents, abrasives, exfoliating agents, colorants, pH modifiers, solvents, vehicle, penetration enhancers, permeation enhancers, pearlizing agents, and any combinations thereof. Amount of the excipients in the formulation can range from about 5% to 99.99% (w/w or w/v). In some embodiments, the formulation comprises one or more GRAS ingredients.

Generally, the pH of intended use of the formulation will generally range from about pH 2 to about pH10, from about pH 3 to about pH 9, from about pH 4 and about pH 8, or from about pH 5.0 to about pH 7.5 or from about pH 5 to about 6.5. Suitable pH adjusting agents which can be used include one or more of organic or inorganic acids and bases including sodium hydroxide, potassium hydroxide, ammonium hydroxide, phosphate buffers, citric acid, acetic acid, fumaric acid, hydrochloric acid, malic acid, nitric acid, phosphoric acid, propionic acid, sulfuric acid, tartaric acid, triethyl amine, and the like.

Typically, the cosmetically acceptable medium for skin care compositions comprises water and other solvents which include, but are not limited to, mineral oils and fatty alcohols. The cosmetically-acceptable medium is from about 10% to about 99.99% by weight of the composition, preferably from about 50% to about 99% by weight of the composition, and can, in the absence of other additives, form the balance of the composition.

As used herein the term "cosmetically acceptable medium" refers to formulations that are used to treat skin, hair and/or nails and contain one or more ingredients used by those skilled in the art to formulate products used to treat skin. The cosmetically acceptable medium can be in any suitable form, i.e., a liquid, cream, emulsion, gel, thickening lotion or powder and will typically contain water, and can contain a cosmetically acceptable solvent and/or one or more surfactants.

The formulation can comprise one or more conventional functional cosmetic or dermatological additives or adjuvants, providing that they do not interfere with the mildness, performance or aesthetic characteristics desired in the final products. The CTFA (The Cosmetic, Toiletry, and Fragrance Association; now known as the Personal Care Products Council) *International Cosmetic Ingredient Dictionary and Handbook*, Eleventh Edition (2006), and *McCutcheon's Functional Materials*, North America and Internationals Editions, MC Publishing Co. (2007) describe a wide variety of cosmetic and pharmaceutical ingredients commonly used in skin care compositions, which are suitable for use in the compositions of the present invention. The compositions of the present invention can contain a wide range of these additional, optional components. The total concentration of added ingredients usually is less than about 20%, preferably less than about 5%, and most preferably less than about 3% by weight of the total composition. Such components include, but are not limited to surfactants, emollients, moisturizers, stabilizers, film-forming substances, fragrances, colorants, chelating agents, preservatives, antioxidants, pH adjusting agents, antimicrobial agents, water-proofing agents, dry feel modifiers, vitamins, plant extracts, hydroxy acids (such as alpha-hydroxy acids and beta-hydroxy acids), and sunless tanning agents.

The formulation can comprise one or more of the following basic cosmetic raw materials, including, but not limited to hydrocarbons, esters, fatty alcohols, fatty acids, emulsifying agents, humectants, viscosity modifiers, and silicone-based materials. The formulations can contain a wide range of these basic components. The total concentration of added ingredients usually is less than 50%, preferably less than 20%, and most preferably less than 10% by weight of the total formulation. Those skilled in the art will appreciate the various concentrations and combinations for employing these basic components to achieve the desired product form.

Suitable lipids which can be used include one or more of hydrocarbons, fatty alcohols, fatty acids, glycerides or esters of fatty acids with $C_1$-$C_{36}$ alkanols. Hydrocarbons can include paraffin or petroleum jelly. Fatty alcohols can include decanol, dodecanol, tetradecanol, hexadecanol or octadecanol. Fatty acids can include $C_6$-$C_{24}$ alkanoic acids such as hexanoic acid, octanoic acid, decanoic acid, dodecanoic acid, tetradecanoic acid, hexadecanoic acid, octadecanoic acid, unsaturated fatty acids such as oleic acid and linoleic acid. Glycerides can include olive oil, castor oil, sesame oil, caprylic/capric acid triglyceride or glycerol mono-, di- and tri-esters with palmitic and/or stearic acid. Esters of fatty acids can include $C_1$-$C_{36}$ alkanols such as beeswax, carnauba wax, cetyl palmitate, lanolin, isopropyl myristate, isopropyl stearate, oleic acid decyl ester, ethyl oleate and $C_6$-$C_{12}$ alkanoic acid esters and the like.

Suitable hydrocarbons include, but are not limited to mineral oil, isohexadecane, squalane, hydrogenated polyisobutene, petrolatum, paraffin, microcrystalline wax, and polyethylene. Suitable oils can include one or more of almond oil, apricot seed oil, borage oil, canola oil, coconut oil, corn oil, cotton seed oil, fish oil, jojoba bean oil, lard oil, linseed oil, boiled macadamia nut oil, mineral oil, olive oil, peanut oil, safflower oil, sesame oil, soybean oil, squalane, sunflower seed oil, tricaprylin (1,2,3 trioctanoyl glycerol), wheat germ oil and the like. The preferred quantity of oil used is in the range of about 5 to about 25% w/w, and more preferably in the range of about 5% to about 20% w/w of the composition.

Suitable esters which can be used include, but are not limited to isopropyl palmitate, octyl stearate, caprylic/capric triglyceride, plant waxes (Canelilla, Caranauba), vegetable oils (natural glycerides) and plant oils (Jojoba).

Suitable fatty alcohols which can be used include, but are not limited to myristyl, cetyl, stearyl, isostearyl, and behenyl.

Suitable emulsifying agents which can be used include, but are not limited to anionic (TEA/K stearate (triethanolamine/potassium stearate), sodium lauryl stearate, sodium cetearyl sulfate, and beeswax/Borax), nonionic (glycerol di-stearate, PEG (polyethyleneglycol)-100 Stearate, Polysorbate 20, steareth 2 and steareth 20), and cationic (distearyldimethylammonium chloride, behenalkonium chloride and steapyrium chloride), polymeric (acrylates/C 10-30 alkyl acrylate crosspolymer, polyacrylamide, polyquaternium-37, propylene glycol, dicaprylate/dicaparate and PPG-1 Trideceth-6), and silicone based materials (alkyl modified dimethicone copolyols), and polyglyceryl esters, and ethoxylated di-fatty esters. Additional suitable emulsifiers/surfactant can include one or more of ionic polysorbate surfactant, Tween® 20, Tween® 40, Tween® 60, Tween® 80, Nonylphenol Polyethylene Glycol Ethers, (alkylphenolhydroxypolyoxyethylene), Poly(oxy-1,2-ethanediyl), alpha-(4-nonylphenol)-omega-hydroxy-, branched (i.e. Tergitol® NP-40 Surfactant), Nonylphenol Polyethylene Glycol Ether mixtures (i.e. Tergitol® NP-70 (70% AQ) Surfactant), phenoxypolyethoxyethanols and polymers thereof such as Triton®, Poloxamer®, Spans®, Tyloxapol®, different grades of Brij, sodium dodecyl sulfate and the like. The preferred quantity of the emulsifiers/surfactant used is in the range of about 0.1% to about 10% w/w of the composition.

Exemplary humectants for use include, but are not limited to propylene glycol, sorbitol, butylene glycol, butylene glycol, hexylene glycol, acetamide MEA (acetylethanolamine), honey, and sodium PCA (sodium-2-pyrrolidone carboxylate), sorbitol, triacetin, and the like.

Viscosity modifiers which can be used in the compositions of the invention include, but are not limited to xanthum gum, magnesium aluminum silicate, cellulose gum, and hydrogenated castor oil.

Suitable thickening agents which can be used include one or more of cellulose polymer, a carbomer polymer, a carbomer derivative, a cellulose derivative, polyvinyl alcohol, poloxamers, polysaccharides and the like.

Suitable emollients which can be used include one or more of caprylic/capric triglycerides, castor oil, ceteareth-20, ceteareth-30, cetearyl alcohol, ceteth 20, cetostearyl alcohol, cetyl alcohol, cetyl stearyl alcohol, cocoa butter, diisopropyl adipate, glycerin, glyceryl monooleate, glyceryl monostearate, glyceryl stearate, isopropyl myristate, isopropyl palmitate, lanolin, lanolin alcohol, hydrogenated lanolin, liquid paraffins, linoleic acid, mineral oil, oleic acid, white petrolatum, polyethylene glycol, polyoxyethylene glycol fatty alcohol ethers, polyoxypropylene 15-stearyl ether, propylene glycol stearate, squalane, steareth-2 or -100, stearic acid, stearyl alcohol, urea and the like.

Suitable preservatives which can be used include one or more of phenoxyethanol, parabens (such as methylparaben and propylparaben), propylene glycols, sorbates, urea derivatives (such as diazolindinyl urea), and the like.

Suitable chelating agents which can be used include one or more of disodium EDTA, edetate trisodium, edetate tetrasodium, diethyleneamine pentaacetate and the like.

In some embodiments, the formulation comprises one or more of alcohols like $C_1$-$C_{12}$ alcohols, diols and triols, glycerol, methanol, ethanol, propanol, octanol and the like.

In some embodiments, the formulation comprises one or more permeation enhancers. Exemplary permeation enhancers include anionic surfactants, such as sodium lauryl sulfate and sodium laurate; cationic surfactants, such as cetylpyridium chloride; non-ionic surfactants, such as poloxamer, Brij, Span, Myrj, and Tween; bile salts; sodium glycodeoxycholate; sodium glycocholate, sodium taurodeoxycholate, sodium taurocholate, Azone®; fatty acids, such as oleic and caprylic acid; cyclodextrins, such as α-, β-, γ-cyclodextrin, methylated β-cylcodextrins; chelators, such as EDTA, sodium citrate and poly acrylates; polymers, such as chitosan, trimethyl chitosan and cationic amino acids, such as poly-L-arginine and L-lysine. Brij is the tradename for a family of nonionic polyoxyethylene commercially available from a number of suppliers. Span is the tradename for a family of sorbitan surfactants, such as sorbitan trioleate (Span 85) and sorbitan tristearate (Span 65) and the like, commercially available from a number of suppliers. Myrj is a tradename for a family of polyethoxylated fatty acid commercially available from a number of suppliers, such as polyoxyethylene monostearate (Myrj 49) and the like. Tween is the tradename for a family of polyoxyethylene sorbitan or polysorbate surfactants, such as polyoxyethylene sorbitan trioleate (Tween 85) and polysorbate 80 (Tween 80) commercially available from a number of suppliers. Azone is a tradename for 1-Dodecylhexahydro-2 h-Azepin-2-One.

In some embodiments, the formulation comprises one or more penetration enhancers. Exemplary penetration enhancers include, but are not limited to fatty acids, bile salts, chelating agents, surfactants, and non-surfactants. Exemplary penetration enhancers include dimethyl sulfoxide; isopropyl myristate; decyl, undecyl or dodecyl alcohol; propylene glycol; polyethylene glycol; C9, C10, C11, C12 or C12-15 fatty alcohols; azone; alkyl pyrrolidones; diethoxy glycol (Transcutol); lecithin; etc. Surfactants can also be used as penetration enhancers.

The formulation disclosed herein can further comprise one or more optional components known for use in personal care products, provided that the optional components are physically and chemically compatible with the essential components described herein, or do not otherwise unduly impair product stability, aesthetics or performance. Individual concentrations of such optional components can range from about 0.001% to about 10% by weight of the compositions.

Non-limiting examples of optional components for use in the composition include a deposition aid, cationic polymers, nonionic polymers, dispersed particles, conditioning agents (silicones and organic conditioning oils), humectant, suspending agent, additional anti-dandruff actives, viscosity modifiers, dyes, nonvolatile solvents or diluents (water soluble and insoluble), pearlescent aids, additional surfactants or nonionic cosurfactants, pediculocides, pH adjusting agents, perfumes, preservatives, chelants, proteins, skin active agents, sunscreens, UV absorbers, vitamins, antioxidants, preserving agents, fillers, surfactants, UVA and/or UVB sunscreens, fragrances, viscosifying agents, wetting agents, anionic polymers, nonionic polymers, amphoteric polymers, viscosity/foam stabilizers, opacifying/pearlizing agents, sequestering agents, stabilizing agents, humectants, anti-static agents, antifreezing agents, buffering agents, dyes, and pigments. These adjuvants are well known in the field of cosmetics and are described in many publications, for example see *Harry's Book of Cosmeticology*, 8th edition, Martin Rieger, ed., Chemical Publishing, New York (2000).

The compositions disclosed herein can also include a deposition aid. The deposition aid is included to effectively enhance deposition of the composition components. The deposition aid can comprise any material that enhances the deposition of the composition components onto the hair, scalp, or skin. In some embodiments, the deposition aids are cationic polymers. The concentration of the deposition aid in the composition should be sufficient to effectively enhance the deposition of the components and typically range from about 0.05% to about 5%, preferably from about 0.075% to about 2.5%, more preferably from about 0.1% to about 1.0%, by weight of the composition.

The compositions disclosed herein can comprise a cationic polymer. Concentrations of the cationic polymer in the composition typically range from about 0.05% to about 3%, preferably from about 0.075% to about 2.0%, more preferably from about 0.1% to about 1.0%, by weight of the composition. Preferred cationic polymers will have cationic charge densities of at least about 0.9 meq/gm, preferably at least about 1.2 meq/gm, more preferably at least about 1.5 meq/gm, but also preferably less than about 7 meq/gm, more preferably less than about 5 meq/gin. The average molecular weight of such suitable cationic polymers will generally be between about 10,000 and 10 million, preferably between about 50,000 and about 5 million, more preferably between about 100,000 and about 3 million.

Suitable cationic polymers for use in the compositions contain cationic nitrogen containing moieties such as quaternary ammonium or cationic protonated amino moieties. The cationic protonated amines can be primary, secondary, or tertiary amines (preferably secondary or tertiary), depending upon the particular species and the selected pH of the composition. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate and methylsulfate. Non limiting examples of cationic polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium containing polymers, including, for example, dimethyldiallylammonium chloride homopolymer, copolymers of acrylamide and dimethyldiallylammonium chloride (referred to in the industry by CTFA as Polyquaternium 6 and Polyquaternium 7, respectively); amphoteric copolymers of acrylic acid including copolymers of acrylic acid and dimethyldiallylammonium chloride (referred to in the industry by CTFA as Polyquaternium 22), terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methylacrylate (referred to in the industry by CTFA as Polyquaternium 47).

Other suitable cationic polymers for use in the composition include polysaccharide polymers, such as cationic cellulose derivatives and cationic starch derivatives. Preferred cationic cellulose polymers are salts of hydroxyethyl cellulose reacted with trimethyl ammonium substituted epoxide, referred to in the industry (CTFA) as Polyquaternium 10 and available from Amerchol Corp. (Edison, N.J., USA) in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the tradename Polymer LM-200.

Other suitable cationic polymers include cationic guar gum and derivatives thereof, such as guar hydroxypropyltrimonium chloride, specific examples of which include the Jaguar series commercially available from Rhone-Poulenc Incorporated and the N-Hance series commercially available from Aqualon Division of Hercules, Inc. Other suitable cationic polymers include quaternary nitrogen-containing cellulose ethers, some examples of which are described in U.S. Pat. No. 3,962,418. Other suitable cationic polymers include copolymers of etherified cellulose, guar and starch, some examples of which are described in U.S. Pat. No. 3,958,581. When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

Polyalkylene glycols having a molecular weight of more than about 1000 are useful herein. Polyethylene glycol polymers useful herein are PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

The composition can also include dispersed particles. The can include at least 0.025% by weight of the dispersed particles, more preferably at least 0.05%, still more preferably at least 0.1%, even more preferably at least 0.25%, and yet more preferably at least 0.5% by weight of the dispersed particles. In some embodiments, it is preferable to incorporate no more than about 20% by weight of the dispersed particles, more preferably no more than about 10%, still more preferably no more than 5%, even more preferably no more than 3%, and yet more preferably no more than 2% by weight of the dispersed particles.

Conditioning agents include any material which is used to give a particular conditioning benefit to skin. The conditioning agents useful in the compositions of the present invention typically comprise a water insoluble, water dispersible, non-volatile, liquid that forms emulsified, liquid particles or are solubilized by the surfactant micelles, in the anionic detersive surfactant component (described above). Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein.

The conditioning agent of the compositions can be an insoluble silicone conditioning agent. The silicone conditioning agent particles can comprise volatile silicone, non-volatile silicone, or combinations thereof. Preferred are non-volatile silicone conditioning agents. If volatile silicones are present, they will typically be incidental to their use as a solvent or carrier for commercially available forms of non-volatile silicone material ingredients, such as silicone gums and resins. The silicone conditioning agent particles can comprise a silicone fluid conditioning agent and can also comprise other ingredients, such as a silicone resin to improve silicone fluid deposition efficiency or enhance glossiness of the hair.

The concentration of the silicone conditioning agent typically ranges from about 0.01% to about 10%, by weight of the composition, preferably from about 0.1% to about 8%, more preferably from about 0.1% to about 5%, more preferably from about 0.2% to about 3%. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609. The silicone conditioning agents for use in the compositions of the present invention preferably have a viscosity, as measured at 25° C., from about 20 to about 2,000,000 centistokes ("csk"), more preferably from about 1,000 to about 1,800,000 csk, even more preferably from about 50,000 to about 1,500,000 csk, more preferably from about 100,000 to about 1,500,000 csk.

The dispersed silicone conditioning agent particles typically have a volume average particle diameter ranging from about 0.01 µm to about 50 µm. For small particle application to hair, the volume average particle diameters typically range from about 0.01 µm to about 41 µm, preferably from about 0.01 µm to about 2 µm, more preferably from about 0.01 µm to about 0.51 µm. For larger particle application to hair, the volume average particle diameters typically range from about 5 µm to about 125 µm, preferably from about 10 µm to about 90 µm, more preferably from about 15 µm to about 70 µm, more preferably from about 20 µm to about 50 µm.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989).

Silicone fluids include silicone oils, which are flowable silicone materials having a viscosity, as measured at 25° C., less than 1,000,000 csk, preferably from about 5 csk to about 1,000,000 csk, more preferably from about 100 csk to about 600,000 csk. Suitable silicone oils for use in the compositions of the present invention include polyalkyl siloxanes, polyaryl siloxanes, polyalkylaryl siloxanes, polyether siloxane copolymers, and mixtures thereof.

Other insoluble, non-volatile silicone fluids having hair conditioning properties can also be used.

Other silicone fluids suitable for use in the compositions are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, *Chemistry and Technology of Silicones*, New York: Academic Press (1968); and in General Electric Silicone Rubber Product Data Sheets SE 30, SE 33, SE 54 and SE 76. Specific non-limiting examples of silicone gums for use in the compositions of the present invention include polydimethylsiloxane, (polydimethylsiloxane) (methylvinylsiloxane) copolymer, polydimethylsiloxane) (diphenyl siloxane) (methylvinylsiloxane) copolymer and mixtures thereof.

Other non-volatile, insoluble silicone fluid conditioning agents that are suitable for use in the compositions of the present invention are those known as "high refractive index silicones," having a refractive index of at least about 1.46, preferably at least about 1.48, more preferably at least about 1.52, more preferably at least about 1.55. The refractive index of the polysiloxane fluid will generally be less than about 1.70, typically less than about 1.60. In this context, polysiloxane "fluid" includes oils as well as gums.

Silicone fluids suitable for use in the compositions of the present invention are disclosed in U.S. Pat. No. 2,826,551, U.S. Pat. No. 3,964,500, U.S. Pat. No. 4,364,837, British Pat. No. 849,433, and Silicon Compounds, Petrarch Systems, Inc. (1984).

Silicone resins can be included in the silicone conditioning agent of the compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Primes of the unit symbols (e.g. M', D', T, and Q') denote substituents other than methyl, and must be specifically defined for each occurrence.

Preferred silicone resins for use in the compositions of the present invention include, but are not limited to MQ, MT, MTQ, MDT and MDTQ resins. Methyl is a preferred silicone substituent. Especially preferred silicone resins are MQ resins, wherein the M:Q ratio is from about 0.5:1.0 to about 1.5:1.0 and the average molecular weight of the silicone resin is from about 1000 to about 10,000.

The conditioning component of the compositions of the present invention can also comprise from about 0.05% to about 3%, by weight of the composition, preferably from about 0.08% to about 1.5%, more preferably from about 0.1% to about 1%, of at least one organic conditioning oil as the conditioning agent, either alone or in combination with other conditioning agents, such as the silicones (described above).

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about C to about C19. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, available from Permethyl Corporation. Hydrocarbon polymers such as polybutene and polydecene are preferred. A preferred hydrocarbon polymer is polybutene, such as the copolymer of isobutylene and butene. A commercially available material of this type is L-14 polybutene from Amoco Chemical Corporation.

Organic conditioning oils for use in the compositions of the present invention can also include liquid polyolefins, more preferably liquid poly-α-olefins, more preferably hydrogenated liquid poly-a-olefins. Polyolefins for use herein are prepared by polymerization of C4 to about C14 olefenic monomers, preferably from about C6 to about C12.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin containing refinery feedstocks or effluents. Preferred hydrogenated a-olefin monomers include, but are not limited to: 1-hexene to 1-hexadecenes, 1-octene to 1-tetradecene, and mixtures thereof.

Other suitable organic conditioning oils for use as the conditioning agent in the compositions of the present invention include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof can include or have covalently bonded thereto other compatible functionalities, such as amides and alkoxy moieties (e.g., ethoxy or ether linkages, etc.).

Specific examples of preferred fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the present invention are mono-carboxylic acid esters of the general formula R'COOR, wherein R' and R are alkyl or alkenyl radicals, and the sum of carbon atoms in R' and R is at least 10, preferably at least 22.

Still other fatty esters suitable for use in the compositions of the present invention are di- and tri-alkyl and alkenyl esters of carboxylic acids, such as esters of C4 to C8 dicarboxylic acids (e.g. C1 to C22 esters, preferably C1 to C6, of succinic acid, glutaric acid, and adipic acid). Specific non-limiting examples of di- and tri-alkyl and alkenyl esters of carboxylic acids include isocetyl stearyol stearate, diisopropyl adipate, and tristearyl citrate. In some embodiments, the composition comprises ester of at least one of lauric acid, and succinic acid have additional anti-acne and/anti-inflammatory properties.

Other fatty esters suitable for use in the compositions of the present invention are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the compositions of the present invention are glycerides, including, but not limited to, mono-, di-, and tri-glycerides, preferably di- and tri-glycerides, more preferably triglycerides. For use in the compositions described herein, the glycerides are preferably the mono-, di-, and tri-esters of glycerol and long chain carboxylic acids, such as C10 to C22 carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin oil and soybean oil. Synthetic oils include, but are not limited to, triolein and tristearin glyceryl dilaurate.

Other fatty esters suitable for use in the compositions of the present invention are water insoluble synthetic fatty esters.

Specific non-limiting examples of suitable synthetic fatty esters for use in the compositions of the present invention include: P-43 (C8-C10 triester of trimethylolpropane), MCP-684 (tetraester of 3,3-diethanol-1,5 pentadiol), MCP 121 (C8-C10 diester of adipic acid), all of which are available from Mobil Chemical Company.

Also suitable for use in the compositions herein are the conditioning agents described by the Procter & Gamble Company in U.S. Pat. Nos. 5,674,478, and 5,750,122. Also suitable for use herein are those conditioning agents described in U.S. Pat. No. 4,529,586 (Clairol), U.S. Pat. No. 4,507,280 (Clairol), U.S. Pat. No. 4,663,158 (Clairol), U.S. Pat. No. 4,197,865 (L'Oreal), U.S. Pat. No. 4,217,914 (L'Oreal), U.S. Pat. No. 4,381,919 (L'Oreal), and U.S. Pat. No. 4,422,853 (L'Oreal).

The compositions can contain a humectant. The humectants can be selected from the group consisting of polyhydric alcohols, water soluble alkoxylated nonionic polymers, and mixtures thereof. The humectants, when used herein, are preferably used at levels by weight of the composition of from about 0.1% to about 20%, more preferably from about 0.5% to about 5%.

Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof.

Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

The compositions of the present invention can further comprise a suspending agent at concentrations effective for suspending water-insoluble material in dispersed form in the compositions or for modifying the viscosity of the composition. Such concentrations range from about 0.1% to about 10%, preferably from about 0.3% to about 5.0%, by weight of the compositions.

Suitable suspending agents include crystalline suspending agents that can be categorized as acyl derivatives, long chain amine oxides, or combinations thereof. These suspending agents are described in U.S. Pat. No. 4,741,855.

The compositions can contain also vitamins and amino acids such as: water soluble vitamins such as vitamin B1, B2, B6, B12, C, pantothenic acid, pantothenyl ethyl ether, panthenol, biotin, and their derivatives, water soluble amino acids such as asparagine, alanine, tryptophan, glutamic acid and their salts, water insoluble vitamins such as vitamin A, D, E, and their derivatives, water insoluble amino acids such as tyrosine, tryptamine, and their salts.

The formulations disclosed herein can also contain pigment materials such as nitroso, monoazo, diazo, carotenoid, triphenyl methanes, triaryl methanes, xanthenes, quinolines, oxazines, azines, anthraquinones, indigoids, thioindigoids, quinacridones, phthalocyianines, botanicals, and natural colors including water soluble dye components. The compositions of the present invention can also contain chelating agents.

In one embodiment, the formulation is a moisturizer cream/gel base. For example, the formulation comprises at least one moisturizing agent. Generally, the formulation can comprise from about 0.01% (by weight) to about 50% (by weight) of the moisturizing agents to impart a moisturizing benefit upon use. It is noted that dryness is one of prime concerns of art known anti-acne topical products. Exemplary moisturizing agents include, but are not limited to, N-Acetyl ethanolamine, aloe vera gel, arginine PCA, chitosan PCA, copper PCA, Corn glycerides, dimethyl imidazolidinone, fructose, glucamine, glucose, glucose glutamate, glucuronic acid, glutamic acid, glycereth-7, glycereth-12, glycereth-20, glycereth-26, glycerin, honey, hydrogenated honey, hydrogenated starch hydrolysates, hydrolyzed corn starch, lactamide MEA, lactic acid, lactose lysine PCA, mannitol, methyl gluceth-10, methyl gluceth-20, PCA, PEG-2 lactamide, PEG-10 propylene glycol, polyamino acids, polysaccharides, polyamino sugar condensate, potassium PCA, propylene glycol, propylene glycol citrate, saccharide hydrolysate, saccharide isomerate, sodium aspartate, sodium lactate, sodium PCA, sorbitol, TEA-lactate, TEA-PCA, urea, xylitol, panthenol, petrolatum, mineral oil, lanolin, lanolin alcohol, tocopherol, esters of tocopherol, alkyl polydimethylsiloxanes, vegetable oils, hydrogenated vegetable oils, fatty acid esters, beeswax, hydrolyzed keratin, hydroxyethyl urea, carboxylic acid amides, mucopolysaccharides, and quaternized nitrogen moisturizing agents. Examples of quaternary nitrogen moisturizing agents include, but are not limited to, hydroxypropyl bis-hydroxyethyldimonium chloride (available as COLA™ Moist 200 from Colonial Chemicals, Inc.), moisturizing agents described in U.S. Pat. No. 6,869,977 (content of which is incorporated herein by reference), choline salts described in U.S. Pat. Nos. 6,475,965 and 6,265,364 (contents of both of which are incorporated herein by reference), carnitine, and combinations thereof. The moisturizing agent can be present in the formulation in any desired amount to give a desired level of moisturization. In some embodiments, the moisturizing agent can be preset in an amount of 0 to about 5. In another embodiment, the quaternary nitrogen moisturizing agent is present in an amount of about 0.1 to about 1% by weight. In another embodiment, the moisturizing agent is present at about 1% by weight.

In some embodiments, the formulation comprises at least one of glycolic acid, lactic acid, sulfur, salicylic acid, and resorcinol.

Some exemplary formulations are described in Tables 2-5.

TABLE 2

Some exemplary cream formulations.

| Phase | Ingredients | A | B | C | Method of preparation |
|---|---|---|---|---|---|
| A | API | 0.2% | 2% | 5% | 1) All ingredients of |
|  | Cetostearyl alcohol | 10.0% | — | 10.0% | phase A were mixed and |
|  | Cetyl alcohol | — | 10.0% | — | heated at 70-80° C. |
|  | Stearyl alcohol | — | 5.0% | — | 2) All ingredients of |
|  | Macrogol Cetostearyl Ether 2 | 5.0% | — | 5.0% | phase B were mixed and stirred to get uniform |
|  | Span 20 | — | 1.0% | — | solution, then phase B |
|  | Apifil | 5.0% | — | — | was also heated to 70-80° C. |
| B | Pemulen TR 1 | — | 0.5% | 0.5% | with continuous |
|  | Macrogol Cetostearyl Ether 20 | 5.0% | — | 5.0% | stirring 3) Phase A was added |
|  | Tween 20 | — | 5.0% | — | into phase B with |
|  | Glycerol | 5.0% | 10.0% | 5.0% | continuous stirring at |
|  | Water | q.s. to 100 | q.s. to 100 | q.s. to 100 | 70-80° C. |
| C | Preservative | 0.1% | 0.1% | 0.1% | 4) Ingredients of phase |
| D | Citric acid/NaOH | q.s. to pH | q.s. to pH | q.s. to pH | C was added into pre-formed cream at 40° C. with continuous stirring 5) Finally phase D was added to get desired pH |

TABLE 3

Some exemplary emugel formulations.

| Phase | Ingredients | A | B | C | Method of preparation |
|---|---|---|---|---|---|
| A | API | 0.1% | 1% | 10% | 1) All ingredients of |
|  | Olive Oil | 5.0% | — | — | phase A was mixed and |
|  | Castor Oil | 5.0% | — | — | heated at 70-80° C. |
|  | Stearyl alcohol | — | 2.0% | 2.0% | 2) All ingredients of |

TABLE 3-continued

Some exemplary emugel formulations.

| Phase | Ingredients | A | B | C | Method of preparation |
|---|---|---|---|---|---|
|  | Oleyl alcohol | — | 2.0% | 20% | phase B was mixed and |
|  | Liquid Paraffin | — | 6.0% | 6.0% | stirred to get uniform |
|  | Span 20 | 2.0% | — | — | solution, then phase B |
|  | Steareth 2 | — | 2.0% | 2.0% | was also heated to 70-80° C. |
| B | Tween 20 | 8.0% | — | — | with continuous |
|  | Steareth 20 | — | 2.0% | 2.0% | stirring |
|  | Carbopol | 1.0% | 1.0% | — | 3) Phase A was added |
|  | Pemulen | — | — | 0.5% | into phase B with |
|  | Propylene glycol | 5.0% | 5.0% | 5.0% | continuous stirring at |
|  | Water | q.s. to 100% | q.s. to 100% | q.s. to 100% | 70-80° C. |
| C | Preservative | 0.1% | 0.1% | 0.1% | 4) Ingredients of phase |
| D | Citric acid/NaOH | q.s. to pH | q.s. to pH | q.s. to pH | C was added into pre-formed emulsion at 40° C. with continuous stirring 5) Finally phase D was added to get desired pH |

TABLE 4

Some exemplary gel formulations.

| Phase | Ingredients | A | B | C | Method of preparation |
|---|---|---|---|---|---|
| A | API | 0.01% | 0.5% | 2% | 1) Ingredients of phase |
|  | Ethanol | 10.0% | 5.0% | 5.0% | A was mixed to |
| B | Tween 20 | 2.0% | — | 2.0% | solubilize drug |
|  | Steareth 20 | — | 2.0% | — | 2) All ingredients of |
|  | Carbopol | 1.0% | — | 1.0% | phase B was mixed and |
|  | Pemulen | — | 0.5% | — | stirred to get uniform |
|  | Propylene glycol | 10.0% | 20.0% | 15.0% | solution, |
|  | Water | q.s. to 100% | q.s. to 100% | q.s. to 100% | 3) Phase A was added |
| C | Preservative | 0.1% | 0.1% | 0.1% | into phase B with |
| D | Citric acid/NaOH/ TEA | q.s. to pH | q.s. to pH | q.s. to pH | continuous stirring 4) Ingredients of phase C was added into pre-formed emulsion with continuous stirring 5) Finally phase D was added to get desired pH |

TABLE 5

Some exemplary lotion formulations.

| Phase | Ingredients | A | B | C | Method of preparation |
|---|---|---|---|---|---|
| A | API | 0.02% | 1.5% | 3% | 1) All ingredients of |
|  | Liquid paraffin | 5.0% | 10.0% | 15.0% | phase A was mixed and |
|  | Olive oil | 1.0% | 1.0% | 1.0% | heated at 70-80° C. |
|  | Glyceryl stearate | 2.0% | 1.0% | — | 2) All ingredients of |
| B | Tween 20 | 2.0% | 5.0% | 10.0% | phase B was mixed and |
|  | Pemulen | — | 0.5% | — | stirred to get uniform |
|  | Ultrez 21 | 1.0% | — | 2.0% | solution, then phase B |
|  | Ethanol | 5.0% | 5.0% | 5.0% | was also heated to 70-80° C. |
|  | Propylene glycol | 10.0% | 10.0% | 10.0% | with continuous |
|  | Water | q.s. to 100% | q.s. to 100% | q.s. to 100% | stirring |
| C | Preservative | 0.1% | 0.1% | 0.1% | 3) Phase A was added |
| D | Citric acid/NaOH/ TEA | q.s. to pH | q.s. to pH | q.s. to pH | into phase B with continuous stirring at 70-80° C. 4) Ingredients of phase C was added into pre-formed lotion at 40° C. with continuous stirring 5) Finally phase D was added to get desired pH |

Without wishing to be bound by a theory, the formulation disclosed herein can provide at least 1.2× increase in area under the curve in a concentration on the skin vs time plot compared with formulations known in the art. Further, the formulation can kill at least 20% more *P. acnes* as compared to direct application of an antibiotic.

The formulations disclosed herein provide formulation technological advances (size optimization, surface modification, and formulation innovations) to improve specificity & efficacy by enhancing penetration & delivery to the target site (sebaceous glands); improving retention to exhibit sustained effect; or easy entry into biofilm enveloped bacteria.

The disclosure further provides the use of the DARTs and formulations discloses herein for treating or preventing at least one bacterial infection condition in a subject. The method generally comprising administering a DART or formulation disclosed herein to a subject in need thereof. In some embodiments, the method is for treating an acne condition in a subject.

The term "acne" includes inflammatory diseases of the pilosebaceous follicles and/or skin glands, and commonly is characterized by papules, pustules, cysts, nodules, comedones, other blemishes or skin lesions. The term "acne" as used herein includes all known types of acne. Some types of acne which can be treated with the composition of the present invention are, for example, acne vulgaris, acne comedo, papular acne, premenstrual acne, preadolescent acne, acne venenata, acne cosmetica, pomade acne, acne detergicans, acne excoriee, gram negative acne, pseudofolliculitis barbae, folliculitis, perioral dermatitis, hiddradenitis suppurativa, cystic acne, acne atrophica, bromide acne, chlorine acne, acne conglobata, acne detergicans, epidemic acne, acne estivalis, acne fulminans, halogen acne, acne indurata, iodide acne, acne keloid, acne mechanica, acne papulosa, pomade acne, premenstral acne, acne pustulosa, acne scorbutica, acne scrofulosorum, acne urticata, acne varioliformis, acne venenata, propionic acne, acne excoriee, gram negative acne, steroid acne, nodulocystic acne and acne rosacea.

Without wishing to be bound by a theory, micronization of besifloxacin can have an impact on its bioactivity. For example, microniztion can enhance besifloxacin's bioactivity or its retention at a desired site. Further, micronization can also effect besifloxacin's stability and amounts in a formulation. Moreover, micronization can also allow optimizing properties of formulations comprising micronized besifloxacin.

Embodiments of the various aspects disclosed herein can also be described by one or more of the numbered paragraphs:

1. A formulation comprising an anti-acne agent and at least one carrier or excipient, wherein the anti-acne agent is in the form of a drug carrier comprising the anti-acne agent and at least one additional compound, said additional compound selected from the group consisting of lipids, oils, polymers, peptides, proteins, carbohydrates, glycolipids, phospholipids, lipoproteins, cationic molecules, and any combinations thereof.
2. The formulation of claim 1, wherein the drug carrier is coated or uncoated.
3. The formulation of paragraph 1 or 2, wherein the drug carrier has a size of about 5 nm to about 20 μm.
4. The formulation of paragraph 1 or 3, wherein the drug carrier has a size of about 5 nm to about 5 μm.
5. The formulation of any of paragraphs further comprising a surface modifier on the surface of the drug carrier.
6. The formulation of any of paragraphs 1-5, wherein the surface modifier is selected from the group consisting of lipids, oils, polymers, peptides, proteins, carbohydrates, glycolipids, phospholipids, lipoproteins, cationic molecules, and any combinations thereof.
7. The formulation of any of paragraphs 1-6, wherein the carrier or excipient is selected from the group consisting of emulsifiers, preservatives, surfactants, oils, lipids, waxes, stabilizers, rheology modifiers or thickening agents (gelling agent), emollients, moisturizers, conditioning agents, fragrances/perfumes, potentiating agents, preservatives, opacifiers, antioxidants, cooling agents, film forming agents, abrasives, exfoliating agents, colorants, pH modifiers, solvents, vehicle, penetration enhancers, pearlizing agents, and any combinations thereof.
8. The formulation of any of paragraphs 1-4, wherein the surface of the drug carrier is substantially free of surface modifier.
9. The formulation of any of paragraphs 1-8, comprising from about 0.1% to about 50% (w/w or w/v) of the carrier or excipient.
10. The formulation of any of paragraphs 1-9, wherein the formulation is formulated for topical, oral or parenteral administration.
11. The formulation of any of paragraphs 1-10, wherein the formulation is an oral dosage, injectable, aerosol or inhalant, lotion, cream, gel, emulgel, oil, serum, powder, spray, ointment, solution, suspension, dispersion, paste, foam, peel, films, mask, patch, stick, roller, impregnated fabric (e.g. a "wipe" or tissue), or any combination thereof.
12. The formulation of any of paragraphs 1-11, further comprising a second anti-acne agent.
13. The formulation of any of paragraphs 1-12, wherein the second anti-acne agent is selected from the group consisting of 8-chloro fluroquinolones, acetretin, adapalene (s), alitretinoin, alpha- or beta-hydroxy acids, antibiotics, antimicrobial peptides, antimicrobials, azelaic acid, benzoyl peroxide, bexarotene, bile salts, biofilm inhibitors, clindamycin, erythromycin, etretinate, glycolic acid, isotretinoin, keratolytic agents, lactic acid, lipoic acid, N-acetylcystein, natural anti-acne agents, octopirox, phenoxyethanol, phenoxypropanol, pyruvic acid, resorcinol, retinoic acid, retinoid(s), salicylic acid, sebostats, sodium sulfacetamide, spironolactone, sulfur, sulfur containing D- or L-amino acids, tazarotene, tea tree oil, tretinoin, triclosan, urea, and any combinations thereof.
14. The formulation of any of paragraphs 1-13, wherein the formulation comprises an 8-chloro fluoroquinolone alone or in combination with another anti-acne agent.
15. The formulation of any of paragraphs 1-14, wherein the formulation comprises besifloxacin and adapalene.
16. The formulation of any of paragraphs 1-14, wherein the formulation comprises 8-chlorofluoroquinolone and an anti-inflammatory agent.
17. The formulation of any of paragraphs 1-14, wherein the formulation comprises 8-chlorofluoroquinolone and retinoic acid or retinoid.
18. The formulation of any of paragraphs 1-17, wherein the second anti-acne agent is in the form of a drug carrier comprising the second anti-acne agent and at least one additional compound, said additional compound selected from the group consisting of lipids, oils, polymers, peptides, proteins, carbohydrates, glycolipids, phospholipids, lipoproteins, cationic molecules, and any combinations thereof.
19. The formulation of any of paragraphs 1-18, wherein the second anti-acne agent drug carrier has a size of about 5 nm to about 50 μm.
20. The formulation of any of paragraphs 1-19, wherein the second anti-acne agent drug carrier has a size of about 100 nm to about 25 μm
21. The formulation of any of paragraphs 1-20, wherein the second anti-acne agent drug carrier comprises a surface modifier on the surface thereof.
22. The formulation of any of paragraphs 1-21, wherein the surface modifier of the second anti-acne agent drug carrier is selected from the group consisting of lipids, oils, polymers, peptides, proteins, carbohydrates, glycolipids, phospholipids, lipoproteins, cationic molecules, and any combinations thereof.

23. The formulation of any of paragraphs 1-20, wherein the surface of the second anti-acne agent drug carrier is substantially free of surface modifier.

24. The formulation of any of paragraphs 1-23, further comprising an additional active agent.

25. The formulation of any of paragraphs 1-24, wherein the additional active agent is an anti-inflammatory-agent, penetration enhancer, anti-oxidant, anti-aging agent, anti-wrinkle agent, skin whitening or bleaching agent, ultraviolet (UV) light absorbing or scattering agent, skin depigmentation agent, skin regenerative agent, scar healing agent, or any combination thereof 26. The formulation of any of paragraphs 1-25, wherein the additional active agent is in the form of a drug carrier comprising a compound selected from the group consisting of lipids, oils, polymers, peptides, proteins, carbohydrates, glycolipids, phospholipids, lipoproteins, cationic molecules, and any combinations thereof.

27. The formulation of any of paragraphs 1-26, wherein the additional active agent drug carrier has a size of about 5 nm to about 100 μm.

28. The formulation of any of paragraphs 1-27, wherein the additional active agent drug carrier has a size of about 100 nm to about 25 μm.

29. The formulation of any of paragraphs 1-28, where in the additional active agent drug carrier comprises a surface modifier on the surface thereof.

30. The formulation of any of paragraphs 1-29, wherein the surface modifier of the additional active agent drug carrier is selected from the group consisting of lipids, oils, polymers, peptides, proteins, carbohydrates, glycolipids, phospholipids, lipoproteins, cationic molecules, and any combinations thereof.

31. The formulation of any of paragraphs 1-30, wherein the surface of the additional active agent drug carrier is substantially free of surface modifier.

32. The formulation of any of paragraphs 1-31, wherein the formulation further comprises a zinc compound.

33. A formulation comprising an antibacterial agent and at least one carrier or excipient, wherein the antibacterial agent is in the form of a drug carrier comprising the antibacterial agent and at least one additional compound, said additional compound selected from the group consisting of lipids, oils, polymers, peptides, proteins, carbohydrates, glycolipids, phospholipids, lipoproteins, cationic molecules, and any combinations thereof.

34. The formulation of paragraph 33, wherein the drug carrier has a size of about 5 nm to about 100 μm.

35. The formulation of paragraph 33 or 34, wherein the drug carrier has a size of about 100 nm to about 25 gam.

36. The formulation of any of paragraphs 33-35 further comprising a surface modifier on the surface of the drug carrier.

37. The formulation of any of paragraphs 33-36, wherein the surface modifier is selected from the group consisting of lipids, oils, polymers, peptides, proteins, carbohydrates, glycolipids, phospholipids, lipoproteins, cationic molecules, and any combinations thereof.

38. The formulation of any of paragraphs 33-37, wherein the surface of the drug carrier is substantially free of surface modifier.

39. The formulation of any of paragraphs 33-38, wherein the carrier or excipient is selected from the group consisting of emulsifiers, preservatives, surfactants, oils, lipids, waxes, stabilizers, rheology modifiers or thickening agents (gelling agent), emollients, moisturizers, conditioning agents, fragrances/perfumes, potentiating agents, preservatives, opacifiers, antioxidants, cooling agents, film forming agents, abrasives, exfoliating agents, colorants, pH modifiers, solvents, vehicle, penetration enhancers, pearlizing agents, and any combinations thereof 40. The formulation of any of paragraphs 33-39, comprising from about 5% to about 99% (w/w or w/v) of the carrier or excipient.

41. The formulation of any of paragraphs 33-40, wherein the formulation is formulated for topical, oral or parenteral administration.

42. The formulation of any of paragraphs 33-41, wherein the formulation is an oral dosage, injectable, aerosol or inhalant, lotion, cream, gel, emulgel, oil, serum, powder, spray, ointment, solution, suspension, dispersion, paste, foam, peel, films, mask, patch, stick, roller, impregnated fabric (e.g. a "wipe" or tissue), or any combination thereof 43. The formulation of any of paragraphs 33-42 further comprising a second antibacterial agent.

44. The formulation of any of paragraphs 33-43, wherein the second antibacterial agent is in the form of a drug carrier.

45. The formulation of any of paragraphs 33-44, wherein the second antibacterial agent drug carrier further comprises a compound selected from the group consisting of lipids, oils, polymers, peptides, proteins, carbohydrates, glyco lipids, phospho lipids, lipoproteins, cationic molecules, and any combinations thereof 46. The formulation of any of paragraphs 33-45, wherein the second antibacterial agent drug carrier has a size of about 5 nm to about 100

47. The formulation of any of paragraphs 33-46, wherein the second antibacterial agent drug carrier has a size of about 100 nm to about 25 μm.

48. The formulation of any of paragraphs 33-47, wherein the second antibacterial agent drug carrier comprises a surface modifier on the surface thereof 49. The formulation of any of paragraphs 33-48, wherein the surface modifier of the second antibacterial agent drug carrier is selected from the group consisting of lipids, oils, polymers, peptides, proteins, carbohydrates, glycolipids, phospholipids, lipoproteins, cationic molecules, and any combinations thereof.

50. The formulation of any of paragraphs 33-47, wherein the surface of the second antibacterial agent drug carrier is substantially free of surface modifier.

51. The formulation of any of paragraphs 33-50 further comprising an additional active agent.

52. The formulation of any of paragraphs 33-51, wherein the additional active agent is an anti-inflammatory-agent, penetration enhancer, permeation enhancer, anti-oxidant, anti-aging agent, anti-wrinkle agent, skin whitening or bleaching agent, ultraviolet (UV) light absorbing or scattering agent, skin depigmentation agent, skin regenerative agent, scar healing agent, or any combination thereof 53. The formulation of any of paragraphs 33-52, wherein the additional active agent is in the form of a drug carrier.

54. The formulation of any of paragraphs 33-53, wherein the additional active agent drug carrier further comprises a compound selected from the group consisting of lipids, oils, polymers, peptides, proteins, carbohydrates, glycolipids, phospholipids, lipoproteins, cationic molecules, and any combinations thereof.

55. The formulation of any of paragraphs 33-54, wherein the additional active agent drug carrier has a size of about 5 nm to about 100 μm.

56. The formulation of any of paragraphs 33-55, wherein the additional active agent drug carrier has a size of about 100 nm to about 25

57. The formulation of any of paragraphs 33-56, wherein the additional active agent drug carrier comprises a surface modifier on the surface thereof.

58. The formulation of any of paragraphs 33-57, wherein the surface modifier of the additional active agent drug carrier is selected from the group consisting of lipids, oils, polymers, peptides, proteins, carbohydrates, glycolipids, phospholipids, lipoproteins, cationic molecules, and any combinations thereof.

59. The formulation of any of paragraphs 33-56, wherein surface of the additional active agent drug carrier is substantially free of surface modifier.

60. The formulation of any of paragraphs 33-59, wherein the formulation further comprises a zinc compound.

61. The formulation of any of paragraphs 33-60, wherein the formulation comprises a moisturizing agent.

62. A Dual Action Rational Therapeutic (DART) molecule that has two distinct anti-bacterial mechanisms of action.

63. A DART molecule that has a β-lactam ring and a quinolone nucleus, or a quinolone nucleus and a nitroheterocycle, or a β-lactam ring and a nitroheterocycle.

64. The molecule of paragraph 62, wherein the molecule inhibits DNA gyrase or topoisomerase IV and transpeptidase-mediated cross-linking of peptidoglycans.

65. The molecule of paragraph 62 or 63, wherein the molecule inhibits isoprenyl pyrophosphate and transpeptidase-mediated cross-linking of peptidoglycans.

66. The molecule of any of paragraphs 62-64, wherein the molecule inhibits isoprenyl pyrophosphate and DNA gyrase of topoisomerase IV.

67. The molecule of any of paragraphs 62-65, wherein the molecule inhibits folate synthesis and DNA gyrase of topoisomerase IV.

68. The molecule of any of paragraphs 62-66, wherein the molecule inhibits folate synthesis and transpeptidase-mediated cross-linking of peptidoglycans.

69. The molecule of any of paragraphs 62-67 that inhibits DNA gyrase or topoisomerase IV and the 30S sub-unit in bacteria.

70. The molecule of any of paragraphs 62-68, wherein the molecule inhibits DNA gyrase or topoisomerase IV and the 50S sub-unit in bacteria.

71. The molecule of any of paragraphs 62-69, wherein the molecule inhibits transpeptidase-mediated cross-linking of peptidoglycans and the 30S or the 50S sub-unit in bacteria.

72. The molecule of any of paragraphs 62-70, wherein the molecule inhibits folate synthesis and the 30S or the 50S sub-unit in bacteria.

73. The molecule of any of paragraphs 62-71, wherein the molecule inhibits isoprenyl pyrophosphate and the 30S or the 50S sub-unit in bacteria.

74. A Dual Action Rational Therapeutic (DART) molecule that has two distinct anti-acne mechanisms of action.

75. The molecule of paragraph 73, wherein the molecule modulates at least two different targets.

76. The molecule of paragraph 73 or 74 wherein the first mechanism is an antibacterial action and the second mechanism of action is inhibition of keratinocyte proliferation and differentiation.

77. The molecule of any of paragraphs 73-75, wherein the first mechanism is an antibacterial action and the second mechanism of action is anti-inflammatory.

78. A Dual Action Rational Therapeutic (DART) molecule which includes two chemical domains, each said chemical domain binding to a distinct active site in target cells, wherein said chemical domains are bound together through a third domain.

79. The molecule of paragraph 77, wherein the third domain is a linker.

80. The molecule of paragraph 77 or 78, wherein the third domain is a cleavable linker.

81. The molecule of paragraph 77 or 78, wherein the third domain is a non-cleavable linker.

82. The molecule of paragraphs 77-80, wherein said third domain is 11-hydroxyundecenic acid; 1,10-decanediol; 1,3-propanediol; 1,5-pentanedil; 10-hydroxydecenic acid; succinic; lactic acid; 3-hydroxypropionic acid; or any combination thereof.

83. The molecule of any of paragraphs 77-81, wherein the third domain increases an activity of at least one of the two chemical domains.

84. The molecule of any of paragraphs 77-82, wherein the third domain has antibacterial or anti-inflammatory activity.

85. The molecule of any of paragraphs 62-83, wherein the molecule is in the form of a drug carrier.

86. The molecule of any of paragraphs 62-84, wherein the drug carrier has a size of about 5 μm to about 100 μm 87. The molecule of any of paragraphs 62-85, wherein the drug carrier has a size of about 100 nm to about 25 μm.

88. The molecule of any of paragraphs 62-86, wherein the drug carrier further comprises a compound selected from the group consisting of lipids, oils, polymers, peptides, proteins, carbohydrates, glycolipids, phospholipids, lipoproteins, cationic molecules, and any combinations thereof.

89. The molecule of any of paragraphs 62-87, wherein the drug carrier further comprises an additional active agent.

90. The molecule of paragraph 88, wherein the additional active agent is an anti-inflammatory-agent, keratolytic agent, penetration enhancer, anti-oxidant, anti-aging agent, anti-wrinkle agent, skin whitening or bleaching agent, ultraviolet (UV) light absorbing or scattering agent, skin depigmentation agent, skin regenerative agent, scar healing agent, or any combination thereof.

91. The molecule of any of paragraphs 62-89, wherein surface of the drug carrier is substantially free of surface modifier.

92. The molecule of any of paragraphs 62-90, wherein the drug carrier further comprises an additional anti-acne agent.

93. The molecule of any of paragraphs 62-91, wherein the second anti-acne agent is selected from the group consisting of acetretin, adapalene(s), alitretinoin, alpha- or beta-hydroxy acids, antibiotics, antimicrobial peptides, antimicrobials, azelaic acid, benzoyl peroxide, bexarotene, bile salts, biofilm inhibitors, clindamycin, erythromycin, etretinate, glycolic acid, isotretinoin, keratolytic agents, lactic acid, lipoic acid, N-acetylcystein, natural anti-acne agents, octopirox, phenoxyethanol, phenoxypropanol, pyruvic acid, resorcinol, retinoic acid, retinoid(s), salicylic acid, sebostats, sodium sulfacetamide, spironolactone, sulfur, sulfur containing D- or L-amino acids, tazarotene, tea tree oil, tretinoin, triclosan, urea, and any combinations thereof 94. The molecule of any of paragraphs 62-92, wherein the drug carrier further comprises a surface modifier on the surface thereof.

95. The molecule of any of paragraphs 62-93, wherein the surface modifier is a compound selected from the group consisting of lipids, oils, polymers, peptides, proteins, carbohydrates, glycolipids, phospholipids, lipoproteins, cationic molecules, and any combination thereof.

96. A formulation comprising a dual action rational therapeutic molecule of any of paragraphs 62-94 and at least one carrier or excipient.

97. The formulation of paragraph 95, wherein the carrier or excipient is selected from the group consisting of emulsifiers, preservatives, surfactants, oils, lipids, waxes, stabilizers, rheology modifiers or thickening agents (gelling agent), emollients, moisturizers, conditioning agents, fragrances/perfumes, potentiating agents, preservatives, opacifiers, antioxidants, cooling agents, film forming agents, abrasives, exfoliating agents, colorants, pH modifiers, solvents, vehicle, penetration enhancers, permeation enhancers, pearlizing agents, and any combinations thereof.

98. The formulation of paragraph 95 or 96 comprising from about 5% to about 99% (w/w or w/v) of the carrier or excipient.

99. The formulation of any of paragraphs 95-97, wherein the formulation is formulated for topical, oral or parenteral administration.

100. The formulation of any of paragraphs 95-98, wherein the formulation is an oral dosage, injectable, aerosol or inhalant, lotion, cream, gel, emulgel, oil, serum, powder, spray, ointment, solution, suspension, dispersion, paste, foam, peel, films, mask, patch, stick, roller, impregnated fabric (e.g. a "wipe" or tissue), or any combination thereof.

101. The formulation of any of paragraphs 95-99 further comprising a second anti-acne agent.

102. The formulation of any of paragraphs 95-100, wherein the second anti-acne agent is selected from the group consisting of acetretin, adapalene(s), alitretinoin, alpha- or beta-hydroxy acids, antibiotics, antimicrobial peptides, antimicrobials, azelaic acid, benzoyl peroxide, bexarotene, bile salts, biofilm inhibitors, clindamycin, erythromycin, etretinate, glycolic acid, isotretinoin, keratolytic agents, lactic acid, lipoic acid, N-acetylcystein, natural anti-acne agents, octopirox, phenoxyethanol, phenoxypropanol, pyruvic acid, resorcinol, retinoic acid, retinoid(s), salicylic acid, sebostats, sodium sulfacetamide, spironolactone, sulfur, sulfur containing D- or L-amino acids, tazarotene, tea tree oil, tretinoin, triclosan, urea, and any combinations thereof 103. The formulation of any of paragraphs 95-101, wherein the second anti-acne agent is in the form of a drug carrier.

104. The formulation of any of paragraphs 95-102, wherein the second anti-acne agent drug carrier further comprises a compound selected from the group consisting of lipids, oils, polymers, peptides, proteins, carbohydrates, glycolipids, phospholipids, lipoproteins, cationic molecules, and any combinations thereof 105. The formulation of any of paragraphs 95-103, wherein the second anti-acne agent drug carrier has a size of about 5 nm to about 100 μm.

106. The formulation of any of paragraphs 94-103, wherein the second anti-acne agent drug carrier has a size of about 100 nm to about 25 μm.

107. The formulation of any of paragraphs 95-105, wherein the second anti-acne agent drug carrier comprises a surface modifier on the surface thereof 108. The formulation of any of claims 95-106, wherein the surface modifier of the second anti-acne agent drug carrier is selected from the group consisting of lipids, oils, polymers, peptides, proteins, carbohydrates, glycolipids, phospholipids, lipoproteins, cationic molecules, and any combinations thereof.

109. The formulation of any of paragraphs 95-105, wherein surface of the second anti-acne agent is substantially free of surface modifier.

110. The formulation of any of paragraphs 95-108 further comprising an additional active agent.

111. The formulation of any of paragraphs 95-109, wherein the additional active agent is an anti-inflammatory-agent, penetration enhancer, anti-oxidant, anti-aging agent, anti-wrinkle agent, skin whitening or bleaching agent, ultraviolet (UV) light absorbing or scattering agent, skin depigmentation agent, skin regenerative agent, scar healing agent, or any combination thereof 112. The formulation of any of paragraphs 95-110, wherein the additional active agent is in the form of a drug carrier.

113. The formulation of any of paragraphs 95-111, wherein the additional active agent drug carrier further comprises a compound selected from the group consisting of lipids, oils, polymers, peptides, proteins, carbohydrates, glycolipids, phospholipids, lipoproteins, cationic molecules, and any combinations thereof 114. The formulation of any of paragraphs 95-112, wherein the additional active agent drug carrier has a size of about 5 nm to about 100 μm.

115. The formulation of any of paragraphs 95-113, wherein the additional active agent drug carrier has a size of about 100 nm to about 25 μm.

116. The formulation of any of paragraphs 95-114, wherein the additional active agent drug carrier comprises a surface modifier on the surface thereof 117. The formulation of any of paragraphs 95-115, wherein the surface modifier of the additional active agent drug carrier is selected from the group consisting of lipids, oils, polymers, peptides, proteins, carbohydrates, glycolipids, phospholipids, lipoproteins, cationic molecules, and any combinations thereof.

118. The formulation of any of paragraphs 95-114, wherein surface of the additional active agent drug carrier is substantially free of surface modifier.

119. The formulation of any of paragraphs 95-117, wherein the formulation further comprises a zinc compound.

120. A method of treating acne condition in a subject comprising administering a therapeutically effective amount of a formulation of any of paragraphs 1-61 and 95-118.

121. The method of any of paragraph 119, wherein the acne condition is caused by antibiotic susceptible bacterial strain.

122. The method of paragraph 119 or 120, wherein the acne condition is caused by antibiotic resistant bacteria.

123. The method of any of paragraphs 119-121, wherein the acne condition is caused by clindamycin-, tetracycline-, doxycycline-, or erythromycin-resistant *Propionbacterium acnes*.

124. The method of any of paragraphs 119-122, wherein the acne condition is caused by clindamycin-, tetracycline-, doxycycline-, or erythromycin-tolerant *Propionbacterium acnes*.

125. A method of treating a bacterial infection in a subject comprising administering a therapeutically effective amount of a formulation of any of paragraphs 1-61 and 95-118.

126. The method of paragraph 124, wherein the infection is caused by a pathogen selected from the group consisting of *Bartonella henselae, Borrelia burgdorferi, Campylobacter jejuni,* Campylobacterfetus, *Chlamydia trachomatis, Chlamydia pneumoniae, Chylamydia psittaci, Simkania negevensis, Escherichia coli* (e.g., O157:H7 and K88), *Ehrlichia chafeensis, Clostridium botulinum, Clostridium perfringens, Clostridium tetani, Enterococcus faecalis, Haemophilius influenzae, Haemophilius ducreyi, Coccidioides immitis, Bordetella pertussis, Coxiella burnetii, Ureaplasma urealyticum, Mycoplasma genitalium, Trichomatis vaginalis, Helicobacter pylori, Helicobacter hepaticus, Legionella pneumophila, Mycobacterium tuberculosis, Mycobacterium bovis, Mycobacterium africanum, Mycobacterium leprae, Mycobacterium asiaticum, Mycobacterium avium, Mycobacterium celatum, Mycobacterium celonae, Mycobacterium fortuitum, Mycobacterium genavense, Mycobacterium haemophilum, Mycobacterium intracellulare, Mycobacterium kansasii, Mycobacterium malmoense, Mycobacterium marinum, Mycobacterium scrofulaceum, Mycobacterium simiae, Mycobacterium szulgai, Mycobacterium ulcerans, Mycobacterium xenopi, Corynebacterium diptheriae, Rhodococcus equi, Rickettsia aeschlimannii, Rickettsia africae, Rickettsia conorii, Arcanobacterium haemolyticum, Bacillus anthracis, Bacillus cereus, Lysteria monocytogenes, Yersinia pestis, Yersinia enterocolitica, Shigella dysenteriae, Neisseria meningitides, Neisseria gonorrhoeae, Streptococcus bovis, Streptococcus hemolyticus, Streptococcus mutans, Streptococcus pyogenes, Streptococcus pneumoniae, Staphylococcus aureus, Staphylococcus epidermidis, Staphylococcus pneumoniae, Staphylococcus saprophyticus, Vibrio cholerae, Vibrio parahaemolyticus, Salmonella typhi, Salmonella paratyphi, Salmonella enteritidis, Treponema pallidum, Candida, Cryptcooccus, Cryptosporidium, Giardia lamblia, Microsporidia, Plasmodium vivax, Pneumocystis carinii, Toxoplasma gondii, Trichophyton mentagrophytes, Enterocytozoon bieneusi, Cyclospora cayetanensis, Encephalitozoon hellem, Encephalitozoon cuniculi,* among other bacteria, archaea, protozoa, and fungi.

127. The method of paragraph 124 or 125, wherein the infection is by an antibiotic resistant bacterial strain.

128. The method of any of paragraphs 124 or 125, wherein the infection is by an antibiotic susceptible bacterial strain.

129. The method of any of paragraphs 124-127, wherein the formulation is administered once or daily to said subject as a single dose or a plurality of doses.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials can be used in the practice or testing of the invention, the methods, devices, and materials in this regard are described herein.

As used herein, the term "herein" is means the whole of the disclosure and as such is not meant to be limited to a particular section or subsection of the disclosure.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages can mean±5%, ±4%, ±3%, ±2.5%, ±2%, ±1.5%, ±1%, or ±0.5% of the value being referred to.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

The term "globule" as used herein refers to spherical or quasi-spherical globes, balls or other shaped particles of a substance such as form in biphasic suspensions or emulsions. Also included in the meaning of the term "globule" are finely divided particles of a solid material.

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1

Screening of antibiotics against *P. acnes* strains shows that the response is unpredictable in both clindamycin-sensitive and non-responder strains Examples 2-15 and Tables 6-15 describe some exemplary DART molecules, their synthesis, formulations and uses.

Example 2: Synthesis of DART Molecule 9 (from Table 1A)

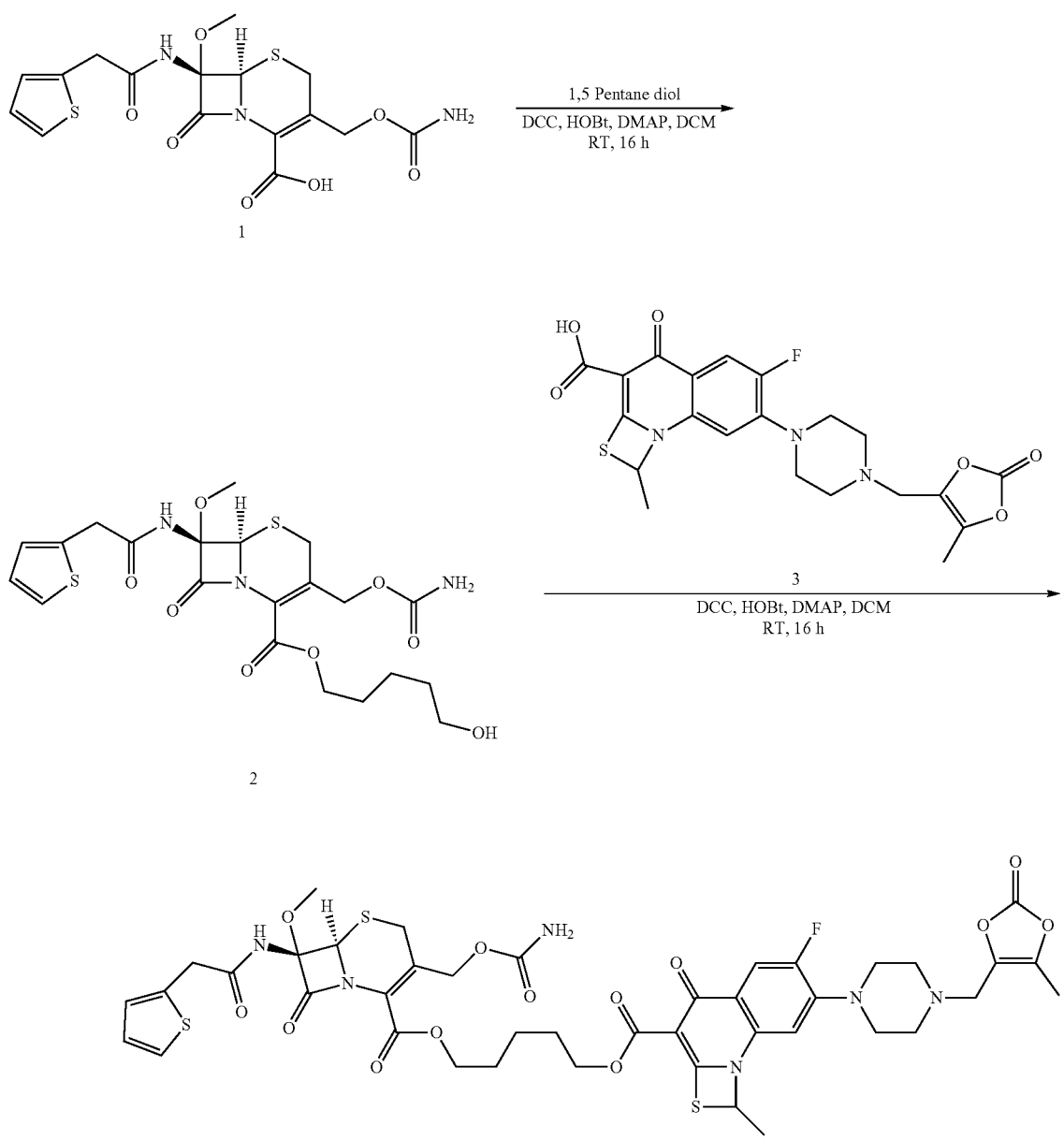

Step 1. Synthesis of 2: To a solution of 1 (1 g, 2.33 mmol) in mixture of dichloromethane (10 ml) and dimethylformamide (1 ml) was added N,N-dicyclohexylcarbodiimide (0.627 g, 3.041 mmol) followed by N-Hydroxybenzatriazole (0.316 g, 2.33 mmol) slowly at ice cold condition and stirred at RT for 2 h to obtain turbid suspension. To this turbid solution pentanediol (0.85 ml, 8.18 mmol) was added followed by 4-dimethylaminopyridine (0.284 g, 2.33 mmol). The final reaction mixture was stirred at RT for 16 h. The white precipitate was filtered and extracted with ethyl acetate. The filtrate was washed with brine solution, dried over sodium sulphate and evaporated to get crude mass. The crude product was purified by flash column chromatography eluting with 1% methanol/dichloromethane to obtain pure compound, 2 (0.9 g, 80% yield).

suspension. The reaction mixture was stirred for 3 hr at RT and compound 2 (0.79 g, 1.55 mmol) was added to this turbid solution followed by addition of 4-dimethylaminopyridine (0.189 g 1.55 mmol). The final solution was stirred at RT for 16 h. The precipitate was filtered, and the filtrate was extracted with ethyl acetate. The organic layer was washed with brine solution and dried over sodium sulphate to obtain the crude product. The crude product was purified by flash column chromatography to get the final product (9) in 50-60% isolated yield.

Example 2: Synthesis of DART Molecule 87 (from Table 1A)

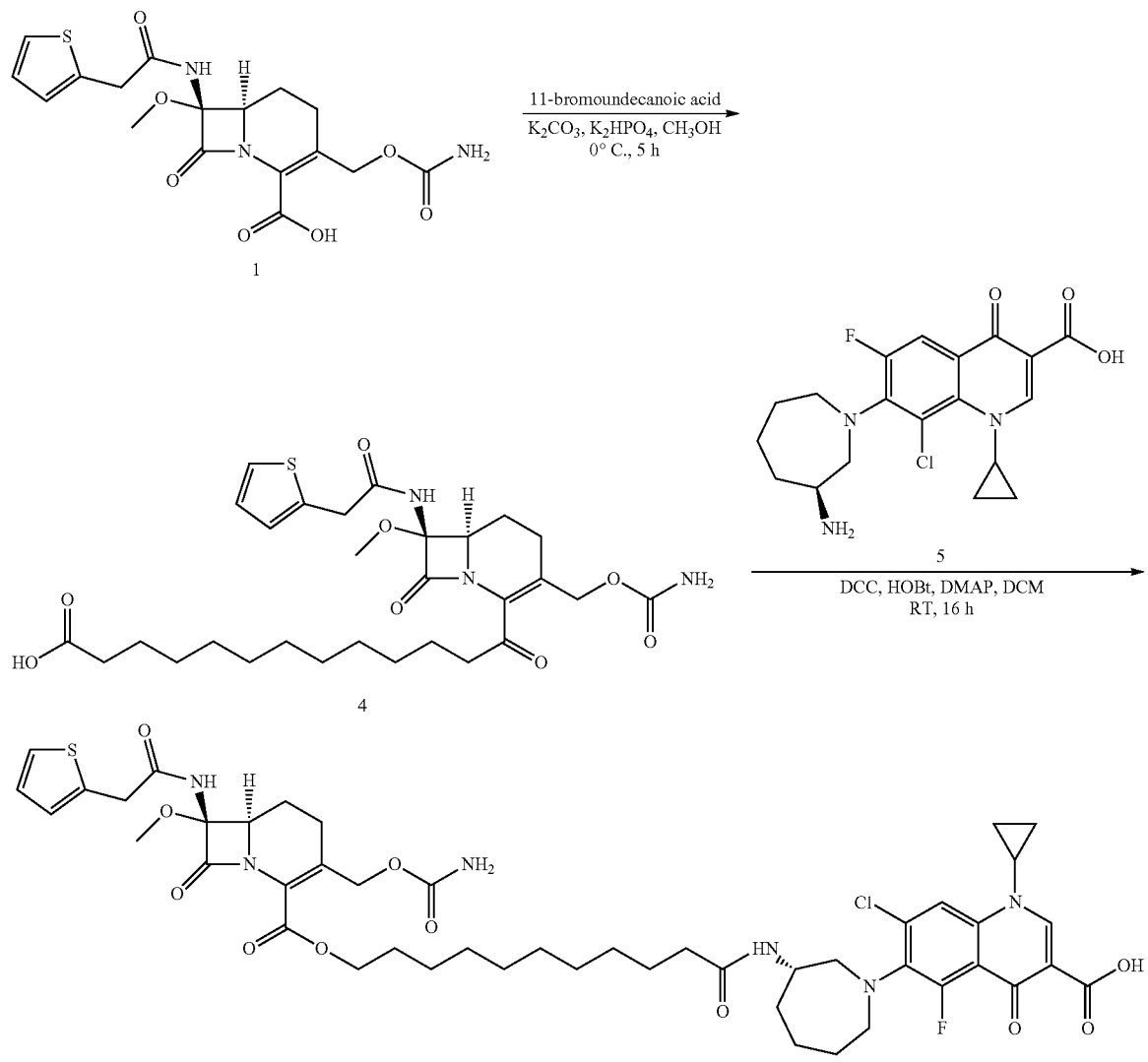

Step 2. Synthesis of DART, 9: To a solution of 3 (0.72 g, 1.55 mmol) in mixture of dichloromethane (10 ml) and dimethylformamide (1 ml) was added dicyclohexylcarbodiimide (0.415 g, 2.05 mmol) followed by N-Hydroxybenzatriazole (0.209 g, 1.55 mmol) at RT to provide turbid Step 1. Synthesis of 4: 11-Bromoundecanoic acid (1.33 g, 5.04 mmol) was pre-mixed with the methanol (0.1 ml) was added into a stirred mixture of 1 (1 g, 2.52 mmol), potassium carbonate (0.243 g, 1.764 mmol), and dipotassium-hydrogenphosphate (0.175 g, 1 mmol) in N,N-dimethylacetamide (15 ml) at 0-5° C. The reaction mixture was stirred at 0° C. for 5 hr and extracted with ethyl acetate (50 ml). The final solution was washed with 3% aqueous sodium bicarbonate solution (10 ml) followed by brine solution (10 ml). The organic solvent was evaporated to give crude mass and finally purified by flash column chromatography. The compound was eluted with 1-3% methanol/dichloromethane to obtain pure compound, 4 (1.2 g, 82% yield).

Step-2: Synthesis of DART, 87: To a solution of Compound 4 (1 g, 1.72 mmol) in dichloromethane (10 ml) and 1 ml dimethylformamide was added dicyclohexylcarbodiimide (0.461 g, 2.23 mmol) followed by N-Hydroxybenzatriazole (0.232 g, 1.72 mmol) at RT to provide turbid suspension. The reaction mixture was stirred for 1 hr at RT. To this turbid solution 5 (0.67 g, 1.72 mmol) was added followed by DMAP (0.210 g, 1.72 mmol) and the reaction mixture was stirred at RT for 16 h. The suspension was filtered and washed with brine solution. The organic layer was dried over sodium sulphate and evaporated to obtain the crude mass. Finally the crude was purified by flash column chromatography using 2-5% methanol/dichloromethane as eluent to obtain the pure compound, 87 with 60-65% isolated yield.

Example 3: Synthesis of DART Molecule 90 (from Table 1B)

Bromo-acetic acid 1-chloromethyl-2-(2-methyl-5-nitro-imidazol-1-yl)-ethyl ester (II) was synthesized according to the following scheme.

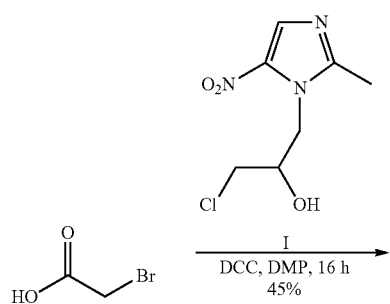

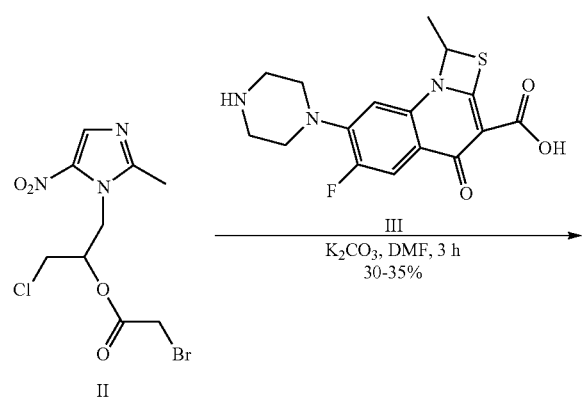

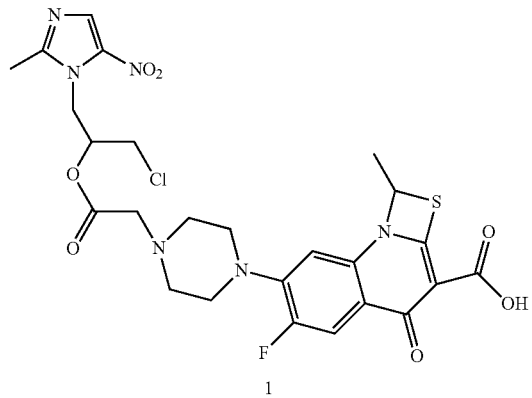

Note: Compound 1 in the scheme corresponds to compound 90 from Table 1B

To a stirred solution of 1-Chloro-3-(2-methyl-5-nitro-imidazol-1-yl)-propan-2-ol, (I) (0.79 g, 3.6 mmol) in dichloromethane (10 ml) was added dicyclohexylcarbadiimide (DCC) (0.9 g, 4.31 mmol) followed by bromoacetic acid (0.5 g, 3.6 mmol) and DMAP (0.44 g, 3.6 mmol) at RT. The reaction mixture was stirred at RT for 16 h. The precipitate was removed by filtration and the organic layer was evaporated to get the crude that was purified by flash column chromatography. The final compound was eluted with 1-2% methanol/dichloromethane mixture. The compound was used for the next step without further characterization.

Synthesis of 7-{4-[1-Chloromethyl-2-(2-methyl-5-nitro-imidazol-1-yl)-ethoxycarbonylmethyl]-piperazin-1-yl}-6-fluoro-1-methyl-4-oxo-4H-2-thia-8b-aza-cyclobuta[a]naphthalene-3-carboxylic acid (1)

To a stirred solution of 6-Fluoro-1-methyl-4-oxo-7-piperazin-1-yl-4H-2-thia-8b-aza-cyclobuta[a]naphthalene-3-carboxylic acid, (III) (0.071 g, 0.2 mmol) in dimethylformamide (10 ml) was added potassium carbonate (0.04 g, 0.3 mmol) followed by addition of compound (II) (0.1 g, 0.3 mmol) and the reaction mixture was stirred at RT for 3 h. The reaction mixture was diluted with ethylacetate, washed two times with water and finally dried over sodium sulphate to obtain the crude mass. The crude was purified by flash column chromatography while eluting with 3-5% methanol/dichloromethane mixture to obtain the pure compound (1), i.e., Compound 90 from Table 1, with 30% isolated yield.

$^1$H-NMR (400 MHz, DMSO) δ ppm: 2.19 (3H, d, J=6.4 Hz, CH$_3$), 2.57 (3H, s, CH$_3$), 2.7 (4H, m, 2×CH$_2$), 3.1-3.3 (2H, s, COCH$_2$), 3.32 (4H, m, 2×CH$_2$), 3.77-3.90(2H, ddd, J$_1$=3.6 Hz, J$_2$=12.4 Hz, J$_3$=35.2 Hz, CH$_2$Cl), 4.40-4.56 (1H, dd, J$_1$=9.6 Hz, J$_2$=14 Hz CHN), 4.76 (1H, d, J=14 Hz, CHN), 5.44 (1H, d, J=5.6 Hz CHOCO), 6.0-6.11 (1H, q, J$_1$=6 Hz, J$_2$=12.4 Hz, CHSN), 6.4 (1H, d, J$_1$=6.8 Hz Ar—H), 7.8 (1H, d, J=14 Hz, Ar—H), 8.04 (1H, s, Ar—H). ESI-MS (m/z): 609 (M+H)$^+$.

Example 4: Synthesis of DART Molecule 91 from Table 1B

2-Methyl-5-nitro-1-oxiranylmethyl-1H-imidazole(IV) was synthesized according to the following scheme.

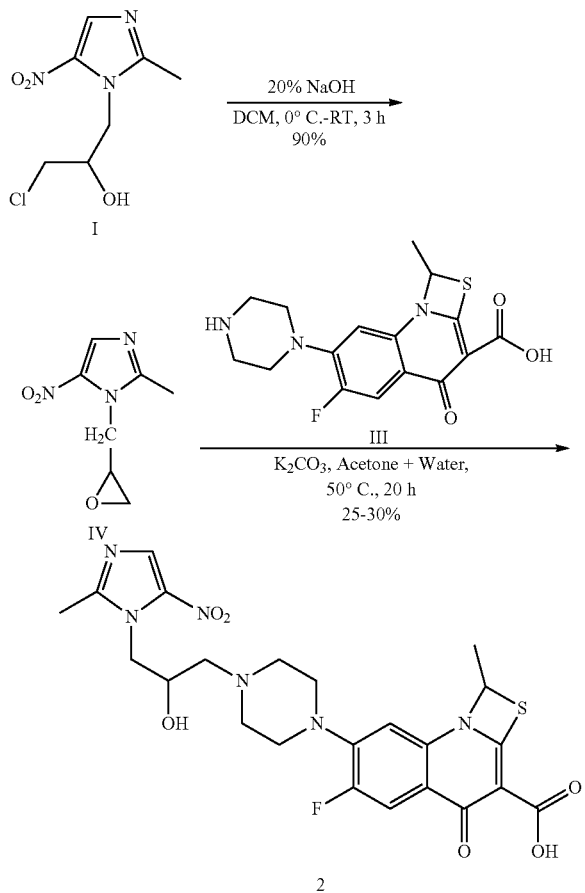

Note:
Compound 2 in the scheme corresponds to compound 91 from Table 1B

To a stirred solution of 1-Chloro-3-(2-methyl-5-nitro-imidazol-1-yl)-propan-2-ol, (I) (0.5 g, 2.27 mmol) in dichloromethane (8 ml) was added 20% Sodium hydroxide (4 ml) at 0° C. The reaction mixture was stirred for 3 h at 0° C. After 3 h the reaction mixture was extracted twice with dichloromethane, the organic layers were combined, washed with brine and finally dried over sodium sulphate to obtain pure product with 90% isolated yield. $^1$H-NMR (400 MHz, CDCl$_3$) δppm: 2.517 (3H, s, CH$_3$), 2.52 (1H, m, CH$_2$), 2.88 (1H, m, CH$_2$), 3.38 (1H, m, CH), 4.17-4.23 (1H, dd, J$_1$=6 Hz, J$_2$=15.2 Hz CH$_2$), 4.85-4.89 (1H, d, J=14.8 CH$_2$).

Synthesis of 6-Fluoro-7-{4-[2-hydroxy-3-(2-methyl-5-nitro-imidazol-1-yl)-propyl]-piperazin-1-yl}-1-methyl-4-oxo-4H-2-thia-8b-aza-cyclobuta[a]naphthalene-3-carboxylic acid (2)

To a stirred solution of 6-Fluoro-1-methyl-4-oxo-7-piperazin-1-yl-4H-2-thia-8b-aza-cyclobuta[a]naphthalene-3-carboxylic acid, (III) (0.2 g, 0.57 mmol) in acetone (15 ml) was added potassium carbonate (0.11 g, 0.19 mmol) dissolved in water (5 ml), followed by addition of epoxy ornidazole, (II) (0.15 g, 0.82 mmol). The reaction mixture was heated at 50° C. for 20 hr. After completion, the reaction mixture was evaporated and extracted twice with dichloromethane. The combined organic layer was dried over sodium sulphate and evaporated to obtain the crude mass. The crude mass was purified by column chromatography by eluting with 10-12% methanol/dichloromethane mixture to obtain the pure compound (2), i.e., Compound 91 from Table 1, with 25-30% isolated yield. $^1$H-NMR (400 MHz, DMSO) δ ppm: 2.12 (3H, d, J=6.4 Hz, CH$_3$), 2.46 (3H, s, CH$_3$), 2.58-2.60 (2H, t, J=5.6 Hz CH$_2$N), 2.66 (4H, m, 2×CH$_2$), 3.2 (4H, m, 2×CH$_2$N), 3.9-4.1 (2H, m, 2×CH$_2$N), 4.63 (1H, d, J=14 Hz, CHOH), 5.15 (1H, d, J=5.2 Hz —OH), 6.39 (1H, d, J=6.4 Hz, CHSN) 6.93 (1H, d, J=7.2 Hz, Ar—H), 7.79 (1H, d, J=14 Hz, Ar—H), 8.04 (1H, s, Ar—H). ESI-MS (m/z): 532.95 (M+H).

Example 5: Synthesis of DART Molecule 94 from Table 1B

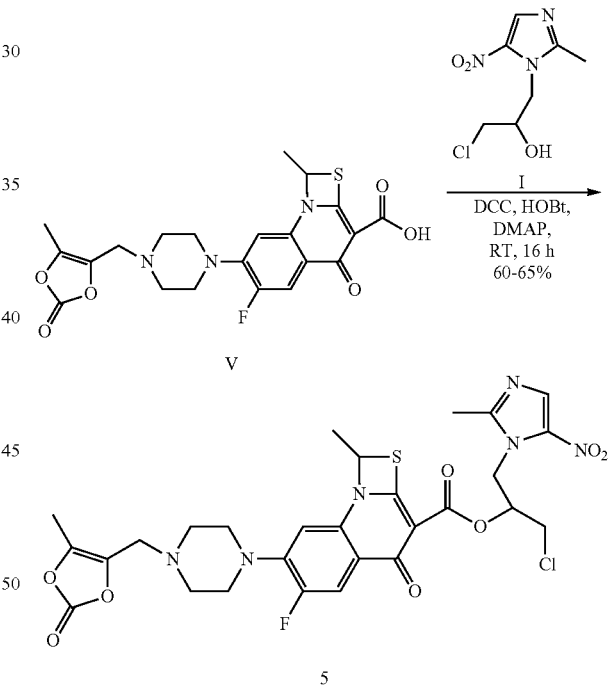

Note: Compound 5 in the scheme corresponds to compound 94 from Table 1B

Synthesis of 6-Fluoro-1-methyl-7-[4-(5-methyl-2-oxo-[1,3]dioxol-4-ylmethyl)-piperazin-1-yl]-4-oxo-4H-2-thia-8b-aza-cyclobuta[a]naphthalene-3-carboxylic acid 1-chloromethyl-2-(2-methyl-5-nitro-imidazol-1-yl)-ethyl ester (5)

To a stirred solution of 6-Fluoro-1-methyl-7-[4-(5-methyl-2-oxo-[1,3]dioxol-4-ylmethyl)-piperazin-1-yl]-4-oxo-4H-2-thia-8b-aza-cyclobuta[a]naphthalene-3-carboxylic acid, (V) (0.5 g, 1.08 mmol) in DMF (20 ml) was added DCC (0.3 g, 1.41 mmol) and HOBt (0.146 g, 1.083 mmol) followed by addition of 1-Chloro-3-(2-methyl-5-nitro-imidazol-1-yl)-propan-2-ol, (I) (0.285 g, 1.3 mmol) and DMAP (0.13 g, 1.08 mmol) at room temperature. The reaction mixture was stirred at RT for 16 h. The precipitate was removed by filtration and the organic layer was evaporated to get the crude mass. Finally it was purified by flash column chromatography eluting with 2-4% methanol/dichloromethane mixture to obtain the pure compound, (5), i.e., Compound 94 from Table 1, with 60% isolated yield. $^1$H-NMR (400 MHz, DMSO) δppm: 2.03 (3H, d, J=5.6 Hz, CH$_3$), 2.12 (3H, s, CH$_3$), 2.5 (3H, s, CH$_3$), 2.62 (4H, m, 2×CH$_2$), 3.22 (4H, m, 2×CH$_2$), 3.95-4.06 (2H, m, CH$_2$Cl), 4.49-4.52 (1H, t, J=10 Hz, CHN) 4.77 (1H, d, J=13.2 Hz, CHN), 5.63(1H, d, J=4.4 Hz, CHOCO), 6.15 (1H, m, CHSN), 6.78 (1H, d, J=7.2, Ar—H), 7.68 (1H, d, J=14, Ar—H), 7.9 (1H, s, Ar—H).

Example 6: Synthesis of DART Molecule 116 from Table 1B

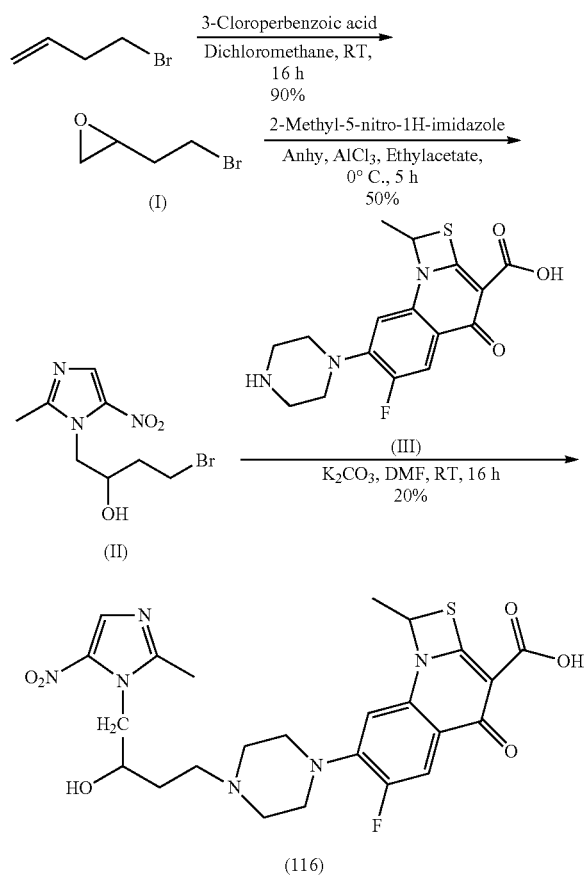

Synthesis of 4-Bromo-1,2-Epoxybutane (I)

A Solution of 3-Chloroperbenzoic acid (55-75% pure, 1.60 g, 9.25 mmol) in 10 ml dichloromethane was added dropwise to a stirred solution of 4-bromo-1-butene (0.5 g, 3.7 mmol) in 20 ml of dichloromethane. After addition, the mixture was stirred at 25° C. for 16 h, to precipitate 3-chlorobenzoic acid. Finally the reaction mixture was evaporated to dryness under vacuum, dissolved in ethyl acetate, washed initially with 4% sodium dithionate followed by saturated sodium bicarbonate and water. Finally the organic layer was dried over sodium sulphate, evaporated and dried under vacuo to obtain the final compound (I) with 90% isolated yield. $^1$H-NMR (400 MHz, CDCl$_3$) δppm: 2.10 (m, 2H, CH$_2$) 2.58 (s, 1H, OCH$_a$) 2.82 (1H, m, OCH$_b$), 3.09 (m, 1H, CH) 3.55 (t, J=6.4, 2H, CH$_2$—Br).

Synthesis of 4-Bromo-1-(2-methyl-5-nitro-imidazol-1-yl)-butan-2-ol (II)

To a stirred solution of 2-methyl-5-nitro-1H-imidazole (0.8 g, 6.3 mmol) in dry ethyl acetate was added anhydrous Aluminium chloride (1.67 g, 12.5 mmol) at 0° C. and allowed to stir for 15 min to dissolve 2-methyl-5-nitro-1H-imidazole. After that 4-bromo-1,2-epoxybutane (I), (1.9 g, 12.5 mmol) was added dropwise into the reaction mixture and the reaction was continued for 5 h at 0° C. The reaction mixture was slowly added into Ice water and pH was adjusted to 1 by adding concentrated HCl. The organic layer was separated, washed with saturated sodium bicarbonate followed by water. The aqueous layer obtained from the first separation adjusted to pH 7.4 using liquor ammonia and extracted with ethyl acetate. The combined organic layer was dried over sodium sulphate and evaporated in vacuo to obtain crude compound rude was purified by flash column chromatography while eluting with 2-3% methanol/dichloromethane mixture to obtain the pure compound (II) with 50% isolated yield. ESI-MS (m/z): 277 (M)$^+$.

Synthesis of 6-Fluoro-7-{4-[3-hydroxy-4-(2-methyl-5-nitro-imidazol-1-yl)-butyl]-piperazin-1-yl}-1-methyl-4-oxo-4H-2-thia-8b-aza-cyclobuta[a]naphthalene-3-carboxylic acid (116)

To a stirred solution of 6-Fluoro-1-methyl-4-oxo-7-piperazin-1-yl-4H-2-thia-8b-aza-cyclobuta[a]naphthalene-3-carboxylic acid, (III) (3 g, 8.6 mmol) in DMF (30 ml) was added potassium carbonate (1.20 g, 8.6 mmol) followed by addition of compound (II) (2 g, 7.2 mmol) and the reaction mixture was stirred at RT for 16 h. The reaction mixture was diluted with ethyl acetate, washed twice with water and finally dried over sodium sulphate to obtain the crude mass. The crude was purified by flash column chromatography while eluting with 3-5% methanol/dichloromethane mixture to obtain the pure compound (116) with 20% isolated yield. $^1$H-NMR (400 MHz, DMSO) δppm: 1.61-1.68 (2H, m, CH$_2$), 2.12 (3H, d, J=6 Hz, CH$_3$), 2.46 (3H, s, CH$_3$), 2.57 (4H, m, 2×CH$_2$), 3.2 (4H, m, 2×CH$_2$), 3.8-4.1 (2H, m, 2×'CH$_2$N), 4.44(1H, m, CHOH), 5.2 (1H, bs, CHOH), 6.4 (1H, q, J$_1$=5.6 Hz, J$_2$=11.6 Hz, CHSN) 6.91 (1H, d, J=7, Ar—H), 7.78 (1H, d, J=13.6 Hz, Ar—H), 8.04 (1H, s, Ar—H). ESI-MS (m/z): 547.08 (M+H)$^+$.

Example 7: Synthesis of DART Molecule 113 from Table 1B

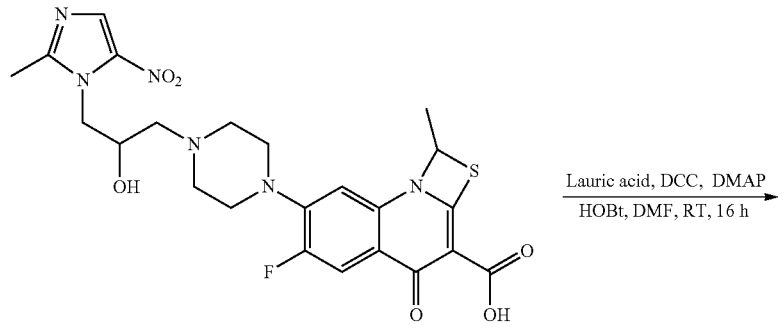

91

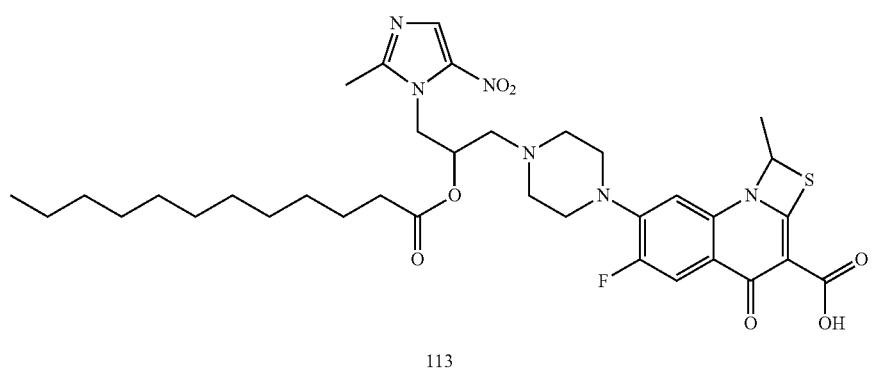

113

Synthesis of 7-{4-[2-Dodecanoyloxy-3-(2-methyl-5-nitro-imidazol-1-yl)-propyl]-piperazin-1-yl}-6-fluoro-1-methyl-4-oxo-4H-2-thia-8b-aza-cyclobuta[a]naphthalene-3-carboxylic acid (113)

To a solution of 91 (0.5 g, 0.94 mmol) in dimethylformamide (15 ml) was added N,N-dicyclohexylcarbodiimide (0.29 g, 1.41 mmol) followed by N-hydroxybenzatriazole (0.13 g, 0.94 mmol) slowly at ice cold condition and stirred at RT for 10 min to obtain turbid suspension. To this turbid solution lauric acid (0.28 g, 1.5 mmol) was added followed by 4-dimethylaminopyridine (0.115 g, 0.94 mmol). The final reaction mixture was stirred at RT for 16 h. The white precipitate was filtered and extracted with ethyl acetate. The filtrate was washed with water and brine solution, dried over sodium sulphate and evaporated to get crude mass. The crude product was purified by flash column chromatography eluting with 2-3% methanol/dichloromethane to obtain pure compound 113 with 35% isolated yield. $^1$H-NMR (400 MHz, CDCl$_3$) δppm: 0.86(3H, t, J=6 Hz, CH$_3$), 1.05-1.38 (18H, m, —CH$_2$), 1.48-1.70(4H, m, —CH$_2$), 1.90-1.93(2H, d, J=11.6 Hz, CH$_3$), 2.16-2.22 (3H, m, CH$_3$), 2.53 (3H, s, CH$_3$), 2.58-2.69 (2H, m, CH$_2$N), 2.69-2.87 (4H, m, 2×CH$_2$), 3.2-3.4 (4H, m, 2×CH$_2$), 4.1-4.25 (2H, m, 2×CH$_2$N), 5.0 (1H, s, CHOH), 6.09(1H, d, J=5.2 Hz, CHSN), 6.41 (1H, d, J=6.8 Hz Ar—H), 7.92 (1H, d, J=14.8 Hz, Ar—H), 8.04 (1H, s, Ar—H). ESI-MS (m/z): 715.2 (M+H)

Example 8: Synthesis of DART Molecule 115 from Table 1B

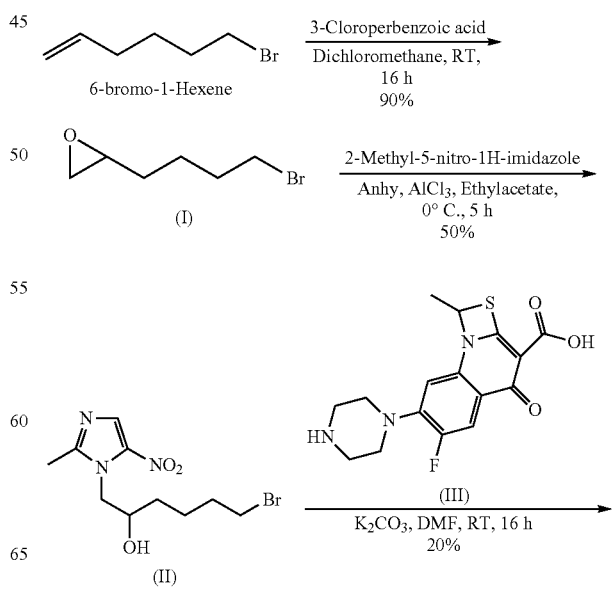

-continued

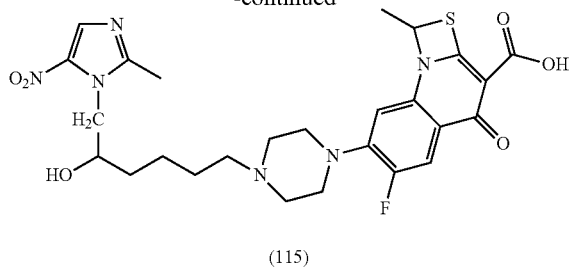

(115)

Synthesis of 2-(4-bromobutyl)-oxirane (I)

A Solution of 3-Chloroperbenzoic acid (55-75% pure, 4.54 g, 18.39 mmol) in 20 ml dichloromethane was added dropwise to a stirred solution of 6-bromo-1-hexene (2 g, 12.26 mmol) in 20 ml of dichloromethane. After addition, the mixture was stirred at 25° C. for 16 h, to precipitate 3-chlorobenzoic acid. Finally the reaction mixture was evaporated to dryness under vacuum, dissolved in ethyl acetate, washed initially with 4% sodium dithionate followed by saturated sodium bicarbonate and water. Finally the organic layer was dried over sodium sulphate, evaporated and dried under vacuo to obtain the final compound (I) with 90% isolated yield. $^1$H-NMR (400 MHz, CDCl$_3$) δ ppm: $^1$H-NMR (400 MHz, CDCl$_3$) δ ppm: 1.48-1.6 (6H, m, CH$_2$) 2.47 (1H, d, J=2.4, OCH) 2.75 (t, J=4, 1H, OCH$_b$), 2.91 (bs, 1H, OCH$_a$) 3.41 (t, J=6.4, 2H, CH$_2$—Br)

Synthesis of 6-Bromo-1-(2-methyl-5-nitro-imidazol-1-yl)-hexan-2-ol (II)

To a stirred solution of 2-methyl-5-nitro-1H-imidazole (0.7 g, 5.5 mmol) in dry ethyl acetate was added anhydrous aluminium chloride (1.46 g, 11 mmol) at 0° C. and allowed to stir for 15 min to dissolve 2-methyl-5-nitro-1H-imidazole. After that 6-bromo-1,2-epoxyhexane (I), (1.96 g, 11.02 mmol) was added dropwise into the reaction mixture and the reaction was continued for 5 h at 0° C. The reaction mixture was slowly added into Ice water and pH was adjusted to 1 by adding concentrated HCl. The organic layer was separated, washed with saturated sodium bicarbonate followed by water. The aqueous layer obtained from the first separation adjusted to pH 7.4 using liquid. ammonia and extracted with ethyl acetate. The combined organic layer was dried over sodium sulphate and evaporated in vacuo to obtain crude compound. Crude was purified by flash column chromatography while eluting with 2-3% methanol/dichloromethane mixture to obtain the pure compound (II) with 50% isolated yield. ESI-MS (m/z): 305.95 (M+H)

Synthesis of 6-Fluoro-7-{4-[5-hydroxy-6-(2-methyl-5-nitro-imidazol-1-yl)-hexyl]-piperazin-1-yl}-1-methyl-4-oxo-4H-2-thia-8b-aza-cyclobuta[a]naphthalene-3-carboxylic acid (115)

To a stirred solution of 6-Fluoro-1-methyl-4-oxo-7-piperazin-1-yl-4H-2-thia-8β-aza-cyclobuta[a]naphthalene-3-carboxylic acid, (III) (1.10 g, 3.16 mmol) in dimethylformamide (30 ml) was added potassium carbonate (0.43 g, 3.16 mmol) followed by addition of compound (II) (0.85 g, 2.63 mmol) and the reaction mixture was stirred at RT for 16 h. The reaction mixture was diluted with ethyl acetate, washed twice with water and finally dried over sodium sulphate to obtain the crude mass. The crude was purified by flash column chromatography while eluting with 3-5% methanol/dichloromethane mixture to obtain the pure compound (115) with 20% isolated yield. $^1$H-NMR (400 MHz, DMSO) δ ppm: 1.61-1.68(6H, m, CH$_2$), 2.1 (3H, d, J=6 Hz, CH$_3$), 2.44 (3H, s, CH$_3$), 2.54 (4H, m, 2×CH$_2$), 3.2 (4H, m, 2×CH$_2$), 3.9-4.1 (2H, m, 2×CH$_2$N), 4.38(1H, d, J=14, CHOH), 5.2 (1H, d, J=4.4, OH), 6.38 (1H, d, J=5.6 Hz, CHSN) 6.9 (1H, d, J=6.8, Ar—H), 7.78 (1H, d, J=14 Hz, Ar—H), 8.02 (1H, s, Ar—H). ESI-MS (m/z): 575 (M+H)

Example 9: Synthesis of DART Molecule 119 from Table 1B

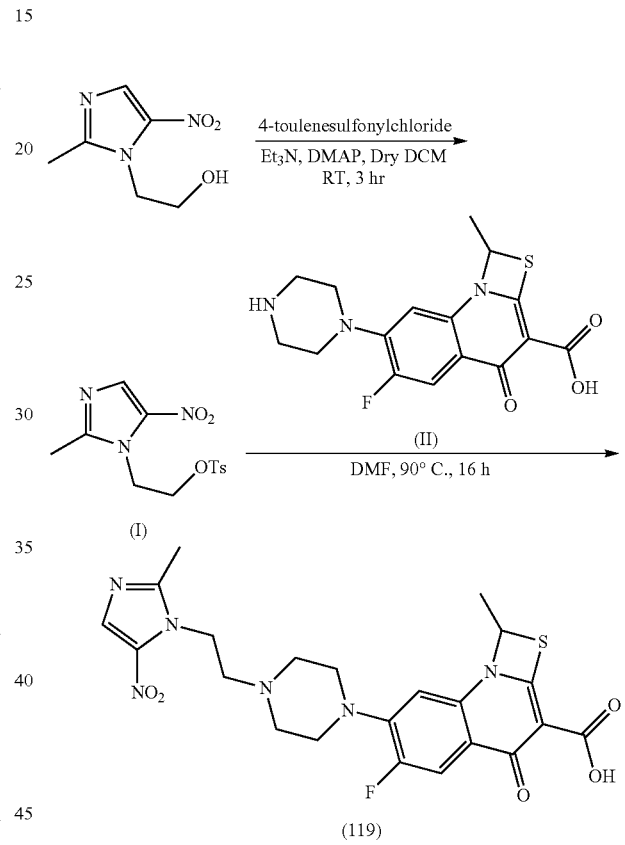

(119)

Synthesis of 2-(2-Methyl-5-nitro-1H-imidazol-1-yl) ethyl 4-methylbenzenesulfonate (I): To a stirred solution of 2-(2-Methyl-5-nitro-imidazol-1-yl)-ethanol (4 g, 16.86 mmol) in dichloromethane (50 ml) was added triethylamine (7.3 ml), 4-toulenesulfonylchloride (6.42 g, 33.72 mmol) followed by 4-dimethylaminopyridine (0.2 g, 1.68 mmol) at 0° C. The reaction mixture was stirred at RT for 3 h. After completion, reaction mixture was washed with water, 5% HCl, sat. NaHCO$_3$ and water. The organic layer was dried over Na$_2$SO$_4$ and evaporated to get crude mass. The crude was purified by flash column chromatography by eluting with 2-3% methanol/dichloromethane to obtain pure compound with 90% isolated yield $^1$H-NMR (400 MHz, CDCl$_3$) δppm: 2.45 (3H, s, Ar—CH$_3$), 2.51(3H, s, —CH$_3$), 4.37(2H, d, J=4.8 Hz, CH$_2$), 4.54(2H, d, J=4.8 Hz, CH$_2$), 7.29(2H, d, J=8.4 Hz, ArH), 7.60(2H, d, J=8.4 Hz, ArH), 7.81(1H, s, ArH).

Synthesis of 6-Fluoro-1-methyl-7-{4-[2-(2-methyl-5-nitro-imidazol-1-yl)-ethyl]-piperazin-1-yl}-4-oxo-4H-2-thia-8b-aza-cyclobuta[a]naphthalene-3-carboxylic acid (119)

To a stirred solution of 6-Fluoro-1-methyl-4-oxo-7-piperazin-1-yl-4H-2-thia-8β-aza-cyclobuta[α]naphthalene-3-carboxylic acid, (II) (5.16 g, 14.76 mmol) in dimethylformamide (100 ml) was added potassium carbonate (2.03 g, 14.76 mmol) followed by addition of compound (I) (2 g, 7.2 mmol) and the reaction mixture was heated at 90° C. for 16 h. The reaction mixture was diluted with ethyl acetate, washed twice with water and finally dried over sodium sulphate to obtain the crude mass. The crude was purified by flash column chromatography while eluting with 4-5% methanol/dichloromethane mixture to obtain the pure compound (119) with 20% isolated yield. $^1$H-NMR (400 MHz, CDCl$_3$) δppm: 2.12 (3H, d, J=6.4 Hz, CH$_3$), 2.52 (3H, s, CH$_3$), 2.64 (4H, m, 2×CH$_2$), 2.72(2H, t, J=6 Hz, CH$_2$), 3.11-3.18 (4H, m, 2×CH$_2$), 4.43-4.49 (2H, m, CH$_2$N), 5.8-5.9 (1H, q, J$_1$=6.4 Hz, J$_2$=12.8 Hz, CHSN), 6.3 (1H, d, J=6.8 Hz, Ar—H), 7.92 (1H, s, Ar—H), 7.95 (1H, s, Ar—H). ESI-MS (m/z): 503 (M+H)

Example 10: Antimicrobial Susceptibility of Clindamycin Sensitive and Resistant *P. acnes*

The antimicrobial susceptibility of *P. acnes* strains against various antibiotics was determined by micro broth dilution method as follows.

Methods:

*P. acnes* (MTCC 1951 and CCARM9010) were cultured in Brain Heart Infusion Agar (BHIA) at 37° C. for 48 hours under anaerobic condition. For MIC test, BHI broth (100 μl) was added into all 96 wells and 100 μl of broth containing different concentrations of cephalothin, cefoxitime, prulifloxacin, nadifloxacin, roxitrhromycin, clindamycin and besifloxacin were added to first well of each row (1A to 1H) and serial (double) dilution was carried out for up to 10 wells (column 1 to column 10 of 96 well plate). For bacterial inoculum, *P. acnes* culture turbidity was adjusted to 0.5 McFarland standard (approximately 1.5×10$^8$) and further diluted (100 times with sterile BHI broth). Diluted *P. acnes* suspension (100 μl) was added to each well except sterility control wells (column 12 of 96 well plate). Inoculated plates were incubated at 37° C. for 72 hours under anaerobic condition. After incubation, MIC was determined by adding Alamar blue dye.

Figure 1B:
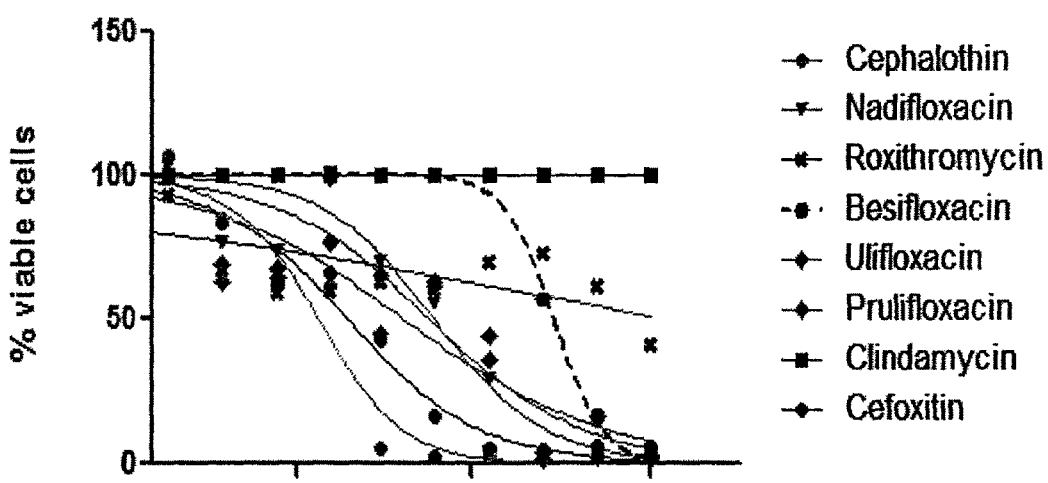

Results:

The MIC results on *P. acnes* strains susceptible to clindamycin indicated that the strain is susceptible to all the antibiotics (FIG. 1A). Interestingly, Clindamycin resistant strain was also resistant to a macrolide, Roxithromycin. (FIG. 1B)

Example 11: Determination of Minimum Inhibitory Concentration (MIC) and Dose Response Curve for Compounds 90, 91, 94, 113, 115 and 116 in Both Clindamycin-Susceptible (MTCC1951) and Clindamycin-Nonresponsive (CCARM 9010) *P. acnes* Strains and Laboratory *S. aureus* Strains Materials:

Brain heart infusion broth, *P. acnes* strains (MTCC 1951 & CCARM 9010), *S. aureus* MTCC 6908, 96 wells plate, Autoclave, Incubator, Anaerobic box with anaerobic gas pack, Plate reader (595 nm), Alamar blue.

Method:

*P. acnes* were cultured in Brain Heart Infusion Agar (BHIA) at 37° C. for 48 hours under anaerobic condition. For MIC test, BHI broth (100 μl) was added into all 96 wells and 100 μl of broth containing drug was added to first well (1A to 1H) and serial (double) dilution was carried out for up to 10 wells (column 1 to column 10 of 96 well plate). For bacterial inoculum, *P. acnes* culture turbidity was adjusted to 0.5 McFarland standard (approximately 1.5×10$^8$ cells/ml) and further diluted (100 times with sterile BHI broth). Diluted *P. acnes* suspension (100 μl) was added to each well except sterility control wells (column 12 of 96-well plate).

The plates were incubated at 37° C. for 48 h under anaerobic condition for *P. acnes* and 37° C. for 24 h for *S. aureus* The plates were read under Bio-Rad plate reader at 595 nm for optical density to generate the dose-response curves. The MIC of the test compound was recorded by addition of Alamar blue dye.

Figure 1C:
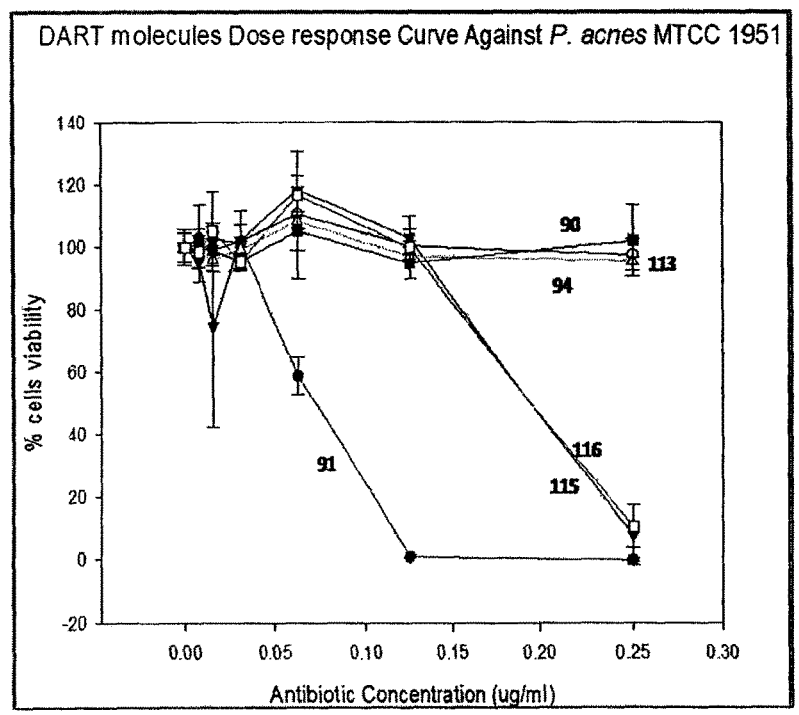
FIGS. 1C and 1D are line graphs showing concentration efficacy curve of DART compounds 90, 91, 94, 113, 115 and 116 in both clindamycin-susceptible (MTCC 1951) (FIG. 1C) and clindamycin-nonresponsive (CCARM 9010) (FIG. 1D) *P. acnes* strains. The molecules have different and unpredictable activity against MTCC1951 and CCARM9010 strains of *P. acnes*. Compound 91 showed highly efficacious bacterial killing profile for both bacterial strains. Compound 90 shows activity in *P. acnes* that do not respond to clindamycin but is ineffective in the *P. acnes* strain that responds to clindamycin.
Figure 1D:
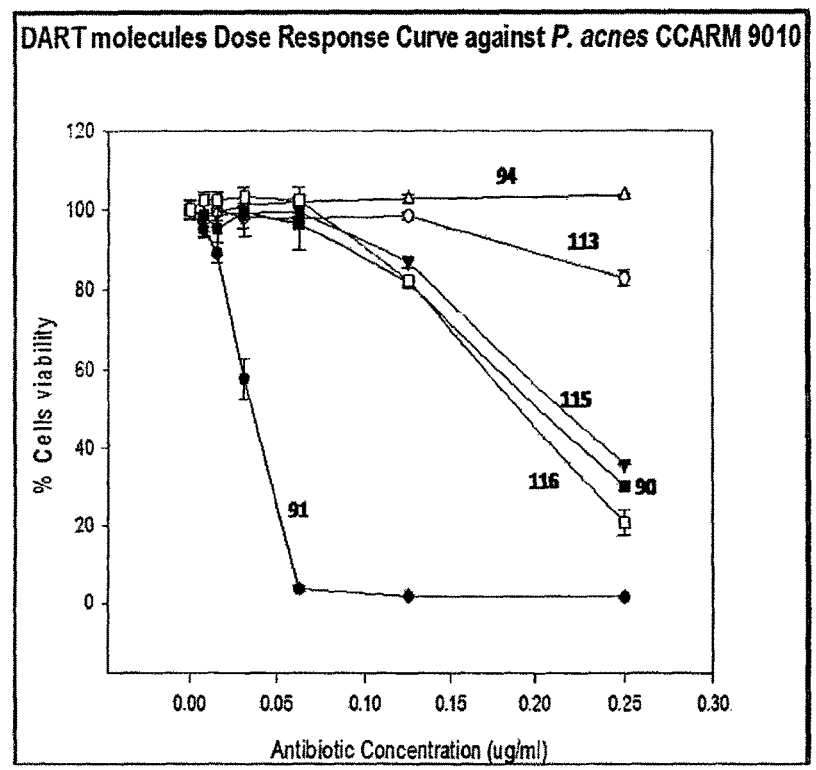

Results:

Table 6 and FIGS. 1C and 1D showed MIC and dose-response curves of different compounds in both susceptible and resistant *P. acnes* strains. The results showed that compound 91 showed lower MIC value and faster bacterial killing profile for both bacterial strains (clindamycin-susceptible and resistant *P. acnes*) in comparison to all other compounds. In contrast compounds 115 and 116, which are only marginally different from 91, exhibited more than double MIC values for both *P. acnes* strains in comparison to MIC value obtained with compound 91. Similarly, compounds 113 and 94 hardly showed any activity against *P. acnes*, which could indicate the importance and involvement of free carbonyl and carboxylic groups towards better activity of the compound. Interestingly the compound 90 was found to be not active in clindamycin-susceptible *P. acnes* but showed promising activity in clindamycin—nonresponder *P. acnes* strain as observed in the dose-response curves of FIGS. 1C and 1D.

In presence of *S. aureus* strain all compounds 90, 91, 115 and 116 have similar activity but compound 113 showed least activities that might be due to steric constrains involved during binding to the target protein (Table 6).

Conclusions:

Compound 91 is a potent anti-acne agent, and an efficacious drug against treatment of both clindamycin-susceptible. In clindamycin resistant *P. acnes* strain also, it showed the highest activity which is better than in the susceptible strain. The same is also reflected in the dose response curve (FIGS. 1C and 1D). In both strains, at a very low concentration, all *P. acnes* bacterium were killed, indicating it overcomes all mechanisms of antibiotic non-responsiveness, i.e. can overcome mechanisms underlying tolerance (described in introduction) as well as resistance. This suggests the structure of compound 91 is unique that shows higher bio-efficacy in comparison to all other compounds against both susceptible and resistant *P. acnes* strains. The wide variability in outcome with structurally-related molecules also highlight the fact that it is not possible to predict efficacy just because of structural similarities. Similarly, the higher MIC value for compound 91 against *S. aureus* in comparison to *P. acnes* proves the specificity of compound 91 towards a particular bacterial strain, and that results seen in a bacterial species is not portable to another disease-causing bacteria.

Purity and bio-activity of compounds 90, 91, 94, 113, 115 and 116 (from Table 1A & 1B)

The purity of all above mentioned DART molecules were evaluated by HPLC and their bio-activity were evaluated in both *P. acnes* susceptible and resistant strains and *S. aureus* susceptible strain. The results are shown in Table 6.

TABLE 6

HPLC purity and MIC values of compounds for both clindamycin susceptible and resistant *P. acnes* strains and a laboratory *S. aureus* strain.

| | MIC | | |
|---|---|---|---|
| Molecules | Susceptible P. acnes (1951) strain (µg/ml) | Resistant P. acnes (9010) strain (µg/ml) | Susceptible S. aureus (6908) strain (µg/ml) |
| 90 | 1.7 | 0.9 | 1.0 |
| 91 | 0.2 | 0.1 | 1.5 |
| 94 | 3.0 | 3.0 | 2.8 |
| 113 | 8.2 | 8.0 | >8.2 |
| 115 | 0.4 | 0.8 | 1.6 |
| 116 | 0.4 | 0.8 | 1.64 |

Example 12: DNA Gyrase Activity Assay with Compounds 90, 91, 94, 113, 115 and 116 with *E. coli* DNA Gyrase Materials:
DNA gyrase assay kit (Topogen Inc.), proteinase K, chloroform, isoamyl alcohol, different test compounds, agarose gel electrophoresis system Method:
DNA super-coiling activity was assayed using DNA gyrase assay kit (Topogen Inc.) with relaxed pHOT1 *E. coli* plasmid DNA according to manufacturer's protocol. The standard reaction mixture (20 µl) contained 35 mM Tris-HCl (pH 7.5), 24 mM KCl, 4 mM $MgCl_2$, 2 mM dithiothreitol, 1.8 mM spermidine, 1 mM ATP, 6.5% glycerol, 0.1 mg/ml bovine serum albumin (BSA), 10 µg/ml relaxed pHOT1 plasmid DNA and 1 U of DNA gyrase. The reaction mixture was incubated at 37° C. for 1 h in presence of selected compounds/fluoroquinolone at different concentrations. The reaction was terminated by addition of ⅕ volume of loading dye (4 µl) followed by proteinase K (50 µg/ml) and again incubated at 37° C. for half an hour. 20 µl chloroform/isoamyl alcohol (24:1) was added to each tube and vortexed briefly. Thereafter, the blue aqueous phase was separated out and analyzed by 1% agarose gel electrophoresis. The gel was stained by ethidium bromide for half an hour and destained with water for 15 mins. The gel was then visualized in a trans-illuminator and photographed.

Figures 2A, 2B:
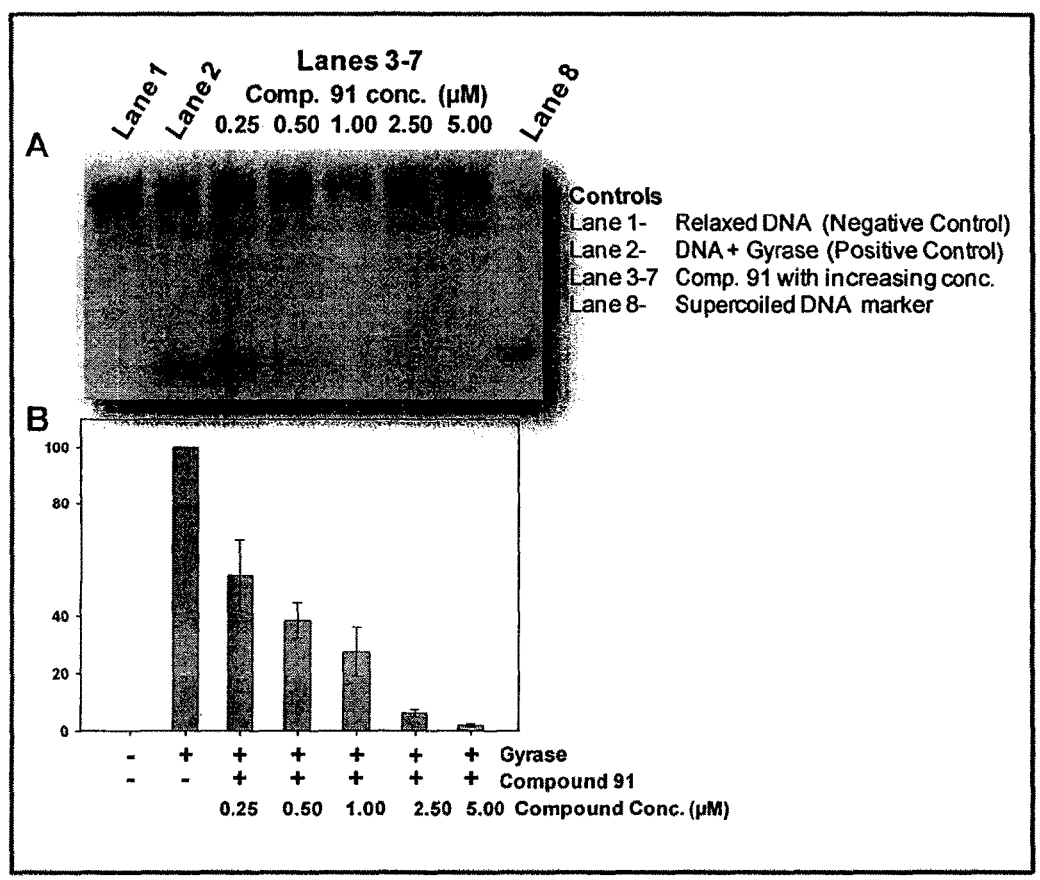
FIGS. 2A and 2B show concentration-dependent inhibition of DNA gyrase activity (super-coiling) by compound 91.

Results: Compounds Inhibit Super-Coiling Activity of DNA Gyrase:
Compound 91 with the best MIC value was first chosen for assessing its effect on DNA gyrase activity. The intensity of super-coiled band was observed at five different concentrations (in the range from 0.25 µM to 5 µM) (FIG. 2A). There was a decrease in super-coiled band in presence of compound 91 (nearly around 54.3% at 0.25 µM to about 2% in presence of 5 µM of compound 91) as compared to compared to the untreated control (100%) (FIG. 2B).

Figure 3A:
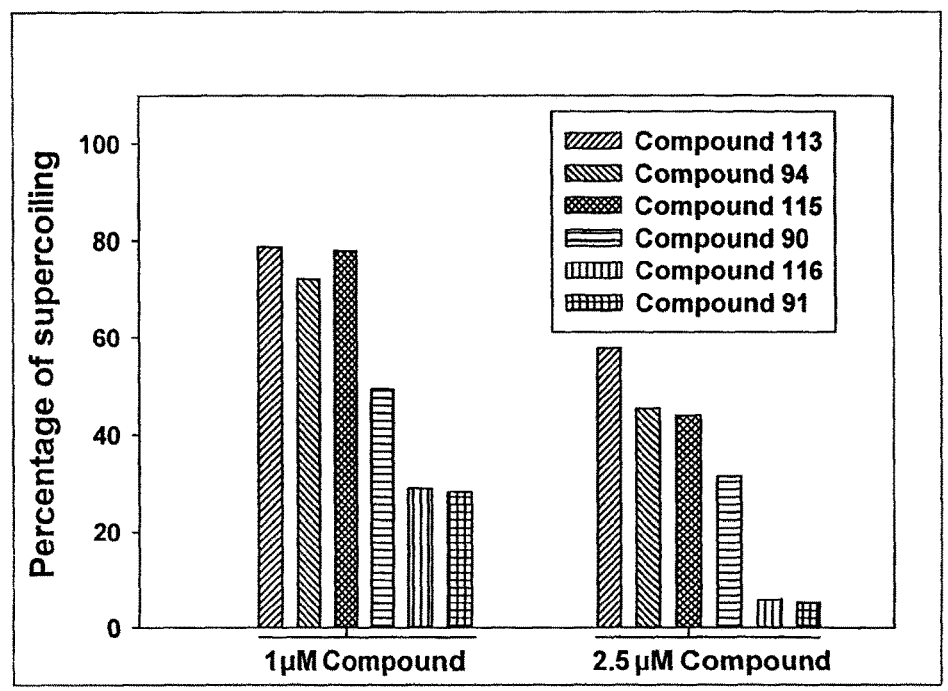
FIG. 3A is a bar graph showing percentage of DNA super-coiling by DNA gyrase in presence of compounds 90, 91, 94, 113, 115 and 116 with relaxed *E. coli* plasmid DNA. Compound 91 and compound 116 seemed to have the best gyrase inhibiting activity among all the comparators. Though this observation is mostly correlated with MIC data against *P. acnes*, yet there is some species-specific advantages is observed with compound 91.

Further, all the compounds 90, 91, 94, 113, 115 and 116 were tested at two concentrations 1 µM and 2.5 µM to check their effect on DNA gyrase activity. FIG. 3A showed that all the compounds were able to inhibit the super-coiling activity of DNA gyrase. However, compounds 91 and 116 are highly potent in this respect as compared to the other compounds showing that minor structural difference between compound 91 and 116 does not affect much in gyrase binding affinity. But higher bacterial killing efficacy of compound 91 than compound 116 as observed in dose response curve (FIGS. 1C & 1D) proved that compound 91 might have unique mode of activity as compared to others.

Figure 3B:
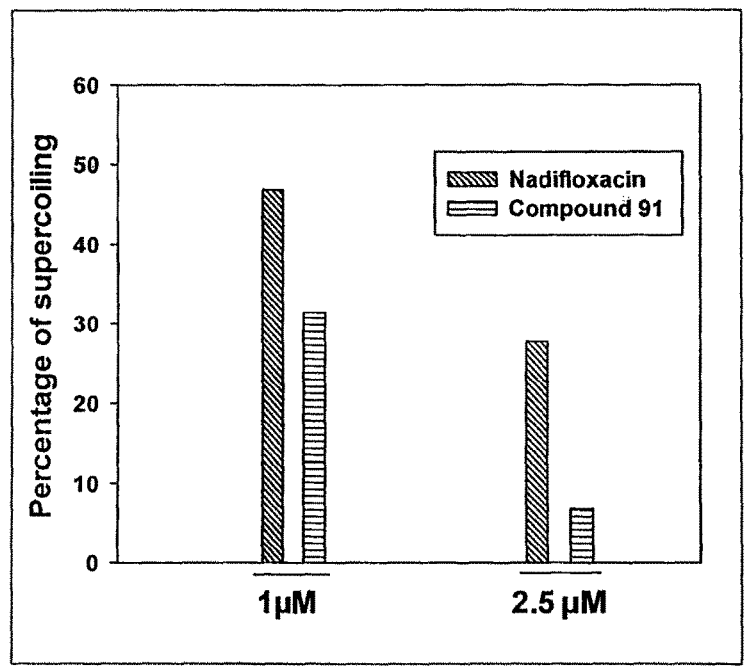
FIG. 3B is a bar graph showing percentage of DNA super-coiling by DNA gyrase in presence of compound 91 and nadifloxacin with relaxed *E. coli* plasmid DNA. Compound 91 shows greater efficacy than Nadifloxacin.

When compound 91 was compared with the known fluoroquinolone nadifloxacin, the former showed better efficacy of inhibiting DNA super-coiling by DNA gyrase than nadifloxacin at both the concentrations tested (FIG. 3B).

Conclusions:
The results obtained from DNA gyrase activity assay suggest that compound 91 is the most potent in binding DNA gyrase and inhibiting its action. Thus, the mechanism of inhibition of bacterial growth is by impeding the DNA gyrase function, thus preventing important cellular functions and eventually cellular death. This compound shows a better antibacterial efficacy and binding affinity in comparison to a known fluoroquinolone, nadifloxacin. These results are in accordance with the results obtained from the MIC data and dose response curves.

Example 13: Mutant Prevention Concentration (MPC) of Compound 91 in Comparison to the Other Known Fluoroquinolones Materials:
Brain heart infusion broth, *P. acnes* MTCC 1951, Petri plate, Autoclave, Incubator, Anaerobic box with anaerobic gas pack.

Method:
*P. acnes* were cultured in Brain Heart Infusion Agar (BHIA) at 37° C. for 48 h under anaerobic condition. 3 to 4 Petri plates containing 48 h *P. acnes* culture was suspended in sterile Phosphate buffer saline, PBS (pH 7.2) and turbidity was adjusted to optical density of 1 at 600 nm ($10^9$ cells/ml). 50 ml of this culture suspension was centrifuged at 4000 rpm for 40 min. The supernatant was discarded and pellet resuspended in 250 µl of sterile PBS. 50 µl of these cell suspensions ($10^{10}$ cells) was spread over the plates containing various concentrations of antibiotics (around MIC range). Plates were incubated at 37° C. for 48 h and the lowest concentration of the drug that allowed no growth was taken as its MPC. If thin film was observed in higher antibiotic concentration plates then thin film was further sub-cultured on drug free plates The growth obtained on drug free plates were then sub-cultured on plates containing drugs (at the concentration at which the thin film was isolated). If growth was not observed in these plates at the end of the incubation period then the same concentration was confirmed to be the MPC for the said compound.

Results:
The Table 7 showed the value of MPC and the ratio of MPC and MIC of compound 91 along with other known fluoroquinolones and clindamycin against *P. acnes*. The MPC/MIC ratio indicates that compound 91 is almost 3 times more active in preventing development of resistance against *P. acnes* than known anti-acne antibiotic, nadifloxacin, new generation fluoroquinolone, ulifloxacin and 2 times with respect to clindamycin. MPC/MIC ratios are found to be close with besifloxacin and compound 91. This concludes both besifloxain and compound 91 are effective molecules for treatment and preventing *P. acnes* and ideal for preventing resistance development against pathogen.

Conclusions:
Unlike MIC testing, which typically uses an inoculum size of approximately $10^4$-$10^5$ cfu/ml, the calculation of the MPC needs a large inoculums (approximately $10^9$-$10^{10}$ cfu/ml). This high inoculum is chosen to ensure the presence of first-step resistant mutants within the susceptible bacterial population. Moreover, MPC/MIC for compound 91 is only 1.5 whereas it is almost 8 for nadifloxacin. The narrower the window between MIC and MPC of an antibiotic molecule the lesser than chance of selective growth of mutants in an in vivo situation. This implies that compound 91 may be more effective than other known anti-acne agents in preventing development of resistance in targeted microbes.

TABLE 7

Mutation prevention concentration (MPC) and ratio of MPC/MIC of the compound 91 and comparison with known fluoroquinolones and lincosamide

| Molecules | MIC (μg/ml) | MPC (μg/ml) | MPC/MIC |
|---|---|---|---|
| Clindamycin | 0.02 | 0.13 | 6.5 |
| Compound 91 | 0.2 | 0.3-0.6 | 1.5-3 |
| Besifloxacin | 0.5 | 2 | 4 |
| Ulifloxacin | 0.13 | 1.2 | 9.2 |
| Nadifloxacin | 0.13 | 1.2 | 9.2 |

Example 14: Zone of Inhibition (ZOI) of Topical Gel Formulation with Compound 91 in Comparison with Other Marketed Formulations Materials:

Brain heart infusion broth, *S. aureus* MTCC 6908, *P. acnes* strains (MTCC 1951 and CCARM 9010), 96 wells plate, Autoclave, Incubator, Anaerobic box with anaerobic gas pack, Plate reader (595 nm), Alamar blue.

Method:

For ZOI test, 100 μl of bacterial suspension (0.5 McFarland standard equal) was spread on BHA plates. Test samples (formulations) were dissolved in water/solvent based on the solubility. Sterile disc (6 mm) were loaded with 10 μl of test samples (with various concentrations of the compound) and were placed on the plates containing bacterial culture. The plates were incubated at 37° C. for 48 h under anaerobic condition for *P. acnes* and 37° C. for 24 h for *S. aureus*, followed by their ZOI measurements.

Results:

The ZOI (measured in cm) of the different test samples are shown for *P. acnes* 1951 (susceptible, Table 8), *P. acnes* 9010 (resistant, Table 9) and *S. aureus* (susceptible, Table 10). The formulation with compound 91 showed bacterial killing profiles against both bacterial strains indicate that compound 91 retain its activity in presence of other excipients present in the formulation. Interestingly ZOI data showed fast bacterial killing with resistant *P. acnes* as compared to susceptible *P. acnes* specially at low drug concentration (1-2 μg) supported by dose response curve as seen in FIGS. 1C and 1D as well as DNA-gyrase assays (FIGS. 2A & 3A). Compound 91 also works in case of *S. aureus* strain and ZOI results support MIC values as seen in Table 6.

Conclusions:

Formulation with compound 91 has activity against certain gram-positive bacterial strains. In case of *P. acnes*, both clindamycin-susceptible and clindamycin non-responder strains, the formulation remains active with compound 91 and preferably more efficacious in clindamycin-nonresponder *P. acnes* supporting the fact drug specific bioactivity.

Tables 8-10. Zone of Inhibition (ZOI) of Topical Gel Formulation with Compound 91 in Comparison for Clindamycin Susceptible *P. acnes* 1951(A), Clindamycin-Nonresponder *P. acnes* 9010 (B) and Laboratory *S. aureus* Strain (B).

TABLE 8

| | ZOI (cm) *P. acnes* 1951 (susceptible) | | | |
|---|---|---|---|---|
| Samples | 1 μg | 2 μg | 4 μg | 8 μg |
| Formulation A (Compound 91) | 0.95 | 1.40 | 2.30 | 2.75 |
| Formulation E (Placebo) | 0 | 0 | 0 | 0 |

TABLE 9

| | ZOI (cm) *P. acnes* 9010 (clindamycin resistant) | | | |
|---|---|---|---|---|
| Samples | 1 μg | 2 μg | 4 μg | 8 μg |
| Formulation A (Compound 91) | 1.60 | 1.85 | 2.15 | 2.45 |
| Formulation E (Placebo) | 0 | 0 | 0 | 0 |

TABLE 10

| | ZOI (cm) *S. aureus* 6908 | | | |
|---|---|---|---|---|
| Samples | 1 μg | 2 μg | 4 μg | 8 μg |
| Formulation A (Compound 91) | 0 | 0.80 | 1.10 | 1.20 |
| Formulation E (Placebo) | 0 | 0 | 0 | 0 |

Example 15: Determination of Anti-Inflammatory Potential of Compound 91 in THP-1 Cells Stimulated by *P. acnes*

Here we selected compound 91 to test anti-inflammatory assay as it showed lower MIC and effective gyrase binding followed by faster bacterial killing profiles. Anti-inflammatory activity of compound 91 in THP-1 cells stimulated with *P. acnes* (ATCC 6919) was studied.

Method: Preparation of Stimulant for Inflammation: *P. acnes* culture suspension was prepared in PBS and the cell number in the suspension was adjusted to approximately $5 \times 10^8$ CFU/ml by measuring the cell density using a Densimat. The bacterial suspension was then heat killed at 80° C. for 30 min and stored at −80° C. until further use.

ELISA to Study Inflammatory Response in THP-1 Cells:

Cells were seeded in a 96-well format ($2 \times 10^5$ THP-1 cells per well) in media containing 10% FBS. The cells were stimulated to induce inflammatory cytokines using 3 McFarland equivalent heat-killed *P. acnes*. Cells in control wells were treated with PBS. One hour after induction with *P. acnes*, test agents were added to the induced cells at appropriate concentrations to be tested (compound 91 at 25 μg/ml). The plates were incubated at 37° C. for 24 hours. After 24 h, the plates were centrifuged to pellet the cells and the supernatants were collected. The cell culture supernatants thus obtained were analyzed for levels of cytokines (IL-1α, IL-1β, IL-6 and IL-8) by ELISA using R&D Systems kits for individual cytokines following the manufacturer's instructions.

Figures 4A, 4B:
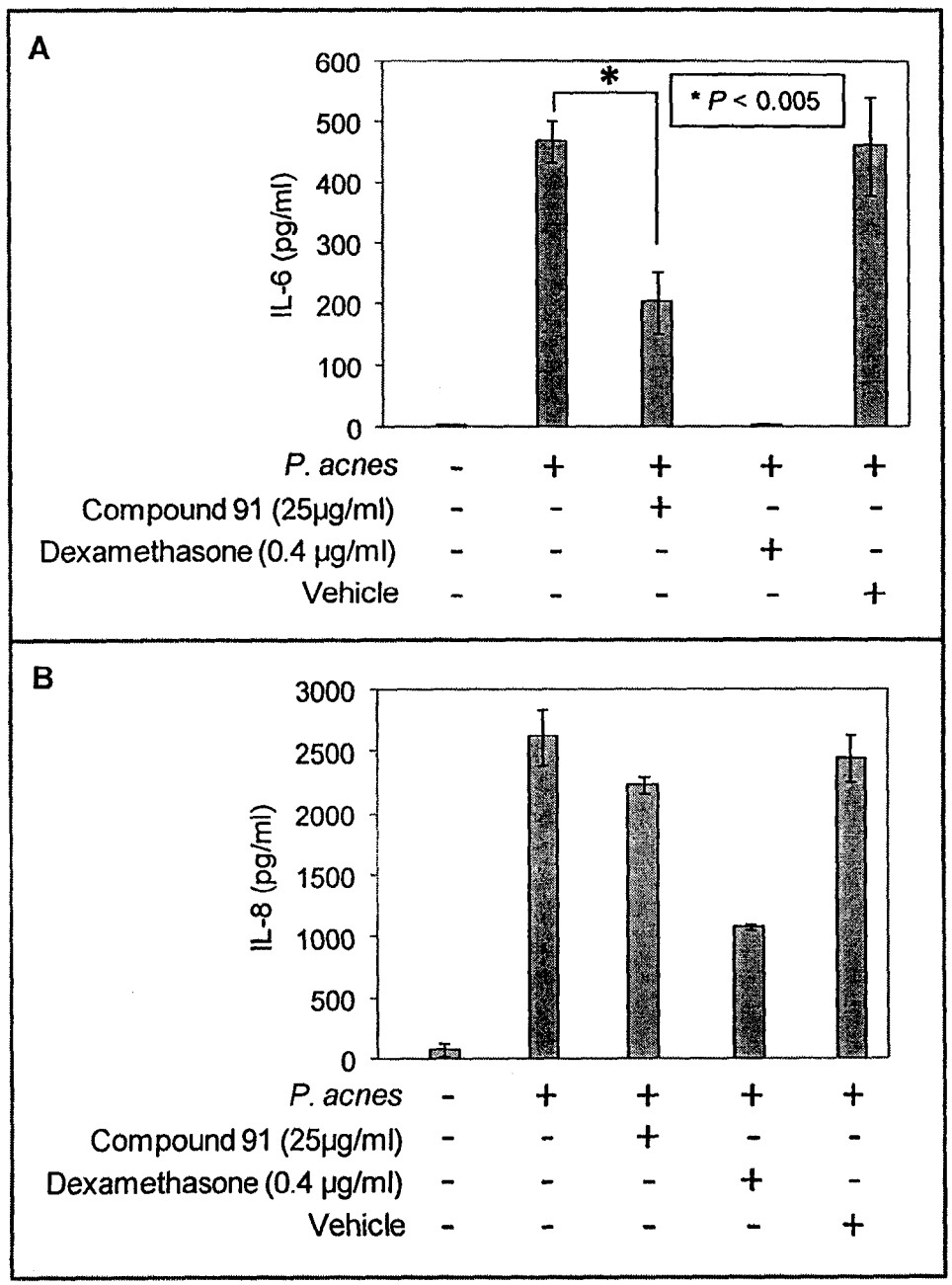
FIGS. 4A and 4B are bar graphs showing the effect of compound 91 on *P. acnes*-induced cytokine IL-6 (FIG. 4A), IL-8 (FIG. 4B) release in THP-1 cells. Compound 91 exerts an anti-inflammatory activity against *P. acnes*-induced cytokine production. Statistical analysis was performed using Student's t-test (*p=0.05; **p=0.005).
Figures 5A, 5B:
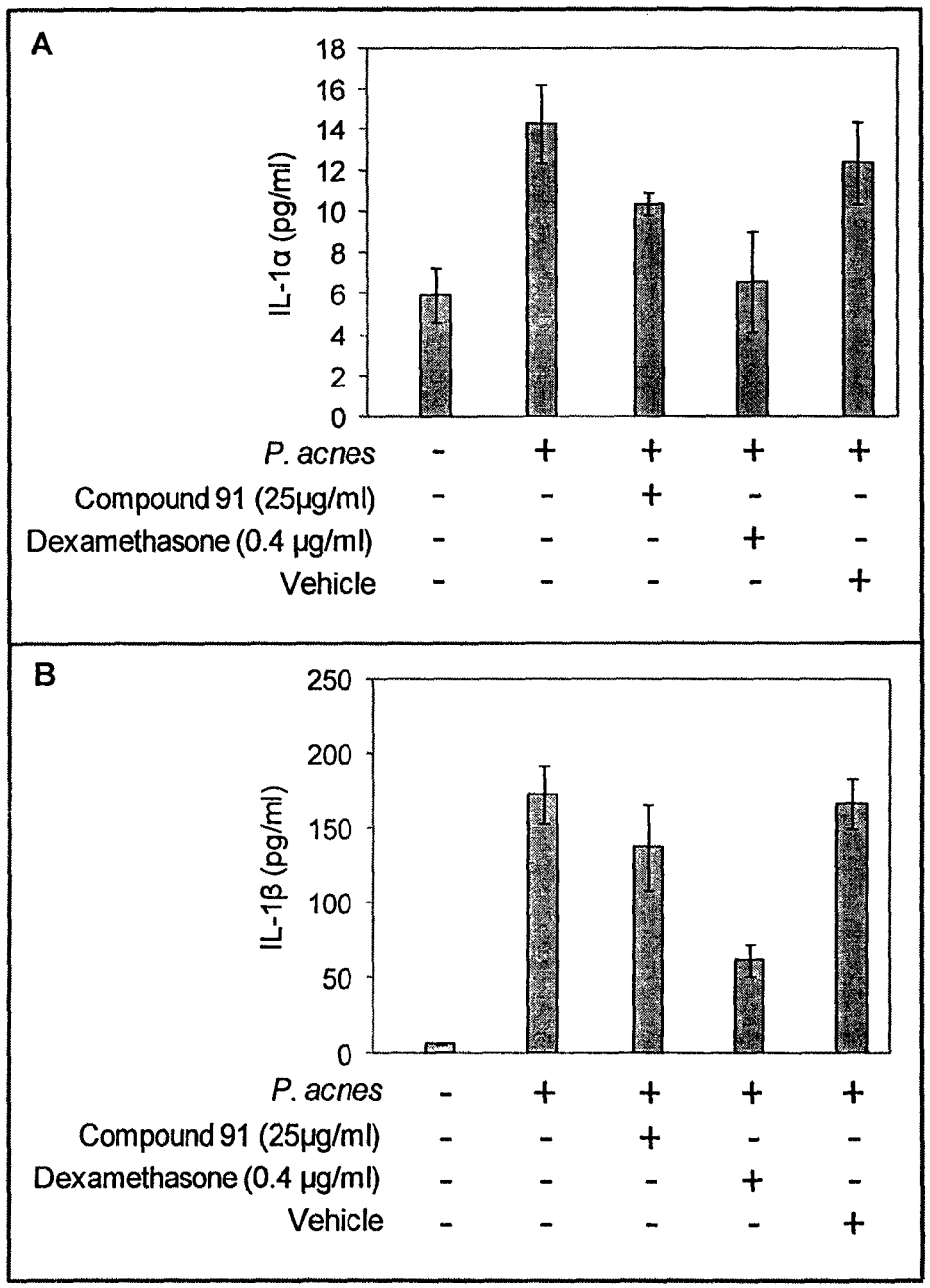
FIGS. 5A and 5B are bar graphs showing the effect of compound 91 on *P. acnes*-induced cytokine IL-1α (FIG. 5A), IL-1β (FIG. 5B) release in THP-1 cells.

Results: Compound 91 Exerts Anti-Inflammatory Action Through the Reduction of IL-6 in *P. acnes*-Induced THP-1 Cells:

THP-1 cells, induced using heat killed *P. acnes*, were treated with 25 μg/ml of compound 91 following which the levels of IL-1α, IL-1β, IL-6 and IL-8 were analyzed in the culture supernatant. At the tested concentration, compound 91 caused a significant reduction (nearly 60%) in *P. acnes*-induced IL-6 levels (FIG. 4A and Table 11). Dexamethasone, the known anti-inflammatory agent, used as a positive control, showed nearly 100% reduction in IL-6 levels. The THP-1 cells showed 90% viability when treated with 25 μg/ml of compound 91 (data not shown). Compound 91 did not have an effect on IL-8 levels in the *P. acnes*-induced THP-1 cells (FIG. 4B). The results presented in FIGS. 5A and 5B show that compound 91 had a small effect on *P. acnes*-induced IL-1α and IL-1β levels (approximately 20-25% reduction as compiled in Table 11). These results suggest that compound 91 is an effective anti-inflammatory agent in a scenario specific to *P. acnes*-induced inflammation.

Conclusions:

The results obtained from the DNA gyrase activity assays (cell-free system) and the anti-inflammatory assays in THP-1 cells indicate that compound 91 has a dual mode of action. One of the mechanism of anti-bacterial effect is mediated by targeting the bacterial DNA gyrase in addition to induction of DNA damage from the nitroheterocycle moiety, while its anti-inflammatory properties are evident from its action on inflammatory mediators in mammalian cells. In the context of acne, this dual mode of action may aid in reducing bacterial population as well as diminishing inflammation at the site of lesions thereby providing faster cure and better patient compliance.

TABLE 11

Percentage reduction by compound 91 in *P. acnes* induced different cytokine IL-1α, IL-1β, IL-6 and IL-8 release in THP-1 cells considering 100% cytokines formation from *P. acnes* induced cells.

| Cytokines | Dexamethasone (25 μg/ml) | Compound 91 (25 μg/ml) |
|---|---|---|
| IL-1β | 64.73% | 20.49% |
| IL-1α | 53.83% | 27.51% |
| IL-6 | 99.54% | 56.76% |
| IL-8 | 58.78% | 14.65% |

Example 16: Topical Formulations with Effective DART Molecule, 91

Both cream and gel formulation was made with effective DART compound 91 where concentration of active is typically in the range from about 0.5% to about 3% by weight or alternatively 0.5% to 2% or most preferably 1.0% to 1.5%. The formulation was maintained at pH typically ranges from pH 4.0 to 8.0 or preferably at pH 4.0 to 6.5 or most preferably at pH 5.0 to 6.0. The concentration of active is sufficient to reduce, treat, or prevent skin infections as well as inflammation at the targeted tissues caused by *P. acnes*, *S. aureus* or *S. epidermis* or other related anaerobic gram positive bacteria.

Based on the solubility profiles of compound 91, fully or partially in different solvents such as dimethyl isosorbide, diethylene glycol monoethyl ether, PEG 400, propylene glycol, benzyl alcohol, and pH 4.0 acetate buffer, three different formulation strategies were adopted to obtain improved pharmacokinetics/pharmacodynamics profiles, high skin penetration properties and better drug deposition characteristics, These should result in faster reduction in bacterial population along with quicker reduction in host immune response, such as inflammation. Such effective formulation with fast onset of action would finally allow reduction of dose and duration of therapy hence ensuring better patient compliance. These formulations would not be restricted to treat infections caused by *P. acnes* (susceptible and resistant strain) but also other skin bacterial infections or skin and skin structure infections or impetigo or atopic dermatitis or rosacea caused by different family of gram positive anaerobic bacteria such as *staphylococcus* sp., *streptococcus* sp. and others (susceptible and resistant strain). More importantly this formulation should work well against resistant bacteria and prevent any further development of resistance Composition Example 1

Topical formulation with partially suspended API (compound 91) in gel formulation using hydroxyethyl cellulose (HEC) as a gelling agent, at pH 5.0-5.5. (Table 12)

TABLE 12

|  | Ingredients | Function | Composition (% w/w) |
|---|---|---|---|
| Phase A | Compound 91 | Active | 1.0 |
|  | Diethylene glycol monoethyl ether | Solvent | 10.0 |
|  | Polyethylene glycol 400 | Humectant | 5.0 |
|  | Propylene glycol | Humectant | 5.0 |
| Phase B | Hydroxyethyl cellulose | Rheology modifier | 1.7 |
|  | Purified Water | Vehicle | q.s to 100 |
| Phase C | Benzyl alcohol | Preservative | 1.0 |
| Phase D | Citric acid | pH modifier | q.s |

Method of Preparation:
1. Hydroxylethyl cellulose was added in portions into measured volume of water by maintaining stirring speed at 100-150 rpm. The mixture was allowed to swell for 1 hour at 80-100 rpm. (Phase B)
2. In a separate vessel, polyethylene glycol 400, propylene glycol, and diethylene glycol monoethyl ether were mixed together and compound 91 was added into the mixture in portions at 400 rpm for ~40-45 min to get a uniform dispersion. (Phase A)
3. The drug dispersion (Phase A) was transferred slowly into phase B and allowed to stir at ~50-100 rpm for ~30 min to form homogenous mixture.
4. Finally, benzyl alcohol was added into the final mixture and mixed for further 30 minutes at 50-100 rpm to obtain a white-to-slightly yellow gel formulation.
5. Finally pH of the gel was maintained at 5.0 to 5.5 using citric acid solution.

Composition Example 2

Topical formulation with partially suspended API (compound 91) in gel formulation using carbopol 980 as a gelling agent at pH 5.0-5.5. (Table 13)

TABLE 13

|  | Ingredients | Function | Composition (% w/w) |
|---|---|---|---|
| Phase A | Compound 91 | Active | 1.0 |
|  | Diethylene glycol monoethyl ether | solvent | 10.0 |

TABLE 13-continued

| | Ingredients | Function | Composition (% w/w) |
|---|---|---|---|
| | Polyethlene glycol 400 | Humectant | 5.0 |
| Phase B | Propylene glycol | Humectant | 5.0 |
| | Carbopol 980 | Rheology modifier | 0.6 |
| | Purified Water | Vehicle | q.s to 100 |
| | Triethanolamine | pH modifier | q.s |
| Phase C | Benzyl alcohol | Preservative | 1.0 |

Method of Preparation:
1. Gelling agent, carbopol 980 was added in portions to a measured volume of water stirring at 100-150 rpm.
2. pH of the gel mixture was adjusted to 5.5 by adding triethanolamine solution to allow swelling of carbopol 980 in water. (Phase B)
3. In a separate vessel, polyethylene glycol, propylene glycol and diethylene glycol monoethyl ether were mixed together and compound 91 was added into the mixture in portions while stirring at 400 rpm for ~40-45 min to get uniform dispersion. (Phase A)
4. This drug dispersion (Phase A) was added slowly into phase B at 50-100 rpm stirring speed for about 30 min.
5. Finally, benzyl alcohol was added into the final mixture and allowed to stir for further 30 minutes at 50-100 rpm to obtain a white-to-slightly yellow gel formulation.
6. After preparation of gel, pH was measured and final pH was maintained at 5.0-5.5.

Composition Example 3

Topical formulation with partially suspended API (compound 91) in gel formulation using propyl gallate as antioxidant and EDTA as a buffering agent/chelating agent at pH 5.0-5.5. (Table 14)

TABLE 14

| | Ingredients | Function | Composition (% w/w) |
|---|---|---|---|
| Phase A | Compound 91 | Active | 1.0 |
| | Diethyleneglycol monoethyl ether | Solvent | 10.0 |
| | Polyethlene glycol 400 | Humectant | 5.0 |
| | Propylene glycol | Humectant | 5.0 |
| Phase B | Hydroxyethyl cellulose | Rheology modifier | 1.7 |
| | Purified Water | Vehicle | q.s to 100 |
| Phase C | Ethylenediaminetetraacetic acid dehydrate | Chelating agent/buffering agent | 0.10 |
| | Benzyl alcohol | Preservative | 1.0 |
| | Propyl gallate | Anti-oxidant | 1.0 |
| Phase D | Citric solution | pH modifier | q.s |

Method of Preparation:
1. Hydroxyethyl cellulose was added in portions into measured volume of water by maintaining stirring speed at 100-150 rpm and allowed to swell for 1 hour at 80-100 rpm. (Phase B)
2. In a separate vessel, polyethylene glycol 400, propylene glycol, and diethylene glycol monoethyl ether were mixed together and compound 91 was added into the mixture in portions while stirring at 400 rpm for ~40-45 min to get uniform dispersion. (Phase A)
3. The drug dispersion (Phase A) was added into Phase B and allowed to stir at ~50-100 rpm for about 30 minutes.
4. Finally ethylenediaminetetraacetic acid dehydrate, benzyl alcohol and propyl gallate were added to the final mixture and stirred for 30 min at 50-100 rpm to obtain white-to-slightly yellow gel formulation.
5. The prepared gel was maintained at pH 5.0 to 5.5 using citric acid solution.

Composition Example 4

Topical formulation with fully suspended API (compound 91) in gel formulation using hydroxyethyl cellulose (HEC) as a gelling agent at pH 5.0-5.5. (Table 15)

TABLE 15

| | Ingredients | Function | Composition (% w/w) |
|---|---|---|---|
| Phase A | Compound 91 | Active | 1.0 |
| | Glycerol | Humectant | 10.0 |
| | Purified Water | Vehicle | 10.0 |
| Phase B | Hydroxyethyl cellulose | Rheology modifier | 1.7 |
| | Purified Water | Vehicle | q.s to 100 |
| Phase C | Sodium sulfite | Preservative | 1.0 |
| Phase D | Citric acid | pH modifier | q.s |

Method of Preparation:
1. Hydroxyethyl cellulose was added in portions into measured volume of water by maintaining stirring speed at 100-150 rpm. The mixture was allowed to swell for 1 h at 80-100 rpm. (Phase B)
2. In a separate vessel, aqueous solution of glycerol was made and compound 91 was added into the mixture in portions at 400 rpm for ~40-45 min to get a uniform dispersion. (Phase A)
3. The drug dispersion (Phase A) was transferred slowly into phase B and allowed to stir at ~50-100 rpm for ~30 min to form homogenous mixture.
4. Finally, propyl paraben was added into the final mixture and mixed for further 30 min at 50-100 rpm to obtain a white-to-slightly yellow gel formulation.
5. Finally pH of the gel was maintained at 5.0 to 5.5 using citric acid solution.

Composition Example 5

Topical formulation with partially suspended API (compound 91) in cream formulation at pH 5.0-5.5 (Table 16)

TABLE 16

| | Ingredients | Function | Composition (% w/w) |
|---|---|---|---|
| Phase A | Compound 91 | Active | 1.00 |
| | Cyclopentasiloxane | Emollient and humectants | 3.00 |
| | Cetostearyl alcohol | Emollient | 2.50 |
| | PEG-2 Stearyl ether | Emulsifier | 2.00 |
| | PEG-21 Stearyl ether | Emulsifier | 2.00 |
| | Dimethylisosorbide | Solubilizer | 5.00 |
| Phase B | Hydroxyethyl cellulose | Rheology modifier | 1.7 |
| | Purified Water | Vehicle | q.s to 100 |
| Phase C | Ethylenediaminetetra-acetic acid dihydrate | Chelating agent | 0.10 |
| | Benzyl alcohol | Preservative | 1.00 |
| Phase D | Citric acid (20% w/w solution in water) | pH modifier | q.s |

Method of Preparation:

1. Hydroxyethyl cellulose was added in portions into measured volume of water by maintaining stirring speed at 500 rpm and heated at 50-55° C. (Phase B)
2. In a separate vessel, PEG-2 Stearyl ether, PEG-21 Stearyl ether and cetostearyl alcohol were heated at 50-55° C. Cyclopentasiloxane and dimethylisosorbide were added into the mixture while stirring at 400 rpm. Compound 91 was added into the final mixture in portions at 400 rpm for ~5-10 min to get uniform dispersion at 50° C. (Phase A)
3. The drug dispersion (Phase A) was added slowly into Phase B and allowed to stir at ~300-400 rpm for about 20-30 min till temperature reach at 40° C.
4. Finally ethylenediaminetetraacetic acid dihydrate and benzyl alcohol were added to the final mixture and stirred for ~30 min at 400 rpm to obtain white-to-slightly yellow cream formulation.
5. Finally pH of the cream formulation is adjusted to 5.0 to 5.5 using citric acid solution.

Composition Example 6

Topical formulation with partially suspended API (compound 91) in cream formulation at pH 5.0-5.5 (Table 17)

TABLE 17

| | Ingredients | Function | Composition (% w/w) |
|---|---|---|---|
| Phase | Compound 91 | Active | 1.00 |
| | Cyclopentasiloxane | Emollient and humectant | 3.00 |
| | Cetostearyl alcohol | Emollient | 2.50 |
| | PEG-20 Sorbitan monolaurate | Emulsifier | 2.00 |
| | Sorbitan monolaurate | Emulsifier | 2.00 |
| | Dimethylisosorbide | Solubilizer | 5.00 |
| Phase B | Carbopol 980 | Rheology modifier | 0.6 |
| | Purified Water | Vehicle | q.s to 100 |
| | Triethanolamine | pH modifier | q.s |
| Phase C | Benzyl alcohol | Preservative | 1.00 |

Method of Preparation:

1. Gelling agent, carbopol 980 was added in portions to a measured volume of water stirring at 100-150 rpm.
2. pH of the gel mixture was adjusted to 5.5 with triethanolamine solution to allow swelling of carbopol 980 in water and heated 50-55° C. (Phase B)
3. In a separate vessel, PEG-20 Sorbitan monolaurate, sorbitan monolaurate, cetostearyl alcohol, Cyclopentasiloxane and dimethylisosorbide were added and heated at 50-55° C. by maintaining stirring at 400-500 rpm. To this final mixture compound 91 was added in portions at 400 rpm for-5-10 min to get uniform dispersion at 50° C. (Phase A)
4. The drug dispersion (Phase A) was slowly transferred into Phase B at 50-55° C. by maintaining stirring speed 400 rpm and was cooled to 40° C. within 20-30 min.
5. Finally, benzyl alcohol was added to the final mixture and allowed to cool to room temperature to finally obtain a white-to-slightly yellow cream formulation.

Example 17: Determination of Minimum Inhibitory Concentration (MIC) of Different Compounds and their Formulations Against *P. acnes* Strains by Using Micro-Broth Dilution Method Materials:

Brain heart infusion broth, *P. acnes* strains (MTCC & CCARM), 96 wells plate, Autoclave, Incubator, Anaerobic box with anaerobic gas pack, Plate reader (600 nm), Alamar blue.

Method:

*P. acnes* (MTCC 3297, MTCC 1951 & CCARM 9010) are cultured in Brain Heart Infusion (BHI) Broth at 37° C. for 48-72 h under anaerobic condition. The test compounds/formulations are initially diluted with suitable solvent and further diluted with BHI broth to get the required concentrations. Samples (100 µl) of different concentrations (prepared by serial dilution) are added to 96-well plate. To the wells, 100 µl of *P. acnes* BHI broth culture is added [culture turbidity adjusted against 0.5 McFarland standard (approx $1.5 \times 10^8$), and further diluted 100-fold with sterile BHI broth]. In addition Growth Control and Sterility Control are created using 100 µl each of *P. acnes* BHI broth culture and plain BHI broth, respectively.

Plates are incubated at 37° C. for 48-72 hrs under anaerobic condition. The plate is read under Bio-Rad plate reader @ 595 nm for optical density to generate the dose-response curves. The MIC of the test compound is recorded by addition of Alamar blue dye.

Examples 18-22 and Tables 18-223 describe some exemplary novel formulations comprising stand-alone API (e.g., besifloxacin), either alone or in combination with adapalene.

Example 18: Micronized Besifloxacin Particle Dispersions (D1)

Preparation:

Besifloxacin is dispersed in surfactant solution (2% aqueous solution of poloxamer 407). The resulting suspension is passed through high pressure homogenizer at about 800 bar. The output dispersion is collected in a beaker and recycled 10 times to yield a dispersion of appropriately sized particles (particle size range of 2 µm to 8 µm). The size distribution is determined by MasterSizer (Malvern Instruments) and mean particle size found to be 4.1 µm [Dv (10)-0.8 µm, Dv (90)-8.9 µm].

Example 19: Preparation of Gel and/Cream Formulations Loaded with Besifloxacin Alone, and its Combination with Adapalene Gel and/Cream formulations containing besifloxacin are formulated as per the compositions shown in Table 18. These gel formulations have off-white to slightly yellow appearance with the pH of 5-5.5 and viscosity of around 5000 mPa·s. The formulations consist of besifloxacin equivalent to 1% w/w, in three different forms (1) micronized suspended besifloxacin HCl (Table 18, GL1, GL2), (2) fully solublised besifloxacin HCl (Table 18, GL4) and (3) besifloxacin particles suspended in cream formulation without sizing (CM1). In addition to stand alone besifloxacin formulation, besifloxacin is combined with the adapalene (0.1%) (Table 18, GL1) to provide both the anti-acne and keratolytic activity in patients suffering from acne.

TABLE 18

Gel and/Cream Formulations for Compositions GL1, GL2, GL3, GL4 and CM1

| Sr. No. | Ingredient | GL1 | GL2 | GL3 | GL4 | CM1 |
|---|---|---|---|---|---|---|
| 1 | Water | q.s | q.s | q.s | q.s | q.s |
| 2 | Carbopol 940 | 1 | 1 | 1 | 0 | 0 |
| 3 | Carbopol 980 NF | 0 | 0 | 0 | 0.8 | 0.6 |
| 4 | Hydroxy Propyl Cellulose-H | 0 | 0 | 0 | 1 | 0 |
| 5 | Allantoin | 0.2 | 0.2 | 0.2 | 0 | 0 |
| 6 | Besifloxacin HCl (equivalent to besifloxacin) | 1 (D1) | 1 (D1) | 0 | 1 | 1 |
| 7 | Adapalene | 0.1 | 0 | 0 | 0 | 0 |
| 8 | Triethanolamine | 1 | 1 | 1 | 0 | 0 |
| 9 | Sodium hydroxide | 0 | 0 | 0 | 0.15 | 0.3 |
| 10 | Glycerol | 5 | 5 | 5 | 0 | 5 |
| 11 | Propylene Glycol | 5 | 5 | 5 | 0 | 0 |
| 12 | PEG 400 | 5 | 5 | 5 | 0 | 0 |
| 13 | Poloxamer 407 | 0.2 | 0.2 | 0.2 | 0 | 0 |
| 14 | Sod. Lauryl Sulphate | 0 | 0 | 0 | 1.6 | 0 |
| 15 | Tween 80 | 0 | 0 | 0 | 8 | 0 |
| 16 | Tween 20 | 0 | 0 | 0 | 4 | 0 |
| 17 | diethylene glycol monoethyl ether | 0 | 0 | 0 | 15 | 0 |
| 18 | Cetyl Alcohol | 0 | 0 | 0 | 0 | 2 |
| 19 | Light Liquid Paraffin | 0 | 0 | 0 | 0 | 5 |
| 20 | Cyclopentasiloxane | 0 | 0 | 0 | 0 | 5 |
| 21 | Steareth 2 | 0 | 0 | 0 | 0 | 2 |
| 22 | Steareth 21 | 0 | 0 | 0 | 0 | 2 |
| 23 | BHT | 0 | 0 | 0 | 0 | 0.1 |
| 24 | Disodium EDTA | 0.1 | 0.1 | 0.1 | 0.05 | 0 |
| 25 | Phenoxyethanol | 0.5 | 0.5 | 0.5 | 0.6 | 0.5 |

Method of Preparation:
(1) Allantoin is heated to 50° C. to dissolve completely and cooled down to RT.
(2) Carbopol is added to above mixture and allowed to swell for 1 to 2 h.
(3) Dispersion of micronized Besifloxacin and adapalene powder is added to the swelled carbopol mixture and allowed to stir for 30 min at 400 rpm.
(4) Then, glycerol, propylene glycol, PEG 400, poloxamer 407 is added followed by the addition of disodium EDTA solubilized in water and then add phenoxyethanol to the above stirring mixture. After addition of all the ingredients, the mixture is allowed to stir for 30 min.
(5) Above mixture is neutralized with triethanolamine and allowed is stirring for 2-3 h at 800 rpm.

Example 20: Preparation of Cream Formulations (CM1) Loaded with Besifloxacin HCl Cream formulation containing suspended Besifloxacin particles are formulated as per the compositions shown in Table 18. This gel formulation has off-white to slightly yellow appearance with the pH of 5-5.5 and viscosity of 3060 mPa·s.

Procedure:
1. Part A: Disperse Besifloxacin in glycerin and deionized water in the main vessel and heat to 70° C.
2. Part B: Heat in cetyl Alcohol, light liquid paraffin, cyclopentasiloxane, steareth 2, and steareth 21 and in a separate vessel to 70° C.
3. Add PART B into PART A with continuous mixing at 70° C. and allow to mix for 15 min. Cool the batch with mixing to 45° C.
4. PART C: Swell the carbopol separately in water for 2 h
5. Add PART C into PART A/B and mix well for 20 min.

Example 21: Minimum Inhibitory Concentration of in-House Besifloxacin Gels (1%) and its Combination with Adapalene (0.1%)

Figure 6:
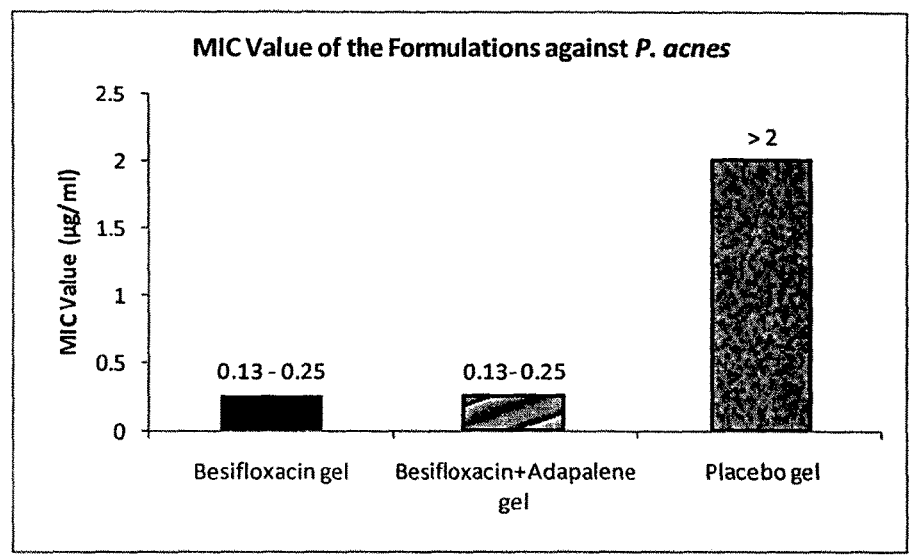
FIG. 6. is a bar graph showing the minimum inhibition value for some exemplary topical gel formulations against *P. acnes*.

Method:
Minimum inhibitory concentration of the test gels (Table 18, GL1 and GL2) are determined by micro broth dilution method against *P. acnes* MTCC 1951 (strain susceptible to *Clindamycin*). BHI broth and BHI agar media were prepared as per the manufacturer's instruction and autoclaved at 121° C. for 15 minutes. *P. acnes* culture is grown in Brain Heart Infusion agar (BHIA) at 37° C. for 48 h under anaerobic condition. For MIC determination testing, gels are dissolved in the solvent and further diluted with BHI broth. Then, 96 wells plate are filled with 100 µl of BHI broth containing drug with different concentration to get the final concentrations of 0.06, 0.13, 0.25, 0.5, 1 and 2 µg/ml in different lanes (lane 1 to lane 6). Remaining lanes of the 96 well plate are used as growth control and sterility control. Finally, *P. acnes* culture suspension (approx $1.5 \times 10^6$) is added in all the wells except sterility control wells and plate is incubated at 37° C. for 48-72 h under anaerobic condition. At the end of 72 h, Alamar blue solution (20 µl) is added into the wells and incubated at 37° C. for 2 h. Plate is visualized for bacterial inhibitions and MIC values of the tested samples are determined. Gel formulation containing Besifloxacin alone, Besifloxacin combination with adapalene and their placebo are analyzed for MIC determinations and results are shown in FIG. 6.

Results:
Minimum inhibitory concentration (MIC) assay showed that MIC values of the besifloxacin in both the formulations (GL1 and GL2) were found to be similar in the range of 0.13 µg/ml to 0.25 µg/ml (FIG. 6).

Example 22: Dose Response Curve (Using Zones of Inhibition) of Gel Containing Besifloxacin Alone, its Combination Containing Adapalene Against *P. acnes*

Agar well-diffusion method is employed to run Zone of Inhibition (ZOI) assays. ZOI is employed to assess the potency of formulations (Table 1, GL1 and GL2) consist of Besifloxacin alone and its combination with adapalene to inhibit the growth of microorganisms under study. ZOI values, determined at different API concentrations, can be used to derive dose-response-curves (DRCs) for efficacy comparison of different formulations.

Method:
*P. acnes* cultured in Brain Heart Infusion (BHI) Broth (37° C., 48 h) under appropriate condition to get the desired CFU count, to be used to inoculate the plates. TSA plates are spreaded with 100 µl of 0.5 McFarland equal bacterial suspension. Sterile disc (6 mm) are loaded with various concentration of gel formulations (equivalent to different Besifloxacin concentration of 0.12, 0.25, 0.5 and 1 µg/ml) and/or controls (100 µl each) and then disc has been placed above the spreaded plates. Thereafter, the treated plates are incubated at 37° C. for 24 h. Readouts are taken after 24 h and effect of combination of two different APIs on anti-acne activity is measured using Zone of Inhibition studies.

Figure 7:
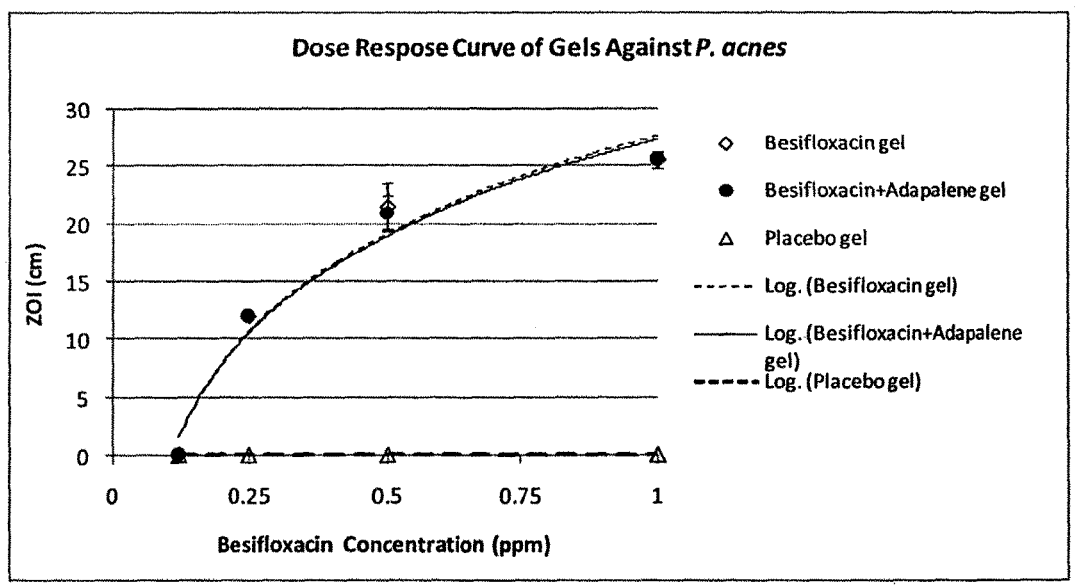
FIG. 7 is a line graph showing the dose response curve of Zone of Inhibition (ZOI) of some exemplary gel formulations against *P. acnes*.

Result:
ZOI assay results showed that both the formulations have similar anti-acne activity as evident from their zone of inhibitions. Adapalene presence in the gel formulation is not affecting the anti-acne activity of the Besifloxacin present in the formulations (FIG. 7).

Example 23: Time Kill Kinetics Evaluation of Gel Containing Besifloxacin Alone, its Combination Containing Adapalene Against *P. acnes*

An activity comparison, by in vitro time-kill kinetics of anti-acne agents using besifloxacin gel (Table 18, GL2) and versus its combination with adapalene gel (Table 18, GL1) has been demonstrated. The time-kill assays are used to evaluate efficacy of antimicrobial agents, either single or in combination.

Figure 8:
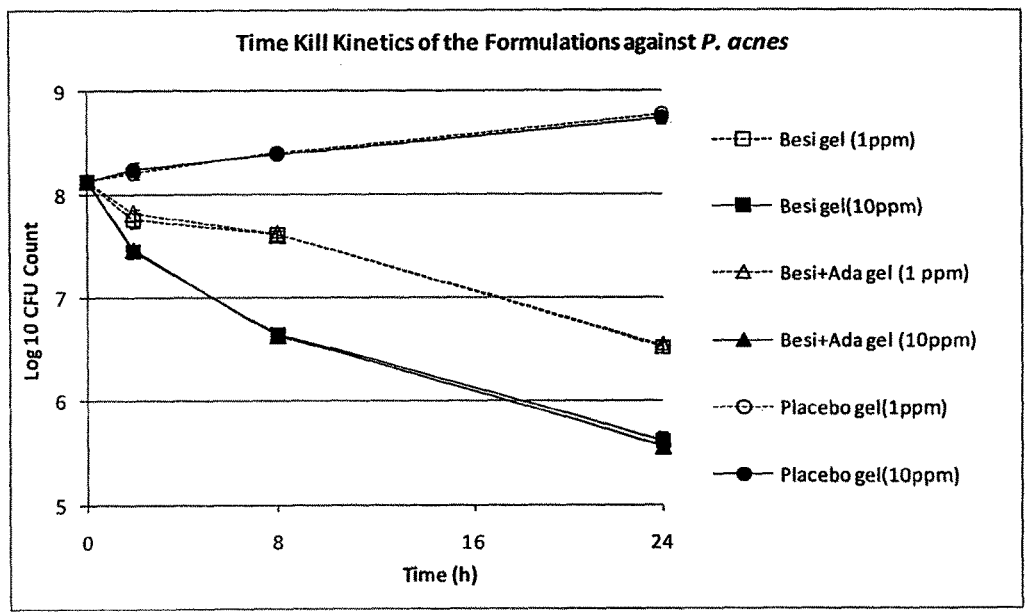
FIG. 8 is a line graph showing the time kill kinetics of some exemplary gel formulations against *P. acnes*.

Method:
*P. acnes* are suspended in brain heart infusion broth (BHI broth) at inoculum concentration of $1.3 \times 10^8$ cells/ml. Cells were taken from a freshly growing (3-7 days old) plate and cell suspension is vortexed to remove the cell clumps as much as possible. The media is then supplemented with appropriate concentrations of gel formulation (equivalent to 1 µg/ml and 10 µg/ml of API) in the reaction mixture. The cultures are incubated on a tube rotator at 37° C. in anaerobic condition for 2 h, 8 h and 24 h. At the end of each time points, aliquots (500) of *P. acnes* cultures are serially diluted with medium and plated on brain heart infusion agar plate. The plates are incubated at 37° C. in $CO_2$ incubator for 3 days. The viable colonies are counted and converted to CFU/ml. The results of time kill study using Besifloxacin gel stand alone and its combination with adapalene concentration are plotted in FIG. 8.

Results:
Time kill assay results showed that both the formulations have similar kill kinetics against *P. acnes*. Presence of adapalene in the gel formulation did not appear to affect the bactericidal activity of the Besifloxacin present in the formulations. Both the formulations also have concentration dependent kill kinetics at two different concentrations of 1 µg/ml and 10 µg/ml (FIG. 8). *P. acnes*'s kill has not been observed with the placebo gel, which indicates that placebo gel is not imparting any anti-bacterial activity.

Example 24: In Vivo Time Kill Kinetics of Gel Containing Besifloxacin Against Clindamycin Resistant *P. acnes*

An activity comparison in in vivo time-kill assay of anti-acne agents using besifloxacin gel and versus placebo gel has been performed in mouse model. This assay is used to determine efficacy of formulation containing antimicrobial agents to kill the pathogen infecting a live animal.

Method:
Clindamycin resistant *P. acnes* cells were grown in brain heart infusion broth (BHI broth) till the cells reached late log phase of growth. Cells were washed twice and resuspended in BHI broth with final inoculum concentration of $2 \times 10^7$ cells/ml. Cell suspension was vortexed and passed through 30 G needles to remove the cell clumps as much as possible. 10 µl of *P. acnes* culture were injected into right ear (dorsal surface) of anesthetized 8-10 weeks old mice by the help of Hamilton syringe (intra dermal injection). After 30 minutes approximately 15 mg of 1% Besifloxacin or Placebo gel formulation was applied on mice right ear (dorsal surface) & properly spreaded with the help of spatula. After 24 hrs. Mice were sacrificed and ears were harvested (0 hrs. Control mice ear had been taken on the same day when *P. acnes* were injected) and placed in microcentrifuge tube. 1 ml of BHI broth added in each tube and then ears were homogenized by mechanical homogenizer. 50 µl of ear homogenates from each tube were plated on BHA plate (containing 0.5 µg/ml Amhotericin-B) after serial dilution. Aliquots (50 µl) of *P. acnes* cultures were serially diluted with medium and plated on brain heart infusion agar plate. The plates were incubated at 37° C. in CO2 incubator for 3 days. The viable colonies were counted and converted to CFU/ml. The results of in vivo time kill study using Besifloxacin gel vs. placebo gel were plotted in FIG. 9.

Figure 9:
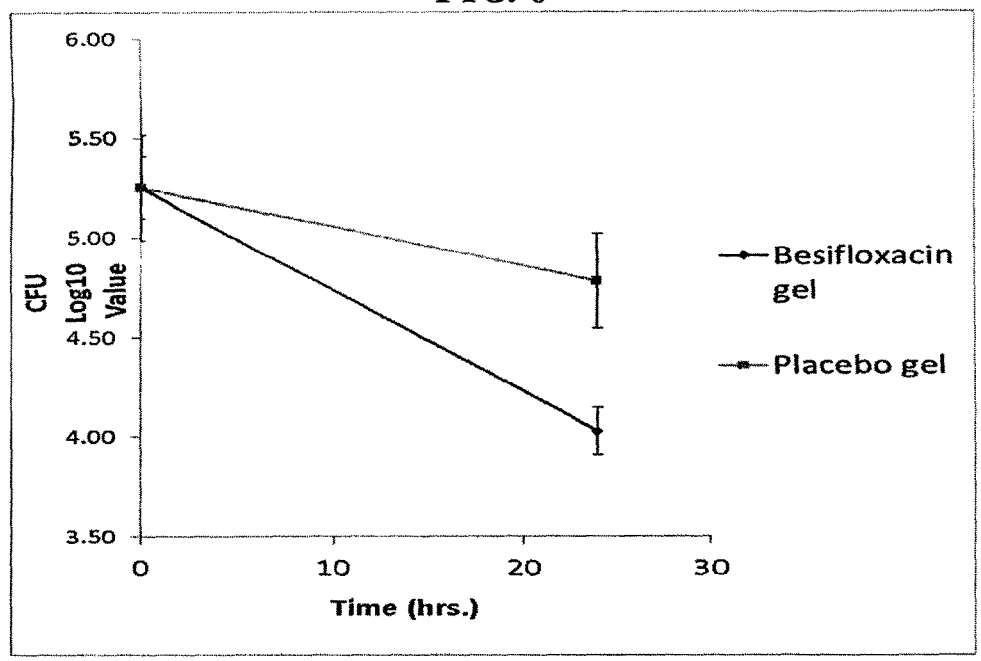
FIG. 9 Graph shows the efficacy of a topical formulation of besifloxacin in *P. acnes* in an in vivo skin infection model. Besifloxacin gel formulation has the ability to clear almost 1.5 log CFU (~95%) of inoculum of clindamycin resistant *P. acnes* within first 24 hours.

Results:
In vivo Time kill assay results showed that Besifloxacin gel formulation have the ability to clear almost 1.5 log CFU (~95%) of inoculum of clindamycin resistant *P. acnes* within first 24 hours (FIG. 9). There were some nominal killing being observed even with the placebo treatment it could largely be attributed to the immuno competency of the host. It further vindicated our claim that not only in in vitro but also in an animal infection model our topical formulations were very effective and could penetrate at the site of infection in sufficient quantity and clear clindamycin resistant infection.

Example 25: Preparation of Spray Formulations Loaded with Besifloxacin Hydrochloride, Clinafloxacin or Sitafloxacin Alone and the Combinations with Adapalene Spray formulations containing besifloxacin Hydrochloride, clinafloxacin, sitafloxacin and combination with adapalene and salicylic acid are formulated as per the compositions shown in Table 19. These formulations have the pH of 4.7-5.5. The formulations consist of actives (besifloxacin hydrochloride, clinafloxacin and sitafloxacin) equivalent to 1% w/w in different formulations (Table 19, S5, S3 and S2). In addition to stand alone formulation, anti-microbial agents are combined with keratolytic agent such as adapalene (0.1%) to provide both the anti-acne and keratolytic activity in patients suffering from acne (Table 19, S1, S4 and S6).

Method of Preparation:

(1) Water is added to a main mixing vessel followed by the addition of sodium hydroxide solution, PEG 1450, methyl gluceth-20 and glycerin in order with mixing.

(2) In a separate vessel, besifloxacin hydrochloride, clinafloxacin or sitafloxacin is added in isopropyl alcohol, propylene glycol, diethylene glycol monethyl ether and ethanol mixture and mixed. All the content of this vessel is added to the main vessel and mixed.

(3) Adapalene is dissolved in N-methyl 2-pyrrolidone and added to main mixing vessel, and mixed.

(4) Salicyclic acid, phenoxyethanol, and sodium hydroxide is added to adjust the pH to 5.0.

(5) Fragrance is added to the stirring mixture and stirred continuously till uniform mixing.

TABLE 19

Spray formulations for compositions S1, S2, S3, S4, S5 and S6

| S. No. | Ingredient | Composition (%) | | | | | |
|---|---|---|---|---|---|---|---|
| | | S1 | S2 | S3 | S4 | S5 | S6 |
| 1 | Water | q.s | q.s | q.s | q.s | q.s | q.s |
| 2 | Sodium hydroxide (18% aq.) | q.s | q.s | q.s | q.s | q.s | q.s |
| 3 | PEG 1450 | 2 | 2 | 2 | 2 | 2 | 2 |
| 4 | Methyl Gluceth-20 | 2.5 | 2.5 | 2.5 | 2.5 | 2.5 | 2.5 |
| 5 | Glycerin | 1 | 1.5 | 2 | 1 | 1 | 1.5 |
| 6 | Besifloxacin | 1 | 0 | 0 | 0 | 1 | 1 |
| 7 | Clinafloxacin | 0 | 0 | 1 | 0 | 0 | 0 |

TABLE 19-continued Spray formulations for compositions S1, S2, S3, S4, S5 and S6

| S. No. | Ingredient | S1 | S2 | S3 | S4 | S5 | S6 |
|---|---|---|---|---|---|---|---|
| 8 | Sitafloxacin | 0 | 1 | 0 | 1 | 0 | 0 |
| 9 | Adapalene | 0.1 | 0 | 0 | 0.1 | 0 | 0 |
| 10 | Isopropyl alcohol | 20 | 20 | 20 | 20 | 20 | 0 |
| 11 | diethylene glycol monethyl ether | 1 | 1 | 1 | 1 | 1 | 1 |
| 12 | Propylene glycol | 1.5 | 1.5 | 1.5 | 1.5 | 1.5 | 1.5 |
| 13 | Ethyl alcohol | 0 | 0 | 0 | 0 | 0 | 20 |
| 14 | N-methyl 2-pyrrolidone | 3 | 0 | 0 | 3 | 0 | 0 |
| 15 | Salicylic acid | 0 | 0 | 0 | 0 | 0 | 2 |
| 16 | Sodium hydroxide | q.s | q.s | q.s | q.s | q.s | q.s |
| 17 | Phenoxyethanol | 1 | 1 | 1 | 1 | 1 | 1 |
| 18 | Fragrance | 0.4 | 0.4 | 0.4 | 0.4 | 0.4 | q.s |

Example 26: Preparation of Face Wash Formulations Loaded with Besifloxacin Hydrochloride, Clinafloxacin or Sitafloxacin Alone and the Combinations with Adapalene Facewash formulations containing besifloxacin, clinafloxacin, or sitafloxacin and the combination with adapalene or salicylic acid are formulated as per the compositions shown in Table 20. These facewash formulations have pH of 4.7-6 and viscosity of around 1500-5000 mPa·s. The formulations consist of actives (besifloxacin hydrochloride, clinafloxacin or sitafloxacin) equivalent to 1% w/w in different formulations (Table 20, FW5, FW3 and FW2). In addition to stand alone formulation, anti-microbial agents are combined with keratolytic agent such as adapalene (0.1%) to provide both the anti-acne and keratolytic activity in patients suffering from acne (Table 20, FW1, FW4 and FW6).

Method of Preparation:
(1) In a main mixing vessel, water is added. Then carbopol aqua SF-1 is added slowly at a low speed (70-80 rpm) of mixing.
(2) In the same vessel, sodium C14-16 olefin sulfonate (40%) and sodium lauryl ether sulphate (28.6%) are added while stirring.
(3) The mixture is neutralized with sodium hydroxide, adjusting the pH to 6.5 to 7.0. The mixing speed is slightly increased to ensure uniform mixing.
(5) Then cocamidopropylbetaine is added to above mixture with continuous stirring followed by slow additions of disodium EDTA and glycerin.
(6) Besifloxacin hydrochloride, clinafloxacin, or sitafloxacin and adapalene are added to the above stirring main vessel.
(7) Adapalene is dissolved in N-methyl 2-pyrrolidone and added to main mixing vessel, and mixed.
(8) Then, salicylic acid, propylene glycol and PEG-7 glycerylcocoate are added to continuous stirring main vessel.
(8) Finally, pH is adjusted to 5.5 by the addition of citric acid.

TABLE 20

Face wash for compositions FW1, FW2, FW3, FW4, FW5 and FW6

| S. No. | Ingredient | FW1 | FW2 | FW3 | FW4 | FW5 | FW6 |
|---|---|---|---|---|---|---|---|
| 1 | Water | q.s. | q.s. | q.s. | q.s. | q.s. | q.s. |
| 2 | Carbopol aqua SF-1 | 6 | 6 | 6 | 6 | 6 | 6 |
| 3 | Sodium C14-16 Olefin Sulfonate | 35 | 35 | 35 | 35 | 35 | 35 |
| 4 | Sodium lauryl ether sulphate | 2 | 2 | 2 | 2 | 2 | 2 |
| 5 | Sodium hydroxide (18% aq.) | q.s. | q.s. | q.s. | q.s. | q.s. | q.s. |
| 6 | Cocamidopropylbetaine (30%) | 10 | 5 | 10 | 10 | 5 | 7 |
| 7 | Disodium EDTA | 0.1 | 0.1 | 0.1 | 0.1 | 0.1 | 0.1 |
| 8 | Glycerin | 5 | 5 | 5 | 5 | 5 | 3 |
| 9 | Besifloxacin | 1 | 0 | 0 | 0 | 1 | 1 |
| 10 | Clinafloxacin | 0 | 0 | 1 | 1 | 0 | 0 |
| 11 | Sitafloxacin | 0 | 1 | 0 | 0 | 0 | 0 |
| 12 | Adapalene | 0.1 | 0 | 0 | 0.1 | 0 | 0 |
| 13 | N-methyl 2-pyrrolidone | 3 | 0 | 0 | 3 | 0 | 0 |
| 14 | Salicylic Acid | 0 | 0 | 0 | 0 | 0 | 1 |
| 15 | Propylene glycol | 0 | 0 | 0 | 0 | 0 | 4 |
| 16 | PEG-7 glycerylcocoate | 1 | 1 | 1 | 1 | 1 | 1 |
| 17 | Citric Acid (50%) | q.s. | q.s. | q.s. | q.s. | q.s. | q.s. |

Example 27: Preparation of Soap Bars Loaded with Besifloxacin Hydrochloride, Clinafloxacin or Sitafloxacin Alone and the Combinations with Adapalene Method of Preparation:

Soap bars containing besifloxacin, clinafloxacin or sitafloxacin are formulated as per the compositions shown in Table 21. The soap bars consist of Besifloxacin hydrochloride equivalent to 1% w/w (Table 21, SB5), clinafloxacin equivalent to 1% w/w (Table 21, SB3), sitafloxacin equivalent to 1% w/w (Table 21, SB2). In addition to stand alone besifloxacin formulation, besifloxacin is combined with adapalene (0.1%) (Table 21, SB1) and salicylic acid (Table 21, SB6) to provide both anti-microbial and keratolytic activity to patients suffering from acne. Similarly, another formulation contains clinafloxacin in combination with adapalene (Table 21, SB4).

Method of Preparation:
(1) Sodium palmitate is blended with remaining ingredients in the mixer.
(2) The mass is passed through the roll mill and plodder followed by billeting and stamping at a temperature between 35° C.-40° C.

TABLE 21

Soap bars for compositions SB1, SB2, SB3, SB4, and SB6

| S. No. | Ingredient | SB1 | SB2 | SB3 | SB4 | SB5 | SB6 |
|---|---|---|---|---|---|---|---|
| 1 | Sodium palmitate | 94.2 | 94.2 | 94.2 | 94.2 | 94.2 | 94.2 |
| 2 | Sodium lauryl ether sulphate | 2 | 2 | 2 | 2 | 2 | 2 |
| 3 | Polyquaternium-39 | 1 | 1 | 1 | 1 | 1 | 1 |
| 4 | Methyl Gluceth-20 | 1 | 1 | 1 | 1 | 1 | 1 |
| 5 | Titanium dioxide | 0.5 | 0.5 | 0.5 | 0.5 | 0.5 | 0 |
| 6 | Besifloxacin | 1 | 0 | 0 | 0 | 1 | 1 |
| 7 | Clinafloxacin | 0 | 0 | 1 | 1 | 0 | 0 |
| 8 | Sitafloxacin | 0 | 1 | 0 | 0 | 0 | 0 |
| 9 | Adapalene | 0.1 | 0 | 0 | 0.1 | 0 | 0 |

TABLE 21-continued

Soap bars for compositions SB1, SB2, SB3, SB4, and SB6

| S. No. | Ingredient | SB1 | SB2 | SB3 | SB4 | SB5 | SB6 |
|---|---|---|---|---|---|---|---|
| 10 | Salicylic acid | 0 | 0 | 0 | 0 | 0 | 0.1 |
| 11 | Oleyl oleate | 0.5 | 0.5 | 0.5 | 0.5 | 0.5 | 0.5 |
| 12 | BHT (Butylated HydroxyToluene) | 0.01 | 0.01 | 0.01 | 0.01 | 0.01 | 0.01 |

Example 28: Preparation of Body Wash Containing Besifloxacin Hydrochloride, Clinafloxacin or Sitafloxacin Alone and the Combinations with Adapalene Method of Preparation:

Body wash formulations containing besifloxacin, clinafloxacin or sitafloxacin and adapalene or salicylic acid are formulated as per the compositions shown in Table 22. The body wash formulations consist of besifloxacin equivalent to 1% w/w (Table 22, BW5), sitafloxacin equivalent to 1% w/w (Table 22, BW2) and clinafloxacin equivalent to 1% w/w (Table 22, BW3). In addition to stand alone besifloxacin formulation, besifloxacin is combined with the adapalene (0.1%) and salicylic acid (2%) (Table 22, BW1, BW6), to provide both anti-acne and keratolytic activity in acne patients. Similarly, another formulation contains clinafloxacin in combination with adapalene (Table 22, BW4).

TABLE 22

Body Wash for Compositions BW1, BW2, BW3, BW4, BW5 and BW6

| S. No. | Ingredient | BW1 | BW2 | BW3 | BW4 | BW5 | BW6 |
|---|---|---|---|---|---|---|---|
| 1 | Water | q.s. | q.s. | q.s. | q.s. | q.s. | q.s. |
| 2 | Disodium EDTA | 0.1 | 0.1 | 0.1 | 0.1 | 0.1 | 0.1 |
| 3 | Carbopolaqua SF-1 | 1 | 1 | 1 | 1 | 1 | 1 |
| 4 | Ammonium lauryl sulphate (30%) | 30 | 30 | 30 | 30 | 30 | 30 |
| 5 | Propylene glycol | 5 | 5 | 5 | 5 | 5 | 5 |
| 6 | Besifloxacin | 1 | 0 | 0 | 0 | 1 | 1 |
| 7 | Clinafloxacin | 0 | 0 | 1 | 1 | 0 | 0 |
| 8 | Sitafloxacin | 0 | 1 | 0 | 0 | 0 | 0 |
| 9 | Adapalene | 0.1 | 0 | 0 | 0.1 | 0 | 0.1 |
| 10 | N-methyl 2-pyrrolidone | 3 | 0 | 0 | 3 | 0 | 3 |
| 11 | Ethanol | 4 | 4 | 4 | 4 | 4 | 4 |
| 12 | Propyl paraben | 0.03 | 0.03 | 0.03 | 0.03 | 0.03 | 0.03 |
| 13 | Methyl gluceth-10 | 0.3 | 0.3 | 0.3 | 0.3 | 0.3 | 0.3 |
| 14 | Disodium laureth sulfosuccinate (39%) | 2 | 2 | 2 | 2 | 2 | 2 |
| 15 | Fragrance | 0.5 | 0.5 | 0.5 | 0.5 | 0.5 | 0.5 |
| 16 | Triethanolamine | q.s. | q.s. | q.s. | q.s. | q.s. | q.s. |

Method of Preparation:
(1) In main mixing vessel, disodium EDTA is dissolved in water.
(2) Carbpol aqua SF-1 is added to the main vessel.
(3) Then it is stirred for 10 min followed by the addition of ammonium lauryl sulphate.
(4) Then propylene glycol, besifloxacin hydrochloride, clinafloxacin, or sitafloxacin are added to above mixture with continuous stirring.
(5) Adapalene is dissolved in N-methyl 2-pyrrolidone and added to main mixing vessel, followed by its mixing.
(6) While stirring remaining ingredients are added to the above mixture.
(7) Finally, neutralization is done with triethanolamine and pH is adjusted to 5.5-6.0.

Example 29: Preparation of Lotion Formulations Loaded with Besifloxacin Hydrochloride, Clinafloxacin or Sitafloxacin Alone and the Combinations with Adapalene Lotion formulations containing besifloxacin are formulated as per the compositions shown in Table 23. These lotions have pH of 4.7-5.5 and viscosity of around 2500-6000 mPa·s. The lotions consist of besifloxacin equivalent to 1% w/w (Table 23, L5), sitafloxacin equivalent to 1% w/w Table 3, L2) and clinafloxacin equivalent to 1% w/w (Table 23, L3). In addition to stand alone formulation, besifloxacin is combined with the adapalene (0.1%) (Table 23, L1) or salicylic acid (Table 23, L6) to provide both the anti-acne and keratolytic activity in patients suffering from acne. Similarly, another formulation contains clinafloxacin in combination with adapalene (Table 23, L4).

TABLE 23

Lotion Formulations for Compositions L1, L2, L3, L4 and L5

| S. No. | Ingredient | L1 | L2 | L3 | L4 | L5 | L6 |
|---|---|---|---|---|---|---|---|
| 1 | Water | q.s | q.s | q.s | q.s | q.s | q.s |
| 2 | Disodium EDTA | 0.05 | 0.05 | 0.05 | 0.05 | 0.05 | 0.05 |
| 3 | Carbopol aqua SF-1 | 1 | 1 | 1 | 1 | 1 | 1 |
| 4 | Petrolatum | 1 | 1 | 1 | 1 | 1 | 1 |
| 5 | Cyclomethicone | 0.5 | 0.5 | 0.5 | 0.5 | 0.5 | 0.5 |
| 6 | Sorbitan stearate | 1.4 | 1.4 | 1.4 | 1.4 | 1.4 | 1.4 |
| 7 | Polysorbate 60 | 0.6 | 0.6 | 0.6 | 0.6 | 0.6 | 0.6 |
| 8 | Methyl gluceth-20 | 1 | 1 | 1 | 1 | 1 | 1 |

TABLE 23-continued

Lotion Formulations for Compositions L1, L2, L3, L4 and L5

| S. No. | Ingredient | L1 | L2 | L3 | L4 | L5 | L6 |
|---|---|---|---|---|---|---|---|
| 9 | Cetyl alcohol | 1.6 | 1.6 | 1.6 | 1.6 | 1.6 | 1.6 |
| 10 | Tocopheryl acetate | 0.25 | 0.25 | 0.25 | 0.25 | 0.25 | 0.25 |
| 11 | Besifloxacin | 1 | 0 | 0 | 0 | 1 | 1 |
| 12 | Clinafloxacin | 0 | 0 | 1 | 1 | 0 | 0 |
| 13 | Sitafloxacin | 0 | 1 | 0 | 0 | 0 | 0 |
| 14 | Adapalene | 0.1 | 0 | 0 | 0.1 | 0 | 0 |
| 15 | N-methyl 2-pyrrolidone | 3 | 0 | 0 | 3 | 0 | 0 |
| 16 | Salicylic acid | 0 | 0 | 0 | 0 | 0 | 1 |
| 17 | Propylene glycol | 2 | 2 | 2 | 2 | 2 | 2 |
| 18 | Glycerin | 8 | 8 | 8 | 8 | 8 | 8 |
| 19 | Ethanol | 2 | 2 | 2 | 2 | 2 | 2 |
| 20 | Phenoxyethanol | 1 | 1 | 1 | 1 | 1 | 1 |
| 21 | Sodium hydroxide | q.s | q.s | q.s | q.s | q.s | q.s |

Method of Preparation:
(1) In main mixing vessel, disodium EDTA is dissolved in water. When it is fully dissolved, mixing speed is set at 100 rpm.
(2) Then, carbopol aqua SF-1 is slowly dispersed into water and stirring is continued until complete mixing.
(3) Heat the mixture to 70° C.
(4) Melt petrolatum, cyclomethicone, polysorbate 60, sorbitan strearate, cetyl alcohol in a separate beaker and add it to above mixture. Keep the stirring speed at 200 rpm.
(5) Allow the mixture to cool at 35-40° C. with constant stirring at 200 rpm.
(6) Add tocopheryl acetate to the above mixture after it reaches at 35-40° C.
(7) Besifloxacin hydrochloride, clinafloxacin or sitafloxacin is added to the above mixture by dispersing in water.
(8) Adapalene is dissolved in N-methyl 2-pyrrolidone and added to main mixing vessel, followed by its mixing at 250 rpm.
(9) Dissolve salicylic acid in ethanol, propylene glycol and glycerol and add it to main mixing vessel.
(10) Add phenoxyethanol to the above mixture with constant stirring at 250 rpm.
(11) Neutralize the whole mixture with sodium hydroxide and mix for 30 min.

Example 28 and Table 24 describe some exemplary formulation comprising soublizied API, (e.g., besifloxacin hydrochloride).

Example 30: Approaches Used for the Solublization of Besifloxacin Hydrochloride

Surfactants are known to solubilize the hydrophobic substances by reducing the interfacial tension. In-addition to surfactants, co-solvents or co-surfactants also helps in solubilization of the poorly water-soluble compounds by increasing the wetting property or reducing the interfacial tension of the hydrophobic molecule. In this patent, besifloxacin have been solubilized using surfactants such as sodium lauryl sulfate, tween 80, tween 20 and span 80, and cosolvents/cosurfactants in the delivery vehicles. The presence of the sodium lauryl sulfate greatly enhanced the aqueous solubility of the besifloxacin hydrochloride and used for preparation of topical formulation (Table 24, SC1, SC2 and SC5). The co-solvents such as propylene glycol monocaprylate and diethylene glycol monoethyl ether has been used for the preparation of cream formulations (Table 24, SC3 and SC4).

TABLE 24

Fully solubilized besifloxacin cream formulations

| | | Composition (1% w/w) | | | | |
|---|---|---|---|---|---|---|
| S. No. | Ingredients | SC1 | SC2 | SC3 | SC4 | SC5 |
| 1 | Besifloxacin hydrochloride | 1.09 | 1.09 | 1.09 | 1.09 | 1.09 |
| 2 | Sodium Lauryl sulfate | 2 | 2 | 2 | 2 | 5 |
| 3 | Cetyl alcohol | 2 | 0 | 0 | 0 | 5 |
| 4 | Tween 80 | 0 | 3 | 0 | 3 | 0 |
| 5 | Tween 20 | 0 | 1.5 | 0 | 0 | 0 |
| 6 | Stearyl alcohol | 3 | 0 | 0 | 0 | 0 |
| 7 | Propylene glycol mono caprylate | 0 | 0 | 3 | 0 | 0 |
| 8 | PEG-8 capriccaprylate glyceride | 0 | 0 | 5 | 0 | 0 |
| 9 | Propylene Glycol | 0 | 0 | 0 | 0 | 1 |
| 10 | Diethylene glycol mono-ethyl ether | 0 | 0 | 0 | 15 | 0 |
| 11 | Steareth-21 | 2 | 3 | 3 | 0 | 2 |
| 12 | Cyclopentasiloxane | 4 | 0 | 4 | 3 | 8 |
| 13 | Phenoxy ethanol | 0.5 | 0.5 | 0.5 | 0.5 | 0.5 |
| 14 | Sodium Hydroxide (10% in water) | 1 | 1 | 1 | 1 | 2 |
| 15 | Carbomer homopolymer type C | 0.20 | 0.80 | 0.15 | 0.8 | 0 |
| 16 | Carbopol Ultrez 10 | 0 | 0 | 0 | 0 | 0.3 |
| 17 | Water | q. s. | q. s. | q. s. | q. s. | q. s. |

Examples 31 and 32, and Tables 25 and 26 describe some exemplary formulations comprising suspended API.

Example 31: Preparation of Suspended Drug Loaded Gel Formulations with Minimal Solubilization-Reprecipitation of the Drug Preparation of drug-loaded (suspended form) gel via a conventional method usually leads to exposure of the drug to a wide range of pH conditions, which may lead to, in some instances, solubilization of the drug, and then reprecipitation. This solubilization-reprecipitation phenomenon in most cases leads to change in original particle size, impurity profile or crystal pattern, or others. As an example, besifloxacin.HCl (which shows pH dependent solubility) displays this solubilization-reprecipitation phenomenon, where pH of about 4.5 or below solubilizes the drug to a significant and variable extent. The solubilized besifloxacin then, upon increase in pH (during formulation preparation), reprecipitates, which may result in one or more unwanted changes.

In order to circumvent this issue, a modified approach has been employed to prepare different suspended drug-loaded formulations. Table 25 and the Method of Preparation below details the gel composition and preparation with negligible or minimal drug solubilization-reprecipitation. These gel formulations have off-white appearance with pH of 5.0-6.0 and approx. viscosity of about 3000 to about 5500 mPa·s measured by Viscometer (RheolabQC, C-LTD 80/QC, Anton Paar). The formulations are used against susceptible and resistant acne conditions.

TABLE 25

Besifloxacin•HCl Suspended Gel Formulations
for Compositions GL5, GL6, GL7

| Chemical Name | Composition (% w/w) | | |
|---|---|---|---|
| | GL5 | GL6 | GL7 |
| Besifloxacin•HCl Equivalent to Besifloxacin | 1 | 1.5 | 2 |
| Allantoin | 0.2 | 0.2 | 0.2 |
| Carbomer homopolymer type C | 0.85 | 0.85 | 0.85 |
| Diethylene glycol monoethyl ether | 5 | 5 | 0 |
| Edetate disodium dehydrate | 0.1 | 0.1 | 0.1 |
| Glycerin | 5 | 5 | 5 |
| Phenoxyethanol | 0.7 | 0.7 | 0.7 |
| Polyethylene glycol 400 | 5 | 5 | 5 |
| Sodium hyaluronate | 0.4 | 0.4 | 0.4 |
| Sodium hydroxide solution* | q.s. to adjust pH | q.s. to adjust pH | q.s. to adjust pH |
| Purified water | q.s. | q.s. | q.s. |

Phase A: Purified water, Edetate disodium dehydrate, Allantoin, Carbomer homopolymer type C Phase B: Purified water, Sodium hyaluronate Phase C: Phenoxyethanol, Sodium hydroxide solution Phase D: Glycerin, Besifloxacin.HCl (Equivalent to Besifloxacin), Purified water, Sodium hydroxide solution Phase E: Polyethylene glycol 400, Diethylene glycol monoethyl ether, Phase F: Sodium hydroxide solution Method of Preparation:

1) In a main mixing vessel, edetate disodium and allantoin were dissolved in water. Then carbomer homopolymer type C and hyaluronate sodium were added and allowed to swell at 200 rpm for 60 min. Then phenoxyethanol was added to the carbomer mixture. Then, pH of the mixture was raised to 6.0 with sodium hydroxide solution.

2) In a separate vessel, glycerin and besifloxacin.HCl were dispersed with continuous mixing at 300 rpm for 10 min.

3) Dilute solution of sodium hydroxide was added dropwise to the separate vessel to adjust pH to 5.5.

4) The contents of the above mixture were added to the main mixing vessel with stirring at 200 rpm for 2 hours.

5) Finally, polyethylene glycol and diethylene glycol monoethyl ether were added to the main mixing vessel and mixed for further 20 min.

6) White-to-pale yellow gel was obtained.

Example 32: Preparation of Suspended Drug Loaded Cream Formulation by Avoiding Re-Precipitation of Drug Similarly, cream formulations containing suspended besifloxacin were prepared, with minimal solubilization-reprecipitation, as per the compositions shown in Table 25. These cream formulations have off-white appearance with pH of 5.0-6.0 and approx. viscosity of about 3000 to about 4000 mPa·s (measured by Viscometer (RheolabQC, C-LTD 80/QC), Anton Paar). The formulations were then tested against susceptible and resistant strains of acne.

TABLE 26

Besifloxacin•HCl Suspended Cream Formulations
for Compositions CM2, CM3 and CM4

| Ingredients | Composition (% w/w) | | |
|---|---|---|---|
| | CM 2 | CM 3 | CM 4 |
| Besifloxacin•HCl equivalent to besifloxacin | 1 | 1.5 | 2 |
| Butylated Hydroxytoluene | 0.1 | 0.1 | 0.1 |
| Carbopol 980 (2%) | 30 | 35 | 40 |
| Cetyl alcohol | 1 | 1 | 1 |
| Cyclopentasiloxane | 5 | 5 | 5 |
| Glycerin | 5 | 5 | 5 |
| Light liquid paraffin | 3 | 3 | 3 |
| Phenoxyethanol | 0.5 | 0.5 | 0.5 |
| Sodium hydroxide solution | 2 | 2 | 2 |
| Span 80 | 1 | 0 | 1 |
| Steareth 2 | 2 | 2 | 1 |
| Steareth 21 | 2 | 2 | 1 |
| Stearyl alcohol | 1 | 1 | 1 |
| Purified water | q.s. to 100 | q.s. to 100 | q.s. to 100 |

Phase A: Cyclomethicone, Span 80, Cetyl alcohol, Stearyl alcohol, Light liquid paraffin, Steareth 2, Steareth 21

Phase B: Glycerin, Besifloxacin.HCl equivalent to besifloxacin, Purified water, Sodium hydroxide solution Phase C: Butylated Hydroxytoluene, Phenoxyethanol, Carbopol 980 (2%)

Method of Preparation:

1. In main mixing vessel, besifloxacin was dispersed in glycerol and water with continuous mixing at 300 rpm for 10 minutes.
2. Dilute solution of sodium hydroxide was added dropwise to the main mixing vessel to adjust pH to about 5.5 and heated to 70° C.
3. In a separate vessel, cyclomethicone, span 80, cetyl alcohol, stearyl alcohol, light liquid paraffin, steareth 2 and steareth 21 were heated together to 70° C.
4. Heated mixture of oil phase was added with continuous mixing to the main mixing vessel at 70° C., 200 rpm and allowed to mix for 15 min.
5. The content of the main mixing vessel was allowed to air-cool with mixing to 45° C.
6. Carbopol was allowed to swell in water for 2 h and its pH was adjusted to about 5.5 to 6 with sodium hydroxide solution, which was then added to the main mixing vessel and mixed.
7. Remaining components butylated hydroxytoluene and phenoxyethanol were added to the main mixing vessel and mixed for 20 min.
8. The cream's pH was adjusted to about 5.5 to 6.0 with sodium hydroxide, if required.

Example 33: Preparation of Formulations Containing Combination of Actives (Soluble Anti-Microbial and Suspended Keratolytic Agent)

Gel formulations containing a combination of soluble besifloxacin.HCl and suspended adapalene were prepared as per the compositions shown in Table 27. These gel formulations have pale yellow appearance with pH of around 4.5 and viscosity in the range of 3000 to 5000 mPa·s (measured by Viscometer (RheolabQC, C-LTD 80/QC), Anton Paar). The formulations containing soluble besifloxacin equivalent to 1-2% w/w and partially or fully suspended adapalene equivalent to 0.1% w/w have been prepared to provide anti-acne, keratolytic and anti-inflammatory effects in patients affected from susceptible and resistant acne.

TABLE 27

Besifloxacin•HCl (soluble) and Adapalene (suspended) Containing Gel Formulations for Compositions SL1, SL2 and SL3

| Ingredients | Composition (% w/w) | | |
|---|---|---|---|
| | SL1 | SL2 | SL3 |
| Besifloxacin•HCl Equivalent to Besifloxacin | 1 | 1.5 | 2 |
| Adapalene | 0.1 | 0.1 | 0.1 |
| Allantoin | 0.2 | 0.2 | 0.2 |
| Diethylene glycol monoethyl ether | 11 | 20 | 23.5 |
| Edetate disodium dihydrate | 0.1 | 0.1 | 0.1 |
| Glycerin | 5 | 5 | 5 |
| Hyaluronate Sodium | 0.3 | 0 | 0.3 |
| Hydroxy ethylcellulose | 0.9 | 1.2 | 0.9 |
| Phenoxyethanol | 0.7 | 0.7 | 0.7 |
| Poloxamer | 0.2 | 0.2 | 0.2 |
| Polyethylene glycol 400 | 6 | 7 | 7 |
| Purified water | q.s. to 100 | q.s. to 100 | q.s. to 100 |

Phase A: Purified water, Allantoin, Edetate disodium dihydrate, Hydroxy ethylcellulose
Phase B: Purified water, Hyaluronate Sodium
Phase C: Purified water, Glycerin, Besifloxacin.HCl Equivalent to Besifloxacin, Adapalene, Poloxamer Polyethylene glycol 400, Diethylene glycol monoethyl ether, Phenoxyethanol.

Method of Preparation:
1. In a main mixing vessel, edetate disodium dihydrate and allantoin were dissolved in water at 400 rpm for about 10 minutes.
2. Hydroxyethyl cellulose (HEC) was added in portions to the main mixing vessel at very high speed (about 400-500 rpm).
3. HEC was allowed to swell for 1 h with stirring at about 100-150 rpm.
4. In a separate vessel, hyaluronate sodium was added and allowed to swell for 15-30 minutes, followed by addition to the main mixing vessel.
5. In a separate vessel, glycerin and besifloxacin.HCl were dispersed in water and mixed with glass rod. Then, diethylene glycol monoethyl ether and polyethylene glycol 400 were added to besifloxacin dispersion and mixed. This dispersion was added to main mixing vessel, and allowed to stir at about 100-150 rpm for about 5 minutes.
6. Phenoxyethanol was then added to the main mixing vessel, and mixed at 100-150 rpm until any polymer lumps disappeared completely and clear gel was obtained.
7. Adapalene was dispersed in aqueous solution of poloxamer and added to the main mixing vessel, resulting in white-to-pale yellow opaque gel containing soluble besifloxacin and suspended adapalene.

Example 34 and Table 28 describe some exemplary formulations which are essentially free of a thickening polymer.

Example 34: Preparation of Suspended Drug Loaded Cream Formulation without Use of Polymer as a Viscosity Modifier According to published literature there may be some kind of physical and/or chemical interaction between Carbomer and fluoroquinolones. For which, there may be a need to prepare formulations without Carbomer or Carbomer-like-polymers to avoid any incompatibility issues during the product shelf life. Towards this, an alternative cream formulation, without use of the Carbomer or any other polymer, has been prepared. Cream formulation compositions and procedure is given in Table 28.

TABLE 28

Besifloxacin•HCl Suspended Cream Formulations for Compositions CM5

| Ingredients | Composition (% w/w) |
|---|---|
| Besifloxacin | 1 |
| Butylatedhydroxy toluene | 0.1 |
| Cetyl alcohol | 2 |
| Cyclopentasiloxane | 5 |
| Glycerin | 5 |
| Mineral Oil | 3 |
| Phenoxyethanol | 0.7 |
| Polyoxyl 2 Stearyl Ether | 2 |
| Polyoxyl 21 Stearyl Ether | 2 |
| Stearyl alcohol | 2 |
| Sodium hydroxide | q.s. to pH >5.5 |
| Purified Water | q.s. to 100.0 |

Phase A: Cetyl alcohol, Stearyl alcohol, Mineral Oil, Cyclopentasiloxane, Polyoxyl 2 Stearyl Ether, Polyoxyl 21 Stearyl Ether
Phase B: Glycerin, Besifloxacin,
Phase C: Sodium hydroxide, Purified Water
Phase D: Butylatedhydroxy toluene, Phenoxyethanol
Phase E: Sodium hydroxide Method of Preparation
1) Phase B: Glycerol and API were mixed together in main mixing vessel,
2) Phase C: Sodium Hydroxide and water were mixed together and added slowly into phase B in the main mixing vessel and the contents heated to 60-65° C.,
3) Phase A excipients were mixed together and heated at 60-65° C., followed by adding to the main mixing vessel with continuous overhead stirring at about 600 rpm,
4) The contents of the main mixing vessel are then allowed to cool to about 40° C.,
5) To this mixture contents of Phase D were added and mixed for 15 min,
6) Finally pH of the formulation was adjusted to 5.5-6.0 using phase E Example 35 and Tables 29-32 describe some exemplary formulations comprising different polymeric or non-polymeric viscosity modifiers or gelling agents

Example 35: Use of Different Polymers for Viscosity Regulation of Formulations Containing Solubilized Besifloxacin.HCl The purpose of gel formulations to be prepared was to have acceptable viscosities, while the active drug remains in soluble form. This becomes challenging, when the pH required for drug solubilizing or stabilizing a solubilized drug is outside the normal range of about 5.0 to about 7.0 for topical products. For example, besifloxacin.HCl goes in solution, of course with proper choice of excipients, when the pH is adjusted to below 5.0, for example in the range 4.0-4.5. Not many polymers (without affecting gel sensorial parameters) were found to be able to furnish acceptable viscosities to the gel formulations, in this pH range.

Different polymers (and their different grades) like carbomer, hydroxypropyl cellulose, hydroxypropyl methyl cellulose, hydroxyethyl cellulose, sodium hyaluronate, and other polymers were used to prepare gels with acceptable viscosities, wherein the active drug was desired to be in a solubilized state.

Gel formulation containing soluble besifloxacin.HCl was attempted to prepare using Carbomer as per the composition and procedure given in Table 25. Although the drug could be solubilized at pH 4.5, the Carbomer used in required amount was not able to impart acceptable viscosity to the formulation. The resulting formulation had viscosity about 1000-1800 mPa·s (measured by Viscometer (RheolabQC, C-LTD 80/QC), Anton Paar).

TABLE 29

Besifloxacin•HCl Solubilized Gel Formulation Prepared Using Carbomer for Compositions SL4

| Phase | Ingredients | Composition (% w/w) |
|---|---|---|
| A | Glycerin | 5.0 |
|   | Besifloxacin•HCl equivalent to Besifloxacin | 1 |
| B | Purified Water | q.s. to 100.0 |
|   | Carbomer Homopolymer Type C | 0.9 |
|   | Allantoin | 0.2 |
|   | Edetate Disodium Dihydrate (EDTA) | 0.1 |
|   | Phenoxyethanol | 0.7 |
|   | Sodium Hyaluronate | 0.4 |
| C | Polyethylene glycol 400 | 6 |
|   | Diethylene glycol monoethyl ether | 11 |

Method of preparation:
1) Phase A: Glycerol and besifloxacin were mixed together in a separate vessel,
2) Phase B: In a main mixing vessel, allantoin and EDTA were solubilized in water with stirring at 200 rpm, then carbomer was sprinkled over it slowly and allowed to swell for 45 min,
3) Sodium hyaluronate was sprinkled into the above mixture and allowed to swell for 15 min, followed by addition of Phenoxyethanol and mixing,
5) Phase A was transferred into the main mixing vessel with continuous stirring at 200 rpm, and mixed for 30 min,
6) Polyethylene glycol 400 and diethylene glycol monoethyl ether were added to the main mixing vessel and mixed for 15 min at 150 rpm Hydroxypropyl Cellulose and Hydroxypropyl Methyl Cellulose are widely used in oral and topical pharmaceutical formulations and available in number of different grades that can furnish wise viscosity ranges. Formulations containing solubilized besifloxacin were prepared using hydroxypropyl cellulose or hydroxypropyl methyl cellulose as viscosity modifiers (Table 30). Although acceptable viscosities of about 3000 mPa·s (measured by Viscometer (RheolabQC, C-LTD 80/QC), Anton Paar) were observed using both the polymers, the sensorials were not acceptable.

TABLE 30

Besifloxacin•HCl Solubilized Gel Formulations Prepared Using Hydroxypropyl Cellulose and Hydroxypropyl Methyl Cellulose for Compositions SL5 and SL6

| | | Compositions (% w/w) | |
|---|---|---|---|
| Phase | Ingredients | SL5 | SL6 |
| A | Glyceroin | 5.0 | 5.0 |
|   | Besifloxacin•HCl | 1.09 | 1.09 |

TABLE 30-continued

Besifloxacin•HCl Solubilized Gel Formulations Prepared Using Hydroxypropyl Cellulose and Hydroxypropyl Methyl Cellulose for Compositions SL5 and SL6

| | | Compositions (% w/w) | |
|---|---|---|---|
| Phase | Ingredients | SL5 | SL6 |
| B | Purified Water | q.s. to 100.0 | q.s. to 100.0 |
|   | Hydroxypropyl Cellulose | 1.5 | 0 |
|   | Hydroxypropyl Methyl Cellulose | 0 | 1 |
|   | Allantoin | 0.2 | 0.2 |
|   | Edetate Disodium Dihydrate (EDTA) | 0.1 | 0.1 |
|   | Phenoxyethanol | 0.7 | 0.7 |
|   | Sodium Hyaluronate | 0.4 | 0.4 |
| C | Polyethylene Glycol 400 | 6 | 6 |
|   | Diethylene glycol monoethyl ether | 11 | 11 |

Method of Preparation:
1) Phase A: Glycerin and besifloxacin hydrochloride were mixed together in a separate vessel,
2) Phase B: In a main mixing vessel, allantoin and Edetate Disodium Dihydrate were solubilized in water with stirring at 200 rpm, then hydroxypropyl cellulose or hydroxypropyl methyl cellulose was sprinkled over it slowly and allowed to swell for 45 minutes,
3) Sodium hyaluronate was sprinkled into the above mixture and allowed to swell for 15 minutes, followed by addition of phenoxyethanol,
5) Phase A was slowly added into the main mixing vessel with continuous stirring at 200 rpm, and mixed for 30 min,
6) Polyethylene Glycol 400 and Diethylene glycol monoethyl ether were added to the main mixing vessel and mixed for 15 min at 150 rpm Hydroxyethyl cellulose is another widely used excipients in oral and topical pharmaceutical formulations and available in number of different viscosity grades. Formulation containing solubilized besifloxacin.HCl was prepared using hydroxyethyl cellulose as viscosity modifiers (Table 31). Using this polymer, the prepared gel could display good sensorials, at pH of about 4.5, along with other parameters like acceptable viscosity and soluble drug.

TABLE 31

Besifloxacin•HCl Solubilized Gel Formulations Prepared Using Hydroxyethyl Cellulose for Compositions SL7, SL8 and SL9

| | Composition (% w/w) | | |
|---|---|---|---|
| Ingredients | SL7 | SL8 | SL9 |
| Besifloxacin•HCl | 1.09 | 1.09 | 1.09 |
| Allantoin | 0.2 | 0.2 | 0.2 |
| Diethylene glycol monoethyl ether | 11 | 13 | 11 |
| Edetate Disodium Dihydrate (EDTA) | 0.1 | 0.1 | 0.1 |
| Glycerin | 5 | 5 | 5 |
| Hydroxy ethyl cellulose | 0.9 | 1 | 1.1 |
| Phenoxyethanol | 0.7 | 0.7 | 0.7 |
| Polyethylene Glycol400 | 6 | 7 | 6 |
| Sodium hyaluronate | 0.3 | 0.3 | 0.3 |
| Purified Water | q.s. to 100 | q.s. to 100 | q.s. to 100 |

Phase A: Purified water, Allantoin, Edetate Disodium Dihydrate (EDTA), Hydroxy ethyl cellulose
Phase B: Purified water, Sodium hyaluronate
Phase C: Purified Water, Glycerin, Besifloxacin.HCl, Polyethylene Glycol 400, Diethylene glycol monoethyl ether, Phenoxyethanol Method of Preparation
1) In a main mixing vessel, EDTA and allantoin were dissolved in water at 400 rpm for 10 min,
2) Then, hydroxy ethyl cellulose was sprinkled to the main mixing vessel at very high speed (around 400-500 rpm) and allowed to swell for 1 h at 100-150 rpm,
3) In a separate vessel, sodium hyaluronate was taken and allowed to swell with water for 15-30 minutes. Then, added to the main mixing vessel,
4) In another vessel, glycerin and besifloxacin HCl were dispersed in water and mixed with glass rod. To this dispersion, diethylene glycol monoethyl ether and polyethylene glycol 400 were added and mixed,
5) Above dispersion was added to the main mixing vessel, and allowed to stir at 100-150 rpm for 5 min,
6) Finally, phenoxyethanol was added to the main mixing vessel, and mixed at 100-150 rpm until polymer lumps disappears, if any and clear gel is obtained.

Example 36: Preparation of Gel Formulations Loaded with Different Concentrations of Suspended Besifloxacin.HCl to Observe the Effect on Viscosities of Formulations Containing Hydroxyethyl Cellulose Gel formulations containing different concentrations of besifloxacin hydrochloride were formulated using hydroxyethyl cellulose as thickening agent as per the compositions shown in Table 32.

TABLE 32

Gel Formulations with Different Concentrations of Suspended Besifloxacin•HCl Using Hydroxyethyl Cellulose for Compositions GL09, GL10, GL11, GL12 and GL13

| Chemical Name | Composition (% w/w) | | | | |
|---|---|---|---|---|---|
| | GL09 | GL10 | GL11 | GL12 | GL13 |
| Besifloxacin•HCl (Equivalent to Besifloxacin) | 0 | 1 | 2 | 4 | 8 |
| Allantoin | 0.2 | 0 | 0 | 0.2 | 0.2 |
| Diethylene glycol monoethyl ether | 5 | 5 | 5 | 5 | 5 |
| Edetate disodium dehydrate (EDTA) | 0.1 | 0.1 | 0.1 | 0.1 | 0.1 |
| Glycerin | 5 | 5 | 5 | 5 | 5 |
| Hydroxy ethyl cellulose | 0.9 | 0.9 | 0.9 | 0.9 | 0.9 |
| Phenoxyethanol | 0.7 | 0.7 | 0.7 | 0.7 | 0.7 |
| Polyethylene glycol 400 | 5 | 5 | 5 | 5 | 5 |
| Sodium hyaluronate | 0.4 | 0.4 | 0.4 | 0.4 | 0.4 |
| Sodium hydroxide solution | q.s. to pH 5.5 | q.s. to pH 5.5 | q.s. to pH 5.5 | q.s. to pH 5.5 | q.s. to pH 5.5 |
| Purified water | q.s. | q.s. | q.s. | q.s. | q.s. |

Phase A: Purified water, Edetate disodium dihydrate (EDTA), Allantoin, Hydroxy ethyl cellulose
Phase B: Purified water, Sodium hyaluronate
Phase C: Phenoxyethanol, Sodium hydroxide solution
Phase D: Glycerin, Besifloxacin.HCl (Equivalent to Besifloxacin), Purified water, Sodium hydroxide solution
Phase E: Polyethylene glycol 400, Diethylene glycol monoethyl ether
Phase F: Sodium hydroxide solution Method of Preparation:
1) In a main mixing vessel, edetate disodium and allantoin were dissolved in water. Then hydroxyethyl cellulose was added in portion to the main mixing vessel while stirring at 100 rpm using over-head stirrer. Gelling agent was allowed to swell at 100 rpm for 30 min to get proper hydration.
2) Hydrated hyaluronate sodium were added to main mixing vessel and mixed. Then phenoxyethanol was added to the mixture. Then, pH of the mixture was raised to 6.0 with sodium hydroxide solution.
3) In a separate vessel, glycerin and besifloxacin.HCl were dispersed with continuous mixing at 300 rpm for 10 min.
4) Dilute solution of sodium hydroxide was added drop-wise to the separate vessel to adjust pH to 5.5.
5) The contents of the above mixture were added to the main mixing vessel with stirring at 200 rpm for 2 hours.
6) Finally, polyethylene glycol and diethylene glycol monoethyl ether were added to the main mixing vessel and mixed for further 20 min.
7) White-to-pale yellow gel was obtained.

Results:
No viscosity drop was observed in hydroxyethyl cellulose based gels. Gels with besifloxacin.HCl concentration upto 4% w/w (equivalent to besifloxacin) were found to have acceptable consistency and sensorial characteristics. Results of viscosities of gel compositions are given in Table 33.

TABLE 33

Viscosities of Gel Compositions at Different Concentrations of Besifloxacin•HCl

| Sr. No. | Composition | Besifloxacin•HCl equivalent to besifloxacin (% w/w) | Viscosity (mPa · s) |
|---|---|---|---|
| 1 | GL09 | 0 | 3842 |
| 2 | GL10 | 1 | 4028 |
| 3 | GL11 | 2 | 4198 |
| 4 | GL12 | 4 | 3842 |
| 5 | GL13 | 8 | 4827 |

Example 37. Preparation of Gel Formulations Loaded with Different Concentrations of Suspended Besifloxacin.HCl to Observe the Effect on Viscosities of Formulations Containing Carbomer Gel formulations containing different concentrations of besifloxacin hydrochloride were formulated as per the compositions shown in Table 34. These formulations were formulated with carbomer to observe the effect of concentration of besifloxacin.HCl on viscosities.

TABLE 34

Gel Formulations with Different Concentrations of Suspended Besifloxacin•HCl Using Carbomer for Compositions GL14, GL15, GL16 and GL17

| Chemical Name | Composition (% w/w) | | | |
|---|---|---|---|---|
| | GL14 | GL15 | GL16 | GL17 |
| Besifloxacin•HCl (Equivalent to Besifloxacin) | 0 | 1 | 1.5 | 10 |
| Allantoin | 0.2 | 0 | 0.2 | 0.2 |
| Carbomer homopolymer type C | 0.85 | 0.85 | 0.85 | 0.85 |
| Diethylene glycol monoethyl ether | 5 | 5 | 5 | 5 |
| Edetate disodium dehydrate (EDTA) | 0.1 | 0.1 | 0.1 | 0.1 |
| Glycerin | 5 | 5 | 5 | 5 |
| Phenoxyethanol | 0.7 | 0.7 | 0.7 | 0.7 |
| Polyethylene glycol 400 | 5 | 5 | 5 | 5 |

TABLE 34-continued

Gel Formulations with Different Concentrations of Suspended
Besifloxacin•HCl Using Carbomer for Compositions
GL14, GL15, GL16 and GL17

| Chemical Name | Composition (% w/w) | | | |
|---|---|---|---|---|
| | GL14 | GL15 | GL16 | GL17 |
| Sodium hyaluronate | 0.4 | 0.4 | 0.4 | 0.4 |
| Sodium hydroxide solution | q.s. to pH 5.5 | q.s. to pH 5.5 | q.s. to pH 5.5 | q.s. to pH 5.5 |
| Purified water | q.s. | q.s. | q.s. | q.s. |

Phase A: Purified water, Edetate disodium dehydrate (EDTA), Allantoin, Carbomer homopolymer type C Phase B: Purified water, Sodium hyaluronate Phase C: Phenoxyethanol, Sodium hydroxide solution Phase D: Glycerin, Besifloxacin.HCl Equivalent to Besifloxacin, Purified water, Sodium hydroxide solution Phase E: Polyethylene glycol 400, Diethylene glycol monoethyl ether Phase F: Sodium hydroxide solution Method of Preparation:

1) In a main mixing vessel, edetate disodium and allantoin were dissolved in water. Then carbomer homopolymer type C and hyaluronate sodium were added and allowed to swell at 200 rpm for 60 minutes. Then phenoxyethanol was added to the carbomer mixture. Then, pH of the mixture was raised to 6.0 with sodium hydroxide solution.

2) In a separate vessel, glycerin and besifloxacin.HCl were dispersed with continuous mixing at 300 rpm for 10 min.

3) Dilute solution of sodium hydroxide was added drop-wise to the separate vessel to adjust pH to 5.5.

4) The contents of the above mixture were added to the main mixing vessel with stirring at 200 rpm for 2 h.

5) Finally, polyethylene glycol and diethylene glycol monoethyl ether were added to the main mixing vessel and mixed for further 20 min.

6) White-to-pale yellow gel was obtained.

Results:

Addition of besifloxacin.HCl to the gels has led to drop in viscosity in a concentration dependent fashion, although a minimum viscosity of about 3000 mPa·s can be considered acceptable. However, viscosities lower than 3000 mPa·s would not be acceptable for desirable flow properties (from tube) and application on skin (by patients). Results of viscosities of gel compositions are given in Table 35.

TABLE 35

Viscosities of Gel Compositions With Different Concentrations of Besifloxacin•HCl

| S. No. | Composition | Besifloxacin•HCl (% w/w) equivalent to besiflexacin (% w/w) | Viscosity* (mPa · s) |
|---|---|---|---|
| 1 | GL14 | 0 | 5833 |
| 2 | GL15 | 1 | 4322 |
| 3 | GL16 | 1 | 3582 |
| 4 | GL17 | 10 | 1310 |

*measured by Viscometer (RheolabQC, C-LTD 80/QC), Anton Paar

Example 38: Preparation of Gel Formulations Containing Suspended Nadifloxacin, Prulifloxacin, Ulifloxacin, Besifloxacin.HCl and Combinations with Adapalene; Prepared Using Hydroxyethyl Cellulose as Thickening Agent Gel formulations containing suspended nadifloxacin, purlifoxacin, ulifloxacin and besifloxacin were formulated alone and in their combination with adapalene as per the compositions shown in Table 36 These formulations had pH of 5.5-6 and viscosity of around 4000-6000 mPa·s.

TABLE 36

Gel Formulations Loaded With Nadifloxacin, Prulifloxacin, Ulifloxacin and Combination with Adapalene
(Compositions GA1, GA2, GA3, GA4 and GA5)

| Chemical Name | Composition (% w/w) | | | | |
|---|---|---|---|---|---|
| | GA1 | GA2 | GA3 | GA4 | GA5 |
| Adapalene | 0 | 0 | 0 | 0.1 | 0.1 |
| Besifloxacin•HCl equivalent to besifloxacin | 0 | 0 | 0 | 0 | 1 |
| Nadifloxacin | 1 | 0 | 0 | 0 | 0 |
| Prulifloxacin | 0 | 1 | 0 | 1 | 0 |
| Ulifloxacin | 0 | 0 | 1 | 0 | 0 |
| Allantoin | 0.2 | 0.2 | 0.2 | 0.2 | 0.2 |
| Citric acid solution | 0.15 | 0.15 | 0.15 | 0.15 | 0.15 |
| Diethylene glycol monoethyl ether | 5 | 5 | 5 | 5 | 5 |
| Edetate disodium dehydrate | 0.1 | 0.1 | 0.1 | 0.1 | 0.1 |
| Glycerin | 5 | 5 | 5 | 5 | 5 |
| Hyaluronate Sodium | 0.2 | 0.2 | 0.2 | 0.2 | 0.2 |
| Hydroxy ethyl cellulose | 1.2 | 1.2 | 1.2 | 1.2 | 1.2 |
| Phenoxyethanol | 0.7 | 0.7 | 0.7 | 0.7 | 0.7 |
| Poloxamer 407 | 0 | 0 | 0 | 0.2 | 0.2 |
| Polyethylene glycol 400 | 5 | 5 | 5 | 5 | 5 |
| Sodium hydroxide solution | q.s. | q.s. | q.s. | q.s. | q.s. |
| Purified water | q.s. | q.s. | q.s. | q.s. | q.s. |

Phase A: Purified water, Edetate disodium dihydrate, Allantoin, Hydroxy ethyl cellulose Phase B: Purified water, Hyaluronate Sodium Phase C: Glycerin, Besifloxacin.HCl equivalent to besifloxacin, Nadifloxacin, Prulifloxacin, Ulifloxacin, Purified water, Sodium hydroxide solution Phase D: Purified water, Poloxamer 407, Adapalene Phase E: Polyethylene glycol 400, Diethylene glycol monoethyl ether Phase F: Phenoxyethanol Phase G: Citric acid solution, Sodium hydroxide solution Method of Preparation:

Stepwise procedure to prepare gel is mentioned below—

1) In a main mixing vessel, edetate disodium and allantoin were dissolved in water. Then hydroxyethyl cellulose and hylauronate sodium were added and allowed to swell at 100 rpm for 60 min.

2) Then phenoxyethanol was added to the above mixture. Then, pH of the mixture was raised to 6.0 with sodium hydroxide solution.

3) In a separate vessel, glycerin and besifloxacin.HCl were dispersed with continuous mixing at 300 rpm for 10 minutes.

4) Dilute solution of sodium hydroxide was added drop-wise to the separate vessel to adjust pH to 5.5.

5) The contents of the above mixture were added to the main mixing vessel with stirring at 200 rpm for 2 h.

6) In a separate vessel, adapalene was dispersed in aqueous solution of poloxamer 407. This adapalene dispersion was transferred to the main mixing vessel.

7) Finally, polyethylene glycol and diethylene glycol monoethyl ether were added to the main mixing vessel and mixed for further 20 min.
8) White-to-pale yellow gel was obtained.

Example 39: Preparation of Gel Formulations Containing Combination of Suspended Besifloxacin.HCl and Adapalene; Prepared Using Carbomer as Rheology Modifier Gel formulation containing suspended besifloxacin in combination with adapalene was prepared as per the compositions shown in Table 37. The formulation had pH of 5.5-6 and viscosity of around 4063 mPa·s at shear rate of 25 $s^{-1}$

TABLE 37

Gel Formulations Loaded With Suspended Besifloxacin•HCl in Combination with Adapalene for Compositions GL19

| Chemical Name | Composition (% w/w) GL19 |
|---|---|
| Besifloxacin•HCl equivalent to besifloxacin | 1 |
| Adapalene | 0.1 |
| Allantoin | 0.2 |
| Carbomer homopolymer type C | 0.85 |
| Diethylene glycol monoethyl ether | 5 |
| Edetate disodium dehydrate | 0.1 |
| Glycerin | 5 |
| Hyaluronate sodium | 0.4 |
| Phenoxyethanol | 0.7 |
| Poloxamer 407 | 0.2 |
| Polyethylene glycol 400 | 5 |
| Sodium hydroxide solution | q.s. |
| Purified water | q.s. to 100 |

Phase A: Purified water, Edetate disodium dihydrate, Allantoin, Carbomer homopolymer type C
Phase B: Purified water, Hyaluronate sodium
Phase C: Sodium hydroxide solution
Phase D: Glycerin, Besifloxacin.HCl equivalent to besifloxacin, Purified water, Sodium hydroxide solution
Phase E: Purified water, Poloxamer 407, Adapalene
Phase F: Polyethylene glycol 400, Diethylene glycol monoethyl ether
Phase G: Phenoxyethanol
Phase H: Sodium hydroxide solution Method of Preparation:
1) In a main mixing vessel, edetate disodium and allantoin were dissolved in water. Then carbomer and hylauronate sodium were added and allowed to swell at 100 rpm for 120 min.
2) Then phenoxyethanol was added to the above mixture. Then, pH of the mixture was raised to 6.0 with sodium hydroxide solution.
3) In a separate vessel, glycerin and besifloxacin.HCl were dispersed with continuous mixing at 300 rpm for 10 min.
4) Dilute solution of sodium hydroxide was added drop-wise to the separate vessel to adjust pH to 5.5.
5) The contents of the above mixture were added to the main mixing vessel with stirring at 200 rpm for 2 h.
6) In a separate vessel, adapalene was dispersed in aqueous solution of poloxamer 407. This adapalene dispersion was transferred to the main mixing vessel.
7) Finally, polyethylene glycol and diethylene glycol monoethyl ether were added to the main mixing vessel and mixed for further 20 minutes.
8) White-to-pale yellow gel was obtained.

Example 40: Gel Formulations Containing Besifloxacin Hydrochloride

Gel Formulations Containing Besifloxacin Hydrochloride were Prepared Using carbomer as gelling agent as per the compositions shown in Table 38. The gel formulations with acceptable viscosities (3500-15000 m·Pa·s) and pH range (5.5 to 6.0) were obtained.

TABLE 38

| | Composition (% w/w) | |
|---|---|---|
| Chemical Name | GL20 | GL21 |
| Besifloxacin•HCl (Equivalent to Besifloxacin) | 1 | 2 |
| Diethylene glycol monoethyl ether | 5 | 0 |
| Edetate disodium dehydrate (EDTA) | 0.1 | 0.05 |
| Allantoin | 0.2 | 0.5 |
| Glycerin | 5 | 5 |
| Carbopol 980 | 0 | 1.2 |
| Carbopol 940 | 1.0 | 0 |
| Propylene Glycol | 0 | 8 |
| Poloxamer 407 | 0 | 0.2 |
| Phenoxyethanol | 0.7 | 0 |
| Polyethylene glycol 400 | 5 | 5 |
| Methyl paraben | 0 | 0.3 |
| Propyl paraben | 0 | 0.03 |
| Triethanolamine | q.s. | q.s. |
| Purified water | q.s. | q.s. |

Method of Preparation:
1) In main mixing vessel, edetate disodium, allantoin and poloxamer were dissolved in water, followed by addition of carbomer while stirring at 200 rpm using over-head stirrer. Gelling agent was allowed to swell at 200 rpm for 2 h.
2) Phenoxyethanol or parabens was/were added to the above mixture. Then, pH of the mixture was raised to 5.5-6.0 using triethanolamine solution.
3) In a separate vessel, glycerin and besifloxacin.HCl were dispersed with continuous mixing at 500 rpm for 20 minutes. Dilute solution of triethanolamine was added drop-wise to adjust pH to 5.5 to 6.0.
4) The contents of the above mixture were added to the main mixing vessel with stirring at 200 rpm for 2 hours.
5) Finally, polyethylene glycol, propylene glycol and diethylene glycol monoethyl ether were added to the main mixing vessel at a stirring rate of 200 rpm for further 20 min.
6) If needed, pH for this mixture was further adjusted to 5.5 to 6.0 using triethanolamine and the mixture is stirred for 2 h to obtain white-to-pale yellow gel.

Example 41: Gel Formulations Containing Besifloxacin Hydrochloride Having Hydroxyethyl Cellulose and Sodium Hyaluronate as Gelling Agents Gel formulations containing besifloxacin hydrochloride were prepared using hydroxyethyl cellulose and sodium hyaluronate as gelling agents as per the compositions shown in Table 39. The gel formulations with acceptable viscosities (3500-15000 m·Pa·s) and pH range (5.5 to 7.0) were obtained.

TABLE 39

| Chemical Name | Composition (% w/w) | | | | |
|---|---|---|---|---|---|
| | GL22 | GL23 | GL24 | GL25 | GL26 |
| Besifloxacin•HCl (Equivalent to Besifloxacin) | 1 | 4 | 2 | 1 | 2 |
| Diethylene glycol monoethyl ether | 5 | 5 | 5 | 5 | 5 |
| Edetate disodium dehydrate (EDTA) | 0.1 | 0.1 | 0.1 | 0.1 | 0.1 |
| Glycerin | 5 | 5 | 5 | 5 | 5 |
| Hydroxyethyl cellulose | 0.9 | 1.2 | 1.5 | 1.75 | 1.5 |
| Phenoxyethanol | 0.7 | 0.7 | 0.7 | 0.7 | 0.7 |
| Polyethylene glycol 400 | 5 | 5 | 5 | 5 | 5 |
| Sodium hyaluronate | 0.4 | 0.9 | 0.2 | 0 | 0 |
| Sodium hydroxide solution | q.s. | q.s. | q.s. | q.s. | q.s. |
| Purified water | q.s. | q.s. | q.s. | q.s. | q.s. |

Method of Preparation:

1) In main mixing vessel, edetate disodium was dissolved in water, followed by addition of hydroxyethyl cellulose (HEC) while stirring at 200 rpm using over-head stirrer. HEC was allowed to swell at 200 rpm for 2 h.
2) In a separate vessel, sodium hyaluronate was allowed to swell in water under stirring for 1 hr. After the completion of swelling of both the thickening agents, swelled sodium hyaluronate was added to the main mixing vessel.
3) Phenoxyethanol and diethylene glycol monoethyl ether were added to the above mixture. Then, pH of the mixture was raised to 5.5-6.0 using sodium hydroxide solution.
4) In a separate vessel, glycerin and besifloxacin.HCl were dispersed with continuous mixing at 500 rpm for 20 minutes. Dilute solution of sodium hydroxide was added drop-wise to adjust pH to 5.5 to 6.0.
5) The contents of the above mixture were added to the main mixing vessel with stirring at 200 rpm for 2 hours.
6) Finally, polyethylene glycol was added to the main mixing vessel at a stirring rate of 200 rpm for further 20 min.
7) If needed, pH for this mixture was further adjusted to 5.5 to 7.0 using sodium hydroxide solution and the mixture is stirred for 2 h to obtain white-to-pale yellow gel.

Example 42: Gel Formulations Containing Besifloxacin Hydrochloride with Different Combinations of Carbomer, Hydroxyethyl Cellulose and Sodium Hyaluronate as Gelling Agents Gel formulations containing besifloxacin hydrochloride were prepared using different combinations of carbomer, hydroxyethyl cellulose and sodium hyaluronate as gelling agents as per the compositions shown in Table 40. The gel formulations with acceptable viscosities (3500-15000 m·Pa·s) and pH range (5.5 to 7.0) were obtained.

TABLE 40

| Chemical Name | Composition (% w/w) | | | | |
|---|---|---|---|---|---|
| | GL27 | GL28 | GL29 | GL30 | GL31 |
| Besifloxacin•HCl (Equivalent to Besifloxacin) | 1 | 1 | 2 | 4 | 1 |
| Diethylene glycol monoethyl ether | 5 | 5 | 5 | 5 | 5 |
| Edetate disodium dehydrate (EDTA) | 0.1 | 0.1 | 0.1 | 0.1 | 0.1 |
| Glycerin | 5 | 5 | 5 | 5 | 5 |
| Hydroxyethyl cellulose | 1.5 | 1.5 | 0.5 | 1.0 | 0.8 |
| Carbomer | 0.7 | 0.3 | 1.2 | 0.4 | 0.8 |
| Phenoxyethanol | 0.7 | 0.7 | 0.7 | 0.7 | 0.7 |
| Polyethylene glycol 400 | 5 | 5 | 5 | 5 | 5 |
| Sodium hyaluronate | 1.0 | 0.2 | 0 | 0.2 | 0.4 |
| Sodium hydroxide solution | q.s. | q.s. | q.s. | q.s. | q.s. |
| Purified water | q.s. | q.s. | q.s. | q.s. | q.s. |

Method of Preparation:

1) In main mixing vessel, edetate disodium was dissolved in water, followed by addition of carbomer and/or hydroxyethyl cellulose (HEC) while stirring at 200 rpm using over-head stirrer. Carbomer and HEC were allowed to swell at 200 rpm for 2 h.
2) In a separate vessel, sodium hyaluronate was allowed to swell in water under stirring for 1 hr. After the completion of swelling of both the thickening agents, swelled sodium hyaluronate was added to the main mixing vessel.
3) Phenoxyethanol and diethylene glycol monoethyl ether were added to the above mixture. Then, pH of the mixture was raised to 5.5-6.0 using sodium hydroxide solution.
4) In a separate vessel, glycerin and besifloxacin.HCl were dispersed with continuous mixing at 500 rpm for 20 minutes. Dilute solution of sodium hydroxide was added drop-wise to adjust pH to 5.5 to 6.0.
5) The contents of the above mixture were added to the main mixing vessel with stirring at 200 rpm for 2 hours.
6) Finally, polyethylene glycol was added to the main mixing vessel at a stirring rate of 200 rpm for further 20 min.
7) If needed, pH for this mixture was further adjusted to 5.5 to 7.0 using sodium hydroxide solution and the mixture is stirred for 2 h to obtain white-to-pale yellow gel.

Example 43: Stability Studies of Besifloxacin.HCl Suspended Gel (GL15)

Prepared Using Carbomer

Besifloxacin.HCl suspended gels were packed in laminated tubes and charged for stability studies under accelerated condition (40° C.±2° C., 75% RH±5%). These gels were evaluated for physical appearance, pH, viscosity, assay and content uniformity at initial time ($T_0$), 2 weeks ($T_{2w}$) and one month ($T_{1m}$).

Results:

Results suggest that gel is stable under tested time durations. Results are mentined below in Table 41.

TABLE 41

Evaluation of stability samples of besifloxacin•HCl gel (GL15) put on accelerated stability conditions

| | | Period of Stability Study | | |
|---|---|---|---|---|
| Tests | Specification | Initial ($T_0$) | 2 weeks ($T_{2w}$) | 1 month ($T_{1m}$) |
| Description | White to pale yellow, homogeneous gel | white gel of uniform consistency | white gel of uniform consistency | white gel of uniform consistency |
| pH | 5.0-6.0 | 5.5-6.0 | 5.5-6.0 | 5.5-6.0 |
| Viscosity @ 25° C., 20 rpm* | 2500-5000 mPa · s | 4322 mPa · s | 4212 mPa · s | 4069 mPa · s |
| Assay | 0.95%-1.05% | 1.01% | 0.987% | 0.983% |
| Content Uniformity | 95%-105% | 100.95%-100.44% | 98.00%-99.00% | 98.00%-99.00% |
| Phenoxyethanol Content | 0.63%-0.77% | 0.71% | 0.68% | 0.69% |

*measured by Viscometer (RheolabQC, C-LTD 80/QC), Anton Paar

Example 44: Stability Studies of Besifloxacin.HCl Suspended Gel (GL10) Prepared Using Hydroxyethyl Cellulose Besifloxacin.HCl suspended gels were packed in laminated tubes and charged for stability studies under accelerated condition (40° C.±2° C., 75% RH±5%). These gels were evaluated for physical appearance, pH, viscosity, assay and content uniformity at initial time ($T_0$), 2 weeks ($T_{2w}$) and one month ($T_{1m}$).

Results:

Results suggest that gel is stable under tested time durations. Results are mentined below in Table 42.

TABLE 42

Evaluation of stability samples of besifloxacin•HCl gel (GL10) put on accelerated stability conditions

| | | Period of Stability Study | | |
|---|---|---|---|---|
| Tests | Specification | Initial ($T_0$) | 2 weeks ($T_{2w}$) | 1 month ($T_{1m}$) |
| Description | White to pale yellow, homogeneous gel | white gel of uniform consistency | white gel of uniform consistency | white gel of uniform consistency |
| pH | 5.0-6.0 | 5.5-6.0 | 5.5-6.0 | 5.5-6.0 |
| Viscosity @ 25° C., 20 rpm* | 2500-5000 mPa · s | 4028 mPa · s | 3674 mPa · s | 3638 mPa · s |
| Assay | 0.95%-1.05% | 1.05% | 1.04% | 1.02[14]% |
| Phenoxyethanol Content | 0.63%-0.77% | 0.73% | 0.73% | 0.69% |

*measured by Viscometer (RheolabQC, C-LTD 80/QC), Anton Paar

Example 45: Stability Studies of Besifloxacin.HCl Suspended Cream (CM02)

Prepared Using Carbomer

Besifloxacin.HCl suspended creams were packed in laminated tubes and charged for stability studies under accelerated condition (40° C.±2° C., 75% RH±5%). These creams were evaluated for physical appearance, pH, viscosity, assay and content uniformity at initial time ($T_0$) and one month ($T_{1m}$).

Results:

Results suggest that gel is stable under tested time durations. Results are mentined below in Table 43.

TABLE 43

Evaluation of stability samples of besifloxacin•HCl cream (CM02) put on accelerated stability conditions

| | | Period of Stability Study | |
|---|---|---|---|
| Tests | Specification | Initial ($T_0$) | 1 month ($T_{1m}$) |
| Description | White to pale yellow, homogeneous cream | white homogeneous cream | white homogeneous cream |
| pH | 5.0-6.0 | 5.5-6.0 | 5.5-6.0 |

TABLE 43-continued

Evaluation of stability samples of besifloxacin•HCl cream (CM02) put on accelerated stability conditions

| | | Period of Stability Study | |
|---|---|---|---|
| Tests | Specification | Initial ($T_0$) | 1 month ($T_{1m}$) |
| Viscosity @ 25° C., 20 rpm* | 2500-5000 mPa · s | 3084 mPa · s | 2499 mPa · s |
| Assay | 0.95%-1.05% | 1.01% | 0.987% |
| Phenoxyethanol Content | 0.63%-0.77% | 0.76% | 0.70% |

*measured by Viscometer (RheolabQC, C-LTD 80/QC), Anton Paar

Example 46: Stability Studies of Besifloxacin.HCl Suspended Cream (CMOS)

Prepared without Use of Polymer

Besifloxacin.HCl suspended creams were packed in laminated tubes and charged for stability studies under accelerated condition (40° C.±2° C., 75% RH±5%). These creams were evaluated for physical appearance, pH, viscosity, assay and content uniformity at initial time ($T_0$) and one month ($T_{1m}$).

Results:

Results suggest that gel is stable under tested time durations. Results are mentined below in Table 44.

TABLE 44

Evaluation of stability samples of besifloxacin•HCl cream (CM05) put on accelerated stability conditions

| | | Period of Stability Study | |
|---|---|---|---|
| Tests | Specification | Initial ($T_0$) | 1 month ($T_{1m}$) |
| Description | White to pale yellow, homogeneous cream | white homogeneous cream | white homogeneous cream |
| pH | 5.0-6.0 | 5.5-6.0 | 5-5.5 |
| Viscosity @ 25° C., 20 rpm* | 1500-3500 mPa · s | 1936 mPa · s | 1908 mPa · s |
| Assay | 0.95%-1.05% | 0.97% | 0.967% |
| Preservative Content (Phenoxyethanol) | 0.63% to 0.77% | 0.75% | 0.70% |

*measured by Viscometer (RheolabQC, C-LTD 80/QC), Anton Paar

Example 47: Stability Studies of Besifloxacin.HCl Soluble Gel (SL7)

Prepared Using Hydroxyethyl Cellulose

Besifloxacin.HCl suspended creams were packed in laminated tubes and charged for stability studies under accelerated condition (40° C.±2° C., 75% RH±5%). These creams were evaluated for physical appearance, pH, viscosity, assay and content uniformity at initial time ($T_0$) and one month ($T_{1m}$).

Results:

Results suggest that gel is stable under tested time durations. Results are mentined below in Table 45.

TABLE 45

Evaluation of stability samples of besifloxacin•HCl soluble gel (SL7) put on accelerated stability conditions

| | | Period of Stability Study | | |
|---|---|---|---|---|
| Tests | Specification | Initial ($T_0$) | 2 weeks ($T_{2w}$) | 1 month ($T_{1m}$) |
| Description | Pale yellow transparent gel | Pale yellow transparent gel | Pale yellow transparent gel | Pale yellow transparent gel |
| pH | 4.0-5.0 | 4.5-5.0 | 4.5-5.0 | 4.5 |
| Viscosity @ 25° C., 20 rpm* | 2500-5000 mPa · s | 3045 mPa · s | 2661 mPa · s | 2700 mPa · s |
| Assay | 0.95%-1.05% | 0.99% | 1.00% | 0.99% |
| Phenoxyethanol Content | 0.63%-0.77% | 0.71% | 0.73% | 0.71% |

*measured by Viscometer (RheolabQC, C-LTD 80/QC), Anton Paar

Example 48: Determination of the Antibacterial Efficacy Against Antibiotic-Nonrespoder *P. acnes* of Besifloxacin (API) by Time Kill Experiment Procedure:

*P. acnes* (CCARM 9010) Aqueous Suspension (0.5 McFarland standard equivalent) was centrifuged at 2000 rpm for 20 min, pellet was resuspended in Brain Heart Infusion (BHI) broth. Resultant *P. acnes* suspension was kept for overnight (16 h) incubation in anaerobic box at 37° C. Stock solution of besifloxacin.HCl (1 mg/ml) was prepared in dimethyl sulphoxide (DMSO) which was further diluted with BHI broth to achieve working stock of besifloxacin.HCl (25 µg/ml). Then reaction mixture was prepared by adding 900 µl of *P. acnes* 0.5 McFarland standard culture (after 16 h incubation) to 100 µl of besifloxacin.HCl working stock solution (25 µg/ml), final besifloxacin.HCl concentration in reaction mixture was 2.5 µg/ml. Reaction mixture (1 ml) was incubated at 37° C. for 24 h in an anaerobic box in two sets—(1) tube with *P. acnes* with 2.5 µg/ml Besifloxacin.HCl and 2) broth control without besifloxacin.HCl. At predetermined time points (1 h, 6 h and 24 h), cells were collected and plated in duplicate after serial dilution in Brain Heart Infusion agar plate. Plates were allowed to grow for 3 days at 37° C. in anaerobic box. After incubation, plates were counted to determine colony forming units (CFU) and log reduction was calculated. In a similar experimental set-up, water was used as solvent instead of DMSO and effects of solvents on time kill kinetics were also studied.

Figure 12:
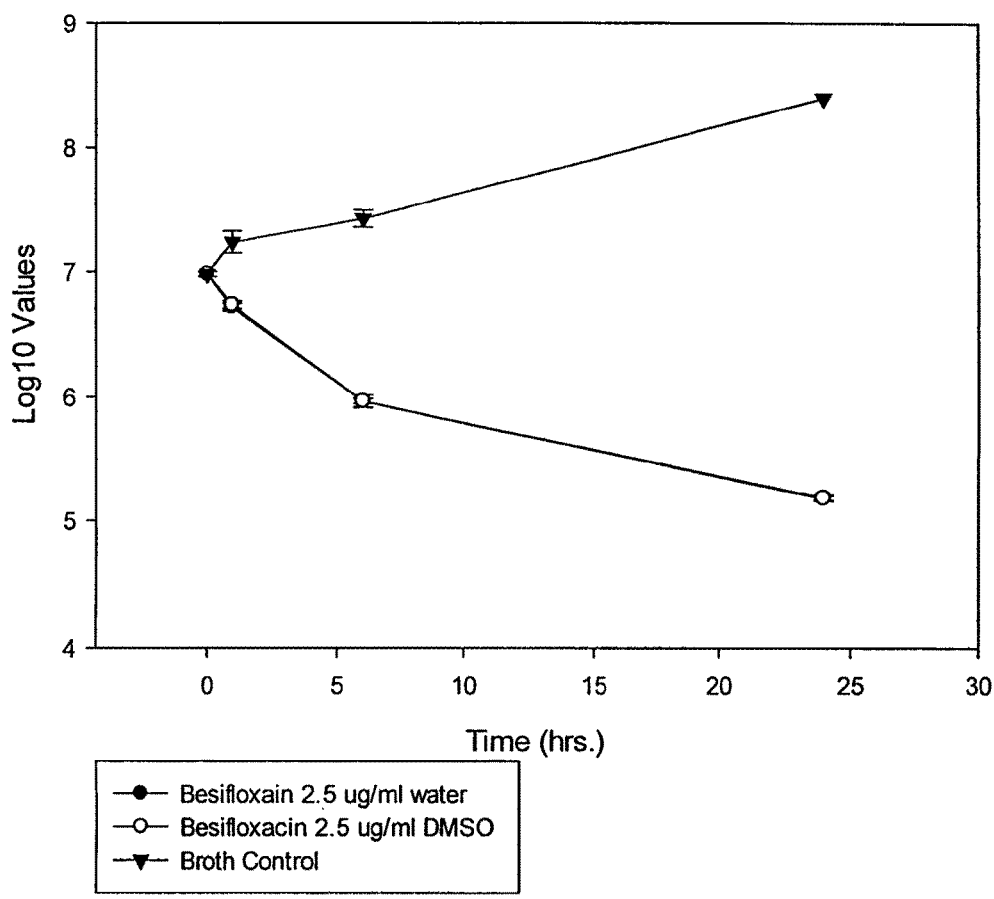
FIG. 12 is a line graph showing time kill kinetics of besifloxacin against *P. acnes* (CCARM 9010).

Results:

Besifloxacin.HCl sample (prepared as 1 mg/ml stock in water and DMSO) showed similar time kill kinetics against *P. acnes* (CCARM 9010) at all the tested time point (Table 46 and FIG. 12)

TABLE 46

Time kill kinetics of Besifloxacin•HCl against *P. acnes*, studied at concentration of 2.5 µg/ml at 1 h, 6 h, and 24 h.

| | Log 10 value of *P. acnes* against different treatment groups | | |
|---|---|---|---|
| Time (h) | Besifloxacin•HCl in water (2.5 µg/ml) | Besifloxacin•HCl in DMSO (2.5 µg/ml) | Broth Control |
| 0 | 7.0 ± 0.02 | 7.0 ± 0.02 | 7.0 ± 0.02 |
| 1 | 6.7 ± 0.03 | 6.7 ± 0.03 | 7.2 ± 0.09 |

TABLE 46-continued

Time kill kinetics of Besifloxacin•HCl against *P. acnes*, studied at concentration of 2.5 μg/ml at 1 h, 6 h, and 24 h.

| Time (h) | Besifloxacin•HCl in water (2.5 μg/ml) | Besifloxacin•HCl in DMSO (2.5 μg/ml) | Broth Control |
|---|---|---|---|
| Log 10 value of *P. acnes* against different treatment groups | | | |
| 6 | 6.0 ± 0.02 | 6.0 ± 0.05 | 7.4 ± 0.07 |
| 24 | 5.2 ± 0.02 | 5.2 ± 0.02 | 8.4 ± 0.0 |

Example 49: Antimicrobial Susceptibility of *P. acnes* Isolated from Acne Patients (Clinical Isolates)

The antimicrobial susceptibility of *P. acnes* isolates against various antibiotics was determined by micro broth dilution method as follows—

Procedure:

*P. acnes* were cultured in Brain Heart Infusion Agar (BHIA) at 37° C. for 48 hours under anaerobic condition. For MIC test, BHI broth (100 μl) was added into all 96 wells and 100 μl of broth containing drug was added to first well (1A to 1H) and serial (double) dilution was carried out for up to 10 wells (column 1 to column 10 of 96 well plate). For bacterial inoculum, *P. acnes* culture turbidity was adjusted to 0.5 McFarland standard (approximately $1.5 \times 10^8$) and further diluted (100 times with sterile BHI broth). Diluted *P. acnes* suspension (100 μl) was added to each well except sterility control wells (column 12 of 96 well plate). Inoculated plates were incubated at 37° C. for 72 hours under anaerobic condition. After incubation, MIC was determined by adding Alamar blue dye.

Results:

The MIC results on *P. acnes* clinical isolates susceptible to clindamycin and erythromycin) indicate that all the strains (clindamycin and erythromycin susceptible) are susceptible to clindamycin, erythromycin, minocycline and besifloxacin (Table 47). Interestingly, wide variation in sensitivity to clindamycin and erythromycin were observed in Clindamycin-nonresponded clinical *P. acnes* isolates. All of the antibiotic-nonresponder clinical isolates were found susceptible to besifloxacin. (Table 48).

TABLE 47

*P. acnes* clinical isolates (susceptible to clindamycin and erythromycin) antimicrobial susceptibility against clindamycin, erythromycin, minocycline and besifloxacin

| *P. acnes* strain No. | Actives MIC | | | |
|---|---|---|---|---|
| | Clindamycin (μg/ml) | Erythromycin (μg/ml) | Minocycline (μg/ml) | Besifloxacin (μg/ml) |
| V2-9 | <0.03 | <0.03 | 0.06 | 0.25 |
| V2-10 | <0.03 | <0.03 | 0.06 | 0.25 |
| V3-9 | <0.03 | <0.03 | 0.06 | 0.25 |
| V3-10 | <0.03 | <0.03 | 0.06 | 0.25 |
| V4-6 | <0.03 | <0.03 | 0.06 | 0.25 |
| V4-8 | <0.03 | <0.03 | 0.06 | 0.25 |
| V4-13 | <0.03 | <0.03 | 0.06 | 0.25 |
| V5-2 | <0.03 | <0.03 | 0.06 | 0.5 |
| V5-5 | <0.03 | <0.03 | 0.06 | 0.5 |
| V5-7 | <0.03 | <0.03 | 0.06 | 0.5 |
| V6-5 | <0.03 | <0.03 | 0.06 | 0.5 |
| V6-6 | <0.03 | <0.03 | 0.06 | 0.5 |
| V6-7 | <0.03 | <0.03 | 0.06 | 0.5 |
| V7-3 | <0.03 | <0.03 | 0.06 | 0.5 |

TABLE 47-continued

*P. acnes* clinical isolates (susceptible to clindamycin and erythromycin) antimicrobial susceptibility against clindamycin, erythromycin, minocycline and besifloxacin

| *P. acnes* strain No. | Actives MIC | | | |
|---|---|---|---|---|
| | Clindamycin (μg/ml) | Erythromycin (μg/ml) | Minocycline (μg/ml) | Besifloxacin (μg/ml) |
| V7-4 | <0.03 | <0.03 | 0.06 | 0.5 |
| V7-14 | <0.03 | <0.03 | 0.06 | 0.5 |
| V9-6E | <0.13 | <0.09 | — | 0.5 |
| V12-2E | <0.13 | <0.09 | — | 0.25 |
| V13-3E | <0.13 | <0.09 | — | 0.5 |
| V14-2E | <0.13 | <0.09 | — | 0.5 |
| V15B-1E | <0.13 | 0.19 | — | 0.25 |
| V17-3E | <0.13 | 0.78 | — | 0.5 |
| V18-4E | <0.13 | 0.19 | — | 0.25 |
| V19-2E | <0.13 | <0.09 | — | 0.25 |
| V20-5E | <0.13 | <0.09 | — | 0.25 |

TABLE 48

*P. acnes* clinical isolates (clindamycin resistance) antimicrobial susceptibility against clindamycin, erythromycin, tetracycline and besifloxacin

| *P. acnes* strain No. | Actives MIC | | | |
|---|---|---|---|---|
| | Clindamycin (μg/ml) | Erythromycin (μg/ml) | Tetracycline (μg/ml) | Besifloxacin (μg/ml) |
| V21A-1 | 1-8 | 50-200 | 0.25 | 0.25 |
| V21A-2 | 8-64 | 50-200 | 0.25 | 0.25 |
| V21A-3 | 8-32 | 100-200 | 0.25 | 0.25 |
| V21A-4 | 16-64 | 100-200 | 0.5 | 0.25 |
| V21A-5 | 1 | 100-200 | 0.25 | 0.25 |
| V21A-6 | 1-2 | 100-200 | 0.5 | 0.25 |
| V21A-7 | 0.5-2 | 100-200 | 0.25 | 0.13 |
| V21A-8 | 1-2 | 100-200 | 0.25 | 0.25 |
| V21A-9 | 16-32 | 100-200 | 0.25 | 0.25 |
| V21A-10 | 16-64 | 100-200 | 0.25 | 0.25 |
| V21B-1 | 64 | >200 | 1 | 0.5 |
| V21B-2 | 6-64 | >200 | 0.25 | 0.25 |
| V21B-3 | 64 | >200 | 0.25 | 0.25 |
| V21B-4 | 32-64 | 200 | 0.25 | 0.25 |
| V21B-5 | 1-4 | >200 | 0.5 | 0.5 |
| V21B-6 | 16-64 | >200 | 0.5 | 0.25 |
| V21B-7 | 16-64 | >200 | 0.5 | 0.25 |
| V21B-8 | 16-64 | >200 | 0.5 | 0.25 |
| V3-1 | 0.5 | >150 | 0.3 | 0.5 |
| V3-2 | 0.5 | 150 | 0.5 | 0.5 |
| V3-3 | 0.5 | >150 | 0.3 | 0.5 |

Conclusion:

The MIC results presented in Tables 45-46 shows that *P. acnes* isolated from volunteers V3 and V21 were resistance to clindamycin and erythromycin, but were susceptible to besifloxacin.

Example 50: Comparative In Vivo Pharmacokinetic Profile of Different Gel and Cream Formulations of Besifloxacin Pharmacokinetic (PK) profile of a topical anti-microbial formulation is important from two perspectives. Firstly, It determines whether the formulation can deliver above MIC level concentration of antimicrobial agents to kill the pathogen at the relevant layers of skin for a prolong period of time. Secondly, PK study determines whether penetration of the actives into systemic circulation has crossed the allowable limits. Formulation with better retention in the skin layers and low penetration in blood would be ideal.

Figure 13:
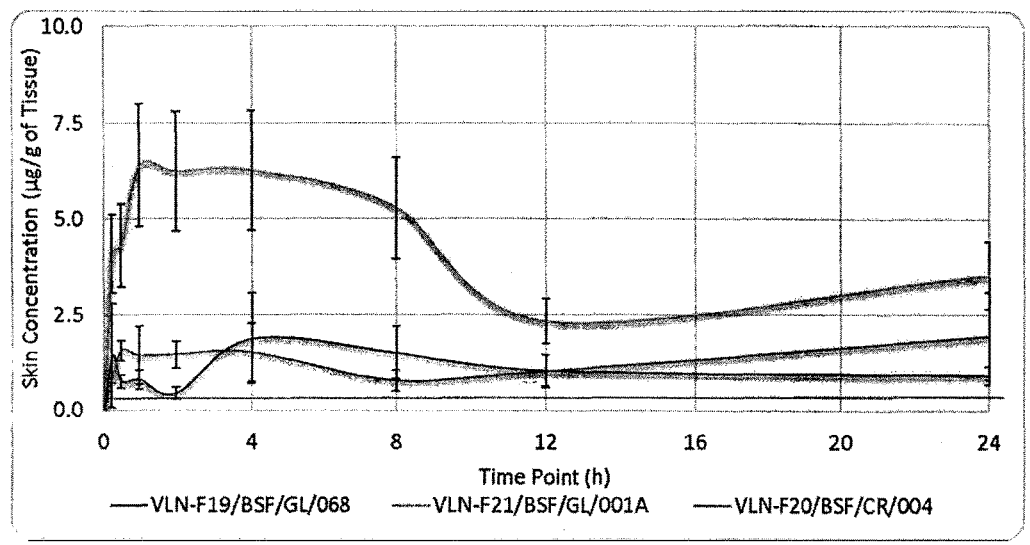
FIG. 13 Graph shows that topical formulations with different excipient compositions for the same antibiotic can result in different profiles in the skin and in systemic circulation of SD rats. Fully suspended 1% Besifloxacin gel (VLN-F19/BSF/GL/068), fully soluble 1% Besifloxacin gel (VLN-F21/BSF/GL/001A) and fully suspended 1% Besifloxacin gel (VLN-F20/BSF/CR/004) were used for comparison purpose. To be efficacious, a formulation should not only be physicochemically compatible with the antibiotic but also enable a sustained concentration of the antibiotic at a concentration greater than MIC level.

Method:

8-10 weeks old Sprague Dawley rats were randomized into three groups according to their body weights. Fully suspended 1% Besifloxacin gel (VLN-F19/BSF/GL/068), fully soluble 1% Besifloxacin gel (VLN-F21/BSF/GL/001A) and fully suspended 1% Besifloxacin gel (VLN-F20/BSF/CR/004) were used for comparison purpose. Animals (4 per time point/formulations) were treated with topical applications of test formulations as a single dermal dose of 50 mg/25 cm2 (hair was clipped from 5×5 cm area in dorsal flank of the animal a day before application). After application 2 minutes were allowed for drying. The application area were then covered with a non-absorbent surgical tape (Tegaderm™). Blood was collected from retro-orbital plexus at pre-dose (0 h), 0.25, 0.5, 1, 2, 4, 8, 12 and 24 h post-dose. At the end of each time point, animals had been euthanized and Tegaderm™ were removed and collected. Then the treated area was gently wiped with water-dipped cotton balls to extract drug efficiently from the top layer or Stratum Corneum. Finally, applied area of the skin was excised. With established extraction procedure. Besifloxacin was extracted from the skin samples. The skin and plasma samples were analyzed by LC-MS/MS to know the concentrations in each matrix and obtained data were used to calculate Cmax, Tmax, t1/2, AUC. The results of PK study using different formulations Besifloxacin gel were plotted in FIG. 13.

Results:

Comparative PK data showed that both fully suspended and fully soluble Besifloxacin gel formulations have the ability to deliver and retain higher than MIC concentration of Besifloxacin in the skin even after 24 hours of application. Their Cmax value is same as the Mutant Prevention Concentration (MPC) of Besifloxacin against *P. acnes*. Though fully soluble one had exhibited higher retention profile in the skin than fully suspended ones, yet all of them showed low penetration in plasma (below detection limit). These data suggest that all three formulations are of sustained release in nature. Therefore unique formularies developed here could penetrate at the site of infection in sufficient quantity without endangering the host safety.

Example 51: Biological Evaluation (Minimum Inhibitory Concentration, Zone of Inhibition Assay and Time Kill Assay) of Besifloxacin.HCl Formulations Against *P. acnes* MTCC 1951 (Susceptible Strain)

Antibacterial activity of besifloxacin formulations were tested against *P. acnes* MTCC 1951 by various antimicrobial susceptibility methods. The following samples were analyzed:

TABLE 49

Besifloxacin•HCl formulations tested against *P. acnes* MTCC 1951

| S. No. | Formulation Details | Code | Besifloxacin•HCl Content (% w/w) |
|---|---|---|---|
| 1 | Besifloxacin•HCl Suspended Cream (1% w/w) | CR/029C | 1.05 |
| 2 | Besifloxacin•HCl Soluble Cream (1% w/w) | CR/003 | 1.17 |
| 3 | Besifloxacin•HCl Suspended Gel (1% w/w) | GL/020 | 1.12 |

Procedures—

*P. acnes* were cultured in Brain Heart Infusion Agar (BHIA) at 37° C. for 48 hours under anaerobic condition. 1) Minimum Inhibitory Concentration (MIC): For MIC test, BHI broth (100 μl) was added into all 96 wells and 100 μl of broth containing drug was added to first well (1A to 1H). Serial (double) dilution was carried out for up to 10 wells (column 1 to column 10 of 96 well plate).

For bacterial inoculums, *P. acnes* culture turbidity was adjusted with 0.5 McFarland standard (approximately 1.5× $10^8$) and further diluted to 100 times with sterile BHI broth. Diluted *P. acnes* suspension (100 μl) was added to each well except sterility control wells (column 12 of 96 well plate). Inoculated plates were incubated at 37° C. for 72 hours under anaerobic conditions. After incubation, MIC was determined by adding Alamar blue dye. 2) Zone of Inhibition (ZOI): For ZOI test, BHA plates were spread with 100 μl of *P. acnes* suspension (0.5 McFarland standard equal). Test samples (drugs/formulations) were dissolved in water/solvent based on the solubility. Sterile disc (6 mm) were loaded with 10 μl of test samples (of various concentration of drug), and were placed above the plates containing *P. acnes* culture. Then, plates were incubated at 37° C. for 48 h, followed by their ZOI measurements. 3) Time Kill Kinetics (TK): For TK Test, *P. acnes* (CCARM 9010) aqueous suspension (0.5 McFarland standard equivalent) was centrifuged at 2000 rpm for 20 min, pellet was resuspended in brain heart infusion (BHI) broth. Resultant *P. acnes* suspension was kept for overnight (16 h) incubation in anaerobic box at 37° C. Stock solution of besifloxacin.HCl (1 mg/ml) was prepared in dimethyl sulphoxide (DMSO) which was further diluted with BHI broth to obtain working stock of besifloxacin.HCl (25 μg/ml). Then reaction mixture was prepared by adding 900 μl of *P. acnes* 0.5 McFarland standard equal culture (after 16 h of incubation) and 100 μl of besifloxacin.HCl working stock (25 μg/ml), to obtain final besifloxacin.HCl concentration in reaction mixture, 2.5 μg/ml. Reaction mixture (1 ml) was incubated at 37° C. in an anaerobic box—(1) tube with *P. acnes* and 2.5 μg/ml Besifloxacin.HCl and 2) broth control without besifloxacin.HCl for 24 h. At predetermined time points (0 h, 2 h, 8 h and 24 h), cells were collected and plated in duplicate after serial dilution in brain heart infusion agar plate. Plates were allowed to grow for 3 days at 37° C. in anaerobic box. After incubation, plates were counted to determine colony forming units (CFU) and log reduction was calculated.

Figure 10:
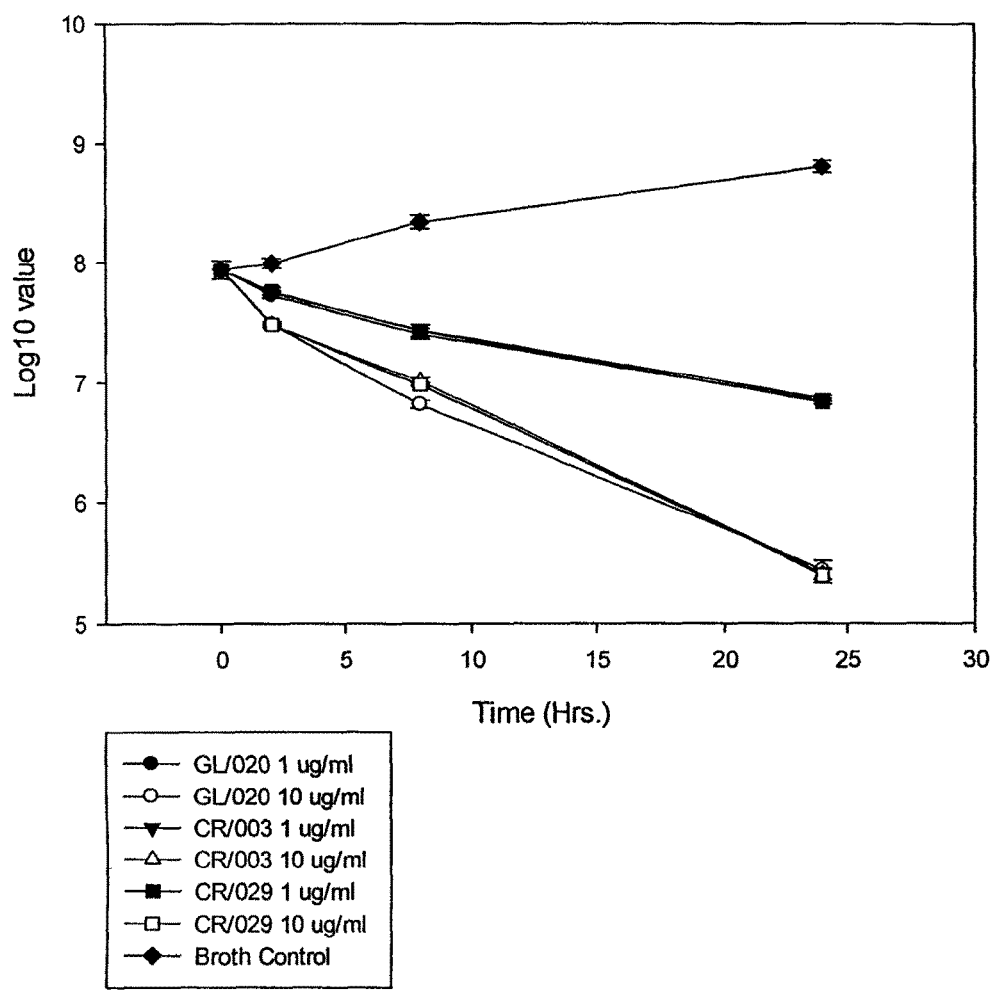
FIG. 10 is a line graph showing time kill kinetics of some exemplary besifloxacin formulations against *P. acnes* MTCC 1951, showing that the composition of the formulation can change the efficacy of an antibiotic.

Results:

Concentration-efficacy-time curves (Table 49-50, FIG. 10) indicate besifloxacin.HCl gel and cream formulations (Table 49) can have differential antibacterial activity against *P. acnes*, suggesting that formulations can modulate the final anti-acne efficacy of an active agent. For the various besifloxacin formulations tested, the MIC values were in the range of 0.13-0.25 μg/ml against *P. acnes* MTCC 1951 (Table 50). Zone of Inhibition assay results display that all besifloxacin formulations (cream and gel) have antibacterial activity against *P. acnes* MTCC 1951. Among the three different tested formulations, ZOI was found to be better with GL/020 (Table 51). Time kill kinetics results indicate that all three formulations (GL/020, CR/003, CR/029C) showed similar activity against *P. acnes* MTCC 1951 at all the time point. In addition, dose dependent differences in kill kinetics were observed in all three formulations between besifloxacin.HCl concentrations of 1 μg/ml and 10 μg/ml. (Table 52 and FIG. 10)

TABLE 50

Minimum Inhibitory concentration (MIC)
MIC of Besifloxacin formulations against *P. acnes* MTCC 1951

| Well No | CR/29C | CR/003 | GL/20 |
|---|---|---|---|
| 1 | 4 | 4 | 4 |
| 2 | 2 | 2 | 2 |
| 3 | 1 | 1 | 1 |
| 4 | 0.5 | 0.5 | 0.5 |
| 5 | 0.25 | 0.25 | 0.25 |
| 6 | 0.13 | 0.125 | 0.13 |
| 7 | 0.1 | 0.1 | 0.1 |
| 8 | 0.03 | 0.03 | 0.03 |
| 9 | 0.02 | 0.02 | 0.02 |
| 10 | 0.01 | 0.01 | 0.01 |
| 11 | GC | GC | GC |
| 12 | SC | SC | SC |
| MIC µg/ml | 0.13 | 0.25 | 0.13 |

TABLE 51

Zone of Inhibition (ZOI) of besifloxacin•HCl gel and cream formulations against *P. acnes*
Besifloxacin Creams ZOI against *P. acnes* MTCC 1951

| Conc. | CR/029C (ZOI cm) | | | CR/003 (ZOI cm) | | | GL/20 (ZOI cm) | | |
|---|---|---|---|---|---|---|---|---|---|
| µg/ml | Rep-1 | Rep-2 | Average | Rep-1 | Rep-2 | Average | Rep-1 | Rep-2 | Average |
| 0.12 | 0 | 0 | 0 | 0 | 0 | 0 | 0 | 0 | 0 |
| 0.25 | 0 | 0 | 0 | 0 | 0 | 0 | 0.8 | 1 | 0.9 |
| 0.5 | 0.8 | 0.8 | 0.8 | 1 | 0.8 | 0.9 | 1.1 | 1.4 | 1.3 |
| 1 | 1.6 | 1.4 | 1.5 | 1.6 | 1.7 | 1.65 | 1.9 | 2.1 | 2 |

TABLE 52

Time Kill Kinetics (TK) of besifloxacin•HCl gel and cream formulations against
*P. acnes* MTCC 1951

Effect of Formulation Treatment on *P. acnes* MTCC 1951 Cell Count (Log10 CFU/ml)

| Time | GL/020 | | CR/003 | | CR/029C | | Broth |
|---|---|---|---|---|---|---|---|
| (h) | 1 µg/ml | 10 µg/ml | 1 µg/ml | 10 µg/ml | 1 µg/ml | 10 µg/ml | Control |
| 0 | 7.94 | 7.94 | 7.94 | 7.94 | 7.94 | 7.94 | 7.94 |
| 2 | 7.73 | 7.48 | 7.75 | 7.48 | 7.76 | 7.48 | 7.99 |
| 8 | 7.40 | 6.82 | 7.44 | 7.01 | 7.43 | 6.98 | 8.34 |
| 24 | 6.84 | 5.44 | 6.86 | 5.40 | 6.83 | 5.39 | 8.81 |
| SD | | | | | | | |
| 0 | 0.07 | 0.07 | 0.07 | 0.07 | 0.07 | 0.07 | 0.07 |
| 2 | 0.03 | 0.01 | 0.02 | 0.01 | 0.03 | 0.03 | 0.04 |
| 8 | 0.04 | 0.03 | 0.01 | 0.03 | 0.05 | 0.02 | 0.06 |
| 24 | 0.02 | 0.08 | 0.03 | 0.04 | 0.02 | 0.06 | 0.05 |

Example 52: Biological Evaluation (Minimum Inhibitory Concentration, Zone of Inhibition Assay and Time Kill Assay) of Besifloxacin.HCl (API and Formulations) Against *S. aureus* MTCC 6908 and *P. acnes* MTCC 1951

Antibacterial activity of besifloxacin API and besifloxacin containing formulation against *S. aureus* MTCC 6908 were determined. The following samples were used for the study.

TABLE 53

Exemplary formulations for determining the antibacterial activity against *S. aureus* MTCC 6908

| S. No. | Samples | Contents |
|---|---|---|
| 1 | BZM-1 | Unmodified besifloxacin |
| 2 | BZM-2 | Stearic acid coated Unmodified BSF |
| 3 | BZM-3 | Stearic acid coated modified BSF |
| 4 | BZM-4 | Stearic acid coated modified BSF |
| 5 | BZM-5 | Stearic acid coated modified BSF |
| 6 | BZM-6 | Placebo gel |
| 7 | BSD-6 | SA coated BSF NPs |
| 8 | BSD-7 | SA coated BSF NPs |
| 9 | BSD-8 | SA coated BSF NPs |
| 10 | BSD-9 | Unmodified BSF |
| 11 | BSD-10 | Stearic acid coated Unmodified BSF |
| 12 | BGB-1 | Unmodified besifloxacin |
| 13 | BGB-2 | Stearic acid coated modified BSF |
| 14 | BGB-3 | Stearic acid coated modified BSF |

TABLE 53-continued

Exemplary formulations for determining the antibacterial activity against *S. aureus* MTCC 6908

| S. No. | Samples | Contents |
|---|---|---|
| 15 | BGB-4 | Stearic acid coated modified BSF |
| 16 | BGB-5 | Uncoated modified BSF |
| 17 | BGB-6 | Lauric Acid coated modified BSF |
| 18 | BSD-1 | LA coated BSF NPs |
| 19 | BSD-2 | LA coated BSF NPs |
| 20 | BSD-3 | Uncoated BSF NPs |
| 21 | BSD-4 | Uncoated BSF NPs |
| 22 | BSD-5 | Uncoated BSF NPs |

TABLE 54

Exemplary formulations for determining the antibacterial activity against *S. aureus* MTCC 6908

| Sample Code | Contents |
|---|---|
| BTK-1 | Unmodified Besifloxacin |
| BTK-2 | Stearic acid coated unmodified besifloxacin |
| BTK-3 | Stearic acid coated modified besifloxacin |
| BTK-4 | Stearic acid coated modified besifloxacin |
| BTK-5 | Stearic acid coated modified besifloxacin |
| BTK-6 | Placebo gel |

Procedure: (1) Minimum Inhibitory Concentration (MIC)

*S. aureus* MTCC 6908 were grown in Tryptone Soya Agar (TSA) at 37° C. for 24 hours. In 96 well plate, 100 µl of Tryptone Soya broth (TSB) was added into all wells and then 100 µl of broth containing drug was added to first well (1A to 1H). Serial (double) dilution was carried out for up to 10 wells (column 1 to column 10 of 96 well plate). *S. aureus* MTCC 6908 culture turbidity was adjusted to 0.5 McFarland standard (approximately $1.5 \times 10^8$) and further 100 times diluted with sterile TSA broth. *S. aureus* MTCC 6908 suspension (100 µl) was added to each well except sterility control. Plates were incubated at 37° C. for 24 hours. After incubation, MIC was determined by adding Alamar blue dye. (2) Zone of Inhibition (ZOI): *S. aureus* MTCC 6908 were grown in Tryptone Soya Agar (TSA) at 37° C. for 24 hours. BHA plates are spreaded with 100 µl of 0.5 McFarland standard equal bacterial suspension. Test samples (drugs/formulations) were dissolved in water/solvent based on the solubility. Sterile disc (6 mm) were loaded with 10 µl of test samples (of various concentration of drug), and were placed above the spreaded plates. Plates were incubated at 37 C for 24 h, followed by ZOI measurement. (3) Time Kill Assay: 0.5 McFarland standard equal *S. aureus* culture was prepared in sterile water. Besifloxacin gels were diluted in Tryptone Soya broth (TSB) to get final concentration of 25 µg/ml. Then 900 µl of *S. aureus* 0.5 McFarland standard equal culture and 100 µl of diluted Besifloxacin gel was mixed to obtain final Besifloxacin concentration, 2.5 µl g/ml. Total reaction mixture (1 ml) was incubated at 37° C. in a tube rotator. After 2 and 6 h exposure, bacterial suspension was placed on Tryptone soya agar plate and incubated at 37° C. for 24 h.

Figure 11:
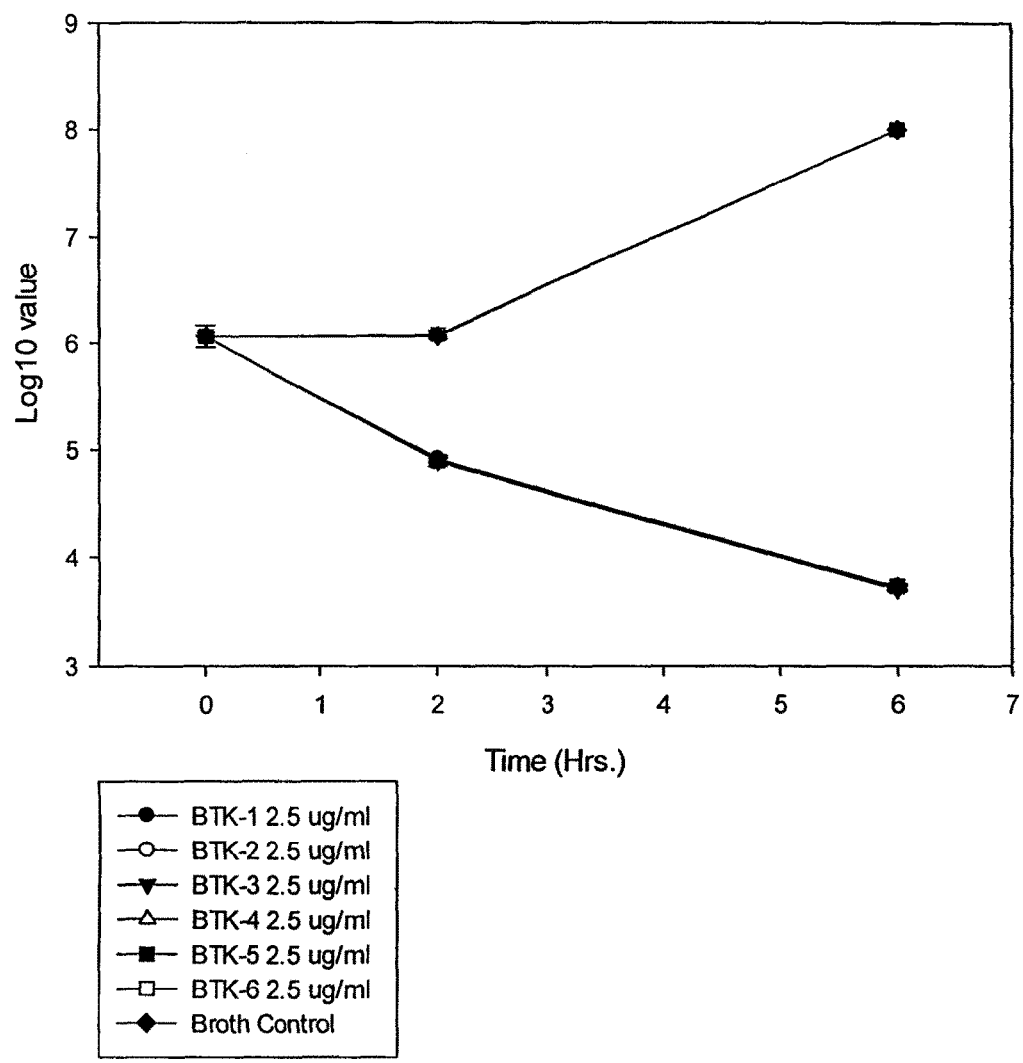
FIG. 11 is a line graph showing time kill kinetics of some exemplary besifloxacin formulations and besifloxacin APIs against *S. aureus*.

Results are shown in Tables 55-56 and FIG. 11. As show in Table 55, MIC results show that all the formulations (BZM1-BZM5 & BGB1-BGB6) were similar in MIC except the placebo gel (BZM 6). Further, Lauric acid coated BSF (BSD1-BSD5) and unmodified BSF (BSD-9) APIs showed similar efficacy in MIC assay, but stearic acid coated APIs (BSD6-BSD10) had less antibacterial efficacy.

As shown in Table 56, zone of inhibition (ZOI) results indicate that all the formulations (BZM1-BZM5) had similar MIC except the placebo gel (BZM 6). There was no difference between unmodified besifloxacin or Stearic acid (SA) coated besifloxacin API based gel. However, stearic acid coated API (BSD-6, BSD-7, BSD-8 and BSD-10) dispersion showed less or no antibacterial efficacy with respect to the unmodified BSF API (BSD 9) dispersion.

As shown in Table 57 and FIG. 11, the time kill results indicate formulations containing unmodified BSF or modified BSF have similar antibacterial kill efficacy. Placebo and growth control showed no undesirable inhibitory growth patterns.

TABLE 55

MIC results
Besifloxacin API/Formulations MIC against *P. acnes* MTCC 1951

| S. No. | Samples | MIC µg/ml | |
|---|---|---|---|
| 1 | BZM-1 | 0.13 | Formulations |
| 2 | BZM-2 | 0.13 | |
| 3 | BZM-3 | 0.13 | |
| 4 | BZM-4 | 0.13 | |
| 5 | BZM-5 | 0.13 | |
| 6 | BZM-6 | >2 | |
| 7 | BGB-1 | 0.13 | |
| 8 | BGB-2 | 0.13 | |
| 9 | BGB-3 | 0.13 | |
| 10 | BGB-4 | 0.13 | |
| 11 | BGB-5 | 0.13 | |
| 12 | BGB-6 | 0.13 | |
| 13 | BSD-1 | 0.25 | API Dispersion |
| 14 | BSD-2 | 0.25 | |
| 15 | BSD-3 | 0.5 | |
| 16 | BSD-4 | 0.5 | |
| 17 | BSD-5 | 0.25 | |
| 18 | BSD-6 | >2 | |
| 19 | BSD-7 | >2 | |
| 20 | BSD-8 | >2 | |
| 21 | BSD-9 | 0.3 | |
| 22 | BSD-10 | <2 | |

TABLE 56

Zone of inhibition
Besifloxacin API & formulations against *S. aureus* MTCC 6908

| | | Besifloxacin 1 µg ZOI (mm) | | | Besifloxacin 2 µg ZOI (mm) | | | Besifloxacin 4 µg ZOI (mm) | | | Besifloxacin 8 µg ZOI (mm) | | |
|---|---|---|---|---|---|---|---|---|---|---|---|---|---|
| S. No. | Samples | Rep-1 | Rep-2 | Avg. | Rep-1 | Rep-2 | Avg. | Rep-1 | Rep-2 | Avg. | Rep-1 | Rep-2 | Avg. |
| 1 | BZM-1 | 21 | 20 | 20.5 | 23 | 23 | 23 | 24 | 24 | 24 | 28 | 27 | 27.5 |
| 2 | BZM-2 | 19 | 20 | 19.5 | 22 | 23 | 22.5 | 25 | 24 | 24.5 | 27 | 27 | 27 |
| 3 | BZM-3 | 20 | 21 | 20.5 | 23 | 23 | 23 | 25 | 25 | 25 | 26 | 26 | 26 |
| 4 | BZM-4 | 21 | 19 | 20 | 23 | 21 | 22 | 24 | 24 | 24 | 24 | 25 | 24.5 |
| 5 | BZM-5 | 19 | 19 | 19 | 21 | 22 | 21.5 | 21 | 22 | 21.5 | 25 | 24 | 24.5 |
| 6 | BZM-6 | — | — | — | — | — | — | — | — | — | — | — | — |
| 7 | BSD-6 | — | — | — | — | — | — | 8 | 8 | 8 | 11 | 12 | 11.5 |
| 8 | BSD-7 | — | — | — | 7 | 7 | 7 | 12 | 11 | 11.5 | 16 | 16 | 16 |
| 9 | BSD-8 | — | — | — | 6 | — | 6 | 13 | 10 | 11.5 | 17 | 16 | 16.5 |
| 10 | BSD-9 | 19 | 19 | 19 | 22 | 20 | 21 | 24 | 24 | 24 | 27 | 26 | 26.5 |
| 11 | BSD-10 | — | — | — | — | — | — | 10 | 8 | 9 | 14 | 13 | 13.5 |

TABLE 57

Time kill
Besifloxacin API/Formulations Time Kill against S. aureus
MTCC 6908

| S. No. | Sample Code | Initial (Log10) | 2 Hrs (Log10) | Log Change | 2 Hrs (Log10) | Log Change |
|---|---|---|---|---|---|---|
| 1 | Growth Control | 6.06 | 6.06 | 0.00 | 8.00 | 1.94 |
| 2 | BTK-1 | 6.06 | 4.91 | -1.15 | 3.73 | -2.33 |
| 3 | BTK-2 | 6.06 | 4.9 | -1.16 | 3.71 | -2.35 |
| 4 | BTK-3 | 6.06 | 4.89 | -1.17 | 3.70 | -2.36 |
| 5 | BTK-4 | 6.06 | 4.9 | -1.16 | 3.72 | -2.34 |
| 6 | BTK-5 | 6.06 | 4.89 | -1.17 | 3.73 | -2.33 |
| 7 | BTK-6 | 6.06 | 6.08 | 0.01 | 8.00 | 1.94 |

Example 53. Minimal Inhibitory Concentration Determination for Besifloxacin.HCl Loaded Formulations (Soluble Besifloxacin.HCl Gel, Suspended Besifloxacin.HCl Gels and Suspended Besifloxacin.HCl Cream) Against Different Strains of P. acnes [MTCC 1951 (Susceptible Strain), CCARM 9010 (Resistant Strain)]

Minimum inhibitory concentrations of gel and cream formulations containing besifloxacin.HCl against two strains of P. acnes [MTCC 1951 (susceptible strain), CCARM 9010 (resistant strain)] were determined. The following samples were used for the study.

TABLE 58

Exemplary formulations for determining the Minimum Inhibitory Concentration (MIC) against P. acnes [MTCC 1951 (susceptible strain), CCARM 9010 (resistant strain)]

| S. No. | Formulation Codes | Code Details | Formulation details |
|---|---|---|---|
| 1 | SL7 | VLN-F21/BSF/GL/001A | Besifloxacin•HCl solublized gel |
| 2 | GL15 | VLN-F21/BSF/GL/002A | Besifloxacin•HCl suspended gel Hydroxyethyl cellulose |
| 3 | GL10 | VLN-F19/BSF/GL/051A | Besifloxacin•HCl suspended gel with carbomer homopolymer Type C |
| 4 | CM02 | VLN-F20/BSF/CR/003A | Besifloxacin•HCl cream with Homopolymer Type C |
| 5 | CM05 | VLN-F20/BSF/CR/004A | Besifloxacin•HCl cream without Homopolymer Type C |

Procedure for Minimum Inhibitory concentration (MIC):
P. acnes were cultured in Brain Heart Infusion Agar (BHIA) at 37° C. for 48 hours under anaerobic condition. For MIC test, BHI broth (100 µl) was added into all 96 wells and 100 µl of broth containing drug was added to first well (1A to 1H) and serial (double) dilution was carried out for up to 10 wells (column 1 to column 10 of 96 well plate). For bacterial inoculum, P. acnes culture turbidity was adjusted to 0.5 McFarland standard (approximately $1.5 \times 10^8$) and further diluted (100 times with sterile BHI broth). Diluted P. acnes suspension (100 µl) was added to each well except sterility control wells (column 12 of 96 well plate). Inoculated plates were incubated at 37° C. for 72 hours under anaerobic condition. After incubation, MIC was determined by adding Alamar blue dye.

Results:
All besifloxacin formulations had shown similar MIC values (0.13-0.25 µg/ml). Results are shown in Table 59.

TABLE 59

Results of MIC of gel and cream formulations against P. acnes [MTCC 1951 (susceptible strain), CCARM 9010 (resistant strain)]

| | | | MIC Value Against Different P. acnes strains (µg/ml) | |
|---|---|---|---|---|
| S. No. | Formulation Codes | Code Details | P. acnes MTCC 1951 | P. acnes CCARM 9010 |
| 1 | SL7 | VLN-F21/BSF/GL/001A | 0.13 | 0.13 |
| 2 | GL15 | VLN-F21/BSF/GL/002A | 0.13 | 0.13 |
| 3 | GL10 | VLN-F19/BSF/GL/051A | 0.13 | 0.25 |
| 4 | CM02 | VLN-F20/BSF/CR/003A | 0.13 | 0.13 |
| 5 | CM05 | VLN-F20/BSF/CR/004A | 0.13 | 0.13 |

Example 54: Minimum Inhibitory Concentration (MIC) Determination of Gel Formulations Loaded with Besifloxacin.HCl/Adapalene/Combination Against P. acnes [MTCC 1951 (Susceptible Strain), CCARM 9010 (Clindamycin-Nonresponderstrain)]

Minimum inhibitory concentrations of gel formulations containing besifloxacin.HCl or adapalene or their combination against P. acnes [MTCC 1951 (susceptible strain), CCARM 9010 (resistant strain)] were determined. The following samples were used for the study.

TABLE 60

Exemplary formulations for determining the Minimum Inhibitory Concentration (MIC) against P. acnes [MTCC 1951 (susceptible strain), CCARM 9010 (resistant strain)]

| S. No. | Formulation Codes | Code Details | Contents |
|---|---|---|---|
| 1 | GL18 | VLN-F19/BSF-ADP/GL/002 | Besifloxacin•HCl (suspended) and Adapalene (suspended) Gel with hydroxyethyl cellulose |
| 2 | GL19 | VLN-F19/BSF-ADP/GL/003 | Besifloxacin•HCl (suspended) and Adapalene (suspended) Gel with homopolymer type C |
| 3 | SS01 | VLN-F17/BSF-ADP/GL/001 | Besifloxacin•HCl (soluble) and adapalene (suspended) with hydroxyethyl cellulose |
| 4 | SL7 | VLN-F21/BSF/GL/001A | Besifloxacin•HCl solublized gel |
| 5 | AD01 | VLN-F19/ADP/GL/001 | Gel containing suspended Adapalene |

Procedure for Minimum Inhibitory concentration (MIC):
P. acnes were cultured in Brain Heart Infusion Agar (BHIA) at 37° C. for 48 hours under anaerobic condition. For MIC test, BHI broth (100 µl) was added into all 96 wells and 100 µl of broth containing drug was added to first well (1A to 1H) and serial (double) dilution was carried out for up to 10 wells (column 1 to column 10 of 96 well plate). For bacterial inoculum, P. acnes culture turbidity was adjusted to 0.5 McFarland standard (approximately $1.5 \times 10^8$) and further diluted (100 times with sterile BHI broth). Diluted P. acnes suspension (100 µl) was added to each well except sterility control wells (column 12 of 96 well plate). Inoculated plates were incubated at 37° C. for 72 hours under anaerobic condition. After incubation, MIC was determined by adding Alamar blue dye.

Results:

All the formulations except gel containing adapalene alone had shown similar MIC (0.13 µg/ml) against *P. acnes* [MTCC 1951 (susceptible strain), CCARM 9010 (resistant strain). Results are shown in Table 61.

TABLE 61

Results of MIC of gel formulations against *P. acnes* [MTCC 1951 (susceptible strain), CCARM 9010 (resistant strain)]

| S. No. | Formulation Codes | Code Details | MIC Value Against Different *P. acnes* strains (µg/ml) | |
|---|---|---|---|---|
| | | | *P. acnes* MTCC 1951 | *P. acnes* CCARM 9010 |
| 1 | GL18 | VLN-F19/BSF-ADP/GL/002 | 0.13 | 0.13 |
| 2 | GL19 | VLN-F19/BSF-ADP/GL/003 | 0.13 | 0.13 |
| 3 | SS01 | VLN-F17/BSF-ADP/GL/001 | 0.13 | 0.13 |
| 4 | SL7 | VLN-F21/BSF/GL/001A | 0.13 | 0.13 |
| 5 | AD01 | VLN-F19/ADP/GL/001 | >4 | >4 |

Example 55: Minimum Inhibitory Concentration (MIC) Determination of Gel and Cream Formulations Loaded with Besifloxacin.HCl Against *S. aureus* MTCC 6908

Minimum inhibitory concentrations of gel and cream formulations containing besifloxacin.HCl against *S. aureus* MTCC 6908 were determined. The samples used for the study were same as those mentioned in Table 58.

Procedure for Minimum Inhibitory Concentration (MIC):

*S. aureus* were cultured in Brain Heart Infusion Agar (BHIA) at 37° C. for 24 hours under anaerobic condition. For MIC test, BHI broth (100 µl) was added into all 96 wells and 100 µl of broth containing drug was added to first well (1A to 1H) and serial (double) dilution was carried out for up to 10 wells (column 1 to column 10 of 96 well plate). For bacterial inoculum, *S. aureus* culture turbidity was adjusted to 0.5 McFarland standard (approximately $1.5 \times 10^8$) and further diluted (100 times with sterile BHI broth). Diluted *S. aureus* suspension (100 µl) was added to each well except sterility control wells (column 12 of 96 well plate). Inoculated plates were incubated at 37° C. for 24 hours. After incubation, MIC was determined by adding Alamar blue dye.

Results:

All the formulations had shown similar MIC (0.25 µg/ml) against *S. aureus* MTCC 6908. Results are shown in Table 62.

TABLE 62

Results of MIC of gel and cream formulations against *S. aureus* MTCC 6908

| Sr. No. | Formulation Codes | Code Details | MIC Value Against *S. aureus* MTCC 6908 (µg/ml) |
|---|---|---|---|
| 1 | SL7 | VLN-F21/BSF/GL/001A | 0.25 |
| 2 | GL15 | VLN-F21/BSF/GL/002A | 0.25 |
| 3 | GL10 | VLN-F19/BSF/GL/051A | 0.25 |
| 4 | CM02 | VLN-F20/BSF/CR/003A | 0.25 |
| 5 | CM05 | VLN-F20/BSF/CR/004A | 0.25 |

Example 56: Minimum Inhibitory Concentration (MIC) Determination of Gel Formulations Loaded with Besifloxacin.HCl/Adapalene/Combination of Both Against *S. aureus* MTCC 6908

Minimum inhibitory concentrations of gel formulations containing besifloxacin.HCl or adapalene or their combination against *S. aureus* MTCC 6908 were determined. The samples used for the study were same as those given in Table 60.

Procedure for Minimum Inhibitory concentration (MIC *S. aureus* were cultured in Brain Heart Infusion Agar (BHIA) at 37° C. for 24 h under anaerobic condition. For MIC test, BHI broth (100 µl) was added into all 96 wells and 100 µl of broth containing drug was added to first well (1A to 1H) and serial (double) dilution was carried out for up to 10 wells (column 1 to column 10 of 96 well plate). For bacterial inoculum, *S. aureus* culture turbidity was adjusted to 0.5 McFarland standard (approximately $1.5 \times 10^8$) and further diluted (100 times with sterile BHI broth). Diluted *S. aureus* suspension (100 µl) was added to each well except sterility control wells (column 12 of 96 well plate). Inoculated plates were incubated at 37° C. for 24 hours. After incubation, MIC was determined by adding Alamar blue dye.

Results:

All the formulations except gel containing adapalene alone had shown similar MIC (0.25 µg/ml) against *S. aureus* MTCC 6908. Results are shown in Table 63.

TABLE 63

Results of MIC of gel formulations against *S. aureus* MTCC 6908

| S. No. | Formulation Codes | Code Details | MIC Value Against *S. aureus* MTCC 6908 (µg/ml) |
|---|---|---|---|
| 1 | GL18 | VLN-F19/BSF-ADP/GL/002 | 0.25 |
| 2 | GL19 | VLN-F19/BSF-ADP/GL/003 | 0.25 |
| 3 | SS01 | VLN-F17/BSF-ADP/GL/001 | 0.25 |
| 4 | SL7 | VLN-F21/BSF/GL/001A | 0.25 |
| 5 | AD01 | VLN-F19/ADP/GL/001 | >4 |

Example 57: In Vitro Time-Kill Kinetic Study of Besifloxacin.HCl Loaded Gel and Cream Formulations Against *Staphylococcus aureus* MTCC 6908

In vitro Time kill kinetic study of gel and cream formulations containing besifloxacin.HCl against *S. aureus* MTCC 6908 was performed. The following samples were used for the study.

TABLE 64

Exemplary formulations (Gel and Cream) for In vitro Time-Kill Kinetic Study against *S. aureus* MTCC 6908

| S. No. | Formulation Code | Code Details | Contents |
|---|---|---|---|
| 1 | SL7 | VLN-F21/BSF/GL/001A | Besifloxacin•HCl solublized gel |
| 2 | GL15 | VLN-F21/BSF/GL/002A | Besifloxacin•HCl suspended gel Hydroxy ethyl cellulose |
| 3 | GL10 | VLN-F19/BSF/GL/051A | Besifloxacin•HCl suspended gel with Carbomer Homopolymer Type C |
| 4 | CM02 | VLN-F20/BSF/CR/003A | Besifloxacin•HCl cream with Carbomer Homopolymer Type C |
| 5 | CM05 | VLN-F20/BSF/CR/004A | Besifloxacin•HCl cream without Carbomer Homopolymer Type C |
| 6 | PP01 | VLN-F19/BSF/GL/070-P | Placebo gel |
| 7 | PP02 | VLN-F20/BSF/CR/004-P | Placebo cream |

Procedure for In-Vitro Time-Kill Assay:

Besifloxacin formulation was diluted in water to prepare 1 mg/ml stock and further diluted in BHI broth to make final concentration of 100 µg/ml. *S. aureus* MTCC 6908 (900 µl) 0.5 McFarland standard equal culture and 100 µl of diluted Besifloxacin (100 µg/ml) were mixed to obtain final Besifloxacin concentration 10 µg/ml in reaction mixture. Total reaction mixture (1 ml) was incubated at 37° C. in an incubator. Post incubation at 1, 3 and 6 h, cells were plated after serial dilution in brain heart infusion agar plate. One tube with two read outs were taken for each sample. Cells were allowed to grow for 16-24 h at 37° C. in incubator.

Results:

All Besifloxacin formulations except Placebo had shown similar antibacterial efficacy against *S. aureus* MTCC 6908 (Approx 2 log reduction at 6 h). Results are shown in Table 65.

Example 58: In Vitro Time-Kill Kinetic Study of Gel Formulations Loaded with Besifloxacin.HCl/Adapalene/Combination of Both Against *Staphylococcus aureus* MTCC 6908

Time kill kinetic study of gel formulations containing besifloxacin.HCl or Adapalene or combination of both against *S. aureus* MTCC 6908 was performed. The following samples were used for the study.

TABLE 66

Exemplary formulations for determining the antibacterial activity against *S. aureus* MTCC 6908

| Sr. No. | Formulation Code | Code Details | Contents |
|---|---|---|---|
| 1 | GL18 | VLN-F19/BSF-ADP/GL/002 | Besifloxacin•HCl and Adapalene gel with Carbomer Homopolymer Type C |
| 2 | GL19 | VLN-F19/BSF-ADP/GL/003 | Besifloxacin•HCl and Adapalene gel with hydroxyl ethyl cellulose |
| 3 | SS01 | VLN-F17/BSF-ADP/GL/001 | Besifloxacin•HCl (solubilized) and Adapalene gel with hydroxyl ethyl cellulose |
| 4 | SL7 | VLN-F21/BSF/GL/001A | Besifloxacin•HCl solublized gel |
| 5 | AD01 | VLN-F19/ADP/GL/001 | Gel containing Adapalene |
| 6 | PP01 | VLN-F19/BSF/GL/070-P | Placebo gel |

Procedure for In Vitro Time-Kill Assay:

Besifloxacin formulation was diluted in water to prepare 1 mg/ml stock and further diluted in BHI broth to make final concentration of 100 µg/ml. *S. aureus* MTCC 6908 (900 µl) 0.5 McFarland standard equal culture and 100 µl of diluted Besifloxacin (100 µg/ml) were mixed to obtain final Besifloxacin concentration 10 µg/ml in reaction mixture. Total reaction mixture (1 ml) was incubated at 37° C. in an incubator. Post incubation at 1, 3 and 6 h, cells were plated after serial dilution in brain heart infusion agar plate. One tube with two read outs were taken for each sample. Cells were allowed to grow for 16-24 h at 37° C. in incubator.

Results:

All Besifloxacin-Adapalene formulations except placebo had shown similar antibacterial efficacy against *S. aureus* MTCC 6908 (approximately 2 log reduction at 6 h. Results are shown in Table 67.

TABLE 65

Results of In-vitro Time-Kill Assay of gel and cream formulations against *S. aureus* MTCC 6908.
Log 10 values (Besifloxacin formulations)

| Time (h) | SL7 GL/001A | GL15 GL/002A | GL10 GL/051A | CM02 CR/003A | CM05 CR/004A | PP01 GL/070-P | PP02 CR/004-P | Broth control |
|---|---|---|---|---|---|---|---|---|
| 0 | 7.42 | 7.42 | 7.42 | 7.42 | 7.42 | 7.42 | 7.42 | 7.42 |
| 1 | 6.54 | 6.56 | 6.50 | 6.54 | 6.53 | 7.57 | 7.58 | 7.61 |
| 3 | 5.78 | 5.80 | 5.77 | 5.88 | 5.91 | 8.02 | 8.07 | 8.10 |
| 6 | 5.52 | 5.52 | 5.53 | 5.51 | 5.54 | 8.97 | 8.98 | 9.00 |
| | | | | SD | | | | |
| 0 | 0.11 | 0.11 | 0.11 | 0.11 | 0.11 | 0.11 | 0.11 | 0.11 |
| 1 | 0.04 | 0.08 | 0.04 | 0.06 | 0.07 | 0.04 | 0.02 | 0.01 |
| 3 | 0.05 | 0.06 | 0.04 | 0.04 | 0.04 | 0.03 | 0.04 | 0.02 |
| 6 | 0.01 | 0.03 | 0.02 | 0.02 | 0.04 | 0.02 | 0.03 | 0.00 |

TABLE 67

Results of In-vitro Time-Kill Assay of gel formulations against S. aureus MTCC 6908.
Log 10 values (Besifloxacin formulations and their combination with Adapalene)

| Time (hr.) | GL18 GL/002 | GL19 GL/003 | SS01 GL/001 | SL7 GL/001A | AD01 ADP/ GL 001 | PP01 GL/070-P | Broth control |
|---|---|---|---|---|---|---|---|
| 0 | 7.53 | 7.53 | 7.53 | 7.53 | 7.53 | 7.53 | 7.53 |
| 1 | 6.25 | 6.34 | 6.31 | 6.34 | 7.57 | 7.54 | 7.59 |
| 3 | 5.81 | 5.80 | 5.76 | 5.76 | 8.16 | 8.20 | 8.24 |
| 6 | 5.48 | 5.47 | 5.49 | 5.49 | 8.84 | 8.91 | 8.92 |
| SD | | | | | | | |
| 0 | 0.04 | 0.04 | 0.04 | 0.04 | 0.04 | 0.04 | 0.04 |
| 1 | 0.02 | 0.01 | 0.07 | 0.07 | 0.02 | 0.01 | 0.02 |
| 3 | 0.01 | 0.02 | 0.02 | 0.05 | 0.02 | 0.00 | 0.02 |
| 6 | 0.02 | 0.05 | 0.05 | 0.03 | 0.04 | 0.01 | 0.03 |

Example 59: In Vitro Time-Kill Kinetic Study of Besifloxacin.HCl Loaded Gel and Cream Formulations Against P. acnes CCARM 9010

In vitro Time kill kinetic study of gel formulations containing besifloxacin.HCl against P. acnes CCARM 9010 was performed. The samples used for the study were same as mentioned in Table 64.

Procedure for In-Vitro Time-Kill Assay:

0.5 McFarland standard equal P. acnes (CCARM 9010) culture was prepared in sterile water. Prepared culture was centrifuged at 2000 rpm for 20 min then supernatant was removed and similar amount of brain heart infusion (BHI) broth was added. P. acnes culture in BHI broth was kept for overnight (16 h.) incubation in anaerobic box at 37° C. Besifloxacin powder was diluted in water and DMSO to prepare 1 mg/ml stock and then both were further diluted in BHI broth to make final concentration of 100 µg/ml. 900 µl of P. acnes 0.5 McFarland culture (after 16 h. incubation) and 100 µl of diluted Besifloxacin (100 µg/ml) were mixed to obtain final Besifloxacin concentration 10 µg/ml in reaction mixture. Total reaction mixture (1 ml) was incubated at 37° C. in an anaerobic box. Post incubation at 2, 8 and 24 h, cells were plated after serial dilution in brain heart infusion agar plate. Cells were allowed to grow for 3 days at 37° C. inside anaerobic box.

Results:

All Besifloxacin formulations except Placebo had shown similar antibacterial efficacy against P. acnes CCARM 9010 (Approx 2 log reduction at 24 hrs). Results are shown in Tables 68.

TABLE 68

Results of In vitro Time-Kill Assay of gel and cream formulations against P. acnes CCARM 9010
Log 10 values (Besifloxacin formulations)

| Time (hr.) | SL7 GL/001A | GL15 GL/002A | GL10 GL/051A | CM02 CR/003A | CM05 CR/004A | PP01 GL/070-P | PP02 CR/004-P | Broth control |
|---|---|---|---|---|---|---|---|---|
| 0 | 8.28 | 8.28 | 8.28 | 8.28 | 8.28 | 8.28 | 8.28 | 8.28 |
| 2 | 7.64 | 7.61 | 7.61 | 7.62 | 7.62 | 8.27 | 8.29 | 8.30 |
| 8 | 6.92 | 6.84 | 6.87 | 6.88 | 6.95 | 8.66 | 8.68 | 8.69 |
| 24 | 6.02 | 6.07 | 6.09 | 6.12 | 6.13 | 9.13 | 9.15 | 9.19 |
| SD | | | | | | | | |
| 0 | 0.03 | 0.03 | 0.03 | 0.03 | 0.03 | 0.03 | 0.03 | 0.03 |
| 2 | 0.01 | 0.01 | 0.03 | 0.01 | 0.03 | 0.02 | 0.02 | 0.00 |
| 8 | 0.03 | 0.01 | 0.02 | 0.04 | 0.04 | 0.01 | 0.03 | 0.02 |
| 24 | 0.06 | 0.07 | 0.06 | 0.04 | 0.08 | 0.02 | 0.01 | 0.02 |

Example 60: In Vitro Time-Kill Kinetic Study of Besifloxacin.HCl Loaded Gel and Cream Formulations Against P. acnes MTCC 1951

In vitro Time kill kinetic study of gel and cream formulations containing besifloxacin.HCl or Adapalene or combination of both against P. acnes MTCC 1951 was performed. The samples used for the study were same as written in Table 64.

Results:

All Besifloxacin formulations except placebo had shown similar antibacterial efficacy against P. acnes MTCC 1951 (approximately 2 log reduction at 24 h). Results are shown in Table 69.

TABLE 69

Results of Time-Kill Assay of gel and cream formulations against
P. acnes MTCC 1951.
Log 10 values (Besifloxacin formulations)

| Time (hr.) | SL7 GL/001A | GL15 GL/002A | GL10 GL/051A | CM02 CR/003A | CM05 CR/004A | PP01 GL/070-P | PP02 CR/004-P | Broth control |
|---|---|---|---|---|---|---|---|---|
| 0 | 8.19 | 8.19 | 8.19 | 8.19 | 8.19 | 8.19 | 8.19 | 8.19 |
| 2 | 7.47 | 7.45 | 7.42 | 7.47 | 7.46 | 8.20 | 8.22 | 8.26 |
| 8 | 6.94 | 6.94 | 6.98 | 7.00 | 6.97 | 8.64 | 8.64 | 8.65 |
| 24 | 6.00 | 5.97 | 6.04 | 6.04 | 6.09 | 9.20 | 9.17 | 9.30 |
|  |  |  |  | SD |  |  |  |  |
| 0 | 0.02 | 0.02 | 0.02 | 0.02 | 0.02 | 0.02 | 0.02 | 0.02 |
| 2 | 0.03 | 0.01 | 0.05 | 0.03 | 0.03 | 0.08 | 0.02 | 0.00 |
| 8 | 0.04 | 0.08 | 0.06 | 0.03 | 0.01 | 0.06 | 0.01 | 0.00 |
| 24 | 0.09 | 0.15 | 0.03 | 0.01 | 0.04 | 0.08 | 0.08 | 0.00 |

Example 61: Determination of Anti-inflammatory Potential of Besifloxacin.HCl, Adapalene in THP-1 Cells Stimulated by P. acnes (ATCC 6919)

Anti-inflammatory activity of besifloxacin.HCl and adapalene in THP-1 cells stimulated with P. acnes (ATCC 6919) was studied.

Procedure:

Preparation of stimulant for inflammation: P. acnes culture suspension was prepared in PBS and the cell number in the suspension was adjusted to approximately $5 \times 10^8$ CFU/ml by measuring the cell density using a Densimat. The bacterial suspension was then heat killed at 80° C. for 30 min and stored at −80° C. until further use.

ELISA to Study Inflammatory Response in THP-1 Cells:

Cells were seeded in a 96-well format ($2 \times 10^5$ THP-1 cells per well) in media containing 10% FBS. The cells were stimulated to induce inflammatory cytokines using 3 McFarland equivalent heat-killed P. acnes. Cells in control wells were treated with PBS. One hour after induction with P. acnes, test agents were added to the induced cells at appropriate concentrations (Besifloxacin at 10 and 30 µg/ml; Adapalene at 0.04 and 0.4 µg/ml). The plates were incubated at 37° C. for 24 hours. After 24 h, the plates were centrifuged to pellet the cells and the supernatants were collected. The cell culture supernatants thus obtained were analyzed for cytokine levels (IL-6 and IL-8) by ELISA using R&D Systems kits for individual cytokines following the manufacturer's instructions.

Results

Figures 14A, 14B:
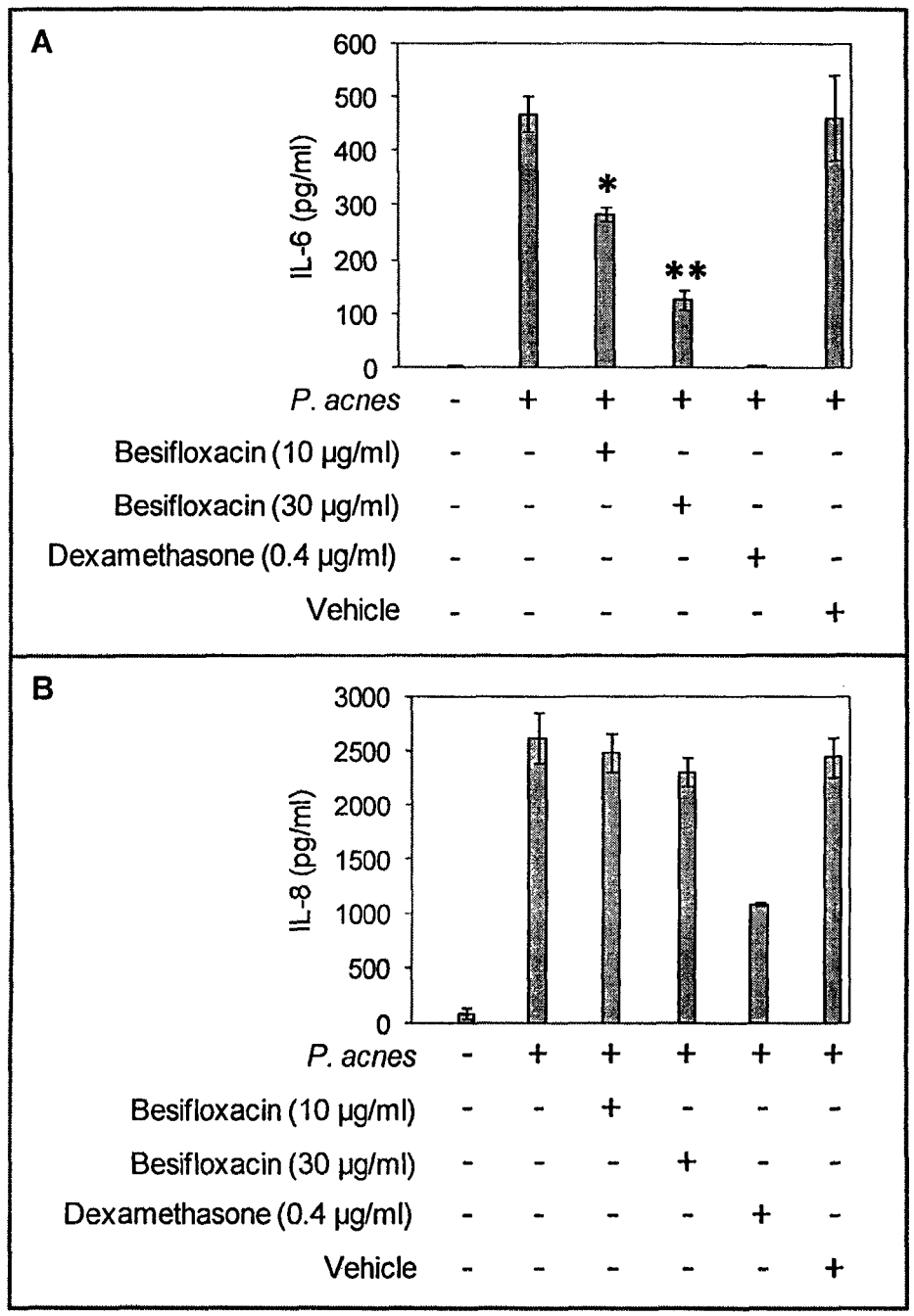
FIGS. 14A and 14B are bar graphs showing the concentration-dependent inhibitory effect of Besifloxacin on *P. acnes*-induced cytokines IL-6 (FIG. 14A) but not IL-8 (FIG. 14B) release in THP-1 cells. Statistical analysis was performed using Student's t-test (*p=0.005; **p=0.0005).

Besifloxacin Inhibits IL-6 Secretion from P. acnes-Induced THP-1 Cells:

In order to study anti-inflammatory effects of besifloxacin in response to P. acnes, THP-1 cells were exposed to heat-killed P. acnes followed by treatment with besifloxacin.HCl at 10 or 30 µg/ml. The culture supernatants were then tested for levels of IL-6 or IL-8 using a colorimetric ELISA. The data presented in FIG. 14A clearly shows that besifloxacin.HCl causes a significant dose-dependent decrease in IL-6 levels induced by P. acnes. However, it does not show similar effect on IL-8 levels (FIG. 14B). The cell viability for each of the tested condition was over 80% compared to untreated cells (data not shown). Dexamethasone, the known anti-inflammatory agent, used as a positive control, showed nearly 100% reduction in IL-6 levels.

Figures 15A, 15B:
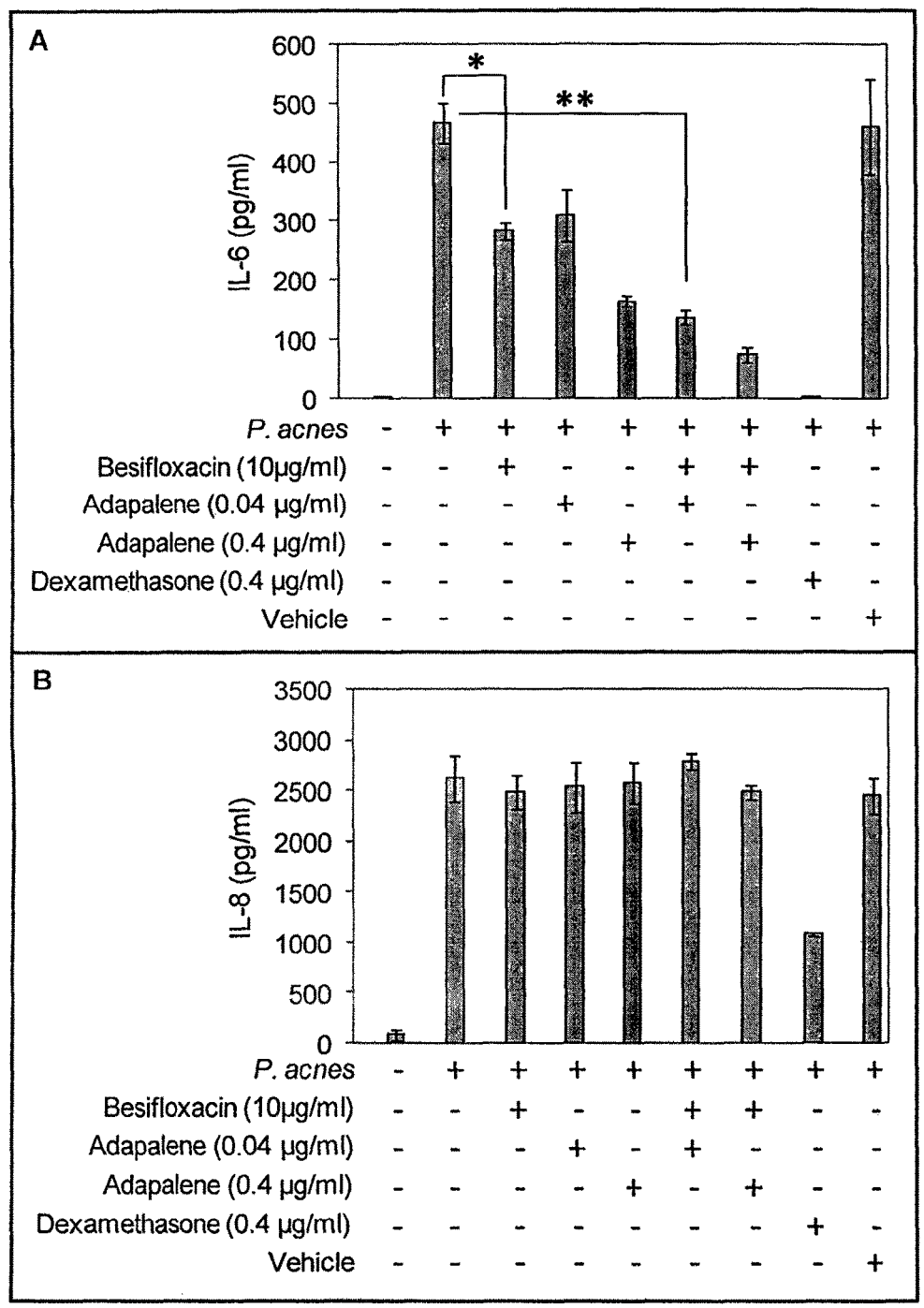
FIGS. 15A and 15B are bar graph showing the combination of Besifloxacin and Adapalene increases the efficacy of inhibiting *P. acnes*-induced cytokines IL-6 (FIG. 15A) but has no effect on IL-8 (FIG. 15B) release in THP-1 cells. Statistical analysis was performed using Student's t-test (*p=0.005; **p=0.001).

Combination of Adapalene and Besifloxacin Shows Additive Inhibitory Effect on IL-6 Secretion by P. acnes-Induced THP-1 Cells:

The effect of a combination of adapalene and besifloxacin.HCl on cytokine secretion by THP-1 cells was studied. For this purpose, THP-1 cells were induced with dead P. acnes and treated with besifloxacin alone (10 µg/ml), adapalene alone (0.04 µg/ml or 0.4 µg/ml) or besifloxacin.HCl and adapalene combinations at the aforementioned concentrations. The results compiled in FIG. 15A show that at the tested concentrations both besifloxacin.HCl and adapalene impart individual anti-inflammatory effects by decreasing the levels of P. acnes-induced IL-6. Further, we observe an additive effect on IL-6 reduction when both besifloxacin-.HCl and adapalene are present compared to their individual effects. Besifloxacin.HCl alone at 10 µg/ml causes approximately 40% reduction in IL-6 levels compared to untreated control. When combined with 0.04 and 0.4 µg/ml adapalene, the IL-6 reduction goes up to 70% and 80% respectively. These effects were however not observed for P. acnes-induced IL-8 levels (FIG. 15B).

Results are presented in Tables 70 and 71 and FIGS. 14 and 15.

TABLE 70

Results of Effect of Besifloxacin•HCl on P. acnes induced cytokine (IL-6, IL-8) release in THP-1 cells as shown in FIG. 14

| | | Expression of Cytokines | | | |
|---|---|---|---|---|---|
| | | IL-6 (pg/ml) | | IL-8 (pg/ml) | |
| Sr. No. | Condition | Mean | SD | Mean | SD |
| 1 | Cells alone | 3.06 | 1.39 | 81.64 | 53.41 |
| 2 | Cells + P. acnes | 468.21 | 34.12 | 2621.6 | 230.38 |
| 3 | Cells + P. acnes + Besifloxacin•HCl (10 µg/ml) | 282.45 | 13.76 | 2484.8 | 169.74 |
| 4 | Cells + P. acnes + Besifloxacin•HCl (30 µg/ml) | 124.58 | 19.2 | 2301.6 | 133.50 |
| 5 | Cells + P. acnes + Dexamethasone (0.4 µg/ml) | 2.15 | 0.52 | 1080.8 | 19.29 |
| 6 | Cells + P. acnes + Vehicle (0.1%) | 461.85 | 80.51 | 2447.0 | 183.10 |

Inference:

There was significant reduction in P. acnes-induced IL-6 levels post drug treatment. However there was no reduction in IL-8 levels.

TABLE 71

Results of Effect of Besifloxacin•HCl and/or Adapalene on *P. acnes* induced cytokine (IL-6, IL-8) release in THP-1 cells as shown in FIG. 15

|  |  | Expression of Cytokines | | | |
|---|---|---|---|---|---|
|  |  | IL-6 (pg/ml) | | IL-8 (pg/ml) | |
| Sr. No. | Condition | Mean | SD | Mean | SD |
| 1 | Cells alone | 3.06 | 1.39 | 81.64 | 53.41 |
| 2 | Cells + *P. acnes* | 468.21 | 34.12 | 2621.64 | 230.38 |
| 3 | Cells + *P. acnes* + Besifloxacin•HCl (10 µg/ml) | 282.45 | 13.76 | 2484.76 | 169.74 |
| 4 | Cells + *P. acnes* + Adapalene (0.04 µg/ml) | 308.82 | 45.54 | 2536.76 | 241.24 |
| 5 | Cells + *P. acnes* + Adapalene (0.4 µg/ml) | 162.76 | 8.45 | 2579.87 | 197.32 |
| 6 | Cells + *P. acnes* + Besifloxacin•HCl (10 µg/ml) + Adapalene (0.04 µg/ml) | 136.70 | 13.06 | 2789.20 | 74.49 |
| 7 | Cells + *P. acnes* + Besifloxacin (10 µg/ml) + Adapalene (0.4 µg/ml) | 72.45 | 13.21 | 2478.09 | 65.87 |
| 8 | Cells + *P. acnes* + Dexamethasone (0.4 µg/ml) | 2.15 | 0.52 | 1080.76 | 19.29 |
| 9 | Cells + *P. acnes* + Vehicle (0.1%) | 461.85 | 80.51 | 2446.98 | 183.10 |

Inference:
1. Besifloxacin.HCl exerts its anti-inflammatory action by decreasing *P. acnes* induced IL-6 levels in THP-1 cells.
2. Addition of adapalene along with besifloxacin.HCl increases the degree of reduction in IL-6 levels and offers enhanced anti-inflammatory effect compared to besifloxacin alone.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein. It is noted that variations and modifications are possible based on the disclosure above without departing from the sprit and scope of the invention.

REFERENCES

Jeremy et al (2003). Journal of Investigative Dermatology; 121: 20-27;
Thibout et al (2014). Journal of Investigative Dermatology; 134: 307-310;
Taglietti et al (2008) Skin Therapy Letter. 2008; 13(5): 6-8;
Regoes et al. (2004) Antimicrob Agents Chemother: 48(10): 3670-6;
Miller et al. (2004) Science; 305 (5690): 1629-31;
Keren et al. (2004) J. Bacteriol; 186: 8172-8180;
Schulzen et al. (2001), Nature 413: 814-821;
Beitru et al. (2003) Antimicrob Agents Chemother.; 47(3): 1112-1114;
Cambau et al. (2009). Antimicrob. Chemother. 63 (3): 443-450;
Kim et al. (2002) Journal of immunology; 169(3): 1535-41;
Liu et al. (2005) Journal of Immunology; 174(5): 2467-2470;
Nagy et al. (2006) Microbes Infect; 8(8): 2195-205;
Lee et al. (2010) Arch Dermatol Res; 302(10): 745-56;
Mouser et al. (2003) J Invest Dermatol; 121(5): 1226-8;
Zasloff et al. (2002) Nature; 415: 389-395;
Epand et al. (1999) Biochim Biophys Acta; 1462: 11-28;
Kabara et al. (1972) Antimicrobn Agents Chemother; 2(1): 23-28; and
De Lucca et al. (2000) Rev. Iberoam. Micol; 17: 116-120

The invention claimed is:
1. A formulation, wherein the formulation comprises:
   (i) 0.5 to 4 (% w/w) Besifloxacin.HCl (Equivalent to Besifloxacin);
   (ii) 2 to 7 (% w/w) diethylene glycol monoethyl ether;
   (iii) 0.1 (% w/w) Edetate disodium dehydrate (EDTA);
   (iv) 2 to 10 (% w/w) glycerin;
   (v) 0.9 to 1.75 (% w/w) hydroxyethyl cellulose;
   (vi) 0 to 0.8 (% w/w) carbomer;
   (vii) 0.3 to 0.7 (% w/w) phenoxyethanol;
   (viii) 2 to 7 (% w/w) polyethylene glycol 400;
   (ix) 0 to 0.5 (% w/w) sodium hyaluronate;
   (x) sodium hydroxide; and
   (xi) purified water.
2. The formulation of claim 1, wherein the formulation further comprises adapalene.
3. The formulation of claim 1, wherein the formulation further comprises a second anti-bacterial agent.
4. A formulation comprising:
   (i) 1 to 4 (% w/w) Besifloxacin.HCl (Equivalent to Besifloxacin);
   (ii) 5 (% w/w) diethylene glycol monoethyl ether;
   (iii) 0.1 (% w/w) Edetate disodium dehydrate (EDTA);
   (iv) 5 (% w/w) glycerin;
   (v) 0.5 to 1.5 (% w/w) hydroxyethyl cellulose;

(vi) 0.3 to 1.2 (% w/w) carbomer;
(vii) 0.7 (% w/w) phenoxyethanol;
(viii) 5 (% w/w) polyethylene glycol 400;
(ix) 0 to 1 (% w/w) sodium hyaluronate;
(x) sodium hydroxide; and
(xi) purified water.

5. The formulation of claim 4, wherein the formulation further comprises adapalene.

6. A method for treating a bacterial infection, comprising administering a therapeutic effective amount of a formulation of claim 1 to a subject in need thereof.

7. The method of claim 6, wherein the bacterial infection is by an antibiotic-resistant bacterial strain.

8. The method of claim 6, wherein bacterial infection is by *P. acnes*.

9. The method of claim 8, wherein *P. acnes* is a drug resistant strain.

10. The method of claim 9, wherein the drug resistant acne is not responding to a therapeutic amount of clindamycin, minocycline, doxycycline, tetracycline or erythromycin.

11. A method for treating a bacterial infection, comprising administering a therapeutic effective amount of a formulation of claim 4 to a subject in need thereof.

12. The method of claim 11, wherein the bacterial infection is by an antibiotic-resistant bacterial strain.

13. The method of claim 11, wherein bacterial infection is by *P. acnes*.

14. The method of claim 13, wherein *P. acnes* is a drug resistant strain.

15. The method of claim 14, wherein the drug resistant stain is not responding to a therapeutic amount of at least one of clindamycin, minocycline, doxycycline, tetracycline and erythromycin.

16. The formulation of claim 4, wherein the formulation further comprises a second anti-bacterial agent.

* * * * *